United States Patent
Oda et al.

(10) Patent No.: US 12,365,906 B2
(45) Date of Patent: Jul. 22, 2025

(54) IMMUNOMODULATORY FUSION PROTEINS AND USES THEREOF

(71) Applicant: Fred Hutchinson Cancer Center, Seattle, WA (US)

(72) Inventors: Shannon K. Oda, Lake Forest Park, WA (US); Philip D. Greenberg, Mercer Island, WA (US); Thomas M. Schmitt, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 18/339,197

(22) Filed: Jun. 21, 2023

(65) Prior Publication Data
US 2024/0218379 A1 Jul. 4, 2024

Related U.S. Application Data

(62) Division of application No. 16/494,729, filed as application No. PCT/US2018/022998 on Mar. 16, 2018, now Pat. No. 11,725,210.

(60) Provisional application No. 62/629,663, filed on Feb. 12, 2018, provisional application No. 62/473,282, filed on Mar. 17, 2017.

(51) Int. Cl.
| | |
|---|---|
| C07K 14/705 | (2006.01) |
| A61K 39/00 | (2006.01) |
| A61K 40/11 | (2025.01) |
| A61K 40/22 | (2025.01) |
| A61K 40/32 | (2025.01) |
| A61K 40/41 | (2025.01) |
| A61K 40/42 | (2025.01) |
| C07K 14/47 | (2006.01) |
| C07K 14/725 | (2006.01) |
| C12N 15/62 | (2006.01) |

(52) U.S. Cl.
CPC .......... *C12N 15/62* (2013.01); *A61K 39/0011* (2013.01); *A61K 40/11* (2025.01); *A61K 40/22* (2025.01); *A61K 40/32* (2025.01); *A61K 40/416* (2025.01); *A61K 40/421* (2025.01); *A61K 40/4243* (2025.01); *C07K 14/4705* (2013.01); *C07K 14/7051* (2013.01); *C07K 14/70521* (2013.01); *C07K 14/70578* (2013.01); *A61K 2239/38* (2023.05); *A61K 2239/48* (2023.05); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,712,149 | A | 1/1998 | Roberts |
| 6,083,751 | A | 7/2000 | Feldhaus et al. |
| 9,163,258 | B2 | 10/2015 | Riddell et al. |
| 9,987,308 | B2 | 6/2018 | Riddell et al. |
| 10,188,749 | B2 | 1/2019 | Stephan et al. |
| 10,350,245 | B2 | 7/2019 | Adair et al. |
| 11,725,210 | B2 | 8/2023 | Oda et al. |
| 2013/0202622 | A1 | 8/2013 | Riddell et al. |
| 2014/0219975 | A1 | 8/2014 | June et al. |
| 2014/0242049 | A1 | 8/2014 | Choi et al. |
| 2014/0314795 | A1 | 10/2014 | Riddell et al. |
| 2016/0008399 | A1 | 1/2016 | Stephan |
| 2016/0083449 | A1 | 3/2016 | Schmitt et al. |
| 2018/0044404 | A1 | 2/2018 | Oda et al. |
| 2018/0353588 | A1 | 12/2018 | Boyd et al. |
| 2018/0369280 | A1 | 12/2018 | Schmitt et al. |
| 2019/0046572 | A1 | 2/2019 | Stephan |
| 2019/0054121 | A1 | 2/2019 | Stephan |
| 2019/0111153 | A1 | 4/2019 | Stephan et al. |
| 2019/0127435 | A1 | 5/2019 | Schmitt et al. |
| 2019/0209671 | A1 | 7/2019 | Dai et al. |
| 2021/0403532 | A1 | 12/2021 | Oda et al. |

FOREIGN PATENT DOCUMENTS

| | | |
|---|---|---|
| AU | 2016226022 B2 | 7/2020 |
| CN | 103965361 A | 8/2014 |
| CN | 110330567 A | 10/2019 |
| EP | 3265481 A1 | 1/2018 |
| WO | WO 2012042480 A1 | 4/2012 |
| WO | WO 2012079000 A1 | 6/2012 |
| WO | WO 2012138858 A1 | 10/2012 |
| WO | WO 2013019615 A2 | 2/2013 |
| WO | WO 2013123061 A1 | 8/2013 |
| WO | WO 2014106839 A1 | 7/2014 |
| WO | WO 2014172584 A1 | 10/2014 |
| WO | WO 2016014535 A1 | 1/2016 |

(Continued)

OTHER PUBLICATIONS

Tarrant et al., Toxicological Sciences 117(1), 4-16 (2010). (Year: 2010).*

(Continued)

*Primary Examiner* — Zachary S Skelding
(74) *Attorney, Agent, or Firm* — Seed IP Law Group LLP

(57) ABSTRACT

The present disclosure relates to immunomodulatory fusion proteins containing an extracellular binding domain and an intracellular signaling domain, wherein binding of a target can generate a modulatory signal in a host cell, such as a T cell. The present disclosure also relates to uses of immune cells expressing such immunomodulatory fusion proteins to treat certain diseases, such as cancer or infectious disease.

43 Claims, 106 Drawing Sheets

Specification includes a Sequence Listing.

(56) References Cited

FOREIGN PATENT DOCUMENTS

| | | |
|---|---|---|
| WO | WO 2016014565 A2 | 1/2016 |
| WO | WO 2016014576 A1 | 1/2016 |
| WO | WO 2016024021 A1 | 2/2016 |
| WO | WO 2016102965 A1 | 6/2016 |
| WO | WO 2016141357 A1 | 9/2016 |
| WO | WO 2016203048 A1 | 12/2016 |
| WO | WO 2018170475 A1 | 9/2018 |

OTHER PUBLICATIONS

Cencioni et al. (Cell Death and Disease (2015) 6, e1741). (Year: 2015).*

Peroumal et al. (Oncotarget, vol. 7, No. 34, pp. 54339-54359, 2016). (Year: 2016).*

Suntharalingam et al., N Engl J Med 2006;355:1018-28. (Year: 2006).*

Alakoskela et al., "Mechanisms for Size-Dependent Protein Segregation at Immune Synapses Assessed with Molecular Rulers," *Biophys. J.* 100(12):2865-2874, 2011.

Anderson et al., "Engineering adoptive T cell therapy to co-opt Fas ligand-mediated death signaling in ovarian cancer enhances therapeutic efficacy," Journal for Immuno Therapy of Cancer 10:e003959, 2022. (14 pages).

Anderson et al., "Obstacles Posed by the Tumor Microenvironment to T cell Activity: A Case for Synergistic Therapies," *Cancer Cell* 31:311-325, Mar. 13, 2017. (15 pages).

Ankri et al., "Human T Cells Engineered To Express a Programmed Death 1/28 Costimulatory Retargeting Molecule Display Enhanced Antitumor Activity," *J. Immunol.* 191(8):4121-4129, 2013.

Arch et al., "4-1BB and Ox40 Are Members of a Tumor Necrosis Factor (TNF)-Nerve Growth Factor Receptor Subfamily That Bind TNF Receptor-Associated Factors and Activate Nuclear Factor κB," *Molecular and Cellular Biology* 18(1):558-565, Jan. 1998. (8 pages).

Bajorath, "Analysis of Fas-ligand interactions using a molecular model of the receptor-ligand interface," *Journal of Computer-Aided Molecular Design* 13:409-418, Jul. 1999. (10 pages).

Barao, "The TNF receptor-ligands 4-1BB-4-1BBL and GITR-GITRL in NK cell responses," *Frontiers in Immunology* 3:402, Jan. 4, 2013. (8 pages).

Brenner, "Errors in Genome Annotation," *Trends in Genetics* 15(4):132-133, 1999.

Chen et al., "Fusion Protein Linkers: Property, Design and Functionality," *Adv Drug Deliv Rev.* 65(10): 1357-1369, 2013 (NIH Public Access Author Manuscript, available in PMC Oct. 15, 2014) (32 pages).

Chen et al., "Molecular mechanisms of T cell co-stimulation and co-inhibition," *Nat Rev Immunol.* 13(4): 227-242, Apr. 2013 (NIH Public Access Author Manuscript, available in PMC Apr. 1, 2014). (30 pages).

Cherkassky et al., "Human CAR T cells with cell-intrinsic PD-1 checkpoint blockade resist tumor-mediated inhibition," *J Clin Invest* 126(8):3130-3144 (2016).

Cheuk et al., "Role of 4-1BB:4-1BB ligand in cancer immunotherapy," *Cancer Gene Therapy* 11(3):215-226, 2004.

Coles et al., "Expression of CD200 on AML blasts directly suppresses memory T-cell function," *Leukemia* 26(9):2148-2151, 2012.

Coles et al., "The immunosuppressive ligands PD-L1 and CD200 are linked in AML T-cell immunosuppression: identification of a new immunotherapeutic synapse," *Leukemia* 29(9):1952-1954, 2015.

Contini et al., "In vivo apoptosis of CD8+ lymphocytes in acute myeloid leukemia patients: involvement of soluble HLA-1 and Fas ligand," *Leukemia* 21: 253-260, 2007.

Dolan et al., "PD-1 Pathway Inhibitors: Changing the Landscape of Cancer Immunotherapy," *Cancer Control* 21(3): 231-237, Jul. 2014. (7 pages).

Dustin et al., "Understanding the Structure and Function of the Immunological Synapse," *CSH Perspectives in Biology* 2(10):a002311, 2010. (14 Pages).

Feldhaus et al., "A CD2/CD28 chimeric receptor triggers the CD28 signaling pathway in CTLL.2 cells," *Gene Therapy* 4(8):833-838, 1997.

Fourcade et al., "CD8(+) T cells specific for tumor antigens can be rendered dysfunctional by the tumor microenvironment through upregulation of the inhibitory receptors BTLA and PD-1," *Cancer Res.* 72(4):887-896, 2012. (15 pages).

Frankel et al., "Characterization of diphtheria fusion proteins targeted to the human interleukin-3 receptor," *Protein Engineering* 13(8):575-581, 2000.

GenBank, "*Homo sapiens* CD2 molecule (CD2), mRNA," Accession No. NM_001767.3, Mar. 15, 2015, 4 pages.

GenBank, "*Homo sapiens* Fas cell surface death receptor (FAS), transcript variant 1, mRNA," Accession No. NM_000043.4, Mar. 15, 2015, 6 pages.

GenBank, "Homo sapiens hepatitis A virus cellular receptor 2 (HAVCR2), mRNA," Accession No. NM_032782.4, Sep. 23, 2018, 5 pages.

GenBank, "*Homo sapiens* lymphocyte activating 3 (LAG3), mRNA," Accession No. NM_002286.5, Jun. 17, 2018, 5 pages.

Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," *Neoplasia* 1(2):123-127, Jun. 1999. (5 pages).

Grassmann et al., "S81. Proffered paper: A new PD1-CD28 chimeric receptor overcomes PD-1-mediated immunosuppression in adoptive T cell therapy," *J. Immunother. Cancer* 2(Suppl. 2):I19, 2014. (1 Page).

Hanada et al., "Augmenting adoptive T cell therapy through universal chimeric costimulators," *J. Immunother. Cancer* 1(Suppl. 1):P14, 2013. (1 Page).

Hatherley et al., "Paired Receptor Specificity Explained by Structures of Signal Regulatory Proteins Alone and Complexed with CD47," *Molecular Cell* 31:266-277, 2008.

Hatherley et al., "Structures of CD200/CD200 Receptor Family and Implications for Topology, Regulation, and Evolution," *Structure* 21(5):820-832, 2013.

Ho et al., "CD200 Is a Marker of LSC Activity in Acute Myeloid Leukemia," *Blood* 128:1705, 2016 (Abstract only) (6 pages).

James et al., "Biophysical Mechanism of T Cell Receptor Triggering in a Reconstituted System," *Nature* 487(7405):64-69, 2012. (HHMI Author Manuscript) (16 Pages).

Jang et al., "Human 4-1 BB (CD137) Signals Are Mediated by TRAF2 and Activate Nuclear Factor-κB," *Biochemical and Biophysical Research Communications* 242:613-620, Jan. 26, 1998. (8 pages).

Jena et al., "Redirecting T-cell specificity by introducing a tumor-specific chimeric antigen receptor," *Blood* 116(7):1035-1044, 2010.

Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, 2009.

Kawalekar et al., "Distinct Signaling of Coreceptors Regulates Specific Metabolism Pathways and Impacts Memory Development in CAR T Cells," *Immunity* 44:380-390, 2016.

Kawasaki et al., "Cancer stem cells, CD200 and immunoevasion," *Trends in Immunology* 29(10):464-468, 2008.

Kawasaki et al., "Co-expression of the toleragenic glycoprotein, CD200, with markers for cancer stem cells," *Biochem Biophys Res Commun.* 364(4):778-782, 2007 (NIH Public Access Author Manuscript, available in PMC Dec. 28, 2007) (11 pages).

Keir et al., "PD-1 and its ligands in tolerance and immunity," *Annu. Rev. Immunol.* 26:677-704, 2008. (Abstract Only)(1 page).

Kharfan-Dabaja et al., "Immunotherapy for chronic lymphocytic leukemia in the era of BTK inhibitors," *Leukemia* 28(3):507-517, 2014.

Kono, "Current status of cancer immunotherapy," *Journal of Stem Cells & Regenerative Medicine* 10(1):8-13, 2014.

Kornmann et al., "Fas and Fas-Ligand Expression in Human Pancreatic Cancer," *Annals of Surgery* 231(3): 368-379, 2000.

(56) References Cited

OTHER PUBLICATIONS

Krause et al., "Antigen-dependent CD28 Signaling Selectively Enhances Survival and Proliferation in Genetically Modified Activated Human Primary T Lymphocytes," *J. Exp. Med.* 188(4):619-626, 1998.

Kuhlmann, "Unleashing T cells for adoptive immunotherapy," https://www.fredhutch.org/en/news/spotlight/2017/12/crd_oda_blood.html, 2017 (3 pages).

Lavrik, "Regulation of Death Receptor-Induced Apoptosis Induced via CD95/Fas and Other Death Receptors," *Molecular Biology* 45(1):150-155, 2011.

Lazar-Molnar et al., "The interchain disulfide linkage is not a prerequisite but enhances CD28 costimulatory function," *Cell Immunol.* 244(2):125-129, 2006. (NIH Public Access Author Manuscript, available in PMC Sep. 12, 2007) (9 pages).

Leccia et al., "Cytometric and Biochemical Characterization of Human Breast Cancer Cells Reveals Heterogenous Myoepithelial Phenotypes," *Cytometry Part A* 81A:960-972, 2012.

Ledbetter et al., "CD28 Ligation in T-Cell Activation: Evidence for Two Signal Transduction Pathways," *Blood* 75(7):1531-1539, 1990. (10 Pages).

Liu et al., "Synthesis of full length recombinant chimeric receptor anti-erbB2 scFv-CD28-ζ and construction of its eukaryotic expression vector," *J Chinese PLA Postgrad Med Sch* 31(4):360-362, 2010 (with English Abstract).

Liu et al., "The role of N-glycosylation of CD200-CD200R1 interaction of classical microglial activation," *Journal of Inflammation* 15(28):1-10, 2018.

Ma et al., "CD28 T cell costimulatory receptor function is negatively regulated by N-linked carbohydrates," *Biochemical and biophysical research communications* 317(1):60-67, 2004.

Ma et al., "Isolation, Culture and Biological Characteristics of Tumor Stem Cells in Human Colorectal Carcinoma," *Cancer Res Prev Treat* 41(4):345-349, 2014 (5 pages) (with English abstract).

Maeda et al., "Engineering of functional chimeric protein G-Vargula Luciferase," *Analytical biochemistry* 249(2):147-152, 1997.

Maus et al., "Antibody-modified T cells: CARs take the front seat for hematologic malignancies," *Blood* 123(17):2625-2635, 2014. (12 Pages).

Milstein et al., "Nanoscale Increases in CD2-CD48-mediated Intermembrane Spacing Decrease Adhesion and Reorganize the Immunological Synapse," *J. Biol. Chem.* 283(49):34414-34422, 2008.

Moreaux et al., "CD200: a putative therapeutic target in cancer," *Biochemical and biophysical research communications* 366(1):117-122, 2008.

Motz et al., "Tumor Endothelium FasL Establishes a Selective Immune Barrier Promoting Tolerance in Tumors," *Nature Medicine* 20(6): 607-615, 2014 (HHS Public Access Author Manuscript, available in PMC Dec. 1, 2014) (26 pages).

Oda et al., "A CD200R-CD28 fusion protein appropriates an inhibitory signal to enhance T-cell function and therapy of murine leukemia," *Blood* 130(22): 2410-2419, 2017.

Oda et al., "A Fas-4-1BB fusion protein converts a death to a pro-survival signal and enhances T cell therapy," *J. Exp. Med.* 217(12): e20191166, 2020 (20 Pages).

Oda et al., "Cheating Death: A Fas-41BB Immunomodulatory Fusion Protein Obviates a Death Signal to Enhance T Cell Function and Adoptive Therapy Targeting Leukemia and Solid Tumors," Conference Program, Retrieved from https://www.keystonesymposia.org/index.cfm?e=Web.Meeting.Program&meetingid=1518&subTab=program [Retrieved Jun. 19, 2018}, 22 pages, 2018.

Oda et al., "Cheating Death: A Fas-41BB Immunomodulatory Fusion Protein Obviates a Death Signal to Enhance T Cell Function and Adoptive Therapy Targeting Leukemia and Solid Tumors," *J. Immunol* 200 (1 Supplement) 179.11, 2018 (4 pages).

Oda et al., Cancer Research, Nov. 2022, vol. 82, No. 22, Supp. Supplement. Abstract No. PR008. Meeting Info: AACR Special Conference: Pancreatic Cancer. Boston, MA, United States. Sep. 13, 2022-Sep. 16, 2022 (2 pages).

Öhlén et al., "Expression of a Tolerizing Tumor Antigen in Peripheral Tissue Does Not Preclude Recovery of High-Affinity CD8+ T Cells or CTL Immunotherapy of Tumors Expressing the Antigen," *The Journal of Immunology* 166:2863-2870, Feb. 15, 2001. (9 pages).

Orlinick et al., "Requirement of Cysteine-rich Repeats of the Fas Receptor for Binding by the Fas Ligand," *The Journal of Biological Chemistry* 272(46):28889-28894, Nov. 14, 1997. (6 pages).

Pakula et al. "Genetic analysis of protein stability and function," *Annual review of genetics* 23(1):289-310, 1989.

Pardoll, "The blockade of immune checkpoints in cancer immunotherapy," *Nat. Rev. Cancer* 12(4):252-264, 2012. (HHS Public Access Author Manuscript, available in PMC May 4, 2016) (31 pages).

Prosser et al., "Primary Human CD8+ T Cells Engineered to Express a PD1-CD28 Chimeric Receptor are Co-Stimulated through the Exploitation of Tumor Expressed PD-L1," *Molecular Therapy* 19 (Supplement 1):S192, 2011.

Prosser et al., "Tumor PD-L1 co-stimulates primary human CD8+ cytotoxic T cells modified to express a PD1:CD28 chimeric receptor," *Mol. Immunol.* 51(3-4):263-272, 2012.

Ramaswamy et al., "Many Checkpoints on the Road to Cell Death: Regulation of Fas-FasL Interactions and Fas Signaling in Peripheral Immune Responses," *Results and Problems in Cell Differentiation*, pp. 17-47, 2009. (31 pages).

Rossy et al., "The integration of signaling and the spatial organization of the T cell synapse," *Front. Immunol.* 3:352, 2012. (12 Pages).

Rudd et al., "CD28 and CTLA-4 coreceptor expression and signal transduction," *Immunol. Rev.* 229(1):12-26, 2009. (Europe PMC Funders Group Author Manuscript, Immunol Rev. Author manuscript available in PMC Oct. 7, 2014) (26 pages).

Shirakabe et al., "Mechanistic insights into ectodomain shedding: susceptibility of CADM1 adhesion molecule is determined by alternative splicing and O-glycosylation," *Scientific Reports* 7:46174, 1-12, 2017.

Siva et al., "Immune modulation by melanoma and ovarian tumor cells through expression of the immunosuppressive molecule CD200," *Cancer Immunol Immunother.* 57:987-996, 2008.

Smith et al., "The challenges of genome sequence annotation or "The devil is in the details,"" *Nature Biotechnology* 15:1222-1223, 1997.

Snauwaert et al., "Can immunotherapy specifically target acute myeloid leukemic stem cells?" *OncoImmunology* 2(2):e22943, 10 pages, 2013.

Soto et al., "MHC-class I-restricted CD4 T cells: a nanomolar affinity TCR has improved anti-tumor efficacy in vivo compared to the micromolar wild type TCR," *Cancer Immunol. Immunother.* 62(2):359-369, 2013. (NIH Public Access Author Manuscript, available in PMC Feb. 1, 2014) (20 pages).

Starling et al., "Analysis of the Ligand Binding Site in Fas (CD95) by Site-Directed Mutagenesis and Comparison with TNFR and CD40," *Biochemistry* 37:3723-3726, Feb. 24, 1998. (4 pages).

Starling et al., "Identification of Amino Acid Residues Important for Ligand Binding to Fas," *Journal of Experimental Medicine* 185(8):1487-1492, Apr. 21, 1997. (6 pages).

Stromnes et al., "Abrogating Cbl-b in effector CD8+ T cells improves the efficacy of adoptive therapy of leukemia in mice," *The Journal of Clinical Investigation* 120(10): 3722-3734, 2010.

Stromnes et al., "Re-adapting T cells for cancer therapy: from mouse models to clinical trials," *Immunol Rev.* 257(1):145-164, 2014 (NIH Public Access Author Manuscript, available in PMC Jan. 1, 2015) (34 pages).

Stromnes et al., "T cells engineered against a native antigen can surmount immunologic and physical barriers to treat pancreatic ductal adenocarcinoma," *Cancer Cell* 28(5): 638-652, 2015 (HHS Public Access Author Manuscript, available in PMC Nov. 9, 2016) (30 pages).

Stumpfova et al., "The immunosuppressive surface ligand CD200 augments the metastatic capacity of squamous cell carcinoma," *Cancer Res.* 70(7):2962-2972, 2010.

(56) References Cited

OTHER PUBLICATIONS

Subramanian et al., "Species- and cell type-specific interactions between CD47 and human SIRPα," *Blood* 107(6): 2548-2556, Mar. 15, 2006 (26 pages).
Takata-Tomokuni et al., "Detection, epitope-mapping and function of anti-Fas autoantibody in patients with silicosis," *Immunology* 116:21-29, Sep. 2005. (10 pages).
Tang et al., "The advantages of PD1 activating chimeric receptor (PD1-ACR) engineered lymphocytes for PDL1+ cancer therapy," *Am. J. Transl. Res.* 7(3):460-473, 2015.
Teague et al., "Interleukin-15 rescues tolerant CD8+ T cells for use in adoptive immunotherapy of established tumors," *Nature Medicine* 12(3):335-341, Mar. 2006. (7 pages).
Tonks et al., "CD200 as a prognostic factor in acute myeloid leukaemia," *Leukemia* 21(3):566-568, 2007.
Van den Borne et al. "The CD200-CD200 Receptor Inhibitory Axis Controls Arteriogenesis and Local T Lymphocyte Influx," PLOS One 9(6):e98820, 2014 (10 pages).
Walton et al., "CRISPR/Cas9-Mediated Trp53 and Brca2 Knockout to Generate Improved Murine Models of Ovarian High-Grade Serous Carcinoma," *Cancer Research* 76(20):6118-6129, Oct. 15, 2016. (13 pages).
Willingham et al., "The CD47-signal regulatory protein alpha (SIRPa) interaction is a therapeutic target for human solid tumors," *Proc. Natl. Acad. Sci. USA* 109(17):6662-6667, 2012.
Yamao et al., "Mouse and Human SHPS-1: Molecular Cloning of cDNAs and Chromosomal Localization of Genes," *Biochemical and Biophysical Research Communications* 231: 61-37, 1997.

\* cited by examiner

IMMUNOMODULATORY FUSION PROTEINS AND USES THEREOF

REFERENCE TO AN ELECTRONIC SEQUENCE LISTING

The contents of the electronic sequence listing (447C1_SeqListing.xml; Size: 372 kilobytes; and Date of Creation: Jun. 21, 2023) is herein incorporated by reference in its entirety.

BACKGROUND

T cell-based immunotherapies began to be developed when tumor-reactive T cells were found among a population of tumor-infiltrating lymphocytes (TILs) (Clark et al., *Cancer Res.* 29:705, 1969). One strategy, known as adoptive T cell transfer, in some contexts involves the isolation of tumor infiltrating lymphocytes pre-selected for tumor-reactivity, clonal expansion of the tumor-reactive T cells induced by anti-CD3 and anti-CD28 antibodies in the presence of IL-2, and finally infusing the expanded cell population back to the tumor-bearing patient (together with chemotherapy and repetitive administration of IL-2) (Dudley et al., *Science* 298:850, 2002). This form of adoptive T cell therapy with tumor infiltrating lymphocytes can be technically cumbersome and leads to complete remission in only a minor fraction of patients with melanoma and is rarely effective in other cancers (Besser et al., *Clin. Cancer Res.* 16:2646, 2010).

Isolation of tumor-reactive T cell clones led to the development of another immunotherapeutic approach—the generation of recombinant T cell receptors (TCRs) specific for particular antigens, which may be introduced into T cells, e.g., using a vector delivery system, to confer specificity for a desired target such as a tumor-associated peptide presented by a major histocompatibility complex (MHC) molecule expressed on a tumor cell (known as human leukocyte antigen (HLA) molecule in humans). Another approach introduces a synthetic receptor, termed a chimeric antigen receptor (CAR), which generally contains an antigen-binding domain, which, e.g., in the context of anti-tumor therapy can bind to a tumor-specific or associated antigen, linked to one or more intracellular component comprising an effector domains, such as a primary signaling domain such as a TCR signaling domain or in some contexts costimulatory signaling domains. Unlike administration of TILs, the basic procedure for engineered TCR or CAR T cell immunotherapy is generally to genetically modify human T cells with a transgene encoding a tumor targeting moiety, ex vivo expansion of the recombinant T cells, and transfusing the expanded recombinant T cells back into patients.

Adoptive T cell therapy using T cells expressing recombinant TCRs has been shown to have a promising clinical benefit, especially in certain B cell cancers. However, effective T cell activation often requires or is enhanced by a concurrent co-stimulatory signal (Chen and Flies, *Nat. Rev. Immunol.* 13: 227-242, 2013). In the tumor microenvironment, co-stimulatory molecules are generally downregulated. As a result, exogenous stimulus via IL-2 is typically needed for T cells that express recombinant TCRs specific for cancer antigens.

Activation of T cells is initiated when the TCR engages a specific peptide presented in MHC on an antigen-presenting cell (APC) (Rossy et al., *Frontiers in Immunol.* 3: 1-12, 2012). The point of interaction of the T cell and the APC becomes the immunological synapse, which is comprised of three concentric supramolecular activation clusters (SMACs), including the central cSMAC, peripheral pSMAC, and the distal dSMAC (Rossy et al., *Frontiers in Immunol.* 3: 1-12, 2012). Within the cSMAC, co-stimulatory receptors can recruit signaling molecules to amplify the TCR signal. Such co-stimulatory receptors can include CD28, and in some contexts form microclusters with the TCR to lower the threshold of activation (Chen and Flies, *Nat. Rev. Immunol.* 13: 227-242, 2013). Access to the cSMAC by transmembrane proteins expressed by T cells may be restricted by the size of the extracellular domain. For example, CD45 has a large ectodomain and is generally excluded from the immunological synapse, thereby preventing its ability to inhibit TCR signaling (James and Vale, *Nature* 487:64-69, 2012).

There remains a need in the immunotherapy field for alternative compositions and methods that provide immunomodulatory signals to host cells for treating various diseases, such as cancer or infections. Presently disclosed embodiments address these needs and provide other related advantages.

BRIEF SUMMARY

In certain aspects, the present disclosure is directed to a fusion protein, comprising an extracellular component that contains a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse.

In some embodiments, a length or spatial distance of a complex formed between the fusion protein and the target or a portion of such fusion protein::target complex (generally the extracellular portion of such complex) is or spans a particular distance, e.g., in some embodiments, is a distance that is less than or less than about a certain distance. In some aspects, a distance of the fusion protein::target complex (or, typically, the extracellular portion thereof) is less than at or about 50 nm, less than at or about 40 nm, less than at or about 30 nm, or less than at or about 20 nm or equal to or less than at or about 15 nm. In some embodiments, it is at or about 10, 11, 12, 13, 14, 15, 16, 17, 18, 19, or 20 nm, such as at or about 14 or 15 nm. In some aspects, the distance is one that is similar to a distance between membranes in an immunological synapse or is a distance that is the same, about the same, or substantially the same, as a distance between the membrane proximal-most portion, e.g., residue, of the extracellular domain of a TCR and the membrane proximal-most portion, e.g., residue, of an MHC (e.g., HLA, such as an MHCI or MHCII) molecule, with respect to a TCR-peptide/MHC complex or the distance spanned by the extracellular portions of such a complex (or spatial distance spanned by the extracellular portion known to be contained within a synapse, such as a complex containing CD8, CD4, CD28, and the respective binding partner or ligand thereof). In some embodiments, spatial distances of complexes refer to a distance between membranes of two different cells, wherein a first cell and a second cell each express on their surface a binding partner that can form a complex between the membranes when the cells are in proximity to each other. In some aspects, the distance is a distance that is the same, about the same, or substantially the same, as a distance spanned by the extracellular portions of a complex formed between a TCR and cognate interaction with an MHC molecule. In some aspects, such as where a fusion protein comprises a binding domain from a molecule ordinarily capable of entering an immunological synapse or co-localizing with an antigen receptor, the distance is similar to or the same as that spanned by a complex formed between the molecule (having the binding domain used in the fusion protein), and a natural binding partner thereof. In some aspects, such as where the fusion protein comprises a binding domain from a molecule ordinarily not capable of entering an immunological synapse or ordinarily not capable of co-localizing with an antigen receptor, the distance is different than, e.g., less than or substantially less than, that spanned by a complex formed between the molecule (having the binding domain or functional portion thereof used in the fusion protein), and a natural binding partner thereof.

In some embodiments, a binding domain within the extracellular component of a fusion protein of this disclosure contains a target-binding portion of a molecule capable of delivering an inhibitory signal, such as of an inhibitory molecule, e.g., an immunoinhibitory molecule, such as an immunoinhibitory receptor or immune checkpoint molecule. In some aspects, such a molecule is a glycoprotein, checkpoint family member. In certain embodiments, the fusion protein comprising a binding domain from a glycoprotein, checkpoint family member or is not a B7 or B7-binding molecule or is not a CD28-B7-superfamily member (e.g., is not a CD28, CTLA4, ICOS, or other B7 family binding molecule) Exemplary glycoprotein, checkpoint family members include CD200R, SIRPα, CD279 (PD-1), CD2, CD95 (Fas), CTLA4 (CD152), CD223 (LAG3), CD272 (BTLA), A2aR, KIR, TIM3, CD300, or LPA5, or a binding variant of any such molecule. In some embodiments, a binding domain within the extracellular component of a fusion protein of this disclosure comprises a binding partner of any of the foregoing, or a binding variant of any such molecule. In some aspects of such embodiments, the intracellular portion of a fusion protein includes a signaling domain capable of delivering a stimulatory, such as a costimulatory, signal to a lymphocyte, such as a T cell, such as a costimulatory region of CD28, 4-1BB, ICOS, or other costimulatory molecule. In some aspects, the intracellular portion of the fusion protein does not include an intracellular signaling domain of the inhibitory molecule, such as of a checkpoint or immunoinhibitory molecule, when the extracellular binding portion is from a checkpoint or immunoinhibitory molecule. In some aspects, a fusion protein does not include a primary signaling domain such as a CD3ζ signaling domain or other domain capable of delivering a primary signal to a T cell.

In certain aspects, the extracellular component or the binding portion thereof contains or is a binding domain of a molecule or ectodomain capable of specifically binding to CD200, such as a binding portion of a CD200R or variant thereof. In some embodiments, the binding domain is or includes a binding region of a molecule or of an ectodomain that is capable of specifically binding to a CD47, such as a SIRP ectodomain or CD47-binding region thereof, such as a SIRPα ectodomain or CD47-binding region thereof. In some embodiments, the binding domain is capable of binding to a PD-L1 or a PD-L2 or a LAG3 molecule. Exemplary targets may be one or more proteins whose expression is increased or upregulated in certain cells or tissues associated with or of a disease or condition to be treated or ameliorated with the fusion proteins and compositions provided herein, such as a tumor cell or tumor microenvironment, or is bound by a receptor generally upregulated on immune cells such as lymphocytes infiltrating a diseased tissue, such as a tumor.

In some embodiments, the extracellular component further includes one or more additional regions or domains, for example, from a molecule other than that from which the binding domain is derived or other than the molecule with which the binding domain shares identity. The one or more additional extracellular domain(s) may include a spacer region, such as one from an immunoglobulin molecule, which may contain all or a portion of a hinge, or constant region domain such as CH2 or CH3 domain, or from another cell surface molecule such as a costimulatory receptor, such as CD28. The additional extracellular domain(s) may include, in some aspects, a multimerization domain, e.g., a dimerization domain or sequence that may promote homo- or heterodimerization with another molecule, such as multimerization of two or more of the fusion proteins. In some embodiments, such a domain includes a portion of an extracellular domain of a CD28 molecule including at least the transmembrane-proximal-most cysteine, and generally an extracellular portion between such cysteine and the membrane, or modified variant thereof. In some aspects, such a domain includes an amino acid sequence as set forth in SEQ ID NO: 32, or portion thereof, or variant thereof such as having at least 90%, 95%, or 99% identity thereto. In some aspects, such a domain may be included in order to facilitate or promote multimerization. In some embodiments, a fusion protein contains an extracellular component including a CD200-binding domain, such as an extracellular portion (or portion thereof, such as a binding domain thereof) of a CD200R, such as an extracellular portion of CD200R having an amino acid sequence as set forth in SEQ ID NO: 25 or encoded by a nucleic acid molecule as set forth in SEQ ID NO: 2, or a CD200-binding portion thereof or variant thereof or binding portion thereof. In some aspects of such embodiments, the extracellular portion of the fusion protein further includes a portion of an extracellular region of CD28, such as up to about 9 to about 12 amino acids thereof (e.g., 9 amino acids or 12 amino acids), and in some aspects including a membrane-proximal-most cysteine residue of a CD28 extracellular region. In some such embodiments, the length of the CD200R portion of the extracellular region is reduced in length corresponding to the number of additional residues in the CD28-derived portion, such as by about 9 to about 12 amino acids (e.g., 9 amino acids or 12 amino acids), or by a sufficient number of amino acids that the distance spanned by the extracellular portion of a complex between the fusion protein and a CD200 molecule is similar to, substantially similar to, or the same as that spanned by the extracellular portion of a complex between a human CD200R, e.g., a CD200R, and CD200; or that spanned by the extracellular portion of a complex between a TCR in cognate interaction with an MHC molecule (e.g., MHC I or MHCII) in binding to a cognate peptide-MHC complex; or that of an immunological synapse. In some aspects, the fusion protein further includes a transmembrane domain, such as a CD28 transmembrane, such as a transmembrane domain encoded by the sequence set forth as SEQ ID NO: 4 or portion thereof, or a modified version thereof, such as a variant modified to contain additional charged regions or residues or hydrophilic residues to facilitate intermolecular interactions. In some embodiments, the protein further includes a CD28 intracellular signaling domain, such as a costimulatory domain of CD28, such as one that is capable of recruiting one or more adapter molecules to a CD28 in response to ligation. In some aspects, the CD28 intracellular domain includes or is a sequence encoded by the nucleotide sequence of SEQ ID NO: 5 or a portion or functional variant thereof.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28 and an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a SIRPα, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD279 (PD-1), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD95 (Fas), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a TIM3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a LAG3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD2, (b) the hydrophobic component comprises a transmembrane domain of a CD28, and (c) the intracellular component comprises an intracellular signaling domain of a CD28.

In some embodiments, the present disclosure is directed to a fusion protein, comprising (a) an extracellular component comprised of a binding domain that specifically binds a target, (b) an intracellular component comprised of an intracellular signaling domain, and (c) a hydrophobic component connecting the extracellular and intracellular components, wherein the extracellular portion of a complex formed by specific binding of the fusion protein to the target (fusion protein::target complex) is of a size, or spans a distance, of (i) up to about a distance between two cell membranes of an immunological synapse, (ii) up to about or substantially the same as a distance spanned by the extracellular portion of a complex between a T cell receptor (TCR) and an MHC-peptide complex specifically bound by the TCR, (iii) up to about or substantially the same as a distance spanned by the extracellular portion of a complex between a natural molecule comprising the binding domain and its cognate binding partner; (iii) less than or up to about 40 nm, 25 nm, 20 nm, 15 nm, or 14 nm; or (iv) any combination thereof; and wherein the extracellular component is or comprises a CD95 (Fas) ectodomain or a functional fragment thereof, and the intracellular component is or comprises a CD137 (4-1BB) intracellular signaling domain or a functional portion thereof.

In some embodiments, the present disclosure is directed to a fusion protein comprising (a) an extracellular component comprised of a binding domain that specifically binds a target, (b) an intracellular component comprised of an intracellular signaling domain, and (c) a hydrophobic component connecting the extracellular and intracellular components, wherein the binding domain is, or has at least 95% identity to, an inhibitory molecule binding domain and the intracellular signaling domain is, or contains at least 95% identity to, a costimulatory or stimulatory molecule binding domain, and wherein the inhibitory molecule is or comprises a CD95 (Fas) ectodomain or a functional fragment thereof, and the costimulatory or stimulatory molecule is or comprises an intracellular signaling domain or a functional portion thereof from CD137 (4-1BB).

In some embodiments, the present disclosure is directed to a fusion protein comprising: (a) an extracellular component comprising an amino acid sequence encoded by a nucleic acid molecule as set forth in SEQ ID NO.:71, (b) a hydrophobic component comprising an amino acid sequence encoded by a nucleic acid molecule as set forth in SEQ ID NO.:197, and (c) an intracellular component comprising an amino acid sequence encoded by a nucleic acid molecule as set forth in SEQ ID NO.:13.

In some embodiments, the present disclosure is directed to a fusion protein comprising: (a) an extracellular component comprising a binding domain with an amino acid sequence as set forth in SEQ ID NO.:72; (b) a hydrophobic component comprising an amino acid sequence as set forth in SEQ ID NO.: 198; and (c) an intracellular component comprising an amino acid sequence as set forth in SEQ ID NO.:36.

In certain aspects, the present disclosure is directed to a nucleic acid molecule encoding a fusion protein as described herein.

In certain aspects, the present disclosure is directed to a vector comprising a nucleic molecule that encodes a fusion protein as described herein.

In certain other aspects, the present disclosure is directed to a host cell comprising a fusion protein, nucleic acid, or vector as described herein.

In certain other aspects, a method of increasing the activity of an immune cell is provided, comprising administering to a subject in need of increased immune cell activity an effective amount of a host cell as described herein.

In other aspects, the present disclosure is directed to a method of enhancing or prolonging an immune response, comprising administering to a subject in need of enhanced or prolonged immune cell activity an effective amount of a host cell as described herein.

In still other aspects, the present disclosure provides a method of stimulating an antigen-specific T cell response, comprising administering to a subject in need of increased immune cell activity an effective amount of a host cell as described herein.

In other aspects, the present disclosure is directed to a method of inhibiting an immunosuppressive signaling pathway, comprising administering to a subject in need thereof an effective amount of a host cell as described herein.

In other aspects, the present disclosure is directed to a method of treating cancer, comprising administering to a subject having cancer a therapeutically effective amount of a host cell as described herein.

In other aspects, the present disclosure is directed to a method of inhibiting immune resistance of cancer cells, comprising administering to a subject in need thereof an effective amount of a host cell as described herein.

In still other aspects, the present disclosure provides a method for treating a tumor, comprising administering to a subject having a tumor a therapeutically effective amount of a host cell as described herein, wherein the administered host cell is capable of proliferating in an immunosuppressive tumor microenvironment.

A method of treating an infection, comprising administering to a subject having the infection a therapeutically effective amount of a host cell as described herein, is also provided by the present disclosure.

These and other aspects of the present invention will become apparent upon reference to the following detailed description and attached drawings.

Expression of Fas-CD28 constructs but not full-length (FL) Fas promoted survival or expansion of T cells upon multiple stimulations in vitro.

Figure 12A:
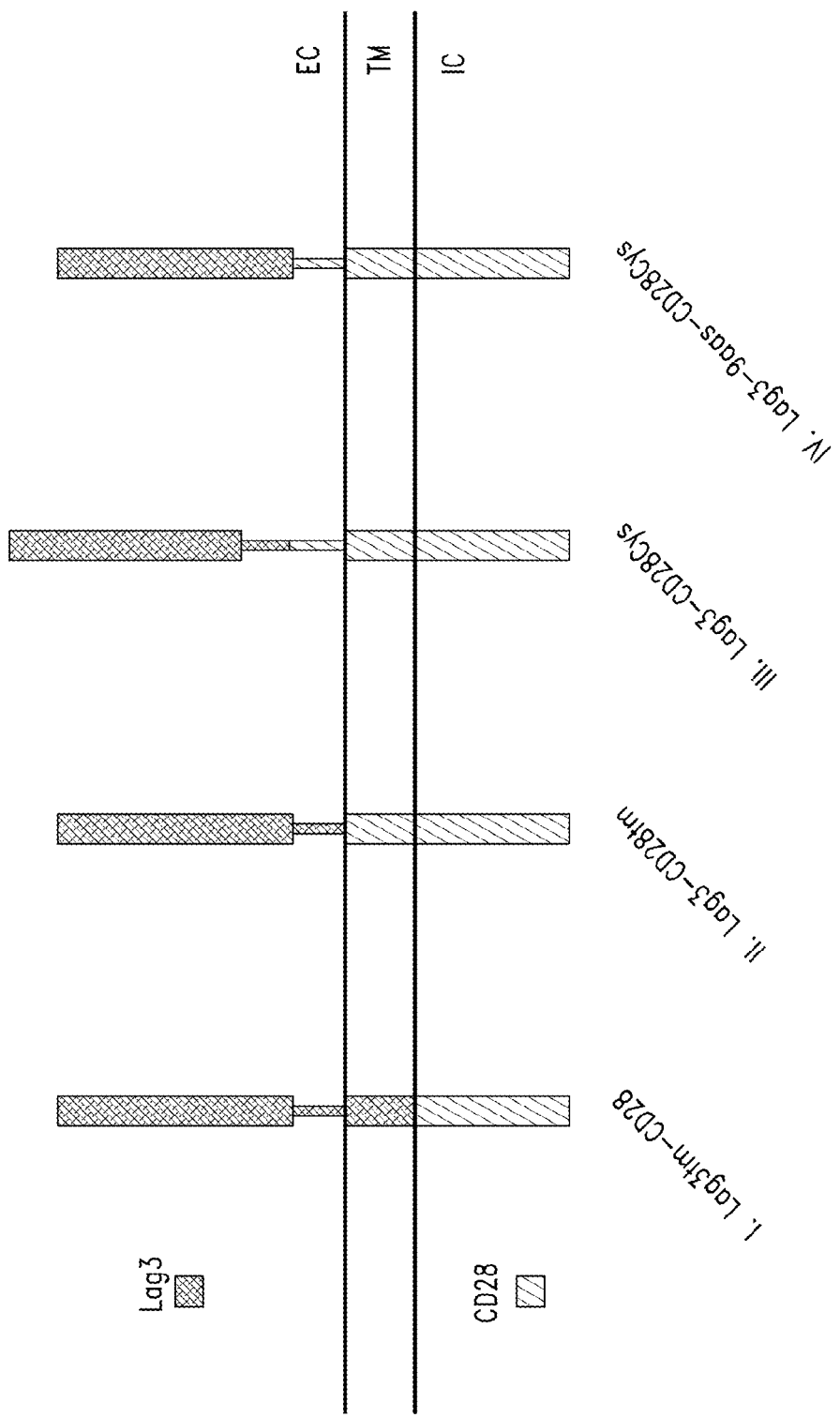
Figure 12B:
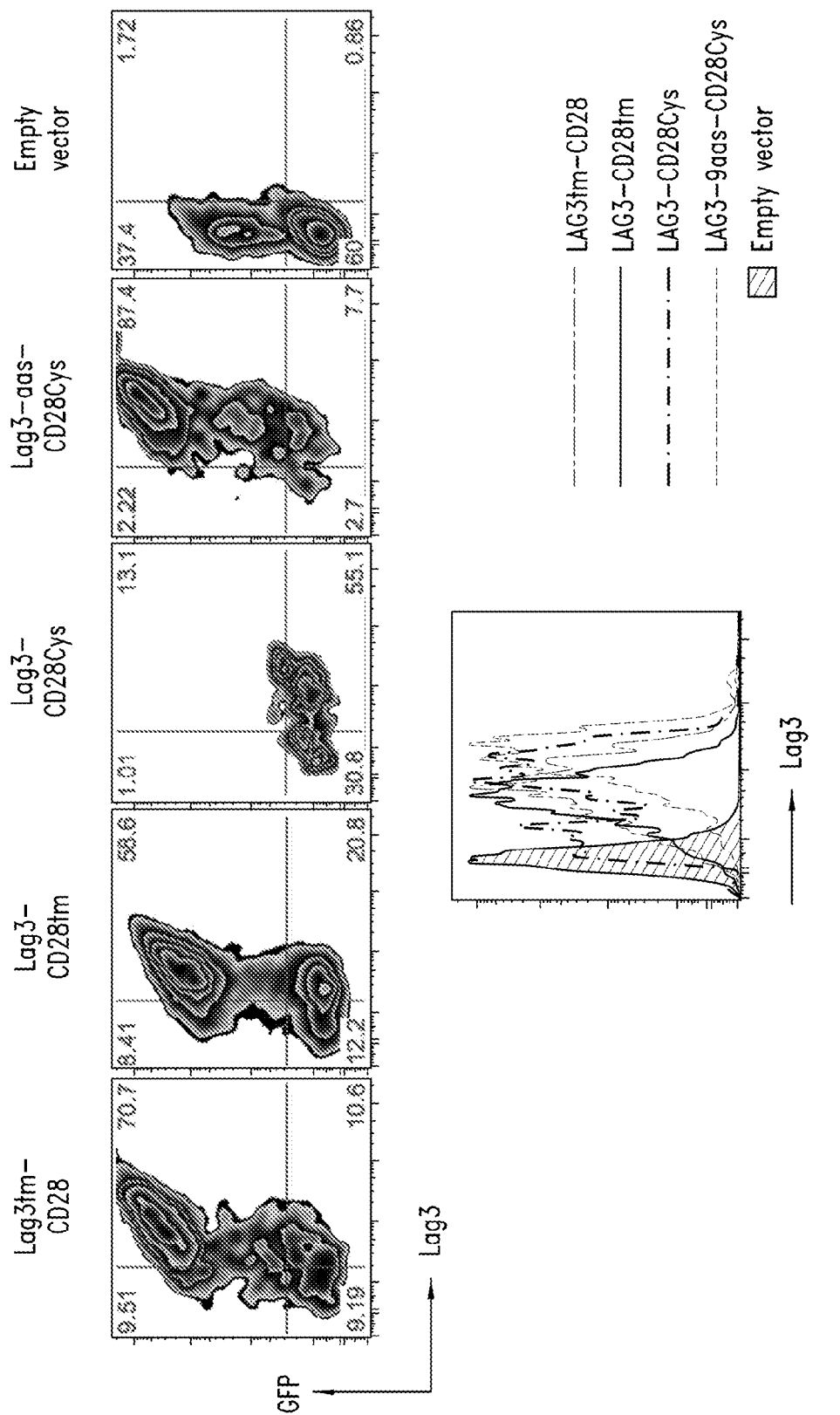

FIGS. 12A and 12B show the structure and expression of fusion proteins comprising LAG3 extracellular components and CD28 co-stimulatory signaling domains. (A) Schematic representation of exemplary LAG3-CD28 constructs. Construct "I" contains LAG3 extracellular ("EC") and transmembrane ("TM") domains and a CD28 intracellular ("IC") signaling domain (LAG3tm-CD28). Construct "II" contains the extracellular domain of LAG3 and the transmembrane and intracellular domains of CD28 (LAG3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of LAG3, wherein the LAG3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of LAG3-CD28 constructs by murine CD8$^+$ T cells, as determined by anti-LAG3 antibody staining and flow cytometry. T cells transduced to express LAG3-CD28 constructs (LAG3tm-CD28; LAG3-CD28tm; LAG3-CD28Cys; LAG3-9aas-CD28Cys) exhibited expression of the constructs, in contrast with control T cells that received empty vector.

Figure 13A:
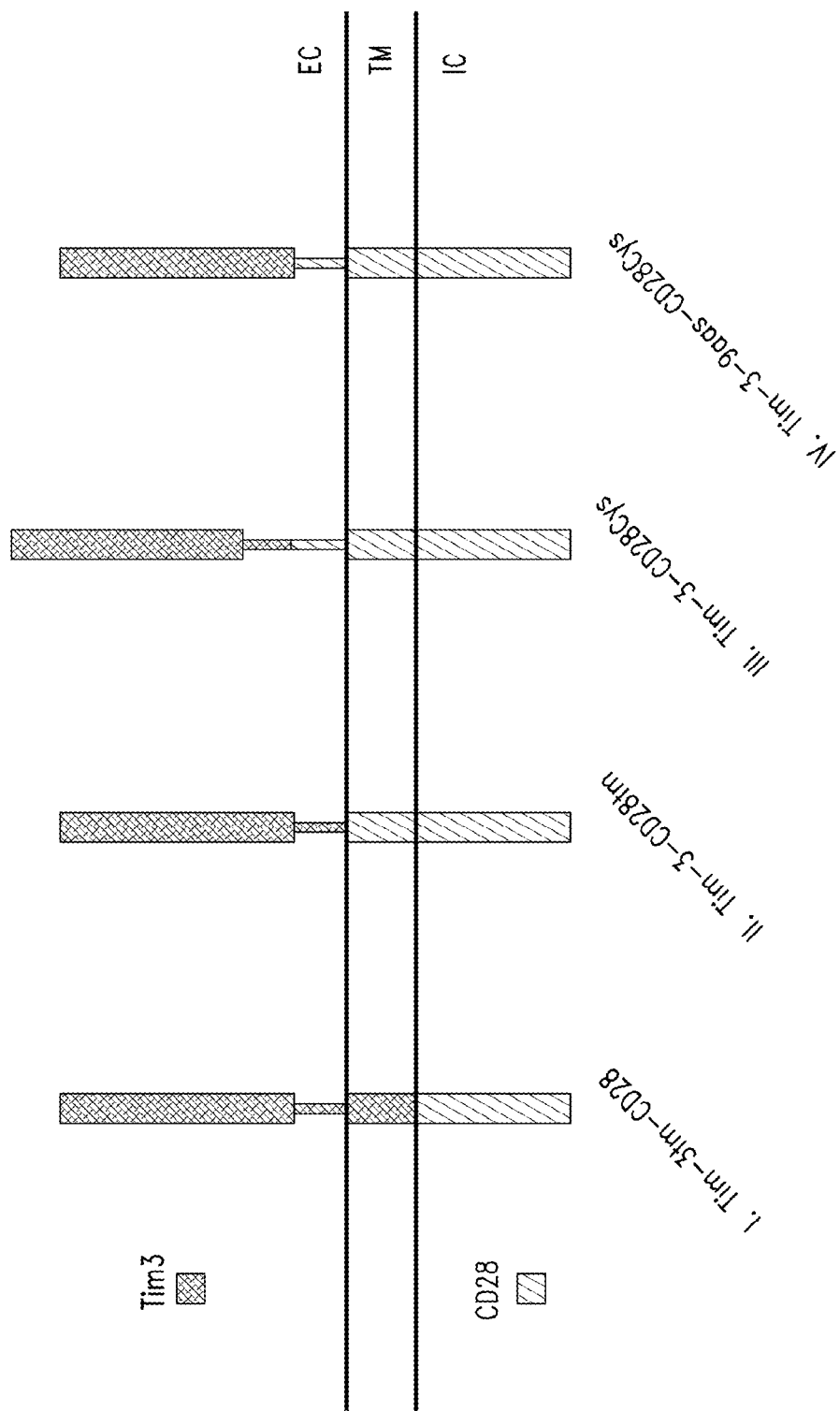
Figure 13B:
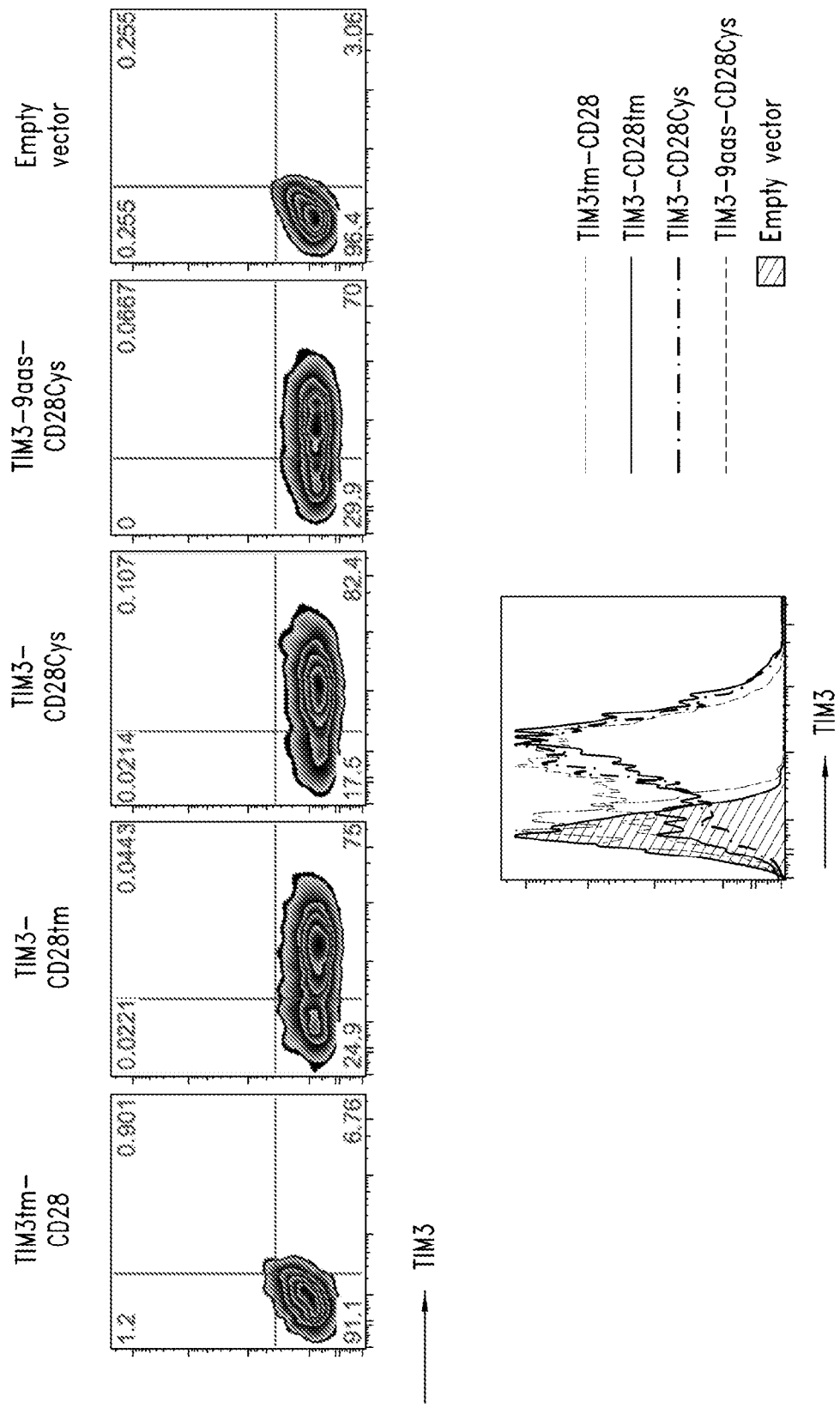

FIGS. 13A and 13B show the structure and expression of fusion proteins comprising TIM3 extracellular components and CD28 co-stimulatory signaling domains. (A) Schematic representation of exemplary TIM3-CD28 constructs. Construct "I" contains TIM3 extracellular ("EC") and transmembrane ("TM") domains and a CD28 intracellular ("IC") signaling domain (TIM3tm-CD28). Construct "II" contains the extracellular domain of TIM3 and the transmembrane and intracellular domains of CD28 (TIM3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of TIM3, wherein the TIM3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of TIM3-CD28 constructs by murine CD8$^+$ T cells, as determined by anti-TIM3 antibody staining and flow cytometry. T cells transduced to express TIM3-CD28 constructs (TIM3tm-CD28; TIM3-CD28tm; TIM3-CD28Cys; TIM3-9aas-CD28Cys) typically exhibited expression of the constructs, in contrast with control T cells that received empty vector.

Figure 14A:
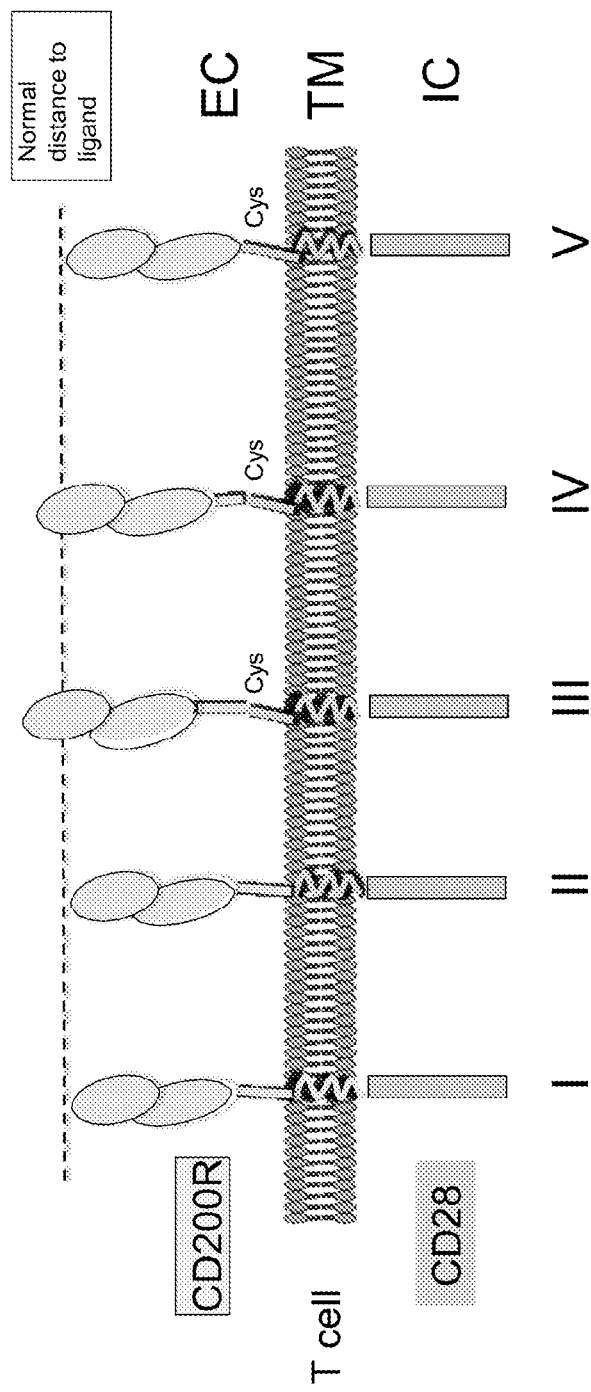
Figure 14B:
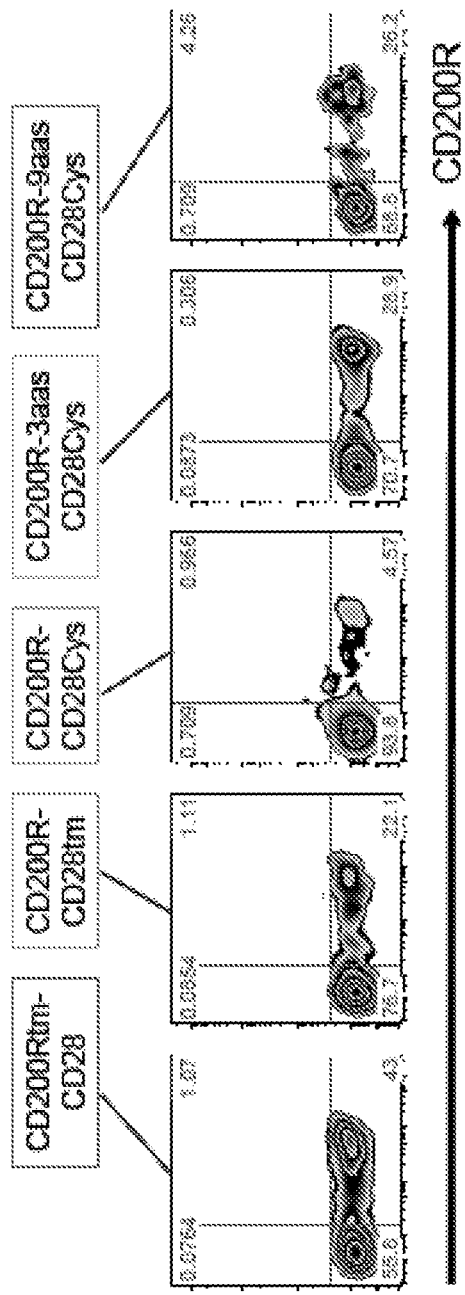

FIGS. 14A and 14B show CD200R-CD28 constructs expressed at high levels on primary murine CD8$^+$ T cells. (A) Schematic illustration of representative CD200R-CD28 constructs. Construct "I" contains CD200R extracellular ("EC") and transmembrane ("TM") domains and a CD28 intracellular ("IC") signaling domain (CD200Rtm-CD28). Construct "II" contains the extracellular domain of CD200R and the transmembrane and intracellular domains of CD28 (CD200R-CD28tm). Constructs "III-V" also incorporate a portion of the extracellular domain of CD28 to the transmembrane-proximal cysteine to promote multimerization and enhance CD28 signaling. To account for any extra extracellular amino acids caused by incorporating the portion of the extracellular domain of CD28 (e.g., from one to about 50 amino acids; such as exemplary murine constructs disclosed here containing an extra three (3) or nine (9) amino acids and exemplary human constructs disclosed here containing an extra nine (9) or twelve (12) amino acids), some constructs have a truncated portion of an extracellular or intracellular domain (e.g., a CD200R that preserves an N linked glycosylation site). For example, construct IV has a truncated portion of CD200R that is truncated by 3 amino acids. Construct V has a truncated portion of CD200R that is truncated 9 amino acids. Constructs "I", "II", and "V" maintain the spatial distance between the cells (e.g., between a T cell and an antigen presenting cell) as indicated by the dashed line, and may co-localize with the TCR within the cSMAC and deliver a strong co-stimulatory signal. (B) Transgenic expression of murine CD200R-CD28 constructs on TCR$_{gag}$ T cells as detected by anti-CD200R antibody.

Figure 15A:
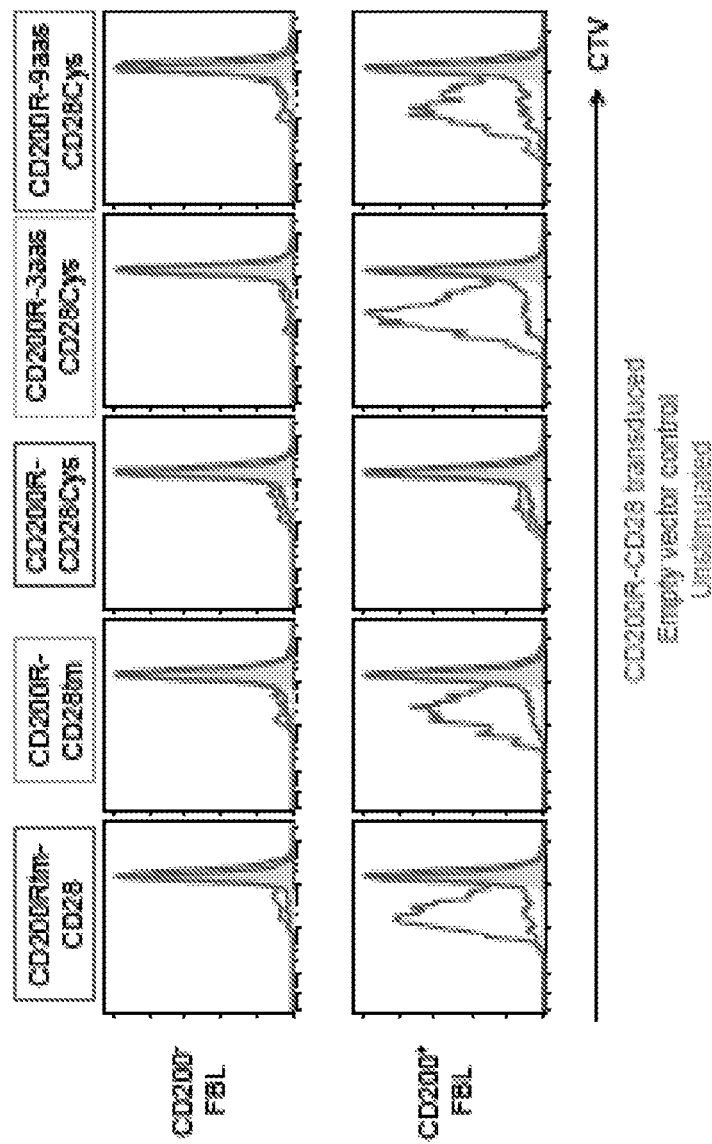
Figure 15B:
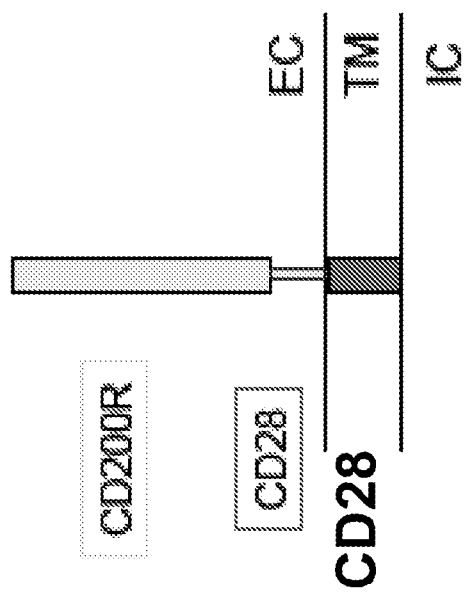
Figure 15C:
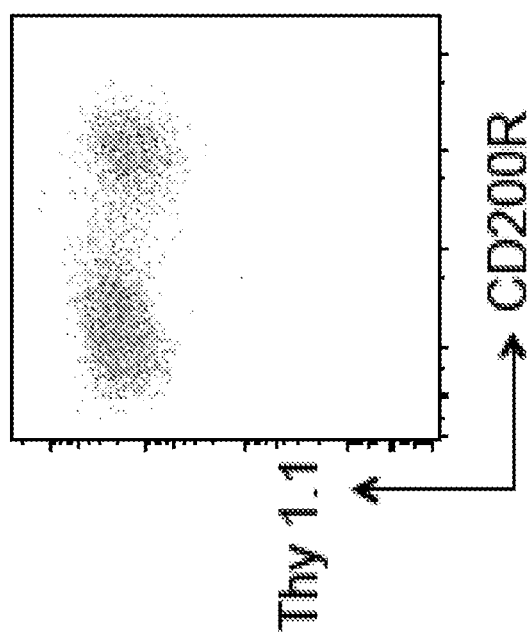
Figure 15D:
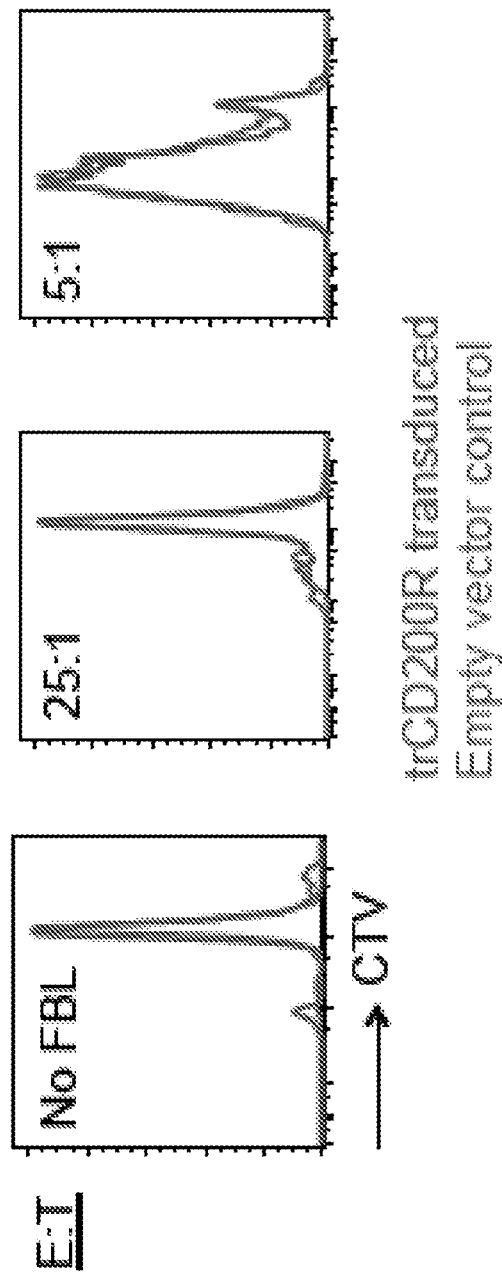
Figure 15E:
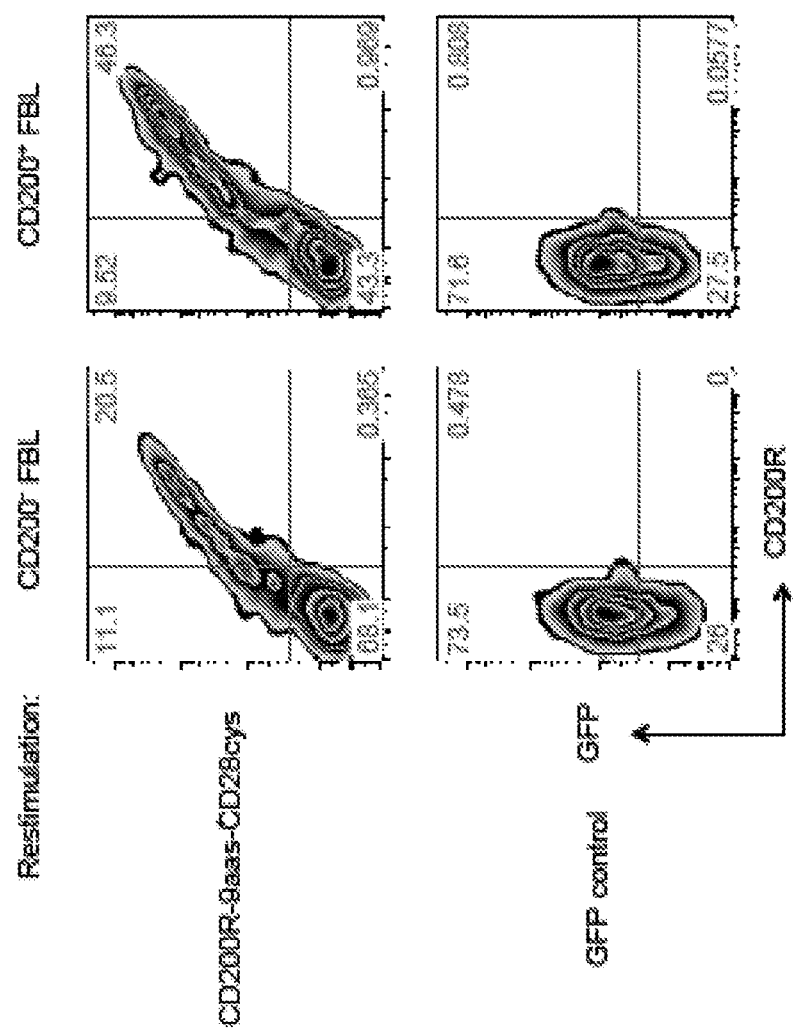
Figure 15F:
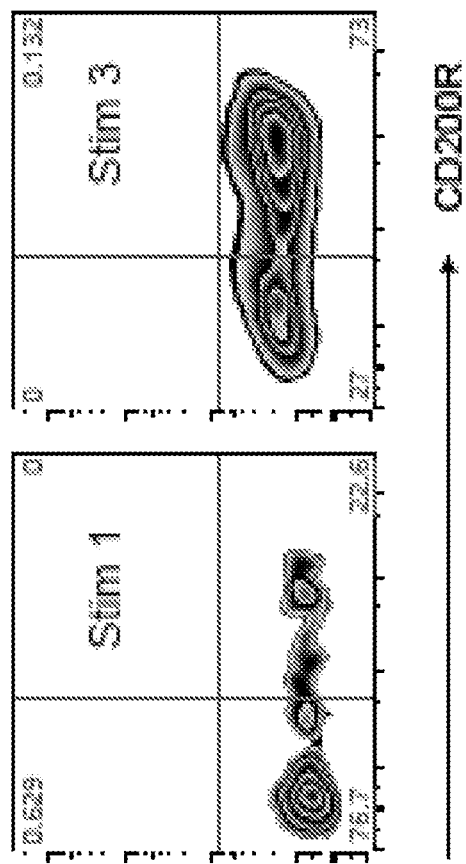
Figure 15G:
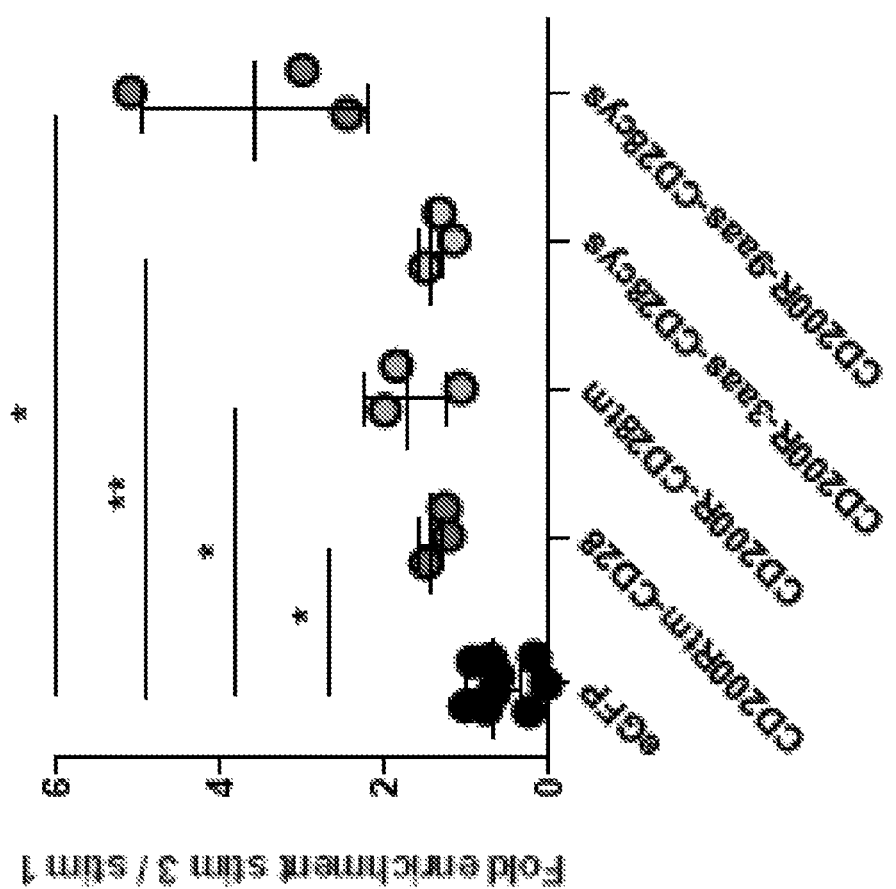
Figure 15H:
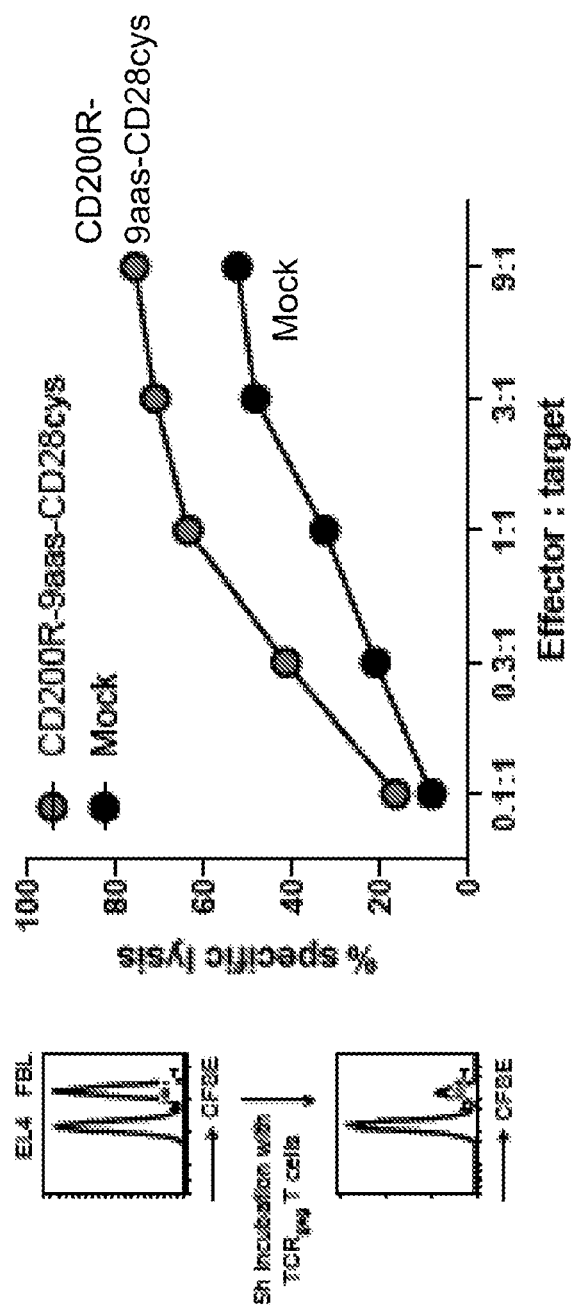
Figure 15I:
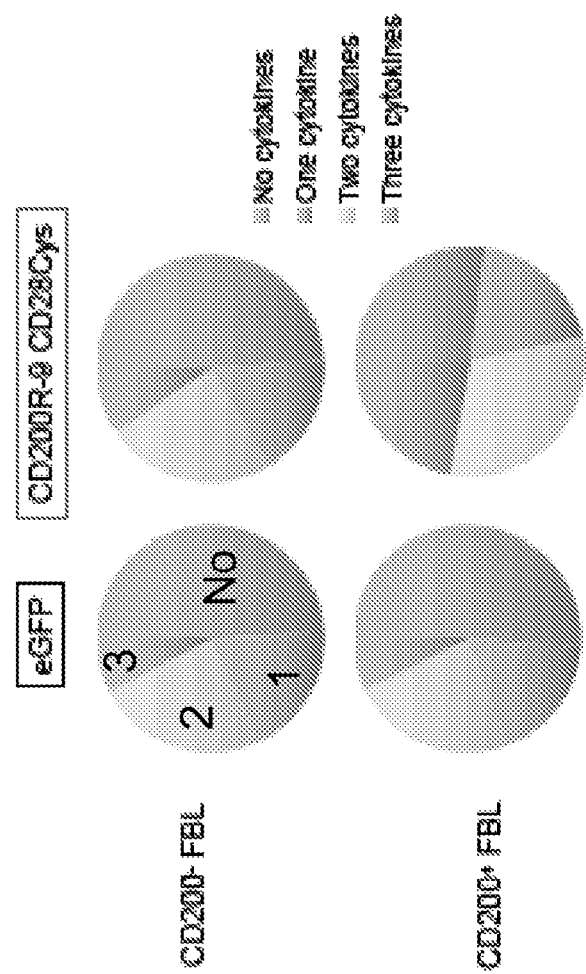
Figure 15J:
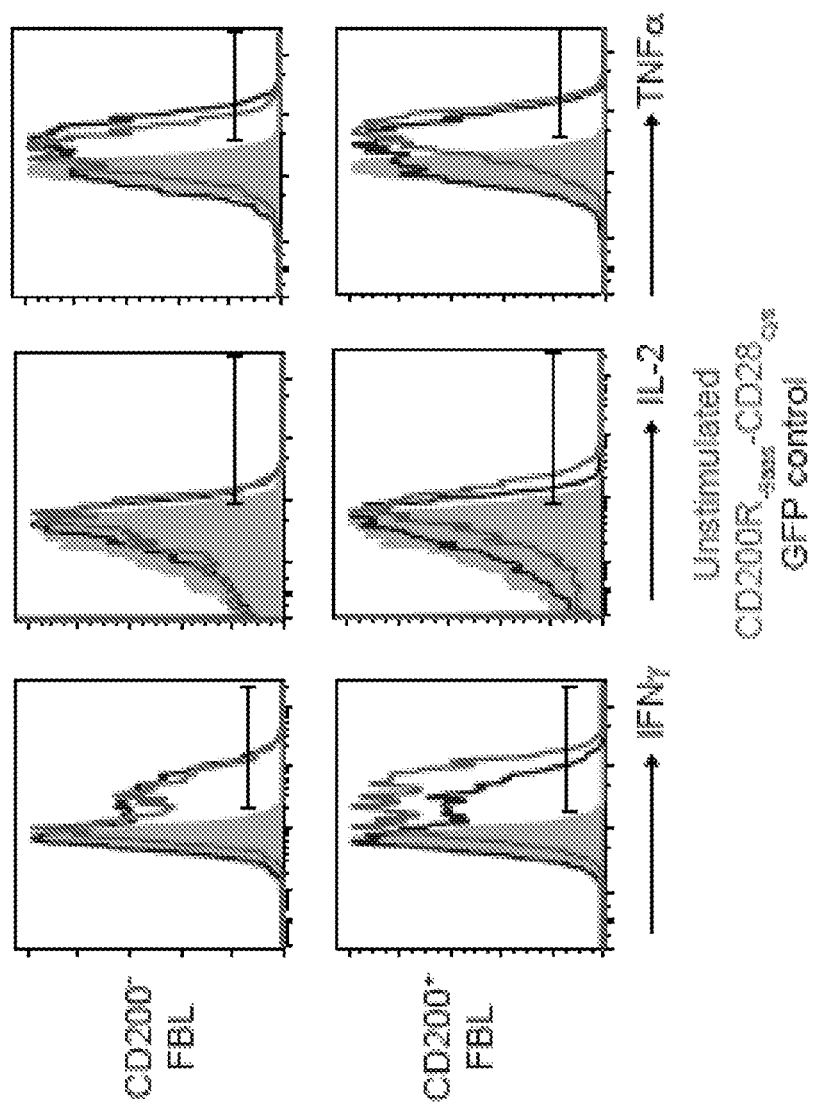
Figure 15K:
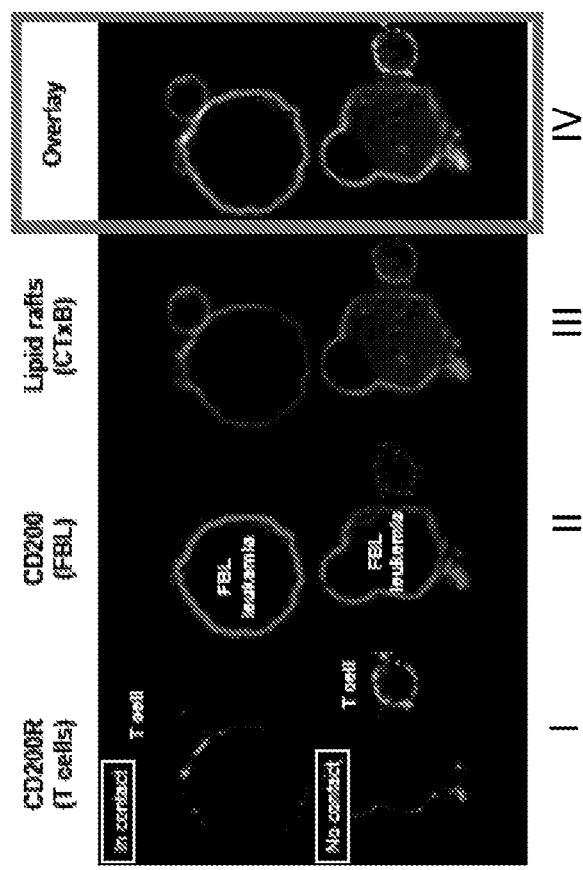
Figure 15L:
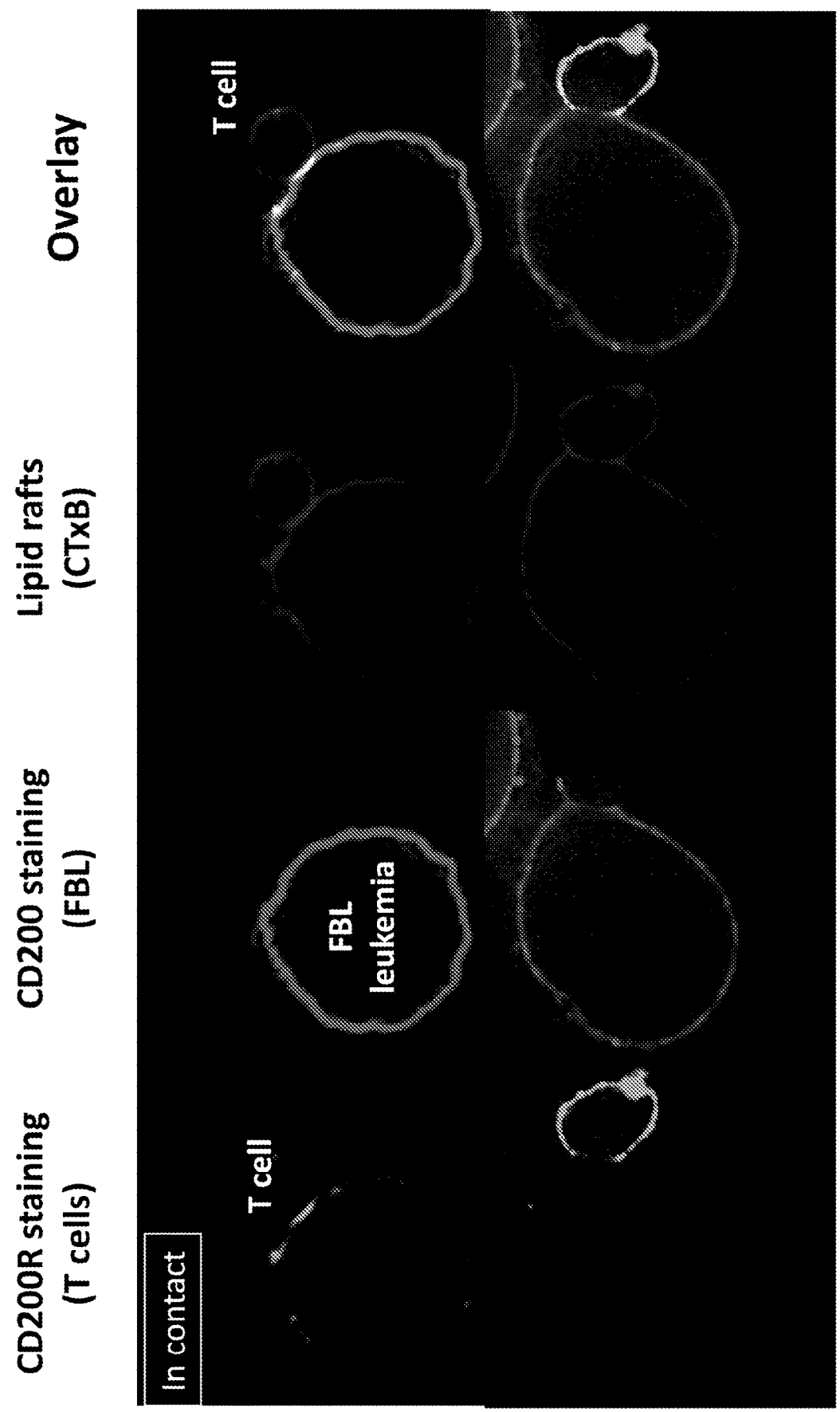
Figure 15M:
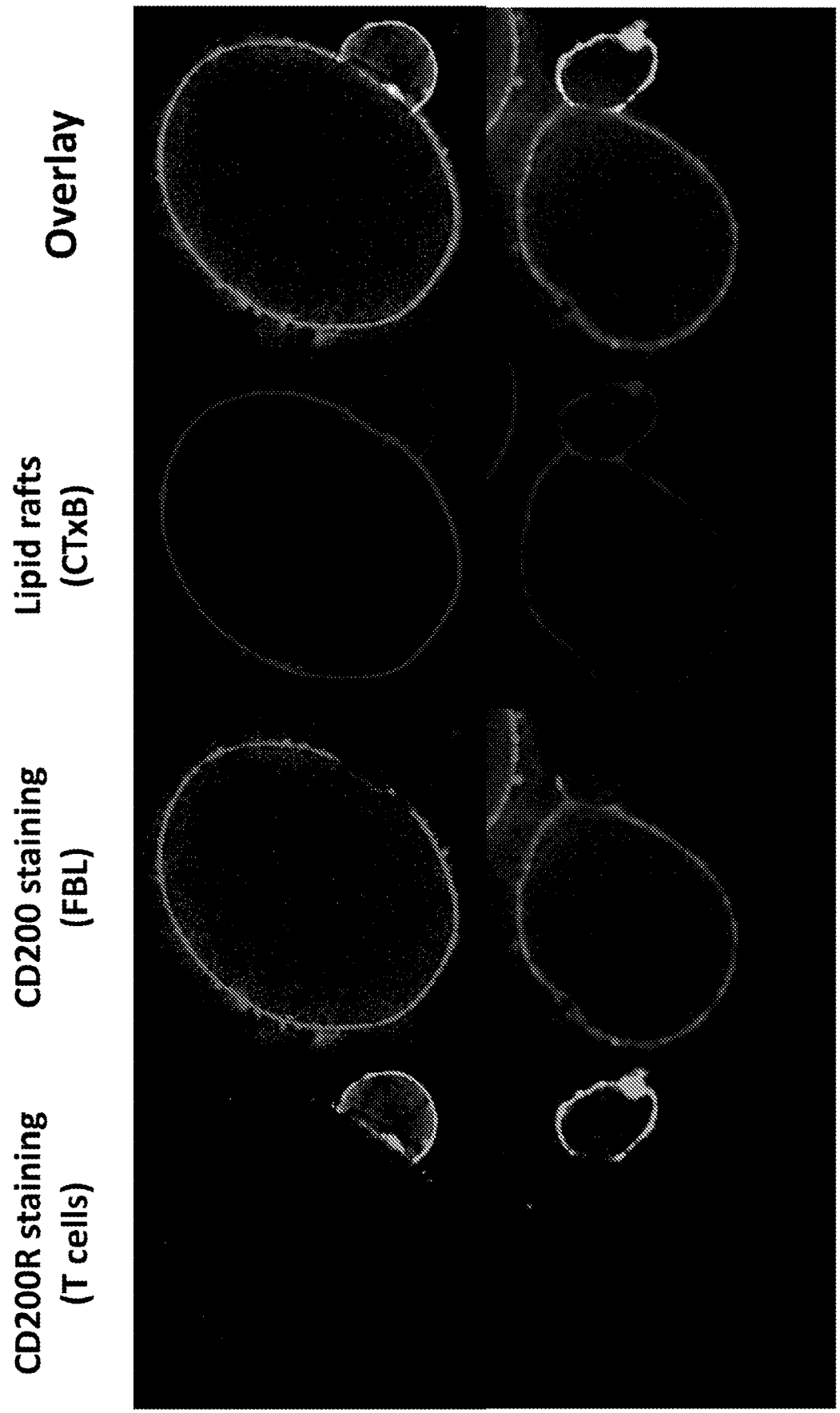
Figure 15N:
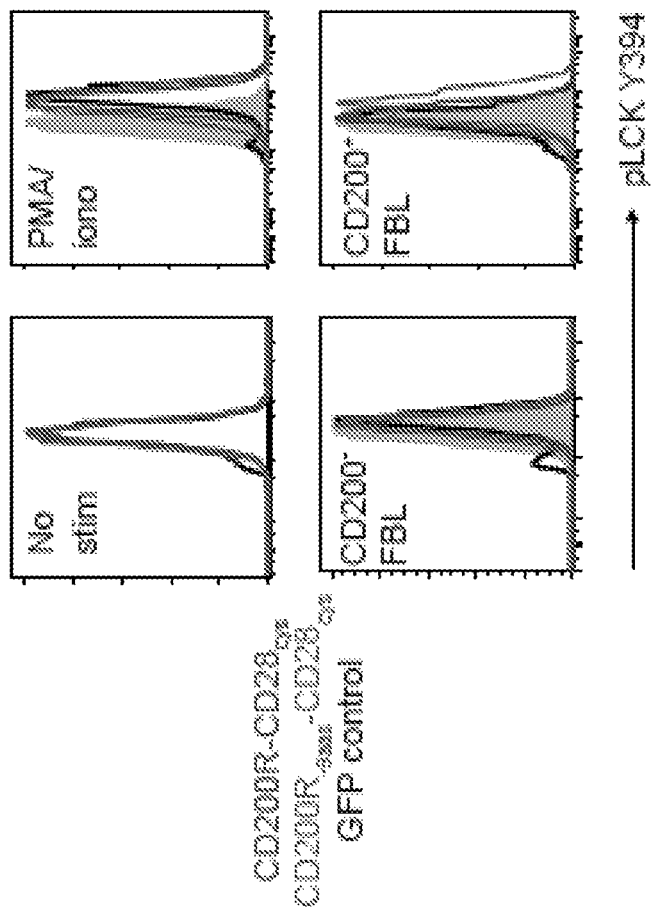

FIGS. 15A to 15N show that CD200R-CD28 constructs promote proliferation, accumulation, and effector function of T cells stimulated by CD200$^+$ tumor target cells in vitro, and accumulate in the immunological synapse. Unless otherwise indicated, all results are representative of at least 2 experiments with similar results. Splenocytes from naive TCR$_{gag}$ mice were stimulated in vitro with anti-CD3, anti-CD28, and recombinant human IL-2 (rhIL-2, 100 U/ml) and transduced with retroviral supernatant for 2 days. Cells were restimulated every 7 days with irradiated FBL and splenocytes and cultured with rhIL-2 (50 U/mL) for up to three stimulations. T cells were used for assays 5-7 days after the last stimulation. (A) Proliferation of CD200R-CD28 and GFP control TCR$_{gag}$ T cells as measured by CellTrace Violet (CTV) dilution, relative to unstimulated cells (shaded). T cells were stimulated with CD200$^-$ FBL (upper panels) or CD200$^+$ FBL (lower panels) for 3 days. (B) Schematic of truncated CD200R (trCD200R). (C) CD28 signaling domain is required for costimulation. Transgenic expression of trCD200R construct on TCRgag T cells as detected by anti-CD200R antibody. (D) Proliferation of trCD200R (blue lines) and GFP control (red lines) TCR$_{gag}$ T cells as measured by CellTrace Violet dilution. T cells were stimulated with CD200$^+$ FBL for 3 days. (E) Restimulation with CD200$^+$ FBL enriches CD200R IFP-transduced T cells. Enrichment of transduced TCR$_{gag}$ T cells in a mixed population including non-transduced TCR$_{gag}$ T cells during 1 cycle of restimulation with irradiated CD200$^-$ (left panels) or CD200+(right panels) FBL, and splenocytes. TCR$_{gag}$ T cells were transduced with CD200R-CD28 (upper panels) or GFP control (lower panels). (F, G) Enrichment of transduced TCR$_{gag}$ T cells in a mixed population including non-transduced TCR$_{gag}$ T cells during weekly cycles of stimulation with irradiated CD200$^+$ FBL and splenocytes. *P<0.05, **P<0.01 (t test). (H) CD200R-9aas-CD28Cys$^+$ CD8$^+$ T cells display enhanced ability to lyse CD200$^+$ FBL cells in vitro. Target tumor cells were labeled with the fluorescent dye 5,6-carboxyfluorescein diacetate succinimidyl ester (CFSE). TCR$_{gag}$ T cells were transduced with CD200R-9aas-CD28Cys or mock-transduced cells (black symbols). Effector TCR$_{gag}$ T cells were incubated at the indicated effector to target ratio with a 1:1 mix of CD200$^+$ FBL and non-specific EL4 control targets for 4 hours. The percentage of FBL of the sum of FBL and control tumor cells was determined by flow cytometry. The percentage lysis was determined by dividing the percent of FBL incubated with T cells by the percent of FBL incubated without T cells. (I) Pie charts depicting the pattern of cytokine production in TCR$_{gag}$ T cells in response to FBL stimulation at a 1:1 ratio. Each slice within the pie chart represents a combination of cytokine staining, including IFNγ, TNFα, and IL-2. (J) Histograms of cytokine production shown in (I), as measured by flow cytometry. Shaded histograms represent GFP control-transduced cells. (K-M) CD200R-9aas-CD28Cys fusion proteins co-localized with lipid rafts, indicating that the fusion proteins concentrate at the region of T cell: target contact, suggesting that the size of the fusion protein can be accommodated within the immunological synapse. Vector transduced TCR$_{gag}$ in vitro expanded effector T cells were combined with FBL at a E:T of 10:1 at 37° C. for 20 minutes. Conjugates were loaded on a μ-Slide VI.4 chamber (Ibidi) for an additional 15 minutes. Fixed cells were stained and visualized by microscopy. In FIG. 15K, the upper panel shows cells in contact, and the lower panel shows cells not in contact. (N) LCK Y394 expression of TCR$_{gag}$ T cells transduced with CD200R-9aas-CD28Cys (red line), CD200R-CD28Cys (blue line), and GFP control (black line) and stimulated for 10 minutes as labeled.

FIGS. 16A to 16E show that T cells transduced with CD200R-9aas-CD28Cys preferentially accumulate in response to tumor challenge in vivo and enhance adoptive immunotherapy of disseminated leukemia. Transduced TCR$_{gag}$ T cells were generated as described in Example 15. C57BL/6 mice were injected with $4\times10^6$ CD200$^+$ FBL cells. Five days later, CD200R.9aas-CD28Cys (Thy1.1 homozygous) and eGFP (Thy1.1 heterozygous) TCR$_{gag}$ T cells were co-injected into Cy-treated FBL-bearing B6 mice at $4\times10^6$ cells/mouse. IL-2 was administered every 2 days ($2\times10^4$ U/dose). On day 8 post-T cell transfer, mice were euthanized and spleens and inguinal lymph nodes harvested. (A) CD200R-9aas-CD28CysTCR$_{gag}$ T cells accumulate in the spleen in response to FBL, relative to empty vector control TCR$_{gag}$ T cells. (B) Phenotype of IFP-transduced T cells is similar to control. Expression of surface markers on TCR$_{gag}$ T cells transduced with CD200R-CD28 (red lines) or non-transduced (blue lines) 5 days after stimulation in vitro. (C) Accumulation of CD200R-9aas-CD28Cys and empty vector control TCR$_{gag}$ T cells in the lymph node (LN) and spleen (Spl) in response to FBL. The fold increase of CD200R-9aas-CD28Cys TCR$_{gag}$ T cells (Thy1.1 hom) was calculated by dividing by the percentage of empty vector control (Thy1.1$^+$ Thy1.2+) TCR$_{gag}$ T cells. (D, E) Expression of surface markers on CD200R-9aas-CD28Cys TCR$_{gag}$ T cells (blue lines), control TCR$_{gag}$ T cells (red lines), and endogenous T cells (shaded) at days 8 (D) and 15 (E). At 15 days post-transfer, CD200R-9aas-CD28Cys TCR$_{gag}$ T cells expressed similar levels of cell surface proteins compared to empty vector control TCR$_{gag}$ T cells.

Figure 17A:
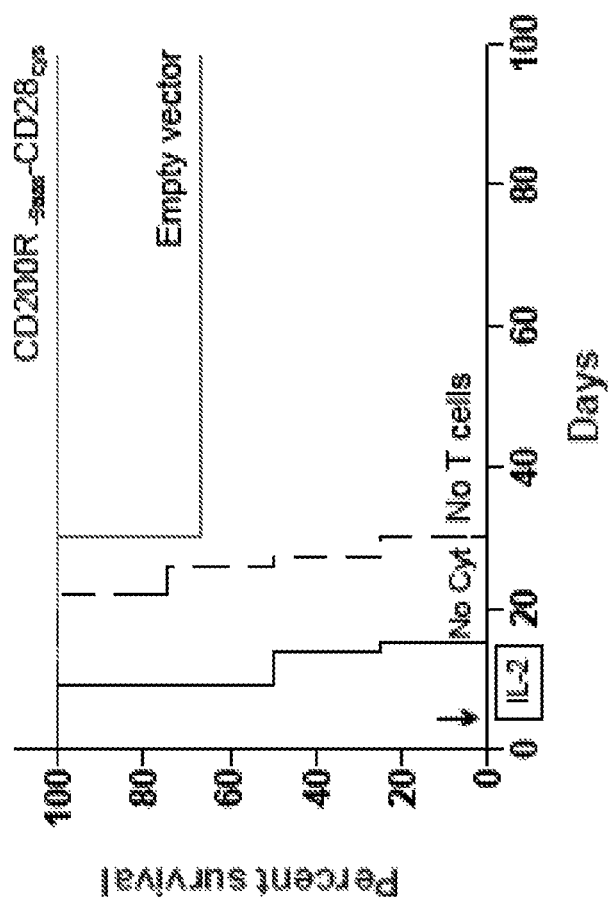
Figure 17B:
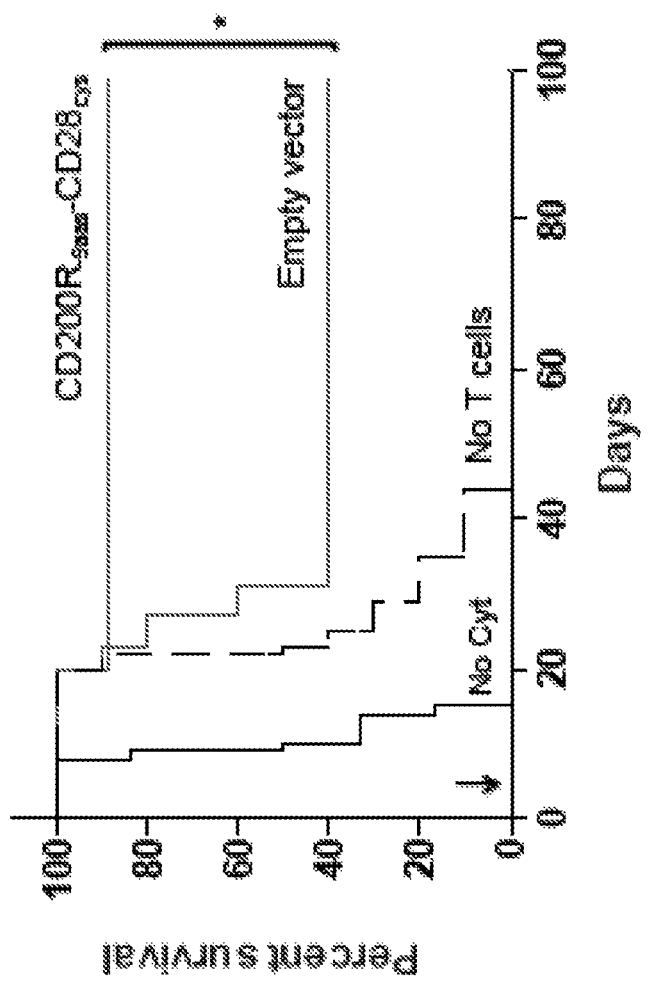

FIGS. 17A and 17B show survival of mice treated in the presence (A) or absence (B) of IL-2 injections. C57BL/6 mice were injected with $4\times10^6$ CD200$^+$ FBL cells. Five days later, CD200R-9aas-CD28Cys, and eGFP TCR$_{gag}$ T cells were injected i.p. into Cy-treated FBL-bearing mice at $10^5$ cells/mouse (indicated by arrow). IL-2 was administered every 2 days for a total of 10 days ($2\times10^4$ U/dose) in a cohort of mice (A). Transfer of CD200R-9aas-CD28Cys TCR$_{gag}$ T cells significantly improved survival in the absence of IL-2 injections (P<0.05, log-rank Mantel-Cox test) (B). In (A), data are from 1 experiment (n=3-4 mice/group). In (B), data were pooled from 3 independent experiments (n=6-10 mice/group).

FIGS. 18A to 18E show that human primary T cells transduced to express a WT1-specific TCR and a CD200Rtm-CD28 fusion protein exhibit enhanced proliferation to target cells that express CD200 and increased cytokine production in response to tumor cells that express CD200. (A) Expression of CD200 on CD34$^+$ cells from a healthy donor leukapheresis (upper panels) or leukemic blasts (lower panels). (B) Expression of the WT1$_{126}$-specific TCR, TCR$_{C4}$, and CD200Rtm-CD28 in primary human T cells. Diagram shows construct combining IFP, TCRα, and TCRβ chains. (C, D) Proliferation of T cells as indicated by CFSE. Cells that proliferate in response to antigen show reduced CFSE fluorescence intensity. T cells transduced with TCR$_{C4}$ or with TCR$_{C4}$ and CD200Rtm-CD28 were stimulated with WT1$_{126}$-pulsed T2 cells. (E) Cytokine production in response to exposure to T2 cells, as measured by flow cytometry. T cells transduced with the TCR$_{C4}$ alone (upper panels) or with both TCR$_{C4}$ and the CD200-targeted IFP (lower panels) were stimulated with a titration of WT1$_{126}$-pulsed T2 cells, as indicated. Relative to control T cells transduced with the TCR$_{C4}$ alone, T cells transduced with both TCR$_{C4}$ and the IFP CD200Rtm-CD28 showed increased cytokine production.

Figure 19A:
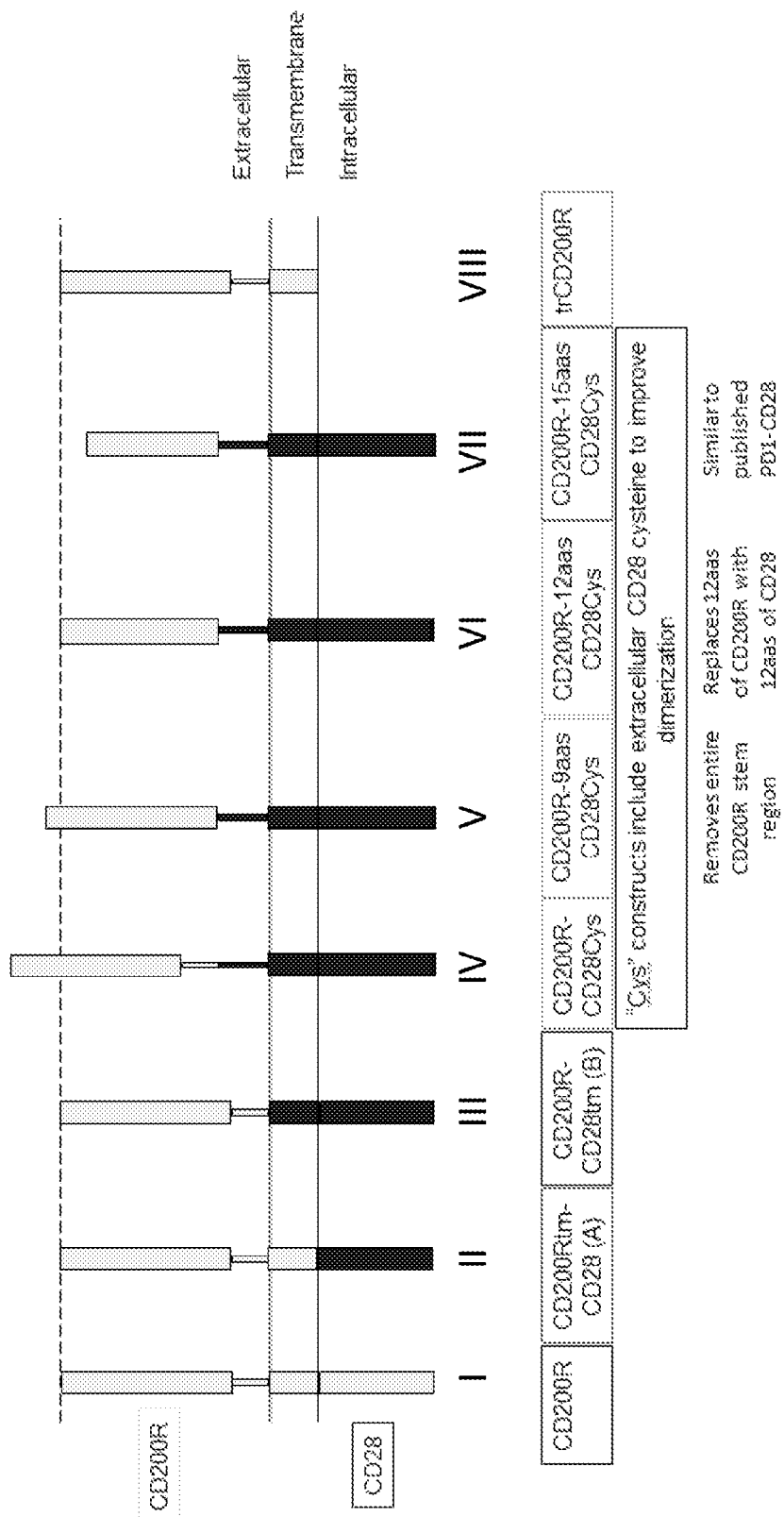
Figure 19B:
Figure 19C:
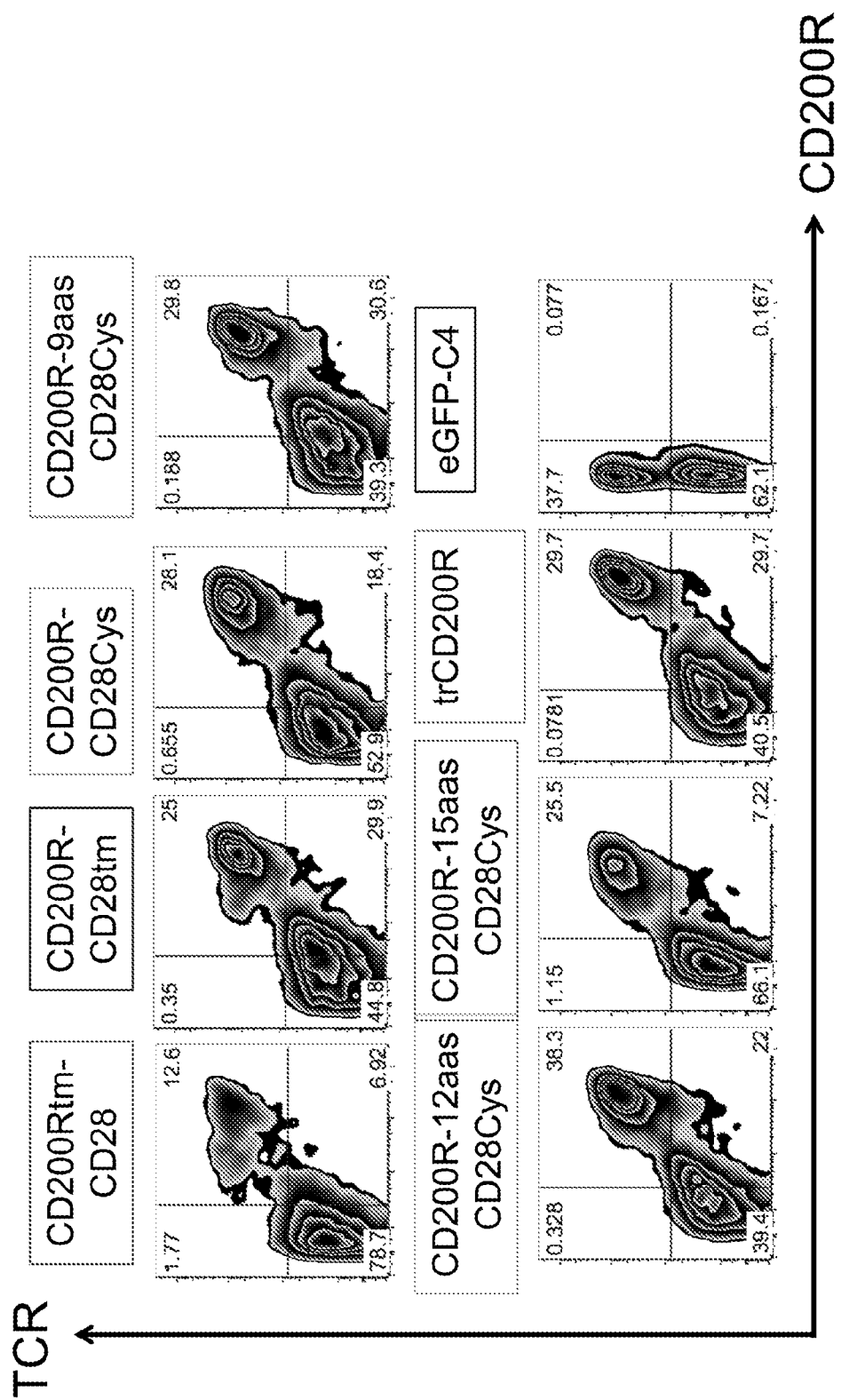

FIGS. 19A to 19C show CD200R-CD28 constructs co-expressed with WT1-specific TCR in primary human T cells. (A) Schematic illustration of representative CD200R-CD28 constructs. (B) Diagram showing construct combining IFP, TCRα, and TCRβ chains. (C) Expression of the WT1$_{126}$-specific TCR, TCR$_{C4}$, and CD200R-CD28 fusion proteins in primary human T cells.

FIGS. 20A to 20D show the results of assays for enrichment of T cells expressing CD200R-CD28 constructs.

FIGS. 21A to 21K show effector function assays (cytokine production, cytotoxicity) for T cells expressing CD200R-CD28 constructs.

Figure 22A:
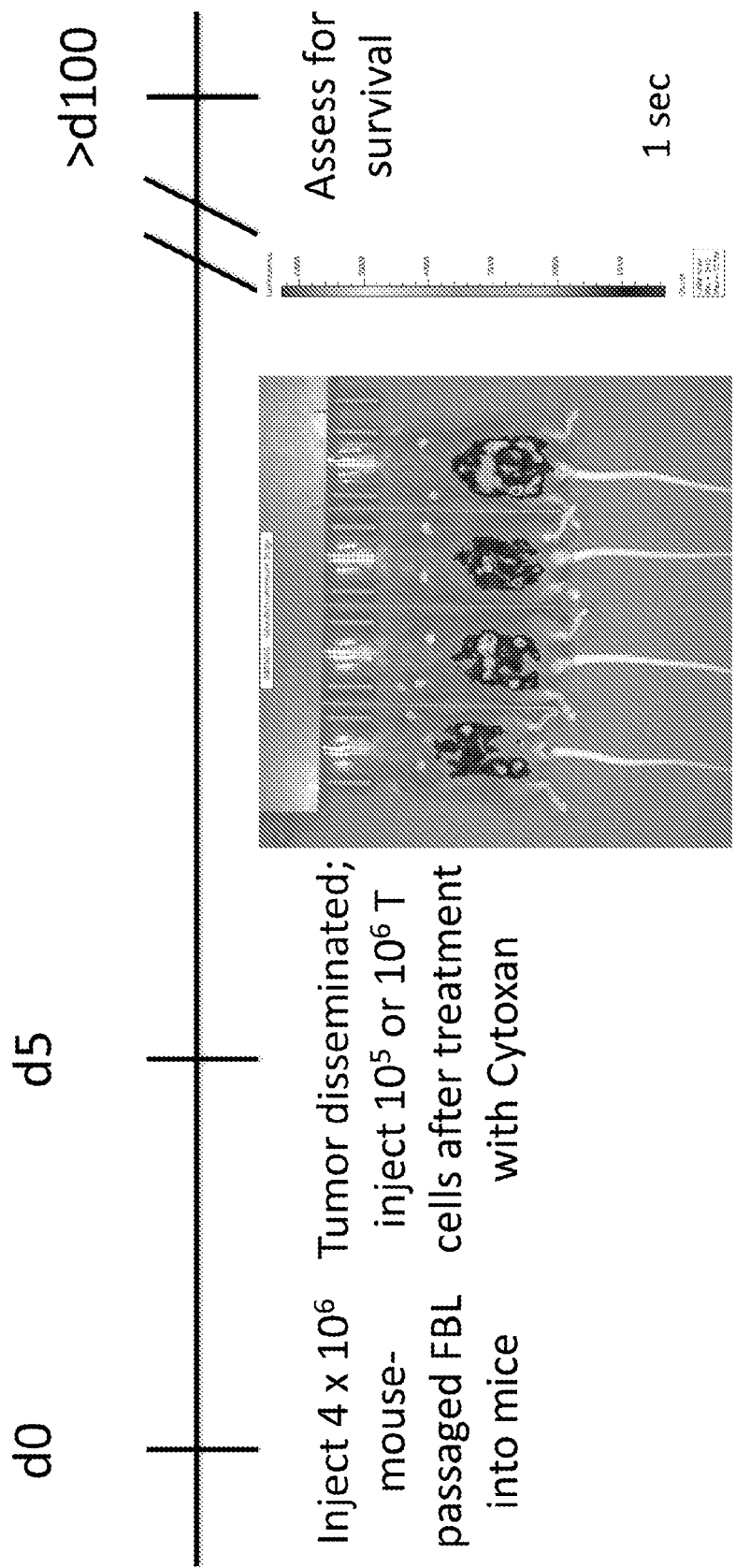
Figure 22B:
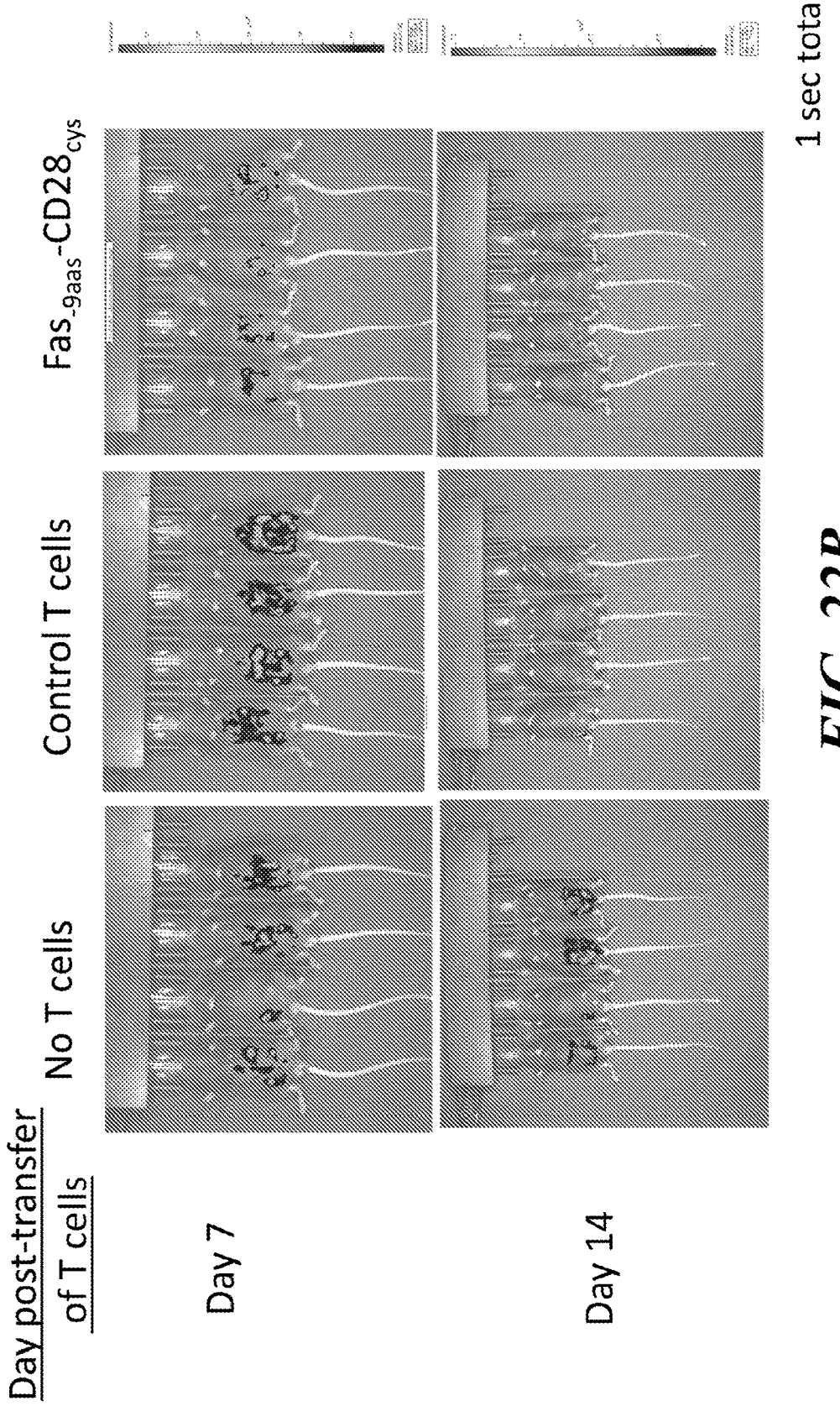
Figure 22C:
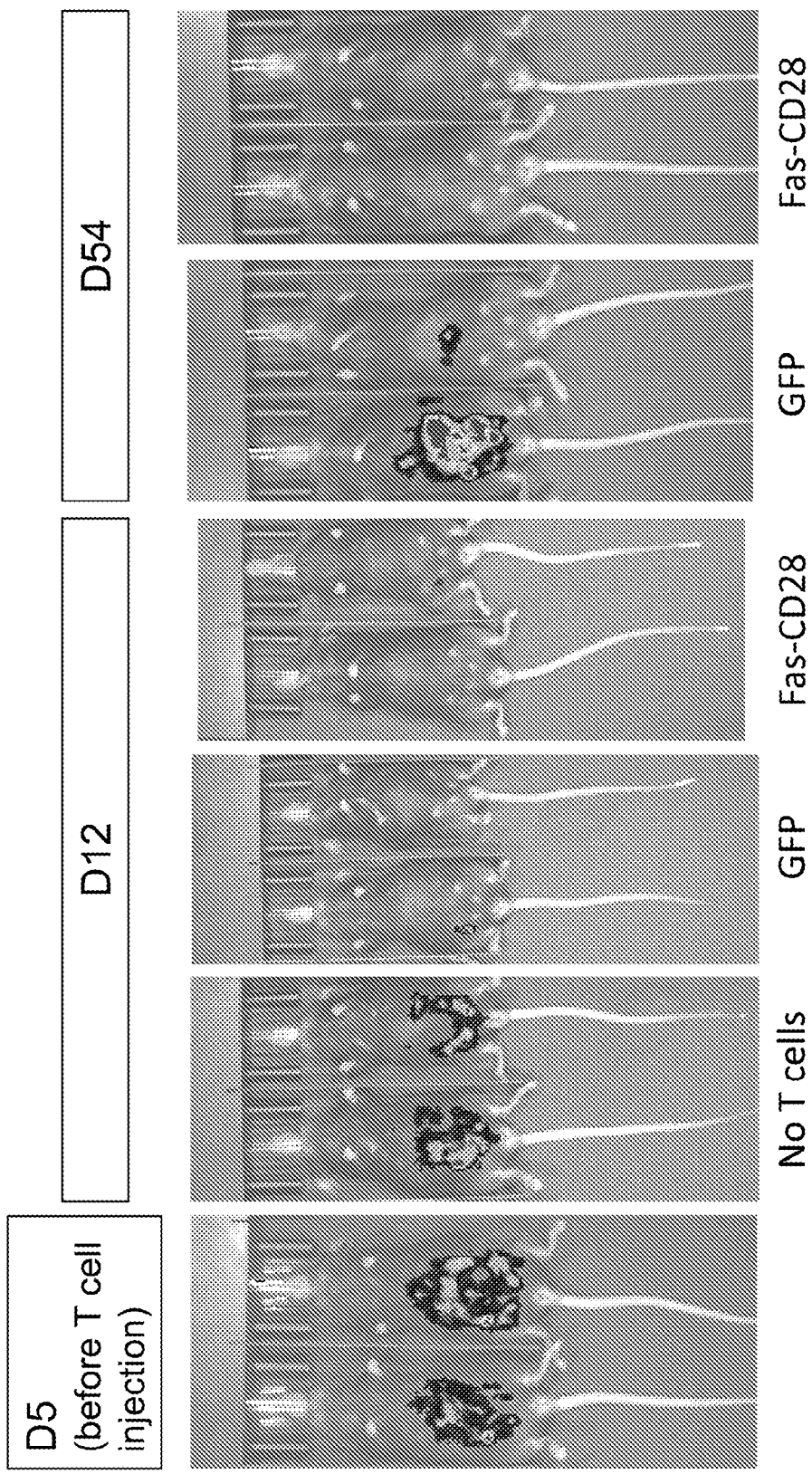
Figure 22D:
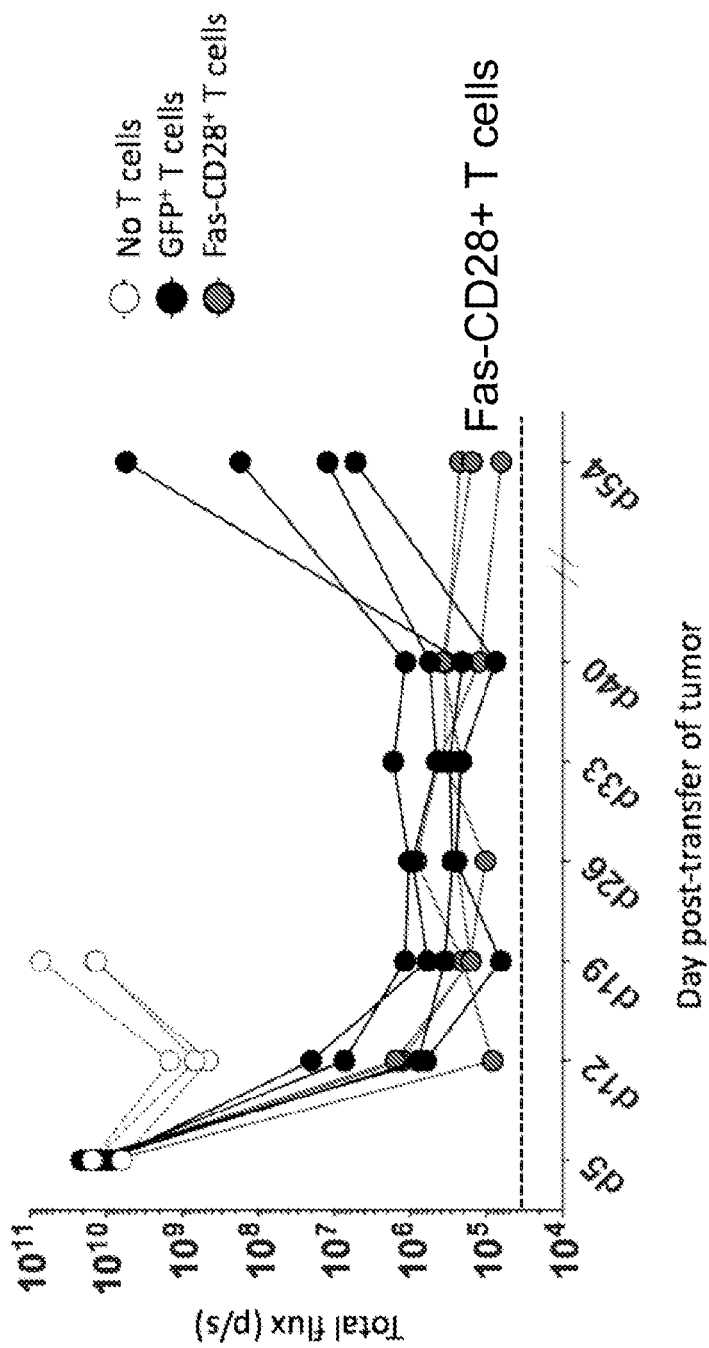

FIGS. 22A to 22D show results of an in vivo study of immunotherapy with T cells expressing Fas IFP constructs. (A) Study design. (B-C) In vivo bioluminescence imaging of firefly luciferase$^+$ FBL tumors in C57BL/6 mice at indicated time points after intraperitoneal inoculation with $4\times10^6$ tumor cells (day 0) and after cyclophosphamide treatment, followed by no additional treatment or adoptive transfer of $10^6$ GFP-transduced or Fas-CD28-transduced TCR$_{gag}$ transgenic CD8$^+$ T cells (day 5). The two mice shown in FIG. 22C are representative of n=4 mice. (D) Biodistribution of FBL tumor cells as quantified by IVIS imaging. FBL tumors in C57BL/6 mice at indicated time points after intraperitoneal inoculation with $4\times10^6$ tumor cells (day 0) and after cyclophosphamide treatment, followed by no additional treatment (white circles) or adoptive transfer of $10^6$ GFP-transduced (black circles) or Fas-CD28-transduced (red circles) TCR$_{gag}$ transgenic CD8$^+$ T cells (day 5).

FIGS. 23A to 23D show that fusion proteins comprising Fas extracellular components and 4-1BB co-stimulatory signaling domains accumulate and proliferate in vitro upon stimulation with tumor cells, and also reduce Fas-induced cell death. (A) Schematic representation of an exemplary Fas-4-1BB construct. The construct contains a Fas extracellular ("EC") domain and 4-1BB transmembrane ("TM") and intracellular ("IC") signaling domains ("Fas-4-1BBtm"). (B) Co-expression of a transgenic TCR and a Fas-4-1BB IFP (Fas-4-1BBtm) in murine T cells. Retroviral supernatant was generated by transfection of Plat-E cells with DNA constructs encoding either TCR$_{gag}$ alone, or TCR$_{gag}$ and Fas-4-1BBtm (SEQ ID NO.:187). Naïve P14 T cells were stimulated with anti-CD3 and anti-CD28, then transduced for 2 days with retroviral supernatant. Five days post-stimulation, transduced T cells were stained with specific antibodies to the TCR and to Fas, and analyzed by flow cytometry. (C) Proliferation of T cells transduced with $TCR_{gag}$ alone or with $TCR_{gag}$ and Fas-4-1BBtm, as measured by CellTrace Violet (CTV) dilution. Transduced P14 T cells were stained with CellTrace Violet (CTV) proliferation dye and were unstimulated (left) or stimulated with FBL tumor cells for 6 days at an effector-to-target ratio of 8:1 (right). T cells were then harvested and analyzed by flow cytometry. (D) Cell death Fas signaling pathway activity in (i) T cells expressing transgenic $TCR_{gag}$ but lacking Fas expression; (ii) wild-type T cells expressing transgenic $TCR_{gag}$; and (iii) T cells expressing transgenic $TCR_{gag}$ and Fas-4-1BBtm. P14 T cells were stimulated and transduced with $TCR_{gag}$ or $TCR_{gag}$+Fas-4-1BBtm IFP. 7 days later, T cells were stained for active caspase-8 expression using the FLICA methodology, as a measure of cell death by the Fas pathway.

Figure 24A:
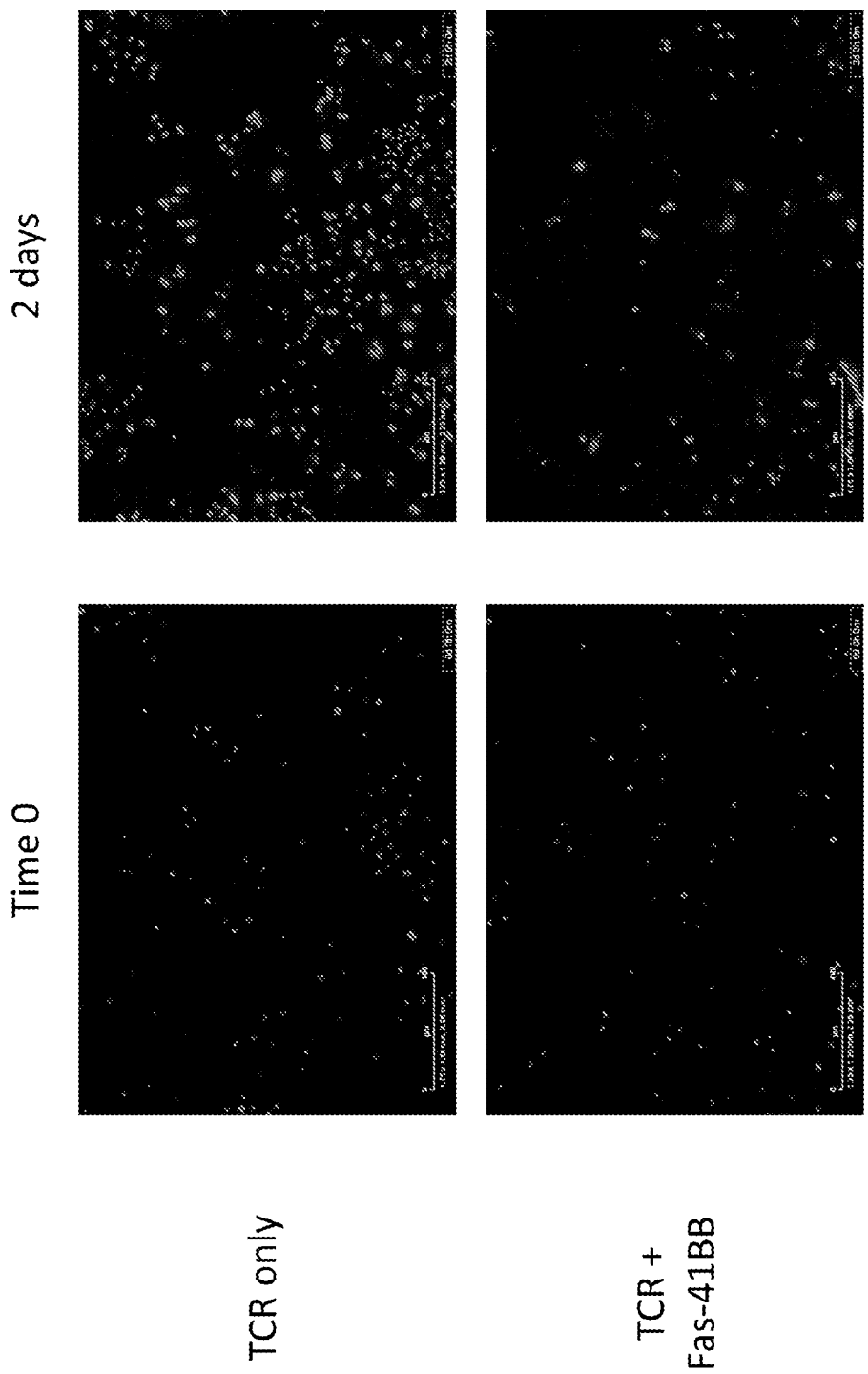
Figure 24B:
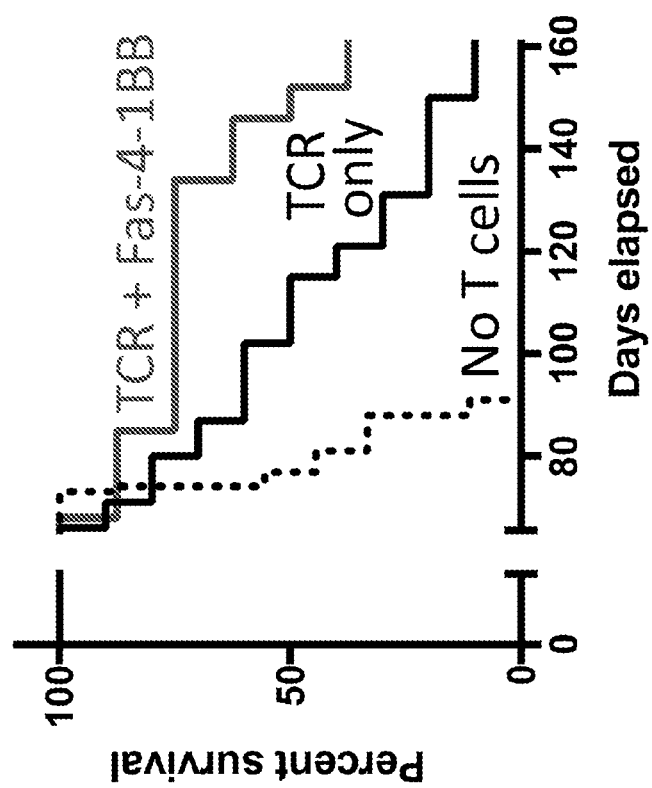

FIGS. 24A to 24B show that Fas-4-1BB T cells control tumor growth and promote survival in an ID8 model of ovarian cancer. (A) Results of an IncuCyte® assay used to quantify killing of ID8 ovarian tumor cells. Murine transduced T cells (anti-mesothelin TCR or anti-mesothelin TCR+Fas-4-1BBtm) were co-incubated with red fluorescent ID8 ovarian tumor cells for two days and ID8 cell growth was quantified by IncuCyte® analysis. Loss of red signal indicates killing of tumor cells. (B) Survival of ID8 mice treated with (i) anti-mesothelin TCR cells or (ii) with anti-mesothelin TCR+Fas-4-1BBtm cells. In the ID8 murine ovarian cancer model, $5 \times 10^6$ ID8 tumor cells were implanted and allowed to disseminate for 6 weeks. Following cyclophosphamide treatment, mice received $10^7$ T cells and $5.0 \times 10^8$ mesothelin-pulsed splenocytes, followed by IL-2 injections for 10 days. Mice were treated every two weeks until euthanized.

FIGS. 25A to 25D show that Fas-4-1BB T cells exhibit greater persistence and promote survival in a KPC mouse model of pancreatic cancer. (A) Ultrasound image of a healthy mouse with normal pancreas (left) and a pancreatic tumor in an "enrolled" mouse (a KPC genetically engineered mouse) (right). (B) Experiment schematic. KPC mice were screened by ultrasound to determine when tumors arise, and were enrolled in the study when a tumor was detected, at approximately 8 weeks of age. Mice were randomly assigned to treatment groups; mice were treated with cyclophosphamide, and those receiving TCR-T cells were injected with $10^7$ each of mesothelin-specific-T cells and mesothelin peptide-pulsed splenocytes post-cyclophosphamide. Beginning 14 days post-enrollment, the T cell/APC infusion (but without cyclophosphamide) was repeated every 2 weeks for a total of 3 infusions, without IL-2 injections. At the end of the study, the mice were assessed for survival. (C) Mice that survived 28 days post final T cell infusion were bled and the persistence of transferred T cells was assessed by detection of congenically marked T cells by flow cytometry. (D) Survival of KPC mice treated with (i) anti-mesothelin TCR cells or (ii) with anti-mesothelin TCR+Fas-4-1BBtm cells.

Figure 26:
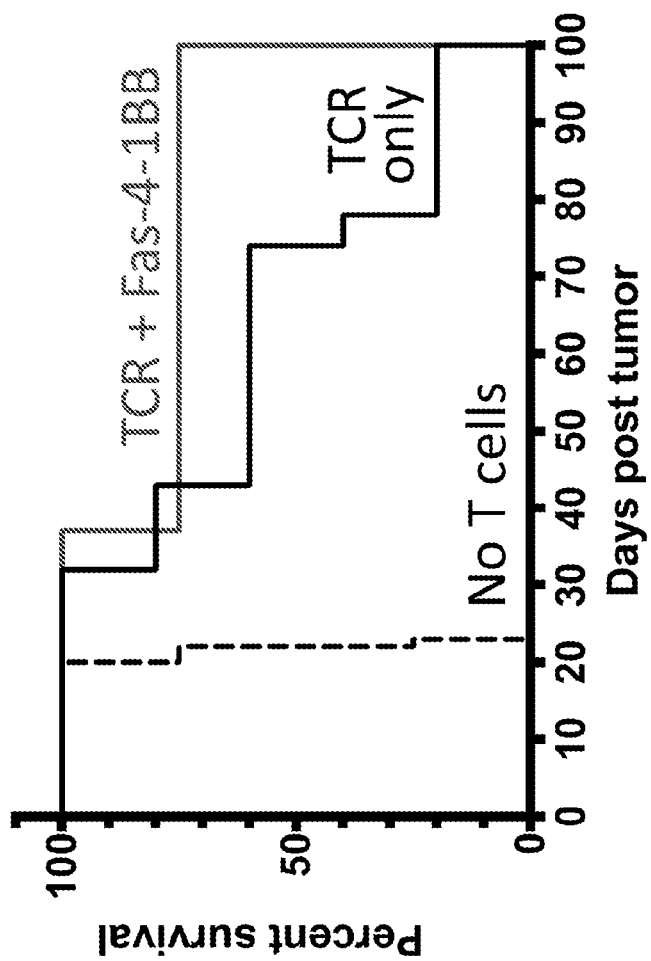

FIG. 26 shows survival of AML model (FBL-injected) mice treated with (i) $TCR_{gag}$ T cells or (ii) with $TCR_{gag}$+Fas-4-1BBtm T cells. Mice were injected with FBL cells. Five days later, mice were treated with cyclophosphamide with or without administration of $10^6$ T cells.

DETAILED DESCRIPTION

The instant disclosure provides fusion proteins that modulate signaling in a host cell, such as an immune cell. For example, fusion proteins of this disclosure can provide an activation or co-stimulatory signal in a human T cell, wherein the T cell may optionally be engineered to have a preferred antigen-specific TCR. These immunomodulatory fusion proteins (IFPs) can interact with ubiquitously expressed targets or with targets that are commonly upregulated or overexpressed in non-normal cells (e.g., a cancer cell). Such IFPs have an extracellular binding domain and an intracellular signaling domain. By transducing T cells with engineered TCRs (e.g., high affinity TCRs) and fusion proteins of this disclosure that generate activation signals, certain embodiments of T cells may no longer require exogenous co-stimulation upon interaction with, for example, a tumor cell.

In certain aspects, the present disclosure provides host cells (e.g., immune cells such as T cells, dendritic cells, NK cells or the like) comprising an IFP, vectors encoding IFPs, and methods of activating T cells comprising an IFP for various therapeutic applications, including the treatment of a disease in subject (e.g., cancer, infectious disease).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, or module or protein includes extensions, deletions, mutations, or any combination thereof (e.g., amino acids at the amino- or carboxy-terminus or between domains) that, in combination, contribute to at most 20% (e.g., at most 15%, 10%, 8%, 6%, 5%, 4%, 3%, 2%, or 1%) of the length of a domain, region, or module or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "heterologous" or "non-endogenous" or "exogenous" refers to any gene, protein, compound, molecule, or activity that is not native to a host cell or a subject, or is any gene, protein, compound, molecule, or activity native to a host or host cell that has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a molecule or activity found in or derived from a host cell, species, or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species, or a combination thereof.

As used herein, the term "endogenous" or "native" refers to a gene, protein, compound, molecule, or activity that is normally present in a host or host cell and has no engineered alterations.

A "binding domain" (also referred to as a "binding region" or "binding moiety"), as used herein, refers to a molecule, such as a peptide, oligopeptide, polypeptide or protein, that possesses the ability to specifically and non-covalently associate, unite, or combine with a target molecule (e.g., CD200, CD47, CD19, CD20, CD22, ROR1, mesothelin, PD-L1, PD-L2, PSMA, WT-1, cyclin-A1). A binding domain includes any naturally occurring, synthetic, semi-synthetic, or recombinantly produced binding partner for a biological molecule or other target of interest or binding protein thereof. In some embodiments, the binding domain is an antigen-binding domain, such as an antibody or T cell receptor (TCR) or functional binding domain or antigen-binding fragment thereof. Exemplary binding domains include receptor ectodomains (e.g., those of CD200R, PD-1, CTLA4, BTLA, CD2, Fas) or binding portions thereof, ligands (e.g., cytokines such as IL35, chemokines) or binding portions thereof, single chain antibody variable regions (e.g., domain antibodies, sFv, scFv, Fab) or binding portions thereof, antigen-binding regions of T cell receptors (TCRs), such as single chain TCRs (scTCRs), or synthetic polypeptides selected for the specific ability to bind to a biological molecule.

In some embodiments, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, or binds to such target molecule while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7 M^{-1}$, at least $10^8 M^{-1}$, at least $109 M^{-1}$, at least $10^{10} M^{-1}$, at least $10^{11} M^{-1}$, at least $10^{12} M^{-1}$, or at least $10^{13} M^{-1}$. "Low affinity" binding domains refer to those binding domains with a $K_a$ of up to $10^7 M^{-1}$, up to $10^6 M^{-1}$, up to $10^5 M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., Ann. N.Y. Acad. Sci. 51:660, 1949; and U.S. Pat. Nos. 5,283,173, 5,468,614, or the equivalent).

As used herein, a "fusion protein" refers to a polypeptide that, in a single chain, has at least two distinct domains, wherein the domains are not naturally found together in a protein. A nucleic acid molecule encoding a fusion protein may be constructed using PCR, recombinantly engineered, or the like, or such fusion proteins can be made using methods of protein synthesis. A fusion protein may further contain other components (e.g., covalently bound), such as a tag or bioactive molecule. In certain embodiments, a fusion protein expressed or produced by a host cell (e.g., T cell) locates to the cell surface, where the fusion protein is anchored to the cell membrane with a portion of the fusion protein located extracellularly (e.g., containing a binding domain) and a portion of the fusion protein located intracellularly (e.g., containing a signaling domain).

A "hydrophobic component," as used herein, means any amino acid sequence having a three-dimensional structure that is thermodynamically stable in a cell membrane, and generally ranges in length from about 15 amino acids to about 30 amino acids. The structure of a hydrophobic component may comprise an alpha helix, a beta barrel, a beta sheet, a beta helix, or any combination thereof. In certain embodiments, a hydrophobic component is comprised of a "transmembrane domain" from a known transmembrane protein, which is a portion of a transmembrane protein that can insert into or span a cell membrane. In further embodiments, a hydrophobic component or transmembrane domain can be disposed between and connect the extracellular and intracellular portions of a fusion protein. Additionally, the hydrophobic component may be modified to contain charged regions or hydrophilic residues to facilitate intermolecular interactions.

As used herein, an "intracellular signaling domain" is an intracellular portion of molecule, such as one used in a fusion protein of this disclosure, that can directly or indirectly promote a response such as a co-stimulatory, positive, or activating biological or physiological response in a cell when receiving the appropriate signal. In certain embodiments, an intracellular signaling domain is part of a protein or protein complex that receives a signal when bound, or itself can bind directly to a target molecule to transmit a signal to other components in the cell. An intracellular signaling domain may directly promote a cellular response when it contains one or more signaling domains or motifs, such as an immunoreceptor tyrosine-based activation motif (ITAM), a kinase domain, a co-stimulatory domain, or the like. In other embodiments, an intracellular signaling domain will indirectly promote a cellular response by associating with one or more other proteins that in turn directly promote a cellular response. In some embodiments, an intracellular signaling domain or functional fragment thereof may be from a CD3E, CD36, CD3ζ, CD25, CD27, CD28, CD40, CD47, CD79A, CD79B, CD134 (OX40), CD137 (4-1BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, Slp76, pTα, TCRα, TCRβ, TRIM, Zap70, PTCH2, or any combination thereof. In some embodiments, an intracellular signaling domain or functional fragment thereof does not comprise a CD3ζ.

A "multimerization domain," as used herein, refers to a polypeptide molecule or region that preferentially interacts or associates with another polypeptide molecule or region, directly or indirectly, wherein the interaction of multimerization domains substantially contribute to or efficiently promote multimerization (i.e., the formation of a dimer, trimer, tetramer, or higher order multimers, which may be a homodimer, heterodimer, homotrimer, heterotrimer, homomultimer, heteromultimer, or the like). For example, multimerization may be due to one or more types of molecular forces, including covalent bonds (e.g., disulfide bonds or bridges), ionic bonds, metallic bonds, electrostatic interactions, salt bridges, dipole-dipole forces, hydrogen bonding, Van der Waals forces, hydrophobic interactions, or any combination thereof. A multimer is stable under appropriate conditions (e.g., physiological conditions, in an aqueous solution suitable for expressing, purifying, or storing recombinant or engineered proteins, or under conditions for non-denaturing or non-reducing electrophoresis). Exemplary multimerization domains may comprise one or more disulfide bonds, zinc finger motif, a leucine zipper motif, helix-turn-helix, helix-loop-helix, or the like.

In certain embodiments, a fusion protein may contain a "linker," which can provide a spacer function to facilitate the interaction of two single chain fusion proteins, or positioning of one or more binding domains, so that the resulting polypeptide structure maintains a specific binding affinity to a target molecule or maintains signaling activity (e.g., effector domain activity) or both. Exemplary linkers include from one to about ten repeats of $Gly_xSer_y$, wherein x and y are independently an integer from 1 to 5.

"Junction amino acids" or "junction amino acid residues" refer to one or more (e.g., about 2-20) amino acid residues between two adjacent motifs, regions, or domains of a fusion protein, such as between a binding domain and an adjacent hydrophobic component, or on one or both ends of a hydrophobic component. Junction amino acids may result from the construct design of a fusion protein (e.g., amino acid residues resulting from the use of a restriction enzyme site during the construction of a nucleic acid molecule encoding a fusion protein). In certain embodiments, junction amino acids form a linker, such as those having from one to about ten repeats of $Gly_xSer_y$, wherein x and y are independently an integer from 1 to 5.

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a $CD4^+$ T cell, a $CD8^+$ T cell, a CD4– CD8– double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or TCM). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+ CD28–, and Qa-1 restricted T cells.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease,* 3rd Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form.

"Major histocompatibility complex molecules" (MHC molecules), which is used interchangeably and is understood to also refer to the human counterpart human leukocyte antigen (HLA molecules), refer to glycoproteins that deliver peptide antigens to a cell surface. MHC class I molecules are heterodimers consisting of a membrane spanning a chain (with three a domains) and a non-covalently associated β2 microglobulin. MHC class II molecules are composed of two transmembrane glycoproteins, α and β, both of which span the membrane. Each chain has two domains. MHC (HLA) class I molecules deliver peptides originating in the cytosol to the cell surface, where peptide:MHC (or peptide: HLA in humans) complex is recognized by $CD8^+$ T cells. MHC (HLA) class II molecules deliver peptides originating in the vesicular system to the cell surface, where they are recognized by $CD4^+$ T cells. An MHC molecule may be from various animal species, including human, mouse, rat, or other mammals.

"Nucleic acid molecule", or polynucleotide, may be in the form of RNA or DNA, which includes cDNA, genomic DNA, and synthetic DNA. A nucleic acid molecule may be double stranded or single stranded, and if single stranded, may be the coding strand or non-coding (anti-sense strand).

A coding molecule may have a coding sequence identical to a coding sequence known in the art or may have a different coding sequence, which, as the result of the redundancy or degeneracy of the genetic code, or by splicing, can encode the same polypeptide.

Variants of the nucleic acid molecules or polynucleotides of this disclosure are also contemplated. Variant polynucleotides are at least 80%, and preferably at least 85%, 90%, 95%, 99%, or 99.9% identical to one of the polynucleotides of defined sequence as described herein, or that hybridizes to one of those polynucleotides of defined sequence under stringent hybridization conditions of 0.015M sodium chloride, 0.0015M sodium citrate at about 65-68° C. or 0.015M sodium chloride, 0.0015M sodium citrate, and 50% formamide at about 42° C. The polynucleotide variants retain the capacity to encode a binding domain or fusion protein thereof having the functionality described herein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015M sodium chloride, 0.0015M sodium citrate at about 65-68° C. or 0.015M sodium chloride, 0.0015M sodium citrate, and 50% formamide at about 42° C. (see Sambrook et al., *Molecular Cloning: A Laboratory Manual,* 2nd Ed., Cold Spring Harbor Laboratory, Cold Spring Harbor, N.Y., 1989).

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, preferred algorithms suitable for determining percent sequence identity and sequence similarity are the BLAST and BLAST 2.0 algorithms, which are described in Altschul et al. (1977) Nucleic Acids Res. 25:3389 and Altschul et al. (1990) J. Mol. Biol. 215:403, respectively.

"Treat" or "treatment" or "ameliorate" refers to medical management of a disease, disorder, or condition of a subject (e.g., a human or non-human mammal, such as a primate, horse, dog, mouse, or rat). In general, an appropriate dose or treatment regimen comprising a host cell expressing a fusion protein of this disclosure, and optionally an adjuvant or adjunctive therapy, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a fusion protein or cell expressing a fusion protein of this disclosure (e.g., CD200R-CD28, SIRPα-CD28, CD200R-41BB, SIRPα-41BB, CD200R-CD28-41BB, SIRPα-CD28-4-1BB or other such fusion proteins), in the context of a disease or condition being treated, refers to that amount of fusion protein or number of cells sufficient to result in amelioration of one or more symptoms of the disease being treated in a statistically significant manner (e.g., reducing infection, reducing tumor size, inhibiting cancer growth or the like).

Immunomodulatory Fusion Proteins (IFPs)

In certain aspects, the present disclosure provides a fusion protein, comprising an extracellular component, a hydrophobic component, and an intracellular component. In some embodiments, the extracellular component includes a binding domain such as one that specifically binds to a target. In some embodiments, the binding domain is from a molecule that ordinarily, e.g., in its natural setting, is capable of delivering a negative or inhibitory signal when bound to its binding partner or ligand or receptor, such as an immunoinhibitory receptor or checkpoint molecule, or the target is an inhibitory receptor or ligand or checkpoint molecule or other inhibitory ligand. In some embodiments, the intracellular component includes a signaling domain, such as a costimulatory signaling domain or signaling region of a molecule generally capable of delivering a costimulatory or positive signal, e.g., to an immune cell. Thus, in some aspects, the fusion proteins are capable of delivering a positive or costimulatory signal in response to a binding event that in a natural setting would result in an inhibitory signal.

In some embodiments, the fusion protein is such that a particular distance is achieved. For example, in some embodiments, a fusion protein::target complex (such as one comprised of an extracellular portion of a complex formed between the fusion protein and the target by specific binding thereto) is of a particular length or spans a particular distance, such as a distance of up to a distance between membranes in an immunological synapse, or that spanned by the extracellular portion of a cognate complex between a TCR and MHC molecule, e.g., following specific recognition thereof by a TCR, or the distance spanned by the extracellular portion of a complex formed between the natural molecule and its natural binding partner. In some embodiments, the distance or length is sufficient to promote the colocalization of a fusion protein with antigen receptor or other signaling molecule when expressed in an immune cell, such as a T cell, or entry into an immunologic synapse.

By way of background, an immunological synapse is an interface between cells, which can form between a variety of cells, such as between immune cells (Rossy et al., *Frontiers in Immunol.* 3: 1-12, 2012; Hatherley et al., *Structure* 21:820, 2013). For example, in the case of a T cell contacting an antigen-presenting cell (APC), an immunological synapse can be formed by the binding of a TCR (found on the surface of a T cell) with an HLA-peptide (MHC-peptide for non-human) complex (found on the surface of, for example, APCs; HLA class I molecules can be found on the surface of all nucleated cells, while HLA class II can conditionally be expressed on all cell types but are regularly found on APCs). In addition, an immunological synapse may be organized into supramolecular activation clusters (SMACs), which can affect lymphocyte activation, direct antigen-HLA (or antigen-MHC) complex presentation to lymphocytes, and direct secretion of cytokines or lytic granules between cells. A SMAC can be comprised of three structures arranged in concentric circles: a central region (cSMAC) containing a high number of TCRs as well as co-stimulatory and inhibitory molecules, a peripheral region (pSMAC) where LFA-1 and talins are clustered, and a distal region (dSMAC) that is enriched for CD43 and CD45 molecules. In certain embodiments, an immunological synapse will span from about 10 nm to about 15 nm. For example, protein interactions found within the immunological synapse, such as the TCR::HLA-peptide interaction or a fusion protein-target interaction, generally span about 14 nm between membranes. In certain embodiments, the width of a SMAC in an immunological synapse does not exceed 15 nm.

In some embodiments, the extracellular span of a fusion protein::target complex is such that it can localize to a particular compartment of an immunological synapse. Some complexes thought to localize to various compartments of the immunological synapse are well-characterized with regard to the length of their extracellular span. For example, the MHC-TCR complex is thought to have an extracellular span of approximately 10-15 nm and more integrin-based complexes are thought to have extracellular spans on the order of approximately 40 nm (Alakoskela et al., *Biophys J* 100:2865, 2011). Additional exemplary complexes include the CD2-CD48 complex, which is thought to have an extracellular span of approximately 12.8 nm (Milstein et al., *J Biol Chem* 283:34414, 2008). Additionally, exemplary ligand-binding molecules thought to localize to the cSMAC include the TCR and MHC complexes, CD2, CD4, CD8, CD28, and ligands thereof (Dustin et al., *CSH Perspectives in Biology* 2:a002311, 2010); thus, it is contemplated that these molecules complexed with their natural ligands are of an appropriate size to localize to the cSMAC.

In some aspects, the length or distance or approximate length or distance of a particular construct or engineered extracellular portion thereof such as an extracellular portion of a fusion protein, or complex of any of the foregoing such as with a binding partner thereof, may be determined or modeled by known methods. In some exemplary models, a protein's tertiary structure, binding domains, and other characteristics may be approximated using an input amino acid or nucleic acid sequence. The tertiary structure of a protein may be used to approximate extracellular portion size, flexibility, and other characteristics useful for determining the approximate length of the extracellular portion of the protein or complex thereof. In general, methods for modeling or approximating the length of the extracellular portion of a protein are known. For example, molbiol-tools.ca and Swiss-Model contain multiple tools useful for predicting protein structure (see also Schwede, T., *Structure* 21:1531, 2013).

In certain embodiments, a fusion protein of this disclosure complexed, associated or interacting with a target is capable of residing within an immunological synapse. In some embodiments, the extracellular portion of a fusion protein::target complex spans an immunological synapse. In other embodiments, a fusion protein::target complex is localized in a supramolecular activation cluster (SMAC), such as a cSMAC. In further embodiments, the extracellular portion of a fusion protein::target complex spans an immunological synapse defined by the extracellular portion of a TCR::HLA-peptide interaction. In still further embodiments, the length of the extracellular portion of a fusion protein::target complex is about 12 nm to about 15 nm, or is about 14 nm.

The distance between the cell membranes of cells interacting in an immunological synapse may be measured by any method known in the art. For example, in particular embodiments, the distance may be measured by a subdiffraction-resolution method or electron microscopy (James and Vale, *Nature* 487:64-69, 2012).

In particular embodiments, a fusion protein as disclosed herein comprises an extracellular portion that extends less than 40 nm from the cell membrane. In some embodiments, a fusion protein as disclosed herein comprises an extracellular portion that extends less than 30 nm from the cell membrane. In some embodiments, a fusion protein as disclosed herein comprises an extracellular portion that extends less than 20 nm from the cell membrane. In some embodiments, a fusion protein as disclosed herein comprises an extracellular portion that extends less than 15 nm from the cell membrane.

In some embodiments, the provided fusion proteins provide the advantage of having an extracellular length or spatial distance as compared to the distance between cell membrane(s) that allows for entry into a synapse or co-localization with antigen receptor, or that mimic a distance or length present in the natural proteins. In some embodiments, where the extracellular portion of the fusion protein includes domain(s) from an additional molecule, which is from a different molecule from which a binding domain is obtained, the length of the extracellular component containing the binding domain is reduced, e.g., truncated, as compared to the extracellular region of the natural molecule, to provide for such similar length or distance. In some embodiments, a fusion protein as described herein comprises an extracellular component comprising an extracellular domain of a cell-surface receptor and a second domain (e.g., a linker or an extracellular domain of a second cell-surface receptor). In some such embodiments, to maintain an extracellular component capable of residing within an immunological synapse or spanning an immunological synapse when complexed with a target molecule, one or more domains of the extracellular component may be truncated.

In some diseases (e.g., cancer), the amplitude and quality of a T cell response resulting from antigen recognition by a T cell receptor (TCR) can be dysregulated (e.g., reduced) due to an imbalance between co-stimulatory and inhibitory signals, which can result in immune resistance. One advantage of certain fusion proteins of the instant disclosure is that a first signal can be converted into a qualitatively different second signal. For example, in some embodiments, the fusion proteins are such that a negative or inhibitory signal can effectively be converted into a positive or co-stimulatory signal to thereby relieve or minimize immune resistance associated with a disease, such as cancer. For example, upon binding to a target that, if bound by its natural binding partner, would result in inhibition or delivery of a negative signal, a fusion protein as provided herein, in some embodiments, is capable of instead delivering a positive, e.g., costimulatory signal, to a cell in which it is expressed, such as in a T cell. In certain embodiments, a fusion protein of this disclosure comprises an extracellular component associated with a negative signal and an intracellular component associated with a positive signal. An exemplary receptor found on the surface of T cells, cytotoxic T-lymphocyte-associated antigen 4 (CTLA4 or CD152), can receive an inhibitory signal when bound by one of its ligands, CD80 or CD86, found on APCs. CTLA4 regulates the amplitude of early stage T cell activation by counteracting the T cell co-stimulatory receptor CD28 (see Rudd et al., *Immunol. Rev.* 229:12, 2009). Another exemplary receptor found on the surface of T cells, programmed cell death protein 1 (PD-1 or CD279), can receive an inhibitory signal when bound by one of its ligands, PD-L1 (B7-H1, CD274) or PD-L2 (B7-DC, CD73), found on APCs. PD-1 limits the activity of T cells in peripheral tissues during inflammation and to minimize autoimmunity (see Keir et al., *Annu. Rev. Immunol.* 26:677, 2008). Representative fusion proteins of this disclosure comprising an extracellular component associated with a negative signal (e.g., CTLA4 or PD-1) and an intracellular component associated with a positive signal (e.g., CD28, CD137) include a CTLA4-CD28 fusion protein, a CTLA4-CD137 fusion protein, a CTLA4-CD28-CD137 fusion protein, a PD1-CD28 fusion protein, a PD1-CD137 fusion protein, or a PD1-CD28-CD137 fusion protein.

Fusion proteins of the instant disclosure may block or reduce the number of inhibitory signals received by an immune cell. For example, in some embodiments, a fusion protein as disclosed herein converts an inhibitory signal into a positive signal, thereby reducing the total number of inhibitory signals received by an immune cell or converting an ordinarily negative or inhibitory signal to a positive one. In other embodiments, a fusion protein as disclosed herein blocks the signaling of a wild-type receptor. For example, dominant negative fusion proteins are included within the scope of the disclosure. In some embodiments, a fusion protein as disclosed herein binds to a wild-type receptor and blocks signaling of the wild-type receptor by forming an oligomer with the wild-type receptor.

Yet another advantage of certain fusion proteins of the instant disclosure is that more than one such fusion protein may be expressed by a cell, providing multiple stimulatory signals. It has been observed that recombinant TCRs possessing multiple co-stimulatory domains may not produce adequate co-stimulatory signaling. Co-expressing multiple immunomodulatory fusion proteins, especially those capable of residing within an immunological synapse, may provide the co-stimulatory signaling necessary for T cells to avoid anergy and proliferate.

In some embodiments, a fusion protein of the instant disclosure operates in trans relative to a TCR or chimeric antigen receptor (CAR) or other antigen receptor. In some embodiments, a fusion protein as disclosed herein operates outside of the immunological synapse.

In yet another aspect, a fusion protein of the instant disclosure allows for enrichment of transduced T cells by restimulation with tumor cells expressing a ligand that binds to the fusion protein, without the need for sorting.

In one exemplary embodiment, a fusion protein comprising (a) an extracellular portion of a CD200R, (b) a transmembrane domain of a CD28, and (c) an intracellular signaling domain of a CD28 is provided. In some embodiments, the extracellular portion further comprises an extracellular portion of a CD28 extending from the CD28 transmembrane domain. In further embodiments, the extracellular portion of the CD200R comprises at least about 231 amino acids from the N-terminus of CD200R. In still further embodiments, the fusion protein further comprises an intracellular signaling domain of a CD137 (4-1BB).

In another exemplary embodiment, the present disclosure provides a fusion protein comprising (a) an extracellular portion of a SIRPα, (b) a transmembrane domain of a CD28, and (c) an intracellular signaling domain of a CD28. In some embodiments, the fusion protein further comprises an extracellular portion of a CD28 extending from the CD28 transmembrane domain. In further embodiments, the extracellular portion of the SIRPα comprises at least about 361 amino acids from the N-terminus of SIRPα. In still further embodiments, the fusion protein further comprises an intracellular signaling domain of a CD137 (4-1BB).

In another exemplary embodiment, the present disclosure provides a fusion protein comprising (a) an extracellular portion of a CD95 (Fas), (b) a transmembrane domain of a CD137 (4-1BB), and (c) an intracellular signaling domain of a CD137 (4-1BB).

In another exemplary embodiment, the present disclosure provides a fusion protein comprising (a) an extracellular portion of a CD95 (Fas), (b) a transmembrane domain of a CD28, and (c) an intracellular signaling domain of a CD137 (4-1BB). In some embodiments, the fusion protein further comprises an extracellular portion of a CD28 extending from the CD28 transmembrane domain.

In another exemplary embodiment, the present disclosure provides a fusion protein, comprising (a) an extracellular component comprised of a binding domain that specifically binds a target, (b) an intracellular component comprised of an intracellular signaling domain, and (c) a hydrophobic component connecting the extracellular and intracellular components, wherein the extracellular portion of a complex formed by specific binding of the fusion protein to the target (fusion protein::target complex) is of a size, or spans a distance, of (i) up to about a distance between two cell membranes of an immunological synapse, (ii) up to about or substantially the same as a distance spanned by the extracellular portion of a complex between a T cell receptor (TCR) and an MHC-peptide complex specifically bound by the TCR, (iii) up to about or substantially the same as a distance spanned by the extracellular portion of a complex between a natural molecule comprising the binding domain and its cognate binding partner; (iii) less than or up to about 40 nm, 25 nm, 20 nm, 15 nm, or 14 nm; or (iv) any combination thereof; and wherein the extracellular component is or comprises a CD95 (Fas) ectodomain or a functional fragment thereof, and the intracellular component is or comprises a CD137 (4-1BB) intracellular signaling domain or a functional portion thereof.

In another exemplary embodiment, the present disclosure provides a fusion protein comprising (a) an extracellular component comprised of a binding domain that specifically binds a target, (b) an intracellular component comprised of an intracellular signaling domain, and (c) a hydrophobic component connecting the extracellular and intracellular components, wherein the binding domain is, or has at least 95% identity to, an inhibitory molecule binding domain and the intracellular signaling domain is, or contains at least 95% identity to, a costimulatory or stimulatory molecule binding domain, and wherein the inhibitory molecule is or comprises a CD95 (Fas) ectodomain or a functional fragment thereof, and the costimulatory or stimulatory molecule is or comprises an intracellular signaling domain or a functional portion thereof from CD137 (4-1BB).

In another exemplary embodiment, the present disclosure provides a fusion protein comprising: (a) an extracellular component comprising an amino acid sequence encoded by a nucleic acid molecule as set forth in SEQ ID NO.:71, (b) a hydrophobic component comprising an amino acid sequence encoded by a nucleic acid molecule as set forth in SEQ ID NO.:197, and (c) an intracellular component comprising an amino acid sequence encoded by a nucleic acid molecule as set forth in SEQ ID NO.:13.

In another exemplary embodiment, the present disclosure provides a fusion protein comprising: (a) an extracellular component comprising a binding domain with an amino acid sequence as set forth in SEQ ID NO.:72; (b) a hydrophobic component comprising an amino acid sequence as set forth in SEQ ID NO.:198; and (c) an intracellular component comprising an amino acid sequence as set forth in SEQ ID NO.:36.

Component parts of the fusion proteins of the present disclosure are further described in detail herein.

Extracellular Component

As described herein, a fusion protein of the present disclosure generally comprises an extracellular component comprising a binding domain that specifically binds a target. Binding of a target by the fusion protein binding domain may (1) block the interaction of target with another molecule (e.g., block or interfere with a receptor-ligand interaction), (2) interfere, reduce or eliminate certain functions of the target (e.g., inhibitory signal transduction), (3) induce certain biological pathways not normally induced when the target is bound (e.g., converting an inhibitory or negative signal into a stimulatory or positive signal), such as in a cell in which the fusion protein is expressed, or any combination thereof. In some embodiments, the fusion proteins as described herein comprise an extracellular portion, wherein the extracellular portion comprises an extracellular portion of protein associated with a negative signal.

Exemplary binding domains of this disclosure may be ectodomains of cell-surface receptors, or binding portions thereof, ectodomains of cell-surface ligands, cytokines (e.g., IL35), chemokines, antibody-based binding domains, TCR-based binding domains, non-conventional binding domains, or any combination thereof. For example, binding domains comprising an ectodomain of CD200R, SIRPα, CD279 (PD-1), CD2, CD95 (Fas), CTLA4 (CD152), CD223 (LAG3), CD272 (BTLA), A2aR, KIR, TIM3, CD300, or LPA5 are within the scope of this disclosure. As used herein, an "ectodomain" from a cell-surface receptor or ligand includes a complete extracellular domain or a functional (binding) fragment thereof. In certain embodiments, an ectodomain comprises a mutated extracellular domain or a functional (binding) fragment thereof that has a higher avidity for target as compared to a wild-type or reference protein. In certain embodiments, an ectodomain comprises a variable-like domain or a CDR of a variable-like domain.

In some embodiments, a fusion protein contains an extracellular component comprising a CD200-binding domain, such as a CD200R ectodomain or CD200-binding portion thereof. By way of background, CD200R is a receptor that binds to CD200, a type-1 membrane protein of the immunoglobulin superfamily (Tonks et al., *Leukemia* 21:566-568, 2007). CD200 has been reported to be upregulated on various malignancies, including leukemias, multiple myeloma, and various solid tumors (e.g., melanoma, breast, and squamous cell carcinoma). In fact, high levels of CD200 expression have been linked with poor prognosis for acute myeloid leukemia (AML), and CD200R signaling has been shown to have an inhibitory effect on T cells (Coles et al., *Leukemia* 26: 2148-2151, 2012). In certain embodiments, a CD200R ectodomain includes a full length extracellular portion of a CD200R protein, a full length mature extracellular portion of a CD200R protein, a binding fragment of an extracellular portion of a CD200R protein, or a binding fragment of an extracellular portion of a CD200R protein along with a portion of the transmembrane domain of CD200R, or any combination thereof.

In further embodiments, a CD200R is encoded by a nucleic acid molecule as set forth in SEQ ID NO.:2. In certain other embodiments, a CD200R ectodomain comprises at least 200 amino acids from the N-terminus of CD200R. In some other embodiments, a CD200R is encoded by a nucleic acid molecule as set forth in SEQ ID NO.:11. In yet other embodiments, an extracellular portion of the CD200R comprises at least 180, 190, 200, 210, 220, 230, 231, 234, or 243 amino acids from the N-terminus of CD200R. For example, in certain embodiments, a CD200R is encoded by the nucleic acid molecule as set forth in SEQ ID NO.:8. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:2.

In some embodiments, a CD200R comprises an amino acid sequence as set forth in SEQ ID NO.:25. In some embodiments, a CD200R comprises an amino acid sequence as set forth in SEQ ID NO.:34. In certain embodiments, a CD200R comprises an amino acid sequence as set forth in SEQ ID NO.:31. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:25.

In some embodiments, a fusion protein contains an extracellular component comprising a CD47-binding domain such as a SIRPα ectodomain or binding portion thereof. By way of background, CD47 is a widely expressed transmembrane protein that plays a role in protecting cells from phagocytosis (Willingham et al., *PNAS* 109: 6662-6667, 2012). Binding of CD47 to SIRPα initiates SIRPα signaling, which inhibits phagocytosis by macrophages. Accordingly, downregulation of SIRPα will result in increased phagocytosis by macrophages. SIRPα is expressed on multiple human tumor types including AML, chronic myelogenous leukemia (CML), acute lymphoblastic leukemia (ALL), Non-Hodgkin lymphoma (NHL), multiple myeloma (MM), lung, bladder, and other solid tumors. In certain embodiments, a SIRPα ectodomain includes a full length extracellular portion of a SIRPα protein, a full length mature extracellular portion of a SIRPα protein, a binding fragment of an extracellular portion of a SIRPα protein, and a binding fragment of an extracellular portion of a SIRPα protein along with a portion of the transmembrane domain of SIRPα, or any combination thereof.

In further embodiments, a SIRPα ectodomain or binding portion thereof is encoded by a nucleic acid molecule as set forth in SEQ ID NO.:17. In certain embodiments, a SIRPα ectodomain comprises at least 300, 310, 320, 330, 340, 350, 360, 361, 370, 373, or more amino acids from the N-terminus of SIRPα. In some other embodiments, a SIRPα is encoded by a nucleic acid molecule as set forth in SEQ ID NO.:21. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:17.

In further embodiments, a SIRPα ectodomain comprises an amino acid sequence as set forth in SEQ ID NO.:40. In some embodiments, a SIRPα comprises an amino acid sequence as set forth in SEQ ID NO.:44. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:40.

In some embodiments, a fusion protein contains an extracellular component comprising a binding domain that binds to PD-L1, PD-L2, or both. In some embodiments, a fusion protein contains an extracellular component comprising a PD-1 ectodomain or ligand-binding portion thereof. In certain embodiments, a PD-1 ectodomain includes a full length extracellular portion of a PD-1 protein, a full length mature extracellular portion of a PD-1 protein, a binding fragment of an extracellular portion of a PD-1 protein, or a binding fragment of an extracellular portion of a PD-1 protein along with a portion of the transmembrane domain of PD-1, or any combination thereof. In certain embodiments, a PD-1 ectodomain comprises at least 80, 90, 100, 110, 120, 125, 130, 132, 135, 137, 140, 149, 150, 155, 158, 160, or 170 amino acids from the N-terminus of PD-1. For example, in certain embodiments, a PD-1 ectodomain is encoded by the nucleic acid molecule as set forth in SEQ ID NO.:91, 93, or 95. In further embodiments, a PD-1 ectodomain comprises at least from about 90 amino acids to at least about 130 amino acids from a PD-1 as set forth in SEQ ID NO.:60. In still further embodiments, a PD-1 ectodomain comprises 170 amino acids from the N-terminus of a PD-1 ectodomain, as set forth in SEQ ID NO.:90. In some embodiments, a PD-1 is encoded by a nucleic acid molecule as set forth in SEQ ID NO.:89. In any of the aforementioned embodiments, a PD-1, a PD-1 ectodomain, or any PD-1 fragment thereof used in a fusion protein of this disclosure is a human PD-1. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:60. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:90. In still further embodiments, there are provided PD-1 binding domains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:89.

In certain embodiments, a PD-1 ectodomain comprises the amino acid sequence as set forth in SEQ ID NO.:92, 94, or 96. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.: 92, 94, or 96. In any of the aforementioned embodiments, a PD-1, a PD-1 ectodomain, or any PD-1 fragment thereof used in a fusion protein of this disclosure is a human PD-1.

In some embodiments, a fusion protein contains an extracellular component comprising a CD2 ectodomain. In certain embodiments, a CD2 ectodomain is encoded by a nucleic acid molecule as set forth in SEQ ID NO.:61. In certain embodiments, a CD2 ectodomain includes a full length extracellular portion of a CD2 protein, a full length mature extracellular portion of a CD2 protein, a binding fragment of an extracellular portion of a CD2 protein, or a binding fragment of an extracellular portion of a CD2 protein along with a portion of the transmembrane domain of CD2, or any combination thereof. In any of the aforementioned embodiments, a CD2, a CD2 ectodomain, or any CD2 fragment thereof used in a fusion protein of this disclosure is a human CD2. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_001767.3. In further embodiments, there are provided CD2 ectodomains s that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:61.

In some embodiments, a CD2 ectodomain comprises an amino acid sequence as set forth in SEQ ID NO.:62. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:62. In any of the aforementioned embodiments, a CD2, a CD2 ectodomain, or any CD2 fragment thereof used in a fusion protein of this disclosure is a human CD2.

In some embodiments, a fusion protein contains an extracellular component comprising a binding domain that binds to FasL. In some embodiments, a fusion protein contains an extracellular component comprising a Fas (CD95) ectodomain. Fas is expressed on tumor-associated vasculature and prevents CD8 cell infiltration by inducing cell death. FasL is expressed in AML, pancreatic, ovarian, and other cancers (Kornmann et al., *Annals of Surgery* 231: 368-379, 2000; Contini et al., *Leukemia* 21: 253-260, 2007; Motz et al., *Nature Medicine* 20: 607-615, 2014). Additionally, many chemotherapeutics have been reported to cause upregulation of FasL on tumors, and FasL can also be upregulated on T cells in response to CD44 engagement. In certain embodiments, a Fas ectodomain includes a full length extracellular portion of a Fas protein, a full length mature extracellular portion of a Fas protein, a binding fragment of an extracellular portion of a Fas protein, and a binding fragment of an extracellular portion of a Fas protein along with a portion of the transmembrane domain of Fas, or any combination thereof. In some embodiments, a Fas ectodomain is encoded by a nucleic acid molecule as set forth in SEQ ID NO.:71. In yet other embodiments, a Fas ectodomain comprises at least 150, 160, 161, 166, 170, or 173 amino acids from the N-terminus of Fas. For example, in certain embodiments, a Fas is encoded by the nucleic acid molecule as set forth in SEQ ID NO.:73. In certain other embodiments, a Fas is encoded by the nucleic acid molecule as set forth in SEQ ID NO.:75. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_000043.4. In still further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:71.

In some embodiments, a Fas ectodomain comprises an amino acid sequence as set forth in SEQ ID NO.:72. In certain embodiments, a Fas ectodomain comprises the amino acid sequence as set forth in SEQ ID NO.:74. In certain other embodiments, a Fas ectodomain comprises the amino acid sequence as set forth in SEQ ID NO.:76. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:72.

In some embodiments, a fusion protein contains an extracellular component comprising a LAG3 (CD223) ectodomain. In certain embodiments, a LAG3 ectodomain includes a full length extracellular portion of a LAG3 protein, a full length mature extracellular portion of a LAG3 protein, a binding fragment of an extracellular portion of a LAG3 protein, and a binding fragment of an extracellular portion of a LAG3 protein along with a portion of the transmembrane domain of LAG3, or any combination thereof. For example, in some embodiments, a LAG3 ectodomain comprises about 420, 416, 415, 413, or 410 amino acids from the N terminus of LAG3. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_002286.5.

In further embodiments, a LAG3 is encoded by a nucleic acid molecule as set forth in SEQ ID NO.:153. In certain other embodiments, a LAG3 ectodomain comprises at least 430, 435, 438, 440, 445, or 450 amino acids from the N-terminus of LAG3. For example, in certain embodiments, a LAG3 is encoded by the nucleic acid molecule as set forth in SEQ ID NO.:161. In any of the aforementioned embodiments, a LAG3, LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:153.

In some embodiments, a LAG3 comprises an amino acid sequence as set forth in SEQ ID NO.:154. In some embodiments, a LAG3 comprises an amino acid sequence as set forth in SEQ ID NO.:162. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:154.

In some embodiments, a fusion protein contains an extracellular component comprising a TIM3 ectodomain. In certain embodiments, a TIM3 ectodomain includes a full length extracellular portion of a TIM3 protein, a full length mature extracellular portion of a TIM3 protein, a binding fragment of an extracellular portion of a TIM3 protein, and a binding fragment of an extracellular portion of a TIM3 protein along with a portion of the transmembrane domain of TIM3, or any combination thereof. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_032782.4.

In further embodiments, a TIM3 is encoded by a nucleic acid molecule as set forth in SEQ ID NO.:167. In certain other embodiments, a TIM3 ectodomain comprises at least 180, 185, 190, 195, or 200 amino acids from the N-terminus of TIM3. For example, in certain embodiments, a TIM3 is encoded by the nucleic acid molecule as set forth in SEQ ID NO.:177. In any of the aforementioned embodiments, a TIM3, TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:167.

In some embodiments, a TIM3 comprises an amino acid sequence as set forth in SEQ ID NO.:168. In some embodiments, a TIM3 comprises an amino acid sequence as set forth in SEQ ID NO.:178. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:168.

A binding domain may be any peptide that specifically binds a target of interest. Sources of binding domains include antibody variable regions from various species (which can be in the form of antibodies, sFvs, scFvs, Fabs, scFv-based grabaody, or soluble VH domain or domain antibodies), including human, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci.* (USA) 95:11804, 1998), spotted ratfish (Nguyen et al., *Immunogen.* 54:39, 2002), or lamprey (Herrin et al., *Proc. Nat'l. Acad. Sci.* (USA) 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of non-conventional binding domains of this disclosure includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:435, 2005 and Hackel et al. (2008) *J. Mol. Biol.* 381:1238-1252), cysteine-knot miniproteins (Vita et al. (1995) *Proc. Nat'l. Acad Sci.* (USA) 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., Proc. Nat'l. *Acad Sci.* (USA) 96:1898, 1999 and Schönfeld et al., *Proc. Nat'l. Acad Sci.* (USA) 106:8198, 2009), V-like domains (see, e.g., US Patent Application Publication No. 2007/0065431), C-type lectin domains (Zelensky and Gready, *FEBS J.* 272:6179, 2005; Beavil et al., *Proc. Nat'l. Acad Sci.* (USA) 89:753, 1992 and Sato et al., *Proc. Nat'l. Acad Sci.* (USA) 100:7779, 2003), mAb² or Fcab™ (see, e.g., PCT Patent Application Publication Nos. WO 2007/098934; WO 2006/072620), armadillo repeat proteins (see, e.g., Madhurantakam et al., *Protein Sci.* 21: 1015, 2012; PCT Patent Application Publication No. WO 2009/040338), affilin (Ebersbach et al., *J. Mol. Biol.* 372: 172, 2007), affibody, avimers, knottins, fynomers, atrimers, cytotoxic T-lymphocyte associated protein-4 (Weidle et al., *Cancer Gen. Proteo.* 10:155, 2013) or the like (Nord et al., *Protein Eng.* 8:601, 1995; Nord et al., *Nat. Biotechnol.* 15:772, 1997; Nord et al., *Euro. J. Biochem.* 268:4269, 2001; Binz et al., *Nat. Biotechnol.* 23:1257, 2005; Boersma and Pluckthun, *Curr. Opin. Biotechnol.* 22:849, 2011).

In some embodiments, a binding domain is a single chain T cell receptor (scTCR) comprising $V_{\alpha/\ominus}$ and $C_{\alpha/\beta}$ chains (e.g., $V_\alpha$-$C_\alpha$, $V_\beta$-$C_\beta$, $V_\alpha$-$V_\beta$) or comprising $V_\alpha$-$C_\alpha$, $V_\ominus$-$C_\ominus$, $V_\alpha$-$V_\beta$ pair specific for a target of interest (e.g., peptide-MHC complex or peptide-HLA complex).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an ectodomain of a molecule having an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to a target of interest.

In certain embodiments, a binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type. In certain embodiments, a TCR has an affinity for a peptide-HLA complex ranging from about 10 M to about 500 M. In further embodiments, a TCR has a high affinity for a peptide-HLA complex ranging from about 10 nM to about 200 pM.

In certain aspects, a fusion protein according to the present disclosure has an extracellular component comprised of a binding domain that specifically binds a target (e.g., a ligand or receptor), wherein the extracellular component optionally includes one or more other functional subcomponents or domains, such as a multimerization domain, a linker, junction amino acids, or any combination thereof.

In certain embodiments, a fusion protein disclosed herein further comprises an additional extracellular region in addition to the binding domain or in addition to the portion derived from the molecule from which the binding domain is derived, such as a spacer or a multimerization domain. For example, in some aspects a multimerization domain is contained in or is a part of the extracellular component of the fusion protein. For example, a multimerization domain may be created by altering (e.g., mutating) the extracellular component, or a multimerization domain may be created by adding 1 to about 50 amino acid residues to the extracellular component. A multimerization domain may be located between the binding domain of the extracellular component and hydrophobic component of a fusion protein of this disclosure. In certain embodiments, a fusion protein expressed on a cell surface comprises a multimerization domain within the extracellular component and is proximal to the cell membrane, within one to 50 amino acids from the hydrophobic component. For example, a fusion protein multimerization domain may comprise one or more cysteine residues located within 30, 25, 20, 15, 14, 13, 12, 11, 10, 9 8, 7, 6, 5, 4, 3, 2, 1 or 0 amino acids from the fusion protein hydrophobic component, wherein such one or more cysteine residues from one fusion protein can form one or more disulfide bridges with one or more other fusion proteins. In some embodiments, the additional extracellular portion is derived from the same molecule from which a transmembrane or stimulatory region of the fusion protein is derived.

In further embodiments, interaction(s) between multimerization domains of two or more fusion proteins substantially contribute to or efficiently promote signal transduction (e.g., immune cell stimulation or activation) as compared to a fusion protein monomer. In certain embodiments, multimerization of fusion proteins promote signal transduction in a host cell in a statistically significant manner over fusion protein monomers. In further embodiments, multimerization of fusion proteins that promotes or enhances signal transduction in a host cell is via a disulfide bridge.

An exemplary multimer is a "dimer," which refers to a biological entity containing two molecules, such as two fusion proteins, associated with each other. Such a dimer is considered a "homodimer" when the two associated fusion proteins have substantially similar or identical amino acid sequences. Similarly, multimerization of three substantially or fully identical fusion proteins is referred to as a "homotrimer." In some embodiments, a multimerization domain comprises at least one cysteine residue, wherein a multimerization domain cysteine residue from a first fusion protein can form a disulfide bridge with a multimerization domain cysteine residue from a second fusion protein. In certain embodiments, a fusion protein dimer forms via a disulfide bridge. In other embodiments, a fusion protein trimer forms via two or more disulfide bridges. Alternatively, a dimer, homodimer, trimer or homotrimer may multimerize via a zinc finger motif or a leucine zipper motif. In still further embodiments, a fusion protein comprises a plurality of multimerization domains, which can be located extracellularly, intracellularly or both.

In some embodiments, a multimerization domain contained in the extracellular component of a fusion protein comprises an extracellular portion extending from the hydrophobic component. For example, in some embodiments, a multimerization domain contained in the extracellular component of a fusion protein comprises an extracellular portion of a CD28 extending from a CD28 transmembrane domain. In some embodiments, an extracellular portion of the CD28 comprises about 5, 6, 7, 8, 9, 10, 11, 12, 13, 14, 15, or up to about 25 amino acids adjacent to the transmembrane domain. In some embodiments, the extracellular portion of the CD28 comprises 9 amino acids or 12 amino acids adjacent to the transmembrane domain. In some embodiments, the extracellular portion of a CD28 comprises the amino acid sequence encoded by a nucleic acid molecule as set forth in SEQ ID NO.:9. In some embodiments, the extracellular portion of a CD28 comprises the amino acid sequence as set forth in SEQ ID NO.:32. In yet another exemplary embodiment, a multimerization domain contained in the extracellular component of a fusion protein comprises an extracellular portion of a CD137 (4-1BB) (e.g., ranging from one to about 50 amino acids) extending from a CD137 (4-1BB) transmembrane domain. In certain embodiments, the multimerization domain and the hydrophobic component are from different proteins. For example, a multimerization domain contained in the extracellular component of a fusion protein comprises an extracellular portion of a CD28 extending from a CD137 transmembrane domain, or comprises an extracellular portion of a CD137 extending from a CD28 transmembrane domain. In any of the aforementioned embodiments, a multimerization domain may further comprise a glycosylation site.

In some embodiments, a fusion protein may contain a linker or junction amino acids connecting, for example, an extracellular component with a multimerization domain or connecting an extracellular component with a hydrophobic component or connecting a hydrophobic component with an intracellular component. In some embodiments, the linker is a $Gly_xSer_y$, wherein x and y are independently an integer from 1 to 5.

In some embodiments, the extracellular component is or comprises a molecule, or portion thereof, that forms a multimer, and the intracellular component is or comprises a molecule, or portion thereof, that forms a multimer of the same number. For example, in some embodiments, the extracelluar component is or comprises a molecule, or portion thereof, that forms a dimer, and the intracellular component is or comprises a molecule, or portion thereof, that also forms a dimer. In some embodiments, the extracelluar component is or comprises a molecule, or portion thereof, that forms a trimer, and the intracellular component is or comprises a molecule, or portion thereof, that also forms a trimer.

A target molecule, which is specifically bound by a binding domain contained in a fusion protein of the present disclosure, may be found on or in association with a cell of interest ("target cell"). Exemplary target cells include an immune cell, a cancer cell, a cell associated with an autoimmune disease or disorder or with an inflammatory disease or disorder, and an infectious organism or cell (e.g., bacteria, virus, virus-infected cell), or any cell presenting antigen complexed with a MHC or human leukocyte antigen (HLA). A cell of an infectious organism, such as a mammalian parasite, is also contemplated as a target cell. In some embodiments, the target is an immunosuppressive ligand. In some embodiments, the target is selected from a CD47, CD58, CD80, CD86, CD95L (FasL), CD200, CD270 (HVEM), CD274 (PD-L1), or GAL9.

Intracellular Component

An intracellular component contained in a fusion protein of the present disclosure will have an intracellular signaling domain, such as an activating domain or a co-stimulatory domain, capable of transmitting functional signals to a cell. In certain embodiments, an intracellular signaling domain will indirectly promote a cellular response by associating with one or more other proteins that directly promote a cellular response. An intracellular signaling domain may include one, two, three or more receptor signaling domains, costimulatory domains, or combinations thereof. Any intracellular component comprising an activating domain, co-stimulatory domain, or both from any of a variety of signaling molecules (e.g., signal transduction receptors) may be used in the fusion proteins of this disclosure.

As used herein, an "intracellular signaling domain" from a cell-surface receptor or ligand includes a complete intracellular domain, a portion comprising an intracellular signaling domain, or a functional (signaling) fragment thereof. In certain embodiments, an intracellular signaling domain comprises a mutated intracellular domain or a functional (signaling) fragment thereof that has increased signaling activity as compared to a wild-type or reference intracellular signaling domain.

A "co-stimulatory molecule" as used herein refers to a receptor or cell-surface molecule that can transduce signals into T cells to positively modulate T cell activation (Chen and Flies, *Nat. Rev. Immunol.* 13: 227-242, 2013). By way of background, T cell activation and proliferation requires two signals mediated through engagement of the T cell antigen-specific receptor (TCR) and a co-stimulatory signal, most typically binding of CD28 by CD80 and CD86 (Ledbetter et al., *Blood* 75:1531, 1990).

An intracellular signaling domain or functional fragment thereof useful in the fusion proteins of this disclosure may be from a CD3E, CD36, CD3ζ, CD25, CD27, CD28, CD40, CD47, CD79A, CD79B, CD134 (OX40), CD137 (4-1BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, S1p76, pTα, TCRα, TCRβ, TRIM, Zap70, PTCH2, or any combination thereof. In some embodiments, an intracellular signaling domain or functional fragment thereof does not comprise a primary signal. In some embodiments, an intracellular signaling domain does not comprise a CD3ζ.

In some embodiments, an intracellular signaling domain of a fusion protein of this disclosure comprises a CD28. CD28 signaling promotes proliferation of T cells stimulated via the TCR (Chen and Flies, *Nat. Rev. Immunol.* 13: 227-242, 2013). CD28 forms disulfide-linked homodimers, as a result of the cysteine residue proximal to the transmembrane domain (Lazar-Molnar et al., *Cell Immunol.* 244: 125-129, 2006). In certain embodiments, a CD28 signaling domain includes a full length intracellular portion of a CD28 protein, a full length mature intracellular portion of a CD28 protein, a signaling fragment of an intracellular portion of a CD28 protein, and a signaling fragment of an intracellular portion of a CD28 protein along with a transmembrane domain or fragment thereof of CD28, or any combination thereof.

In some embodiments, an intracellular signaling domain of a fusion protein contains an intracellular signaling domain of a CD137 (4-1BB). CD137 is a co-stimulatory molecule, wherein binding of CD137 to its ligand (4-1BBL or CD137L) is associated with T cell activation and proliferation (Cheuk et al., *Cancer Gene Therapy* 11: 215-226, 2004). In certain embodiments, a CD137 signaling domain includes a full length intracellular portion of a CD137 protein, a full length mature intracellular portion of a CD137 protein, a signaling fragment of an intracellular portion of a CD137 protein, and a signaling fragment of an intracellular portion of a CD137 protein along with a transmembrane domain or fragment thereof of CD137, or any combination thereof.

In certain embodiments, an intracellular signaling domain comprises a lymphocyte receptor signaling domain or comprises an amino acid sequences having one or a plurality of immunoreceptor tyrosine-based activation motifs (ITAMs). In still further embodiments, an intracellular signaling domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

In some exemplary embodiments, the present disclosure provides a fusion protein having an extracellular component comprising an extracellular portion of a CD200R that specifically binds CD200, an intracellular component comprising an intracellular portion of CD28, and a hydrophobic component connecting the extracellular and intracellular components, provided that a fusion protein::target complex spans a distance similar to a distance between membranes in an immunological synapse.

In particular embodiments, an intracellular component of a fusion protein of the instant disclosure comprises a CD28, a CD137 (4-1BB) or both. For example, in some embodiments, an intracellular component comprises the amino acid sequence encoded by a nucleic acid molecule as set forth in in SEQ ID NO.:5. In some other embodiments, an intracellular component comprises an amino acid sequence encoded by a nucleic acid molecule as set forth in SEQ ID NO.:13. In some embodiments, an intracellular component comprises two intracellular signaling domains, for example, a CD28 and a CD137 (4-1BB). In some embodiments, an intracellular component comprises an amino acid sequence encoded by a nucleic acid molecule as set forth in SEQ ID NO.:5 and the amino acid sequence encoded by the nucleotide sequence as set SEQ ID NO.:13.

Hydrophobic Component

A hydrophobic portion contained in a single chain fusion protein of the present disclosure will allow a fusion protein of this disclosure to associate with a cellular membrane such that a portion of the fusion protein will be located extracellularly and a portion will be located intracellularly (e.g., intracellular signaling domain). A hydrophobic component will generally be disposed within the cellular membrane phospholipid bilayer. In certain embodiments, one or more junction amino acids may be disposed between and connecting a hydrophobic portion with an intracellular signaling domain.

In certain embodiments, a hydrophobic domain is a transmembrane domain, such as one derived from an integral membrane protein (e.g., receptor, cluster of differentiation (CD) molecule, enzyme, transporter, cell adhesion molecule, or the like). In some embodiments, the hydrophobic domain comprises a transmembrane domain found in or derived from an integral membrane protein, wherein the transmembrane domain has been modified by the addition, removal, or replacement of one or more amino acids with at least one different amino acid, or any combination thereof, such as charged or hydrophilic residues that facilitate intermolecular interactions. Thus, the term "hydrophobic domain" includes transmembrane domains having, for example, modifications that may reduce hydrophobicity.

In some embodiments, the hydrophobic component comprises a transmembrane domain of a CD2, CD3R, CD36, CD3ζ, CD25, CD27, CD28, CD40, CD47, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), TIM3, CD300, CD357 (GITR), A2aR, DAP10, FcRα, FcRβ, FcRγ, Fyn, GAL9, KIR, Lck, LAT, LPA5, LRP, NKG2D, NOTCH1, NOTCH2, NOTCH3, NOTCH4, PTCH2, ROR2, Ryk, S1p76, SIRPα, pTα, TCRα, TCRβ, TIM3, TRIM, or Zap70. In particular embodiments, a hydrophobic portion is a transmembrane domain from CD28, CD4, CD8, CD27, or CD137 (4-1BB).

In certain embodiments, a transmembrane domain comprises a CD28 transmembrane domain. In some embodiments, a transmembrane domain comprises or consists of a CD28 transmembrane domain having an amino acid sequence encoded by a polynucleotide having at least 80%, 85%, 90%, 95% or more sequence identity with the polynucleotide of SEQ ID NO.:4. In further embodiments, a transmembrane domain is a CD28 transmembrane domain comprising or consisting of an amino acid sequence encoded by the nucleic acid molecule as set forth in SEQ ID NO.:4. In still further embodiments, a transmembrane domain is a CD28 transmembrane domain having at least 90%, 95% or more sequence identity with the amino acid sequence of SEQ ID NO.:27. In yet further embodiments, a transmembrane domain is a CD28 transmembrane domain comprising or consisting of an amino acid sequence as set forth in SEQ ID NO.:27.

In certain embodiments, a transmembrane domain comprises a CD137 (4-1BB) transmembrane domain. In further embodiments, a transmembrane domain comprises or consists of a CD137 transmembrane domain having an amino acid sequence encoded by a polynucleotide having at least 80%, 85%, 90%, 95% or more sequence identity with the polynucleotide of SEQ ID NO.:197. In particular embodiments, a transmembrane domain is a CD137 transmembrane domain comprising or consisting of an amino acid sequence encoded by the nucleic acid molecule of SEQ ID NO.:197.

In certain other embodiments, a transmembrane domain comprises a CD200R transmembrane domain. In some embodiments, a transmembrane domain comprises or consists of a CD200R transmembrane domain having an amino acid sequence encoded by a polynucleotide having at least 80%, 85%, 90%, 95% or more sequence identity with the polynucleotide of SEQ ID NO.:3. In further embodiments, a transmembrane domain is a CD200R transmembrane domain comprising or consisting of an amino acid sequence encoded by the nucleic acid molecule as set forth in SEQ ID NO.:3.

In certain embodiments, a transmembrane domain comprises a SIRPα transmembrane domain. In some embodiments, a transmembrane domain comprises or consists of a SIRPα transmembrane domain having an amino acid sequence encoded by a polynucleotide having at least 80%, 85%, 90%, 95% or more sequence identity with the polynucleotide of SEQ ID NO.:18. In further embodiments, a transmembrane domain is a SIRPα transmembrane domain comprising or consisting of an amino acid sequence encoded by the nucleic acid molecule as set forth in SEQ ID NO.:18.

In certain embodiments, a transmembrane domain comprises a CD2 transmembrane domain. In some embodiments, a transmembrane domain comprises or consists of a CD2 transmembrane domain having an amino acid sequence encoded by a polynucleotide having at least 80%, 85%, 90%, 95% or more sequence identity with the polynucleotide of SEQ ID NO.:63. In further embodiments, a transmembrane domain is a CD2 transmembrane domain comprising or consisting of an amino acid sequence encoded by the nucleic acid molecule as set forth in SEQ ID NO.:63.

In certain embodiments, a transmembrane domain comprises a Fas transmembrane domain. In some embodiments, a transmembrane domain comprises or consists of a Fas transmembrane domain having an amino acid sequence encoded by a polynucleotide having at least 80%, 85%, 90%, 95% or more sequence identity with the polynucleotide of SEQ ID NO.:77. In further embodiments, a transmembrane domain is a Fas transmembrane domain comprising or consisting of an amino acid sequence encoded by the nucleic acid molecule as set forth in SEQ ID NO.:77.

In certain embodiments, a transmembrane domain comprises a TIM3 transmembrane domain. In some embodiments, a transmembrane domain comprises or consists of a TIM3 transmembrane domain having an amino acid sequence encoded by a polynucleotide having at least 80%, 85%, 90%, 95% or more sequence identity with the polynucleotide of SEQ ID NO.:169. In further embodiments, a transmembrane domain is a TIM3 transmembrane domain comprising or consisting of an amino acid sequence encoded by the nucleic acid molecule as set forth in SEQ ID NO.:169.

In certain embodiments, a transmembrane domain comprises a LAG3 transmembrane domain. In some embodiments, a transmembrane domain comprises or consists of a LAG3 transmembrane domain having an amino acid sequence encoded by a polynucleotide having at least 80%, 85%, 90%, 95% or more sequence identity with the polynucleotide of SEQ ID NO.:155. In further embodiments, a transmembrane domain is a LAG3 transmembrane domain comprising or consisting of an amino acid sequence encoded by the nucleic acid molecule as set forth in SEQ ID NO.:155.

Nucleic Acids and Host Cells

In certain aspects, the present disclosure provides nucleic acid molecules that encode any one or more of the fusion proteins described herein, which may be immunomodulatory fusion proteins (IFPs). Such nucleic acid molecules can be inserted into an appropriate vector (e.g., viral vector or non-viral plasmid vector) for introduction in a host cell of interest (e.g., hematopoietic progenitor cell, T cell).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be converted into a non-natural or recombinant cell (e.g., a non-natural or recombinant T cell) by introducing a nucleic acid that encodes a fusion protein as described herein and whereby the cell expresses a fusion protein.

In certain embodiments, nucleic acid molecules encoding fusion proteins may be codon optimized to enhance or maximize expression in certain types of cells, such as T cells (Scholten et al., *Clin. Immunol.* 119: 135-145, 2006).

In one exemplary embodiment, the present disclosure provides a nucleic acid molecule that encodes a CD200R-CD28 construct (huCD200Rtm-CD28), wherein the extracellular component comprises a CD200R ectodomain, the hydrophobic component comprises the transmembrane domain of a CD200R, and the intracellular component comprises the intracellular signaling domain of a CD28. For example, in one embodiment, a nucleic acid molecule as set forth in SEQ ID NO.:1 is provided. In certain embodiments, the present disclosure provides a huCD200Rtm-CD28 comprising a polynucleotide that is at least 80% or at least 90% identical to a polynucleotide sequence of SEQ ID NO.: 1. In other embodiments, the present disclosure provides a huCD200Rtm-CD28 comprising or consisting of a polynucleotide sequence of SEQ ID NO.:1.

In another exemplary embodiment, the present disclosure provides a nucleic acid molecule that encodes a CD200R-CD28 construct (huCD200R-CD28tm), wherein the hydrophobic component comprises the transmembrane domain of a CD28. For example, in one embodiment, the disclosure provides a nucleic acid molecule as set forth in SEQ ID NO.:6. In certain embodiments, the present disclosure provides a huCD200R-CD28tm comprising a polynucleotide that is at least 80% or at least 90% identical to a polynucleotide sequence of SEQ ID NO.:6. In other embodiments, the present disclosure provides a huCD200R-CD28tm comprising or consisting of a polynucleotide sequence of SEQ ID NO.:6. In further embodiments, a huCD200R-CD28tm protein has an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.: 29.

In other exemplary embodiments, the present disclosure provides a nucleic acid molecule that encodes a CD200R-CD28 construct, wherein the extracellular comprises a truncated extracellular domain of CD200R and an extracellular portion of CD28. For example, the CD200R extracellular domain may be truncated by about 9 to about 15 amino acids. Exemplary CD200R-CD28 constructs of the instant disclosure include those with a 9 amino acid truncation (e.g., huCD200R-9aas-CD28Cys, SEQ ID NO.:7), a 12 amino acid truncation (e.g., huCD200R-12aas-CD28Cys, SEQ ID NO.:10), or a 15 amino acid truncation (e.g., huCD200R-15aas-CD28Cys, SEQ ID NO.:183). The extracellular portion of CD28 comprises, in some embodiments, an amino acid sequence encoded by a nucleic acid molecule as set forth in SEQ ID NO.:9. In certain embodiments, an extracellular portion of CD28 comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:32. In further embodiments, an extracellular portion of CD28 comprises or consists of an amino acid sequence as set forth in SEQ ID NO.:32. In certain other embodiments, a huCD200R-9aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:30. An exemplary huCD200R-9aas-CD28Cys protein comprises or consists of an amino acid sequence as set forth in SEQ ID NO.: 30. In certain other embodiments, a huCD200R-12aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:33. An exemplary huCD200R-12aas-CD28Cys protein comprises or consists of an amino acid sequence as set forth in SEQ ID NO.: 33. In certain other embodiments, a huCD200R-15aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:184. An exemplary huCD200R-15aas-CD28Cys protein comprises or consists of an amino acid sequence as set forth in SEQ ID NO.:184.

In one exemplary embodiment, the present disclosure provides a nucleic acid molecule that encodes a CD200R-CD28-4-1BB construct (huCD200R-9aas-CD28Cystm-41BBic or huCD200R-12aas-CD28Cystm-41BBic), wherein the intracellular component comprises the intracellular signaling domain of CD137 (4-1BB). For example, in one embodiment, the nucleic acid molecule has the nucleotide sequence as set forth in SEQ ID NO.:12 or SEQ ID NO.:14.

In another exemplary embodiment, the present disclosure provides a nucleic acid molecule that encodes a CD200R-CD28-4-1BB construct (huCD200R-9aas-CD28Cys tm ic 41BBic or huCD200R-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:9 or SEQ ID NO.:15.

In other exemplary embodiments, the present disclosure provides a nucleic acid molecule that encodes a SIRPα-CD28 construct. For example, the present disclosure includes a nucleic acid molecule as set forth in SEQ ID NO.:16 (huSIRPαtm-CD28) or SEQ ID NO.:19 (huSIRPα-CD28tm).

In other exemplary embodiments, the present disclosure provides a nucleic acid molecule that encodes a SIRPα-CD28 construct, wherein the extracellular component comprises a truncated extracellular domain of SIRPα and an extracellular portion of CD28. For example, the SIRPα extracellular domain may be truncated by about 8 amino acids to about 15 amino acids. An exemplary SIRPα-CD28 constructs has the CD95 (Fas) extracellular domain truncated by 12 amino acids (e.g., huSIRPα-12aas-CD28Cys, SEQ ID NO.:20).

In one exemplary embodiment, the present disclosure provides a nucleic acid molecule that encodes a SIRPα-CD28-4-1BB construct (huSIRPα-12aas-CD28Cystm-41BBic), wherein the intracellular component comprises the intracellular signaling domain of CD137 (4-1BB). For example, in one embodiment, the nucleic acid of the present disclosure has the nucleotide sequence as set forth in SEQ ID NO.:22.

In another exemplary embodiment, the present disclosure provides a nucleic acid molecule that encodes a SIRPα-CD28-4-1BB construct (huSIRPα-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:23.

In other exemplary embodiments, the present disclosure provides a nucleic acid molecule that encodes a PD-1-CD28 construct. For example, the present disclosure includes a nucleic acid molecule as set forth in SEQ ID NO.:97 (huPD1-CD28Cys).

In other exemplary embodiments, the present disclosure provides a nucleic acid molecule that encodes a PD-1-CD28 construct, wherein the extracellular component comprises a truncated extracellular domain of PD-1 and an extracellular portion of CD28. For example, the PD-1 extracellular domain may be truncated by about 10 amino acids to about 25 amino acids. Exemplary PD-1-CD28 constructs have the PD-1 extracellular domain truncated by 12 amino acids (e.g., huPD1-12aas-CD28Cys, SEQ ID NO.:99), 15 amino acids (e.g., huPD1-15aas-CD28Cys, SEQ ID NO.:101), or 21 amino acids (e.g., huPD1-21aas-CD28Cys, SEQ ID NO.:103).

In other exemplary embodiments, the present disclosure provides a nucleic acid molecule that encodes a CD2-CD28 construct. For example, the present disclosure includes a nucleic acid molecule as set forth in SEQ ID NO.:69 (huCD2-CD28Cys).

In other exemplary embodiments, the present disclosure provides a nucleic acid molecule that encodes a Fas-CD28 construct. For example, the present disclosure includes a nucleic acid molecule as set forth in SEQ ID NO.:83 (huFas-CD28Cys).

In other exemplary embodiments, the present disclosure provides a nucleic acid molecule that encodes a Fas-CD28 construct, wherein the extracellular component comprises a truncated extracellular domain of Fas and an extracellular portion of CD28. For example, the Fas extracellular domain may be truncated by about 7 amino acids to about 15 amino acids. Exemplary Fas-CD28 constructs have the CD95 (Fas) extracellular domain truncated by 7 amino acids (e.g., huFas-7aas-CD28Cys, SEQ ID NO.:85) or 12 amino acids (e.g., huFas-12aas-CD28Cys, SEQ ID NO.:87).

In another exemplary embodiment, the present disclosure provides a nucleic acid molecule that encodes a Fas-4-1BB construct, wherein the extracellular component comprises the entire extracellular domain or a truncated extracellular domain of CD95 (Fas), and the intracellular component comprises the signaling domain of CD137 (4-1BB). In a further embodiment, the nucleic acid molecule encodes a Fas-4-1BB construct wherein the hydrophobic component further comprises the transmembrane portion of CD95 (Fas) or CD137 (4-1BB). For example, in certain embodiments, a Fas-4-1BB construct is encoded by a the nucleic acid molecule having at least 80%, 85%, 90%, 95% or more sequence identity with the polynucleotide sequence of SEQ ID NO.:185. In some embodiments, a Fas-4-1BB construct is encoded by a polynucleotide comprising or consisting of the polynucleotide sequence of SEQ ID NO.:185. In other embodiments, a Fas-4-1BB construct is encoded by a nucleic acid molecule having at least 80%, 85%, 90%, 95% or more sequence identity with the polynucleotide sequence of SEQ ID NO.:187. In some embodiments, a Fas-4-1BB construct is encoded by a polynucleotide comprising or consisting of the polynucleotide sequence of SEQ ID NO.:187. In certain other embodiments, a Fas-4-1BB construct is a huFastm-41BB protein comprising an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:186. An exemplary huFastm-41BB protein comprises or consists of an amino acid sequence as set forth in SEQ ID NO.:186. In certain other embodiments, a Fas-4-1BB construct is a huFas-41BBtm protein comprising an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:188. An exemplary huFas-41BBtm protein comprises or consists of an amino acid sequence as set forth in SEQ ID NO.:188.

In other exemplary embodiments, the present disclosure provides a nucleic acid molecule that encodes a Fas-CD28-41BB construct, wherein the extracellular component comprises an extracellular domain of CD95 (Fas), the hydrophobic component comprises a transmembrane domain of CD28, and the intracellular component comprises the signaling domain of CD137 (4-1BB). In some embodiments, the extracellular component comprises a truncated extracellular domain of CD95 (Fas) and an extracellular portion of CD28. For example, the CD95 (Fas) extracellular domain may be truncated by about 7 to about 15 amino acids. Exemplary Fas-CD28-41BB constructs have the CD95 (Fas) extracellular domain truncated by 7, 9, 12, or 15 amino acids. For example, in some embodiments, the CD95 (Fas) extracellular domain may comprise an amino acid sequence encoded by the nucleic acid sequence as set forth in SEQ ID NO.:73 or 75. The extracellular portion of CD28 may comprise a multimerization domain. The extracellular portion of CD28 may comprise, for example, an amino acid sequence encoded by a nucleic acid sequence as set forth in SEQ ID NO.:9.

In other exemplary embodiments, the present disclosure provides a nucleic acid molecule that encodes a TIM3-CD28 construct. For example, the present disclosure includes a nucleic acid molecule as set forth in SEQ ID NO.:173 (huTIM3-CD28Cys). Also included within the scope of the disclosure is a TIM3-CD28 fusion protein, wherein the extracellular component comprises a truncated extracellular domain of TIM3 and an extracellular portion of CD28. For example, the TIM3 extracellular domain may be truncated by about 8 to about 15 amino acids (e.g., huTIM3-12aas-CD28Cys, SEQ ID NO.:175, has a 12 amino acid truncation).

In other exemplary embodiments, the present disclosure provides a nucleic acid molecule that encodes a LAG3-CD28 construct. For example, the present disclosure includes a nucleic acid molecule as set forth in SEQ ID NO.:163 (huLAG3-CD28Cys). Also included within the scope of the disclosure is a LAG3-CD28 fusion protein, wherein the extracellular component comprises a truncated extracellular domain of LAG3 and an extracellular portion of CD28. For example, the LAG3 extracellular domain may be truncated by about 8 to about 15 amino acids (e.g., huLAG3-12aas-CD28Cys, SEQ ID NO.:159, has a 12 amino acid truncation).

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous nucleic acid sequence encoding a fusion protein or a non-endogenous nucleic acid sequence encoding a fusion protein specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising green fluorescent protein (GFP), an extracellular domain of human CD2, or a truncated human EGFR (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptide, or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g. green fluorescent protein, huEGFRt).

In some embodiments, a vector encoding a fusion protein as disclosed herein may encode more than one fusion protein. For example, a vector may encode two different fusion proteins (e.g., a first fusion protein comprising a PD-1 ectodomain and a second fusion protein comprising a TIM3 ectodomain).

In some embodiments, a vector encoding a fusion protein as disclosed herein may further comprise an antigen-specific TCR. In some embodiments, the antigen-specific TCR is exogenous. In some embodiments, the antigen-specific TCR is specific to a HLA (MHC) class I restricted antigen. In some embodiments, the antigen is a cancer-specific antigen. Embodiments wherein the cancer-specific antigen comprises WT-1, mesothelin, or cyclin-A1 are also within the scope of the disclosure. In still other embodiments, a vector that encodes a fusion protein as disclosed herein further encodes a ligand, which may be CD200, CD47, PD-L1, or CD58. In yet further embodiments, a vector that encodes a fusion protein as disclosed herein further encodes an siRNA for reducing the expression of an endogenous receptor. In some particular embodiments, the endogenous receptor is CD200R, SIRPα, CD279 (PD-1), CD95 (Fas) or CD2.

In some embodiments, host cells capable of expressing a fusion protein of this disclosure on the cell surface are immune cells. In some embodiments, host cells capable of expressing a fusion protein of this disclosure on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., *Leukemia* 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In some embodiments, T cells may be engineered to express a TCR specific to a particular antigen.

In certain embodiments, a host cell transfected to express a fusion protein of this disclosure is a functional T cell, such as a virus-specific T cell, a tumor antigen specific cytotoxic T cell, a naïve T cell, a memory stem T cell, a central or effector memory T cell, γδ T cells, or a CD4+ CD25+ regulatory T cell. In further embodiments, a nucleic acid molecule encoding a fusion protein of this disclosure is introduced into bulk CD8$^+$ T cells, naïve CD8+ T cells, CD8+ $T_{CM}$ cells, CD8+ $T_{EM}$ cells, or any combination thereof. In still further embodiments, a nucleic acid molecule encoding a fusion protein of this disclosure is introduced into bulk CD4$^+$ T cells, naïve CD4$^+$ T cells, CD4+$T_{CM}$ cells, CD4+ $T_{EM}$ cells, or any combination thereof. In other embodiments, a nucleic acid molecule encoding a fusion protein of this disclosure is introduced into a population of T cells enriched for naïve CD8+ T cells and CD8+$T_{CM}$ cells. In still other embodiments, a nucleic acid molecule encoding a fusion protein of this disclosure is introduced into a population of T cells enriched for naïve CD4+ T cells and CD4+$T_{CM}$ cells. In any of the aforementioned embodiments, the T cells further contain a nucleic acid molecule encoding an engineered antigen-specific T cell receptor (TCR), an engineered antigen-specific high affinity TCR, an exogenous co-stimulatory molecule, a chimeric antigen receptor (CAR), or any combination thereof.

In certain embodiments, a host cell transfected to express a fusion protein of this disclosure is a functional natural killer cell.

One or more growth factor cytokines that promote proliferation of T cells expressing a fusion protein of this disclosure may be added to the culture used to expand T cells. The cytokines may be human or non-human. Exemplary growth factor cytokines that may be used promote T cell proliferation include IL2, IL15, or the like.

In certain embodiments, a host T cell transfected to express a fusion protein of this disclosure is a CD4$^+$ T cell that also expresses an antigen-specific high-affinity TCR specific to a HLA (MHC) class I restricted antigen (see Soto et al., *Cancer Immunol Immunother.* 62: 359-369, 2013).

In certain embodiments, a host T cell transfected to express a fusion protein of this disclosure also expresses a recombinant TCR specific to a cancer antigen. In some embodiments, the cancer antigen is a WT1. "WT1" refers to Wilm's tumor 1, a transcription factor that contains four zinc-finger motifs at the C-terminus and a proline/glutamine-rich DNA binding domain at the N-terminus. WT1 has an essential role in the normal development of the urogenital system and is mutated in a small subset of patients with Wilm's tumors. High expression of WT1 has been observed in various cancers, including, breast cancer, ovarian cancer, acute leukemias, vascular neoplasms, melanomas, colon cancer, lung cancer, thyroid cancer, bone and soft tissue sarcoma, and esophageal cancer. Alternative splicing has been noted for WT1.

In certain embodiments, a host T cell transfected to express a fusion protein of this disclosure also expresses a recombinant TCR specific to mesothelin. "Mesothelin" (MSLN) refers to a gene that encodes a precursor protein that is cleaved into two products, megakaryocyte potentiating factor and mesothelin. Megakaryocyte potentiation factor functions as a cytokine that can stimulate colony formation in bone marrow megakaryocytes. Mesothelin is a glycosylphosphatidylinositol-anchored cell-surface protein that may function as a cell adhesion protein. This protein is overexpressed in epithelial mesotheliomas, ovarian cancers and in specific squamous cell carcinomas. Alternative splicing results in multiple transcript variants.

In certain embodiments, a host T cell transfected to express a fusion protein of this disclosure also expresses a recombinant TCR specific to cyclin-A1.

In certain embodiments, a host T cell transfected to express a fusion protein of this disclosure also expresses a CAR.

In still other embodiments, a host cell that expresses a fusion protein as disclosed herein further comprises a ligand, which may be CD200, CD47, PD-L1, or CD58. In yet further embodiments, a host cell that expresses a fusion protein as disclosed herein further expresses an siRNA for reducing the expression of an endogenous receptor. In some particular embodiments, the endogenous receptor is CD200R, SIRPα, CD279 (PD-1), CD95 (Fas), or CD2.

In some embodiments, a host cell that expresses a fusion protein as disclosed herein may express more than one fusion protein. For example, the host cell may express two different fusion proteins (e.g., a first fusion protein comprising a PD-1 ectodomain and a second fusion protein comprising a TIM3 ectodomain).

Uses

Diseases that may be treated with cells expressing fusion proteins as described in the present disclosure include cancer, infectious diseases (viral, bacterial, protozoan infections), immune diseases (e.g., autoimmune), or aging-related diseases (e.g., senescence). Adoptive immune and gene therapy are promising treatments for various types of cancer (Morgan et al., Science 314:126, 2006; Schmitt et al., Hum. Gene Ther. 20:1240, 2009; June, J. Clin. Invest. 117:1466, 2007) and infectious disease (Kitchen et al., PLoS One 4:38208, 2009; Rossi et al., Nat. Biotechnol. 25:1444, 2007; Zhang et al., PLoS Pathog. 6:e1001018, 2010; Luo et al., J. Mol. Med. 89:903, 2011).

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to a fusion protein T cell therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia, and acute myeloid leukemia (AML)) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, a method of treating a subject with the fusion protein as disclosed herein includes treating acute myelocytic leukemia, acute lymphocytic leukemia, acute myeloid leukemia (AML), and chronic myelocytic leukemia.

In particular embodiments, a method of treating a subject with the fusion protein as disclosed herein includes treating pancreatic cancer.

In particular embodiments, a method of treating a subject with the fusion protein as disclosed herein includes treating ovarian cancer.

In particular embodiments, a method of treating disease with a fusion protein as disclosed herein is provided, wherein the disease comprises a solid tumor that expresses CD200 or a tumor that is infiltrated with myeloid cells that are CD200$^+$, and the fusion protein has an extracellular component comprising an extracellular portion of a CD200R.

In particular embodiments, a method of treating disease with a fusion protein as disclosed herein is provided, wherein the disease comprises acute myeloid leukemia (AML) and the fusion protein has an extracellular component comprising an extracellular portion of a CD200R, a SIRPα, a CD95 (Fas), a CD279 (PD-1), or a CD2.

In particular embodiments, a method of treating disease with a fusion protein as disclosed herein is provided, wherein the disease comprises a solid tumor and the fusion protein has an extracellular component comprising an extracellular portion of a TIM3, a CD223 (LAG3), a CD95 (Fas), a CD279 (PD-1), or a CD2.

In particular embodiments, a method of treating disease with a fusion protein as disclosed herein is provided, wherein the disease comprises breast cancer, ovarian cancer, colon cancer, prostate cancer, or multiple myeloma, and the fusion protein has an extracellular component comprising an extracellular portion of a CD200R. In some such embodiments, a CD200R-9aas-CD28Cys fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:7. In certain embodiments, a CD200R-9aas-CD28Cys fusion protein is encoded by a polynucleotide comprising or consisting of a polynucleotide sequence as set forth in SEQ ID NO.:7. In other embodiments, a CD200R-9aas-CD28Cys fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:30. In further embodiments, a CD200R-9aas-CD28Cys fusion protein comprises or consists of an amino acid sequence as set forth in SEQ ID NO.:30.

In particular embodiments, a method of treating disease with a fusion protein as disclosed herein is provided, wherein the disease comprises ovarian cancer, pancreatic cancer, or AML, and the fusion protein has an extracellular component comprising an extracellular portion of a CD95 (Fas). In some such embodiments, a Fastm-4-1BB fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:185. In certain embodiments, a Fastm-4-1BB fusion protein is encoded by a polynucleotide comprising or consisting of a polynucleotide sequence as set forth in SEQ ID NO.:185. In other embodiments, a Fastm-4-1BB fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:186. In further embodiments, a Fastm-4-1BB fusion protein comprises or consists of an amino acid sequence as set forth in SEQ ID NO.:186.

In particular embodiments, a method of treating disease with a fusion protein as disclosed herein is provided, wherein the disease comprises ovarian cancer, pancreatic cancer, or AML, and the fusion protein has an extracellular component comprising an extracellular portion of a CD95 (Fas). In some such embodiments, a Fas-4-1BBtm fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:187. In certain embodiments, a Fas-4-1BBtm fusion protein is encoded by a polynucleotide comprising or consisting of a polynucleotide sequence as set forth in SEQ ID NO.:187. In other embodiments, a Fas-4-1BBtm fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:188. In further embodiments, a Fas-4-1BBtm fusion protein comprises or consists of an amino acid sequence as set forth in SEQ ID NO.:188.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, infection with cytosolic pathogens whose antigens are processed and displayed with HLA (MHC) Class I molecules, are treated with fusion proteins of this disclosure.

A fusion protein of this disclosure may be administered to a subject in cell-bound form (e.g., gene therapy of target cell population (mature T cells (e.g., CD8+ or CD4+ T cells) or other cells of T cell lineage)). In a particular embodiment, cells of T cell lineage expressing fusion proteins administered to a subject are syngeneic, allogeneic, or autologous cells.

Pharmaceutical compositions including fusion proteins of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. The present disclosure provides pharmaceutical compositions comprising cells expressing a fusion protein as disclosed herein and a pharmaceutically acceptable carrier, diluents, or excipient. Suitable excipients include water, saline, dextrose, glycerol, or the like and combinations thereof.

In some embodiments, the disclosure is directed to a method of increasing the activity of an immune cell, enhancing or prolonging an immune response, stimulating an antigen-specific T cell response, inhibiting an immunosuppressive signaling pathway, treating cancer or a tumor, inhibiting immune resistance of cancer cells, or treating an infection, comprising administering to a subject in need thereof an effective amount of a host cell expressing a fusion protein as described herein. In further embodiments, a host cell for use in any of the aforementioned methods further expresses an engineered antigen-specific TCR, an engineered antigen-specific high affinity TCR, a CAR, a co-stimulatory molecule, or any combination thereof. In particular embodiments, methods of treating leukemia are provided, comprising co-expressing a fusion protein as disclosed herein and a recombinant, antigen-specific TCR.

In some embodiments, there are provided methods of inducing or enhancing a Class I HLA response by a CD4+ T cell, comprising administering to a subject in need thereof an effective amount of a CD4+ T cell expressing a fusion protein as described herein. In further embodiments, a host cell for use in inducing or enhancing a Class I HLA response by a CD4+ T cell further expresses an engineered antigen-specific TCR, an engineered antigen-specific high affinity TCR, a CAR, a co-stimulatory molecule, or any combination thereof.

In any of the aforementioned embodiments, the methods are effective in the absence of administering exogenous IL-2.

In some embodiments, there are provided methods for increasing cytokine production in an immune cell (e.g., $CD4^+$ T cell or a $CD8^+$ T cell) of a subject, comprising administering to a subject in need thereof an effective amount of a fusion protein, or a vector encoding the fusion protein, as disclosed herein.

In some embodiments, there are provided methods for increasing cytokine production in an immune cell (e.g., $CD4^+$ T cell or a $CD8^+$ T cell), comprising contacting the immune cell with a fusion protein, or a vector encoding the fusion protein, as disclosed herein. In further embodiments, the immune cell further expresses an engineered antigen-specific TCR, an engineered antigen-specific high affinity TCR, a CAR, a co-stimulatory molecule, or any combination thereof. In some embodiments, the cytokine that is increased comprises interferon gamma (IFNγ), tumor necrosis factor (TNFα), or interleukin-2 (IL-2).

In still other embodiments, a subject of any of the aforementioned methods is further treated with an adjunctive therapy, such as a chemotherapy. Exemplary chemotherapeutic agents include, for example, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™ Bristol-Myers Squibb Oncology, Princeton, N.J.) and docetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

In some embodiments, the adjunctive therapy is a vaccine, an inhibitor of an immunosuppression signal, a B-Raf inhibitor, a MEK inhibitor, a tyrosine kinase inhibitor, a cytotoxic agent, a chemotherapeutic, or any combination thereof. In some embodiments, the inhibitor of an immunosuppression signal is an antibody or siRNA. In some embodiments, the antibody or siRNA is specific for PD-1, PD-L1, PD-L2, CTLA4, LAG3, KIR, CD244, B7-H3, B7-H4, BTLA, HVEM, GAL9, TIM3, A2aR, or any combination thereof.

EXAMPLES

Example 1

CD200R-CD28 Fusion Protein Constructions

Figure 1A:
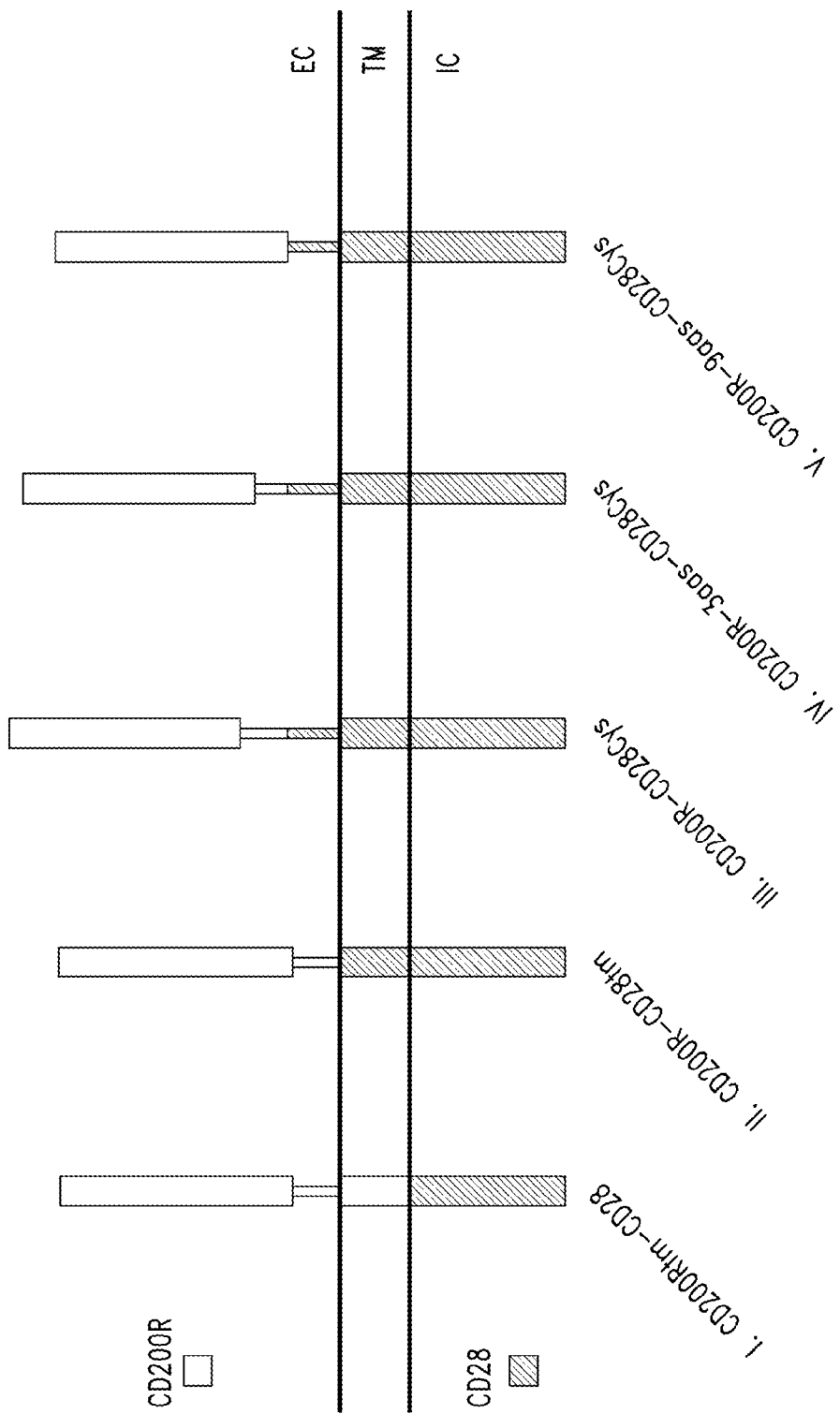
FIGS. 1A and 1B show CD200R-CD28 constructs expressed at high levels on primary murine CD8$^+$ T cells. (A) Schematic representation of exemplary CD200R-CD28 constructs. Construct "I" contains CD200R extracellular ("EC") and transmembrane ("TM") domains and a CD28 intracellular ("IC") signaling domain (CD200Rtm-CD28). Construct "II" contains the extracellular domain of CD200R and the transmembrane and intracellular domains of CD28 (CD200R-CD28tm). Constructs "III-V" also incorporate a portion of the extracellular domain of CD28 to the transmembrane-proximal cysteine to promote multimerization and enhance CD28 signaling. To account for any extra extracellular amino acids (e.g., from one to about 50 amino acids; such as exemplary murine constructs disclosed here contain an extra nine (9) amino acids and exemplary human constructs disclosed here contain twelve (12) amino acids), some constructs have a truncated portion of an extracellular or intracellular domain (e.g., a CD200R that preserves an N linked glycosylation site). For example, construct IV has a truncated portion of CD200R that is truncated by 3 amino acids. Construct V has a truncated portion of CD200R that is truncated 9 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) Transgenic expression of murine CD200R-CD28 constructs on TCR$_{gag}$ T cells as detected by anti-CD200R antibody. The control vector contains green fluorescent protein (GFP).

Exemplary fusion proteins as described herein are illustrated using schematic representations in FIG. 1A. Exemplary fusion proteins include immunomodulatory fusion proteins (IFPs) comprised of the extracellular domain of CD200R or a portion thereof, and an intracellular signaling domain of CD28 or a portion thereof (FIG. 1A, constructs I-V). The hydrophobic component may be comprised of the transmembrane domain of either CD200R (FIG. 1A, construct I) or CD28 (FIG. 1A, constructs II-V), or portions thereof. In some exemplary CD200R-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., FIG. 1A construct III, CD200R-CD28Cys; construct IV, CD200R-3aas-CD28Cys; and construct V, CD200R-9aas-CD28Cys). The extracellular component may comprise all or a portion of the extracellular domain of CD200R. In some embodiments, the extracellular component comprises the entire extracellular domain of CD200R (FIG. 1A, constructs I-III). In other examples, the extracellular component comprises the first 235 amino acids (preserving an N-linked glycosylation site) (e.g., FIG. 1A, construct IV, CD200R-3aas-CD28Cys) or the first 229 amino acids (e.g., FIG. 1A, construct V, CD200R-9aas-CD28Cys) from the N-terminus of CD200R. The size of the extracellular component, which may be manipulated by adjusting the fusion protein construct, may affect the ability of the fusion protein to enter the immunological synapse and co-localize with the TCR within the cSMAC to deliver a strong co-stimulatory signal. Additionally, the CD200R-CD28 construct has the capacity to convert what would typically be an inhibitory signal from the binding of CD200R to its target into a positive signal generated by the CD28 intracellular signaling domain.

An exemplary nucleic acid molecule encoding a CD200R-CD28 fusion protein comprises the following elements (5' to 3'): Extracellular Component (CD200R)-Multimerization Domain (CD28 Cysteine)-Hydrophobic Component (CD28 transmembrane)-Intracellular Component (CD28 intracellular). In some embodiments, a nucleic acid molecule encoding a CD200R-CD28 fusion protein comprises a nucleic acid molecule as set forth in any one of SEQ ID NOS.:47-51 or 1, 6, 7, 10, 12, 14, or 15.

Nucleic acids encoding the constructs were ordered from Invitrogen or generated in-house by PCR then directionally TOPO-cloned into the pENTR™/D-TOPO® vector (Invitrogen), and transferred into the retroviral vector pMP71-attR using Gateway® technology (Invitrogen). In certain embodiments, the nucleic acid molecules encoding IFPs of the instant disclosure were codon optimized before cloning into the pMP71-attR retroviral vector.

Example 2

Transgenic Expression of CD200R-CD28 Constructs

A preclinical mouse model for disseminated leukemia, based on the murine C57BL/6 Friend virus-induced erythroleukemia (FBL) and TCR$_{gag}$ transgenic mice, was used to determine if CD200R-CD28 chimeric receptors can improve T cell function.

TCR transgenic mice were generated to produce CD8$^+$ T cells specific for the gag epitope (TCR$_{gag}$). C57BL/6 (B6) mice were purchased from the Jackson Laboratory. TCR$_{gag}$ transgenic mice express a TCR transgene specific for the Friend virus gag epitope in CD8$^+$ T cell (Öhlén et al., *J. Immunol.* 166: 2863-2870, 2001). All animal studies performed were approved under the University of Washington Institutional Animal Care and Use Committee protocol (Protocol #2013-01). The murine B6 Friend virus induced erythroleukemia (FBL) expresses the F-MuLV encoded gag epitope (peptide CCLCLTVFL (SEQ ID NO.:213)).

CD200R-CD28 chimeric constructs based on murine genes were inserted into the pMP71 retroviral vector and used to transduce primary mouse splenocytes stimulated with anti-CD3 and anti-CD28 antibodies. Constructs were designed as described in Example 1, and ordered from Invitrogen or generated in-house by PCR. The constructs were then directionally TOPO-cloned into the pENTR™/D-TOPO® vector (Invitrogen), and transferred into the retroviral vector pMP71-attR using Gateway® technology (Invitrogen). The retroviral packaging cell line Plat-E (Morita et al., 2000, *Gene Therapy* 7:1063-1066, 2000; Cell Biolabs, Inc.) was transduced with the retroviral vector using effectene transduction reagent (Qiagen). Viral supernatant was collected on days 2 and 3 and then used to transduce TCR$_{gag}$ T cells.

One day prior to the transfection, $TCR_{gag}$ T cells were stimulated with anti-CD3/CD28 and 100 U/mL rhIL-2. Transduction of $TCR_{gag}$ T cells was performed in 12 well plates in the presence of IL-2 and polybrene by spinfection for 90 minutes at 1000 g. FBL cells were transduced with CD200 with polybrene spinfection, similar to T cell transduction, and subsequently sorted to generate a homogenous population.

Figure 1B:
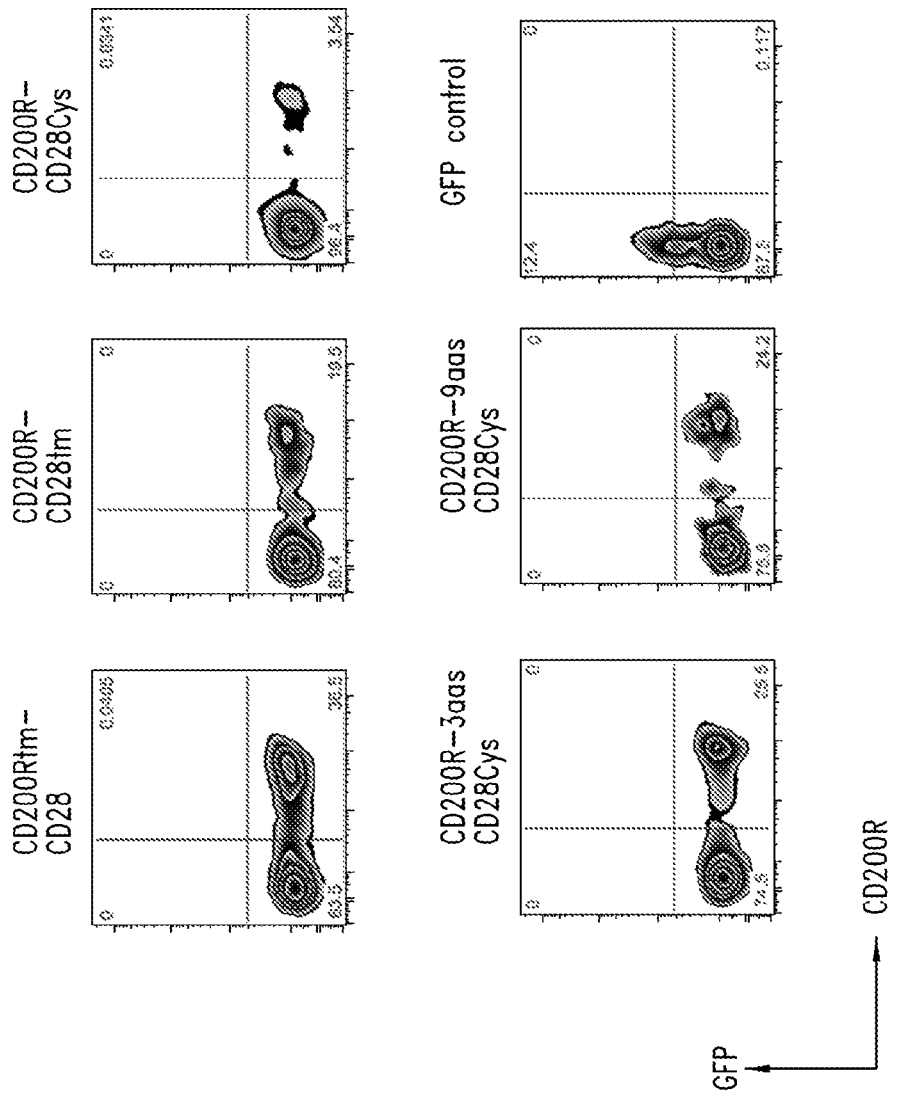

Five days after transduction, CD8+ T cells were analyzed for construct expression by anti-CD200R antibody staining and flow cytometry (FIG. 1B). A vector encoding green fluorescent protein (GFP) was used as a control. Transduction efficiency ranged from 4-36% and the mean fluorescent intensity (MFI) of the transduced cells was similar between constructs.

Example 3

CD200R-CD28 Constructs Promote In Vitro Proliferation, Accumulation, and Effector Function of Transduced T Cells The CD200R-CD28 constructs described in Examples 1 and 2 were assessed for their abilities to promote proliferation, accumulation, and effector function of $TCR_{gag}$ T cells. Expansion of Effector Cells In Vitro $TCR_{gag}$ effector cells were generated in vitro as previously described (Stromnes et al., *J. Clin. Invest.* 120: 3722-34, 2010). Irradiated antigen presenting splenocytes ($5\times10^6$), irradiated FBL ($3\times10^6$), and $TCR_{gag}$ tg cells ($10^6$) were cultured together with IL-2 (50 U/mL) in 10 mL of culture media (IMDM supplemented with non-essential amino acids, 2 µM glutamine, 100 U/mL penicillin/streptomycin, 10% FBS, and 50 µM 2-mercapatoethanol). T cells were restimulated weekly and assessed by flow cytometry 5-7 days after the last stimulation.

In Vitro T Cell Proliferation Assay $TCR_{gag}$ T cells were transduced as in Example 2. To assess T cell proliferation in vitro, $TCR_{gag}$ T cells were stained with CellTrace Violet (CTV, Life Technologies) according to the manufacturer's protocol. CTV-labeled Tg T cells ($10^5$) and GFP control T cells were stimulated with titrating numbers of CD200− FBL or CD200+ FBL cells. After 3 days, CTV dilution of $TCR_{gag}$ T cells was assessed by flow cytometry.

Figure 2A:
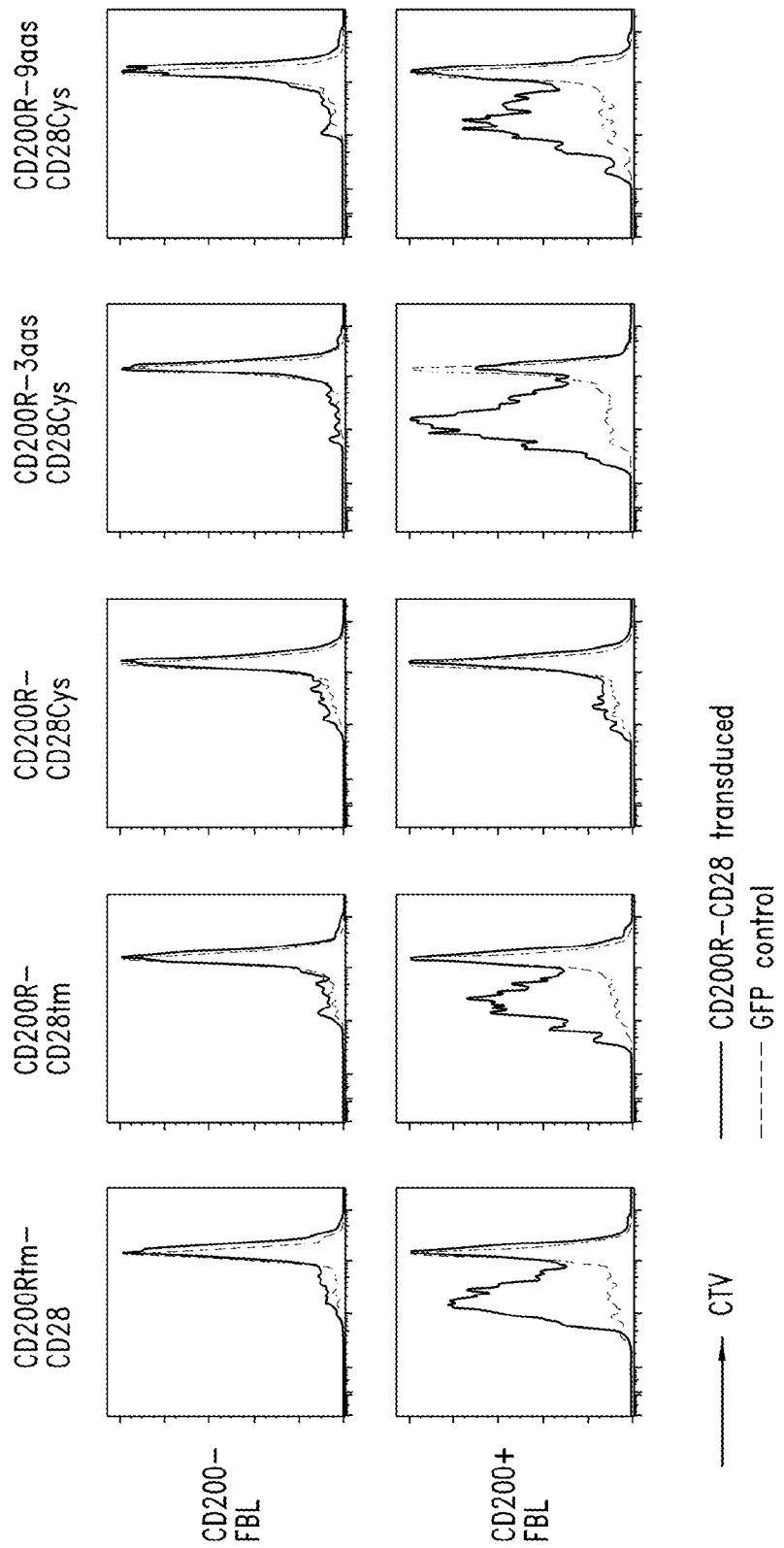
FIGS. 2A to 2G show that CD200R-CD28 constructs promote proliferation, accumulation, and effector function in response to CD200$^+$ tumor target cells in vitro, and accumulate in the immunological synapse. Splenocytes from naive TCR$_{gag}$ mice were stimulated in vitro with anti-CD3, anti-CD28, and recombinant human IL-2 (100 U/ml) and transduced with retroviral supernatant for 2 days. Cells were restimulated every 7 days with irradiated FBL and splenocytes and cultured with rhIL-2 (50 U/mL) for up to three stimulations. T cells were used for assays 5-7 days after the last stimulation. (A) Proliferation of CD200R-CD28 and GFP control TCR$_{gag}$ T cells as measured by CellTrace Violet dilution. T cells were stimulated with CD200$^-$ FBL (upper panels) or CD200$^+$ FBL (lower panels) for 3 days. (B) Preferential expansion/survival of transduced TCR$_{gag}$ T cells during co-culture with non-transduced TCR$_{gag}$ T cells during weekly cycles of stimulation with irradiated CD200$^+$ FBL and splenocytes. (C) Enrichment of transduced T cells. Repeated restimulation with irradiated CD200$^+$ tumor cells enriched the cells transduced with CD200R-9aas-CD28Cys compared to wild-type T cells transduced with an empty GFP control vector. (D) Increased CD200R and CD200 signal intensity at T cell:FBL synapse. Lipid rafts are increased at the immunological synapse (I). CD200R-9aas-CD28Cys fusion proteins co-localized with lipid rafts, indicating that the fusion proteins concentrate within the immunological synapse (III, IV). (E) CD200R-CD28$^+$ CD8$^+$ T cells display enhanced ability to lyse CD200$^+$ FBL cells in vitro. Target tumor cells were labeled with different dilutions of the fluorescent dye 5,6-carboxyfluorescein diacetate succinimidyl ester (CFSE), as indicated. Effector TCR$_{gag}$ T cells transduced with the indicated CD200R-CD28 fusion protein or an empty vector control were incubated at the indicated effector to target ratio with a 1:1 mix of CD200$^+$ FBL (CFSE$^{hi}$) and non-specific EL4 (CFSE$^{lo}$) control targets for 5 hours. The percentage of FBL of the sum of FBL and control tumor cells was determined by flow cytometry. The percentage lysis was determined by dividing the percent of FBL incubated with T cells by the percent of FBL incubated without T cells. (F) Target tumor cells for CFSE assay in (G). Target tumor cells were labeled with different dilutions of the fluorescent dyes CellTrace Violet (CTV) or CFSE. A 1:1:1 mix of EL4 cells (CTV+), CD200$^+$ FBL (CFSE$^{hi}$) and non-specific EL4 (CFSE$^{lo}$) control targets was generated. (G) CFSE cytotoxicity assay. TCR$_{gag}$ T cells were transduced with CD200R-CD28 receptor or GFP control vector. Effector TCR$_{gag}$ T cells were incubated at the indicated effector to target ratio with a 1:1 mix of CD200$^-$ FBL or CD200$^+$ FBL and non-specific EL4 control targets for 4 hours. The percentage of FBL of the sum of FBL and control tumor cells was determined by flow cytometry. The percentage lysis was determined by dividing the percent of FBL incubated with T cells by the percent of FBL incubated without T cells.

Flow cytometry results indicating the number of $TCR_{gag}$ T cells after stimulation with titrating numbers of CD200− FBL cells (upper) or CD200+ FBL (lower) are shown in FIG. 2A. Four of the five CD200R-CD28 constructs tested dramatically improved proliferation of $TCR_{gag}$ T cells in response to CD200+ FBL (blue lines) compared to GFP control-transduced T cells (red lines).

In Vitro T Cell Accumulation Assay

To determine if the enhanced proliferation also resulted in increased accumulation of transduced cells, the proportion of transduced cells in the total $TCR_{gag}$ population over multiple cycles of stimulation with irradiated CD200+ FBL was measured.

Figure 2B:
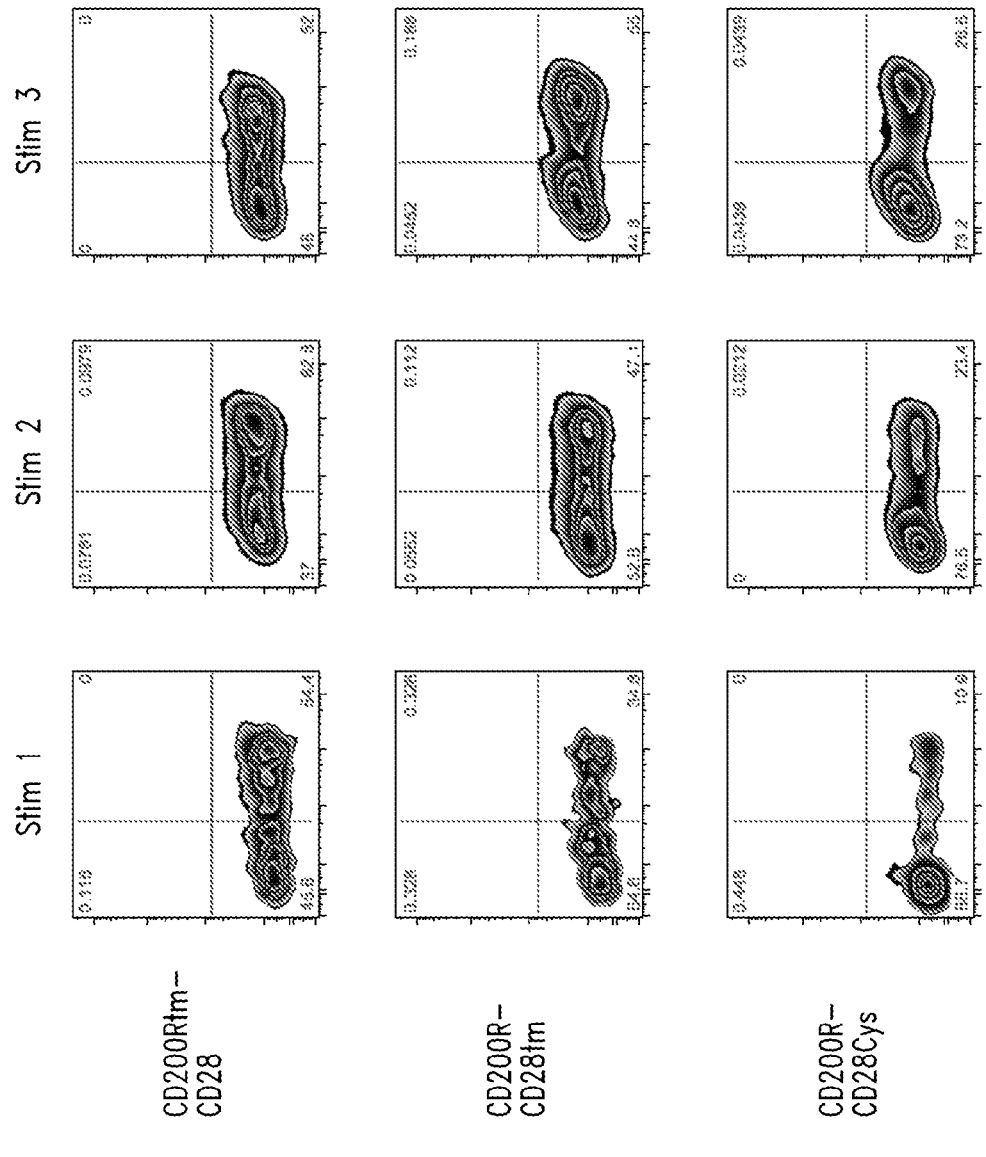
Figure 2B:
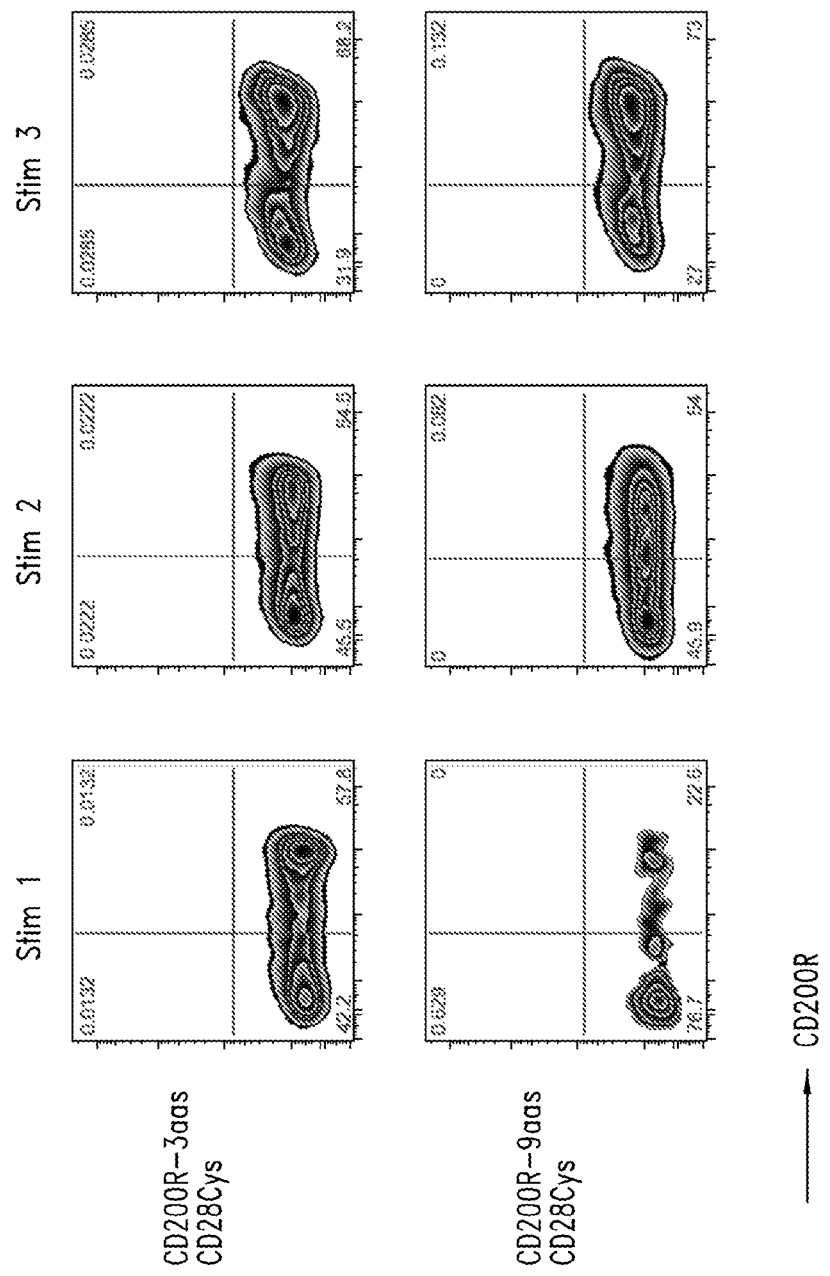

Several of the constructs promoted accumulation of transduced T cells, including CD200R-CD28tm, CD200R-CD28Cys, CD200R-3aas-CD28Cys, and CD200R-9aas-CD28Cys (FIG. 2B). Of these constructs, CD200R-9aas-CD28Cys exhibited the greatest increase in transduced T cells over multiple stimulations, resulting in more than a 3-fold expansion over 3 stimulations.

In Vitro T Cell Enrichment Assay

Figure 2C:
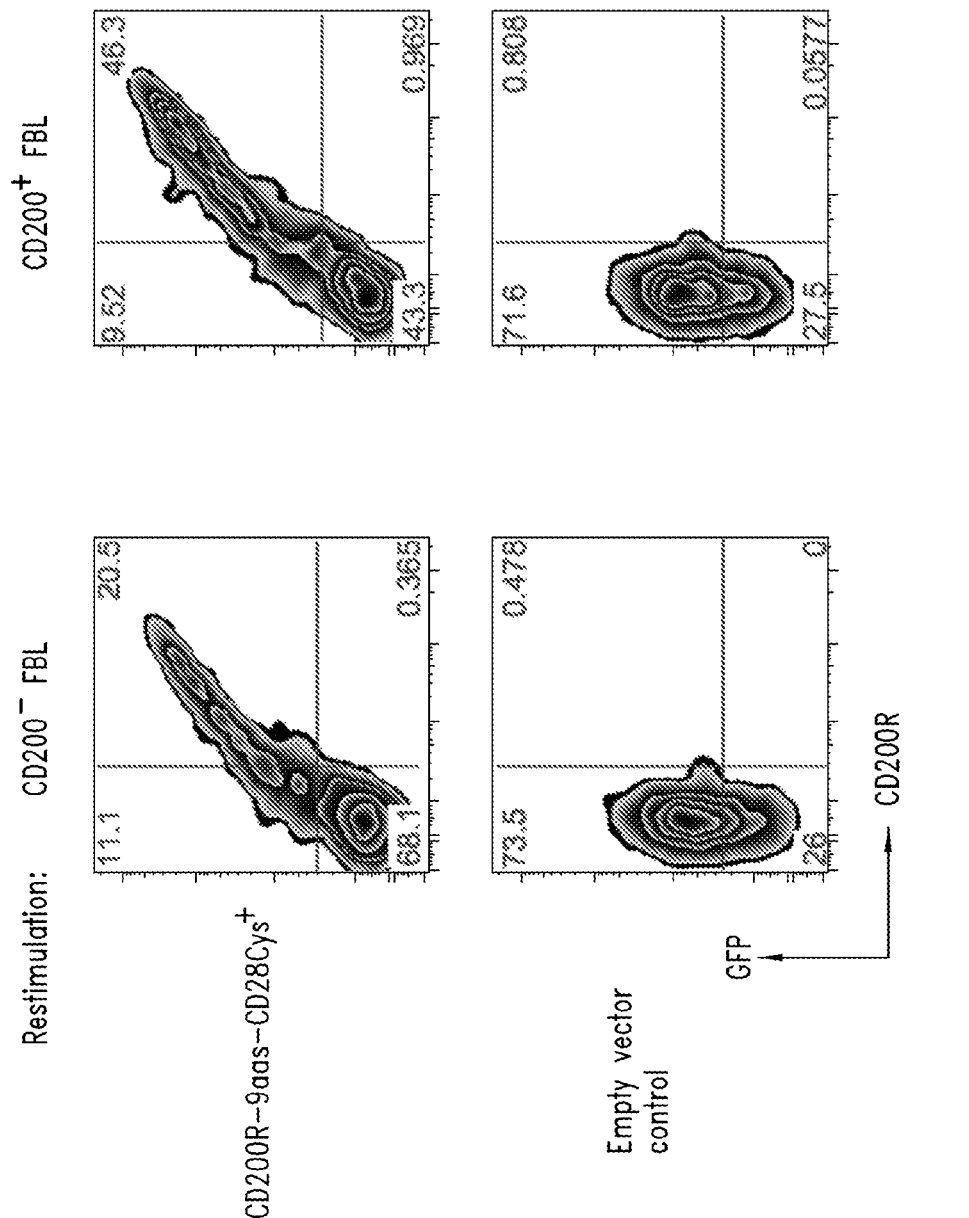

A mixed population of transduced and nontransduced CD8+ T cells were restimulated with CD200+ or CD200− irradiated FBL cells to determine if restimulation would enrich the population for the transduced CD200R-9aas-CD28Cys IFP+ T cells. Repeated restimulation with irradiated CD200+ tumor cells enriched the cells transduced with the IFP compared to wild type T cells, demonstrating that recognition of a target expressing the ligand for the CD200R-9aas-CD28Cys IFP enhances the response (FIG. 2C).

In Vitro Colocalization Assay

Figure 2D:
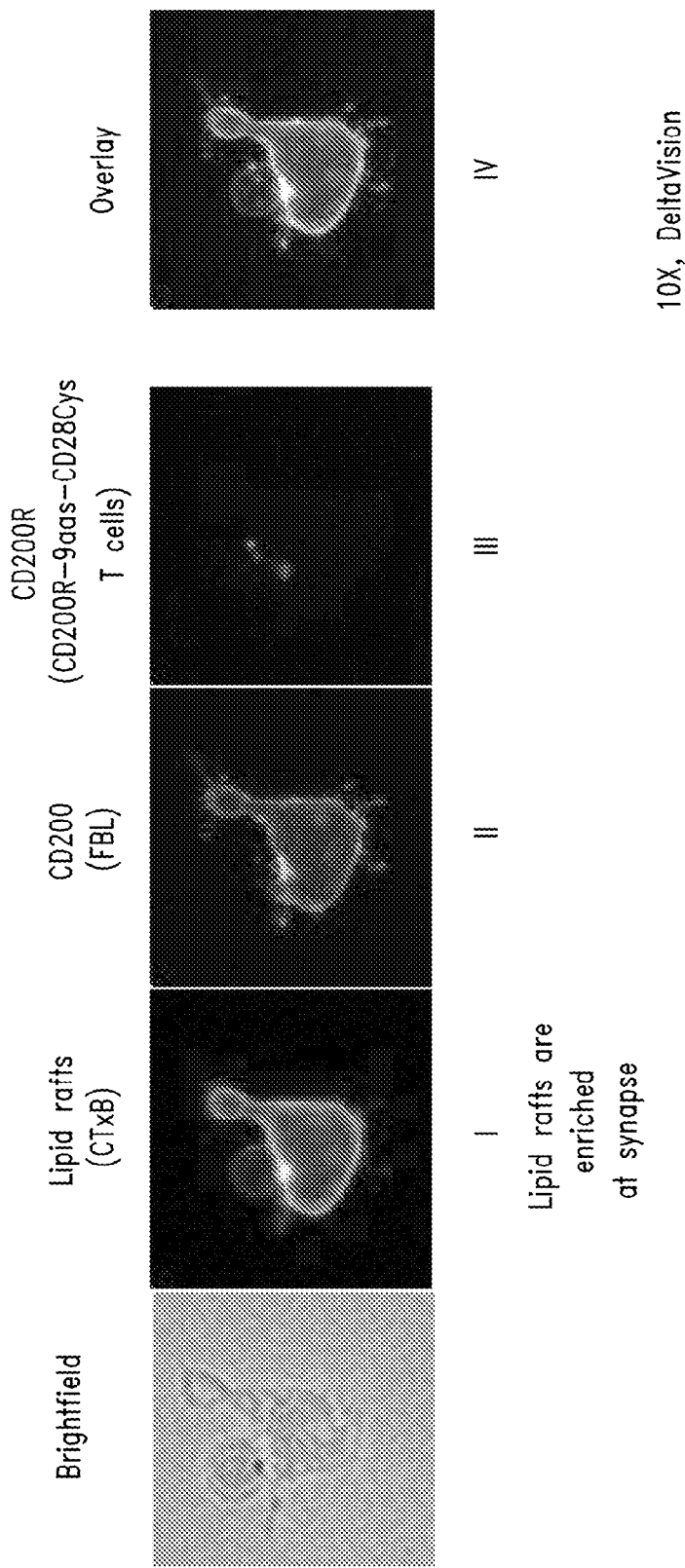

Transduced T cells were imaged by microscopy to determine if the CD200R-9aas-CD28Cys IFP colocalized with the cognate ligand in the immunological synapse (IS) during T cell activation. CTxB was used to stain lipids within the cell membrane, which are enriched at the synapse (FIG. 2D, panel I). Labeled antibodies that target CD200 expressed by the FBL cell (FIG. 2D, panel II) or CD200R expressed by the T cell (FIG. 2D, panel III) were used to visualize the location of the molecules in relation to the IS. CD200 ligand and CD200R colocalized within the IS (FIG. 2D, panel IV), demonstrating that the construct is sized appropriately to be accommodated by the immunologic synapse.

CFSE-Based Cytotoxicity Assay

Increased CD28 signaling also promotes effector function (Chen and Flies, *Nat. Rev. Immunol.* 13: 227-242, 2013). CD200R-CD28 fusion protein-transduced T cells were tested for increased killing of target tumor cells. FBL and control EL4 tumors were incubated for 10 minutes at room temperature with 2.5 µM ($CFSE_{hi}$) or 0.25 µM ($CFSE^{lo}$) CFSE in PBS, respectively. Excess dye was removed by washing tumor cells in serum-containing media. A 1:1 mixture of EL4 and FBL tumor cells was incubated with titrated numbers of CD200R-CD28 or GFP vector transduced $TCR_{gag}$ in vitro expanded effector T cells for 4 hours in 96-well, round-bottom plates at 37° C. and 5% $CO_2$. Specific FBL lysis was determined by flow cytometric analyses of the % $CFSE_{hi}$ (FBL) of total CFSE positive cells (FBL+EL4) remaining in the well.

Figure 2E:
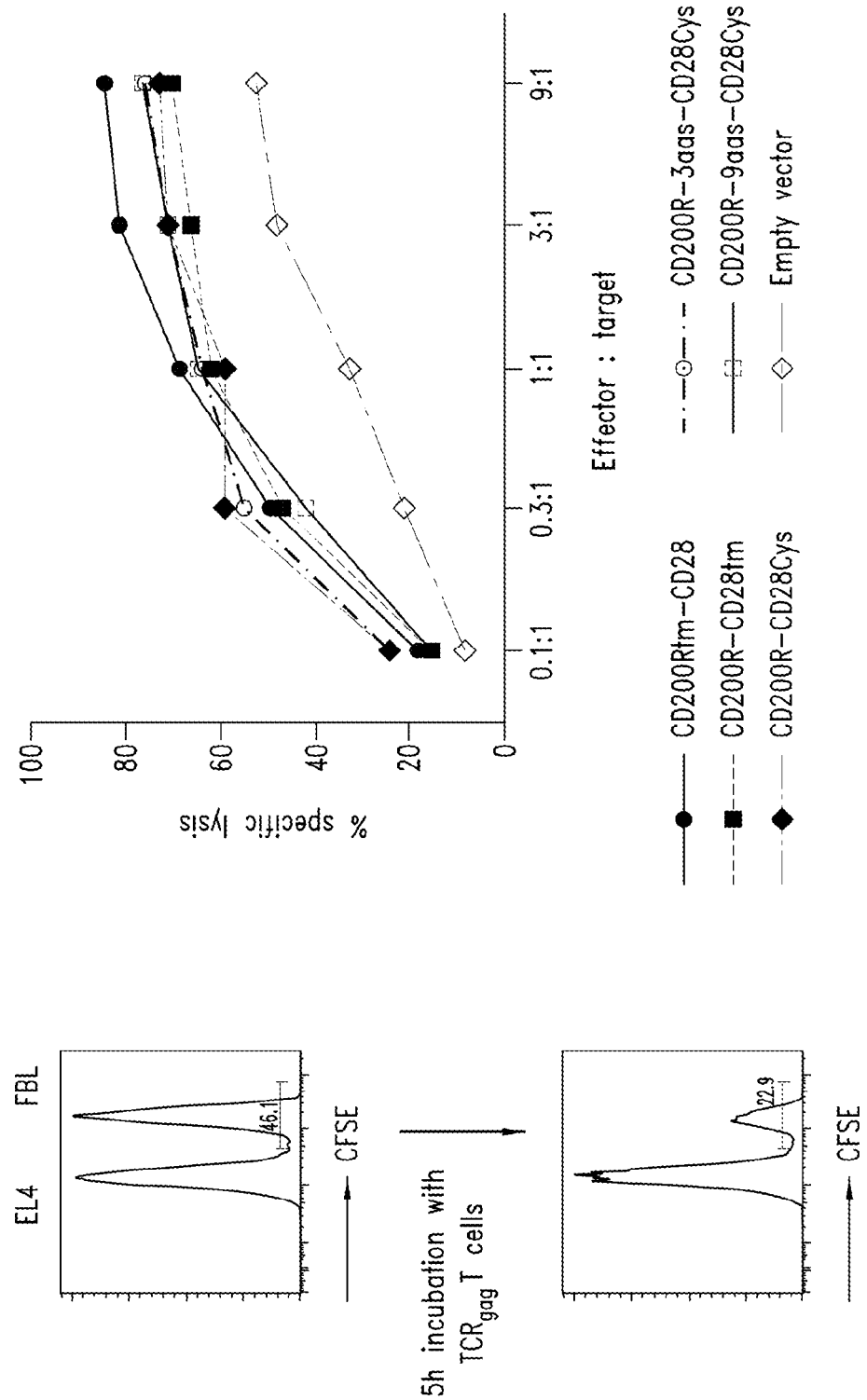
Figure 2F:
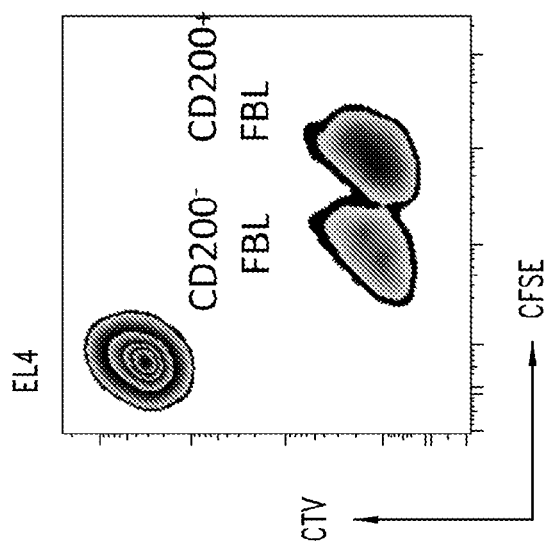
Figure 2G:
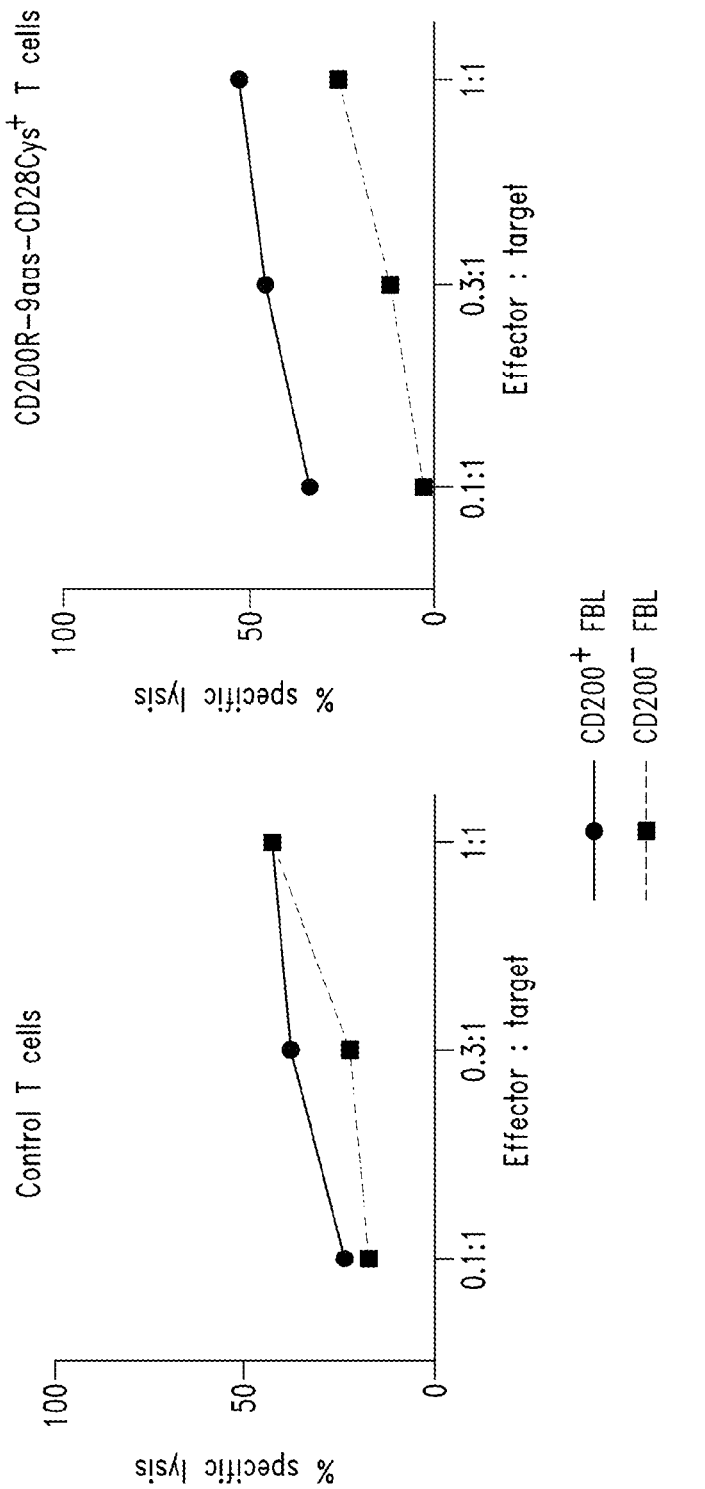

$TCR_{gag}$ T cells transduced with CD200R-CD28 constructs displayed an enhanced ability to lyse FBL tumor in vitro compared to $TCR_{gag}$ T cells transduced with an empty vector (FIGS. 2E, 2G). Target tumor cells were labeled with different dilutions of the fluorescent dyes CellTrace Violet (CTV) or CFSE to generate a 1:1:1 mix of EL4 cells (CTV+), CD200+ FBL ($CFSE^{hi}$) and non-specific EL4 ($CFSE^{lo}$) control targets (FIG. 2F). Additionally, control GFP-transduced $TCR_{gag}$ T cells lysed CD200− FBL and CD200+ FBL at equal efficiencies (FIG. 2G). By contrast, $TCR_{gag}$ T cells transduced with CD200R-9aas-CD28Cys exhibited increased killing of CD200+FBL cells compared to control T cells, lysing over 40% of CD200+ FBL at the lowest E:T ratio tested (FIG. 2G).

Taken together, these data show that CD200R-CD28 constructs function to increase accumulation and the lytic activity of transduced T cells in response to tumor cell stimulation.

Example 4

T Cells Transduced with CD200R-9aas-CD28Cys Exhibit Enhanced Accumulation In Vivo in Response to Recognition of FBL B6 mice were injected with $4\times10^6$ live FBL leukemia intraperitoneal (i.p.) as previously described (Stromnes et al., *J. Clin. Invest.* 120: 3722-34, 2010). After allowing 5 days for the FBL to disseminate, mice received 180 mg/kg cyclophosphamide (Cy, commercially available as Cytoxan®) i.p. at least 6 hours before transfer of the effector T cells. For survival studies, $10^5$ $TCR_{gag}$ T cells which previously underwent 1-3 stimulations in vitro were transferred into tumor-bearing mice. To assess short-term proliferation and accumulation, $2\times10^6$ of each of fusion protein-transduced and a GFP-control-transduced T cells were co-injected into tumor-bearing mice and the mice euthanized for analysis 8 days later. Mice were regularly monitored for tumor burden and euthanized if evidence of tumor progression predicted mortality would occur within 24-48 hours.

Figure 3A:
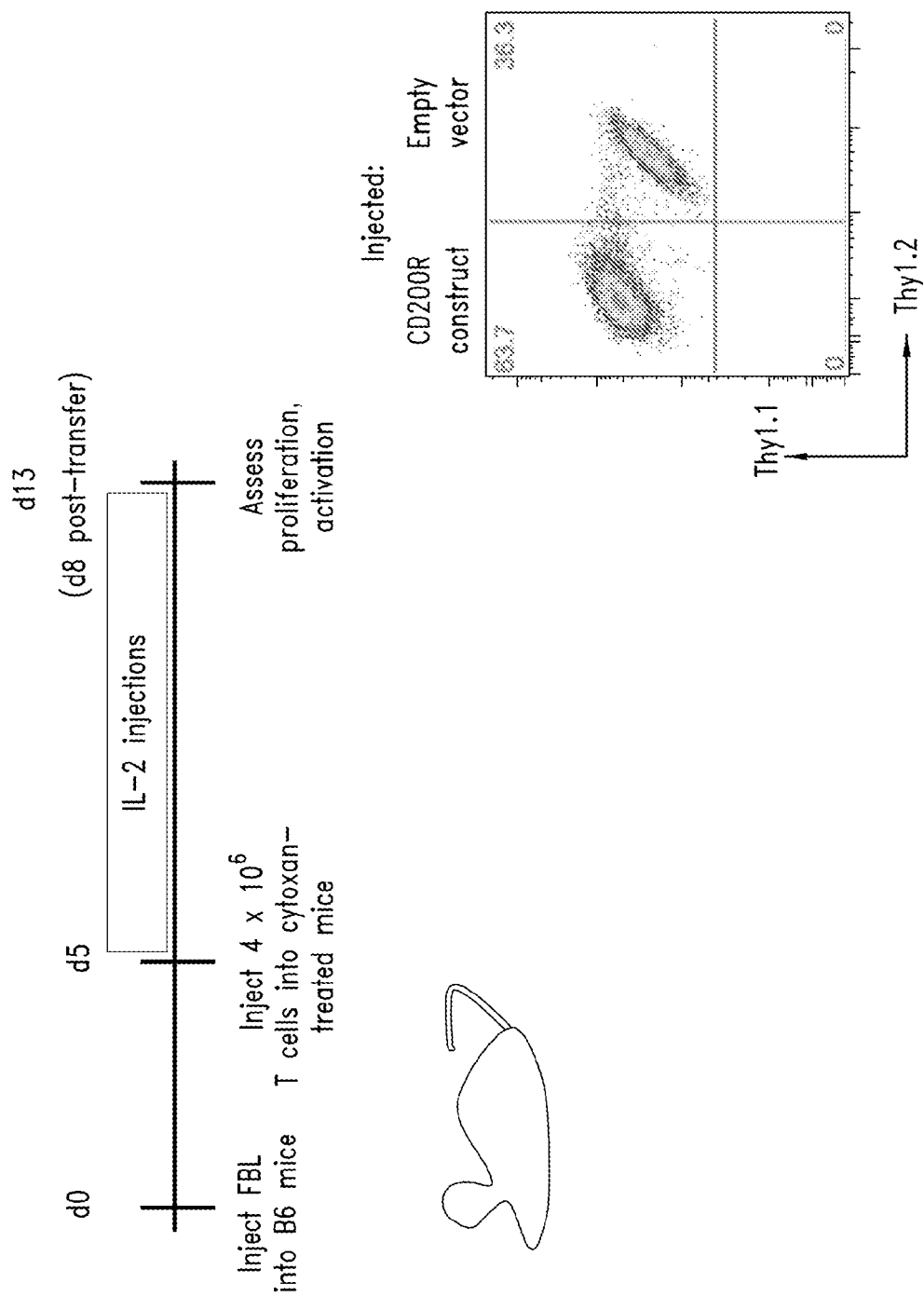
FIGS. 3A to 3D show that T cells transduced with CD200R-9aas-CD28Cys preferentially accumulate in response to tumor challenge in vivo and express surface proteins consistent with an effector phenotype after injection into cyclophosphamide-treated, FBL-bearing mice. Transduced TCR$_{gag}$ T cells were generated as described in Example 2. (A) Experimental schematic. C57BL/6 mice were injected with 4×10$^6$ CD200$^+$ FBL cells. Five days later, CD200R-9aas-CD28Cys (Thy1.1 homozygous) and eGFP control (Thy1.1 heterozygous) TCR$_{gag}$ T cells were co-injected into cyclophosphamide-treated FBL-bearing B6 mice at 4×10$^6$ cells/mouse. IL-2 was administered every 2 days (2×10$^4$ U/dose). On day 8 post-T cell transfer, mice were euthanized and spleens and inguinal lymph nodes harvested. (B) CD200R-9aas-CD28Cys TCR$_{gag}$ T cells accumulate in the spleen in response to FBL. (LN=lymph node; Spl=spleen). (C) Comparison of surface proteins 3 days post-transfer for T cells transduced to express CD200R-9aas-CD28Cys, T cells transduced with an empty vector, and endogenous T cells. CD200R-9aas-CD28Cys TCR$_{gag}$ T cells expressed reduced CD62L compared to control TCR$_{gag}$ T cells, suggesting an effector T cell phenotype. (D) Comparison of surface proteins 15 days post-transfer for cells transduced to express CD200R-9aas-CD28Cys$^+$ T cells, T cells transduced with an empty vector, and endogenous T cells. CD200R-9aas-CD28Cys TCR$_{gag}$ T cells express similar levels of cell surface proteins compared to control TCR$_{gag}$ T cells.
Figure 3B:
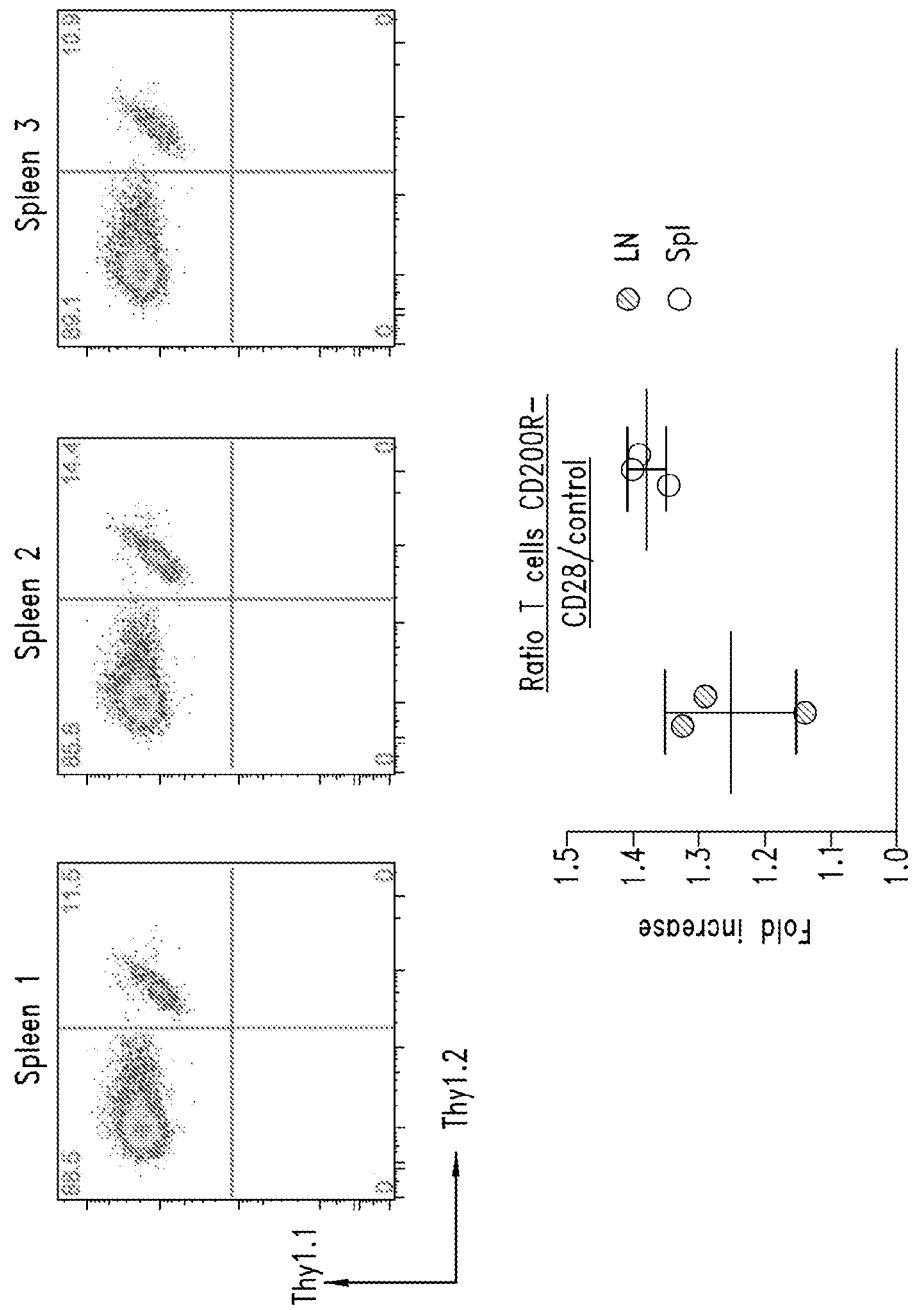
Figure 3C:
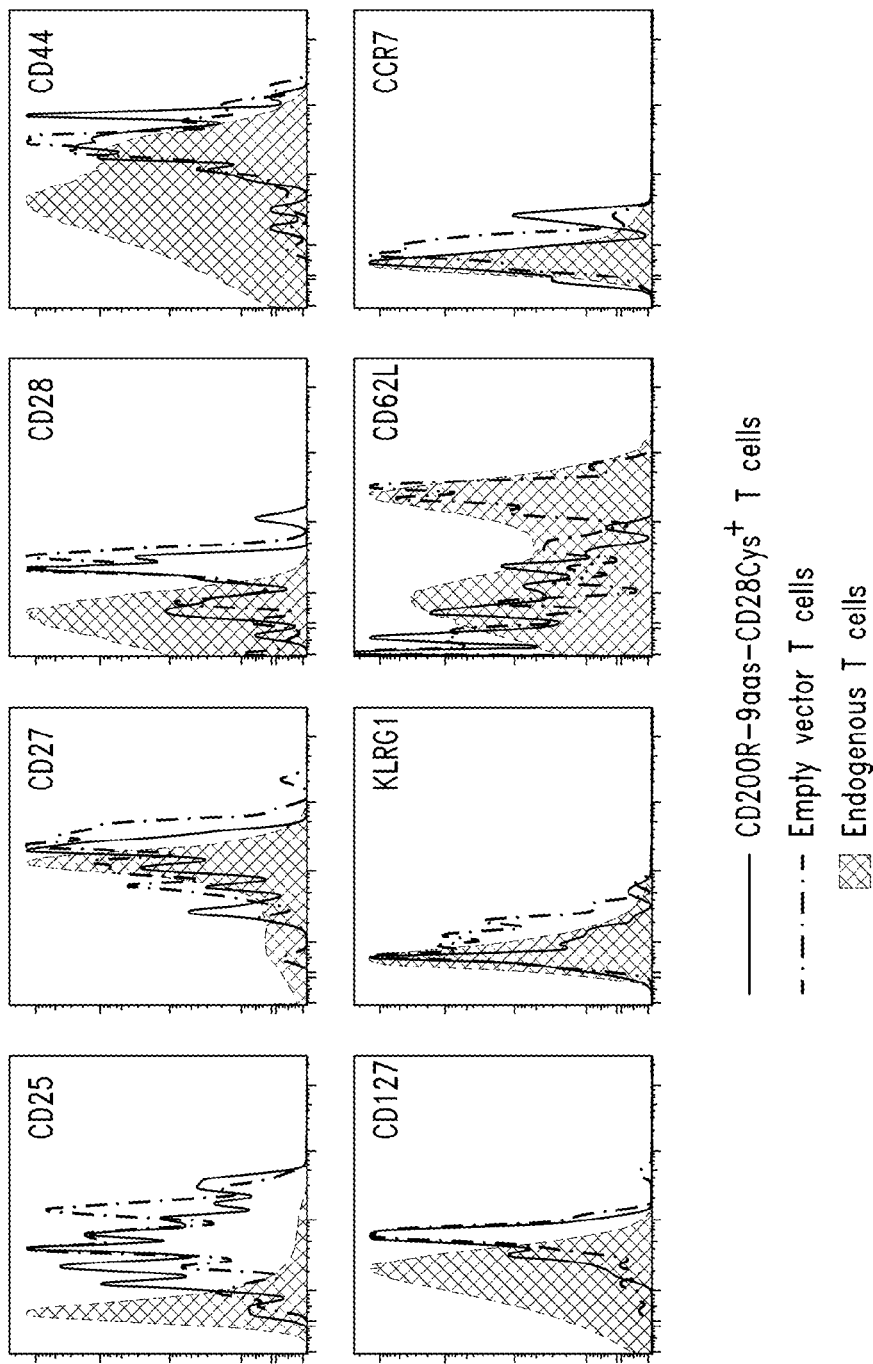
Figure 3D:
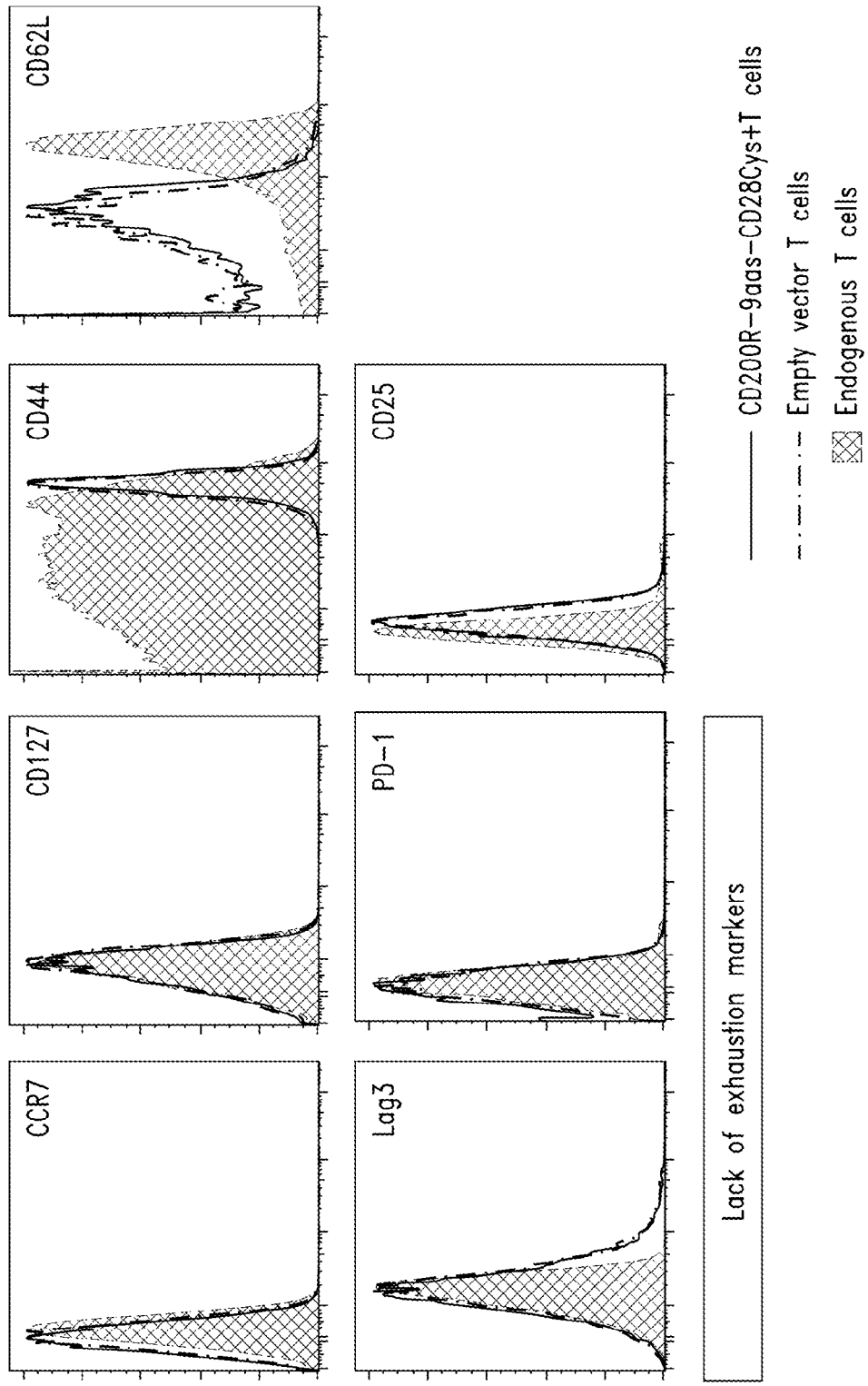

To assess whether CD200R-9aas-CD28Cys fusion protein-transduced T cells exhibited greater proliferation and accumulation in vivo in response to recognition of FBL, a mixed population of fusion protein-transduced and control cells were transferred into tumor-bearing mice and the ratio of cells by ex vivo analysis were compared 8 days after transfer (FIG. 3A). By use of congenic markers, transduced T cells were detected at a 1.2-1.4-fold greater ratio over control cells in both the spleen and lymph nodes relative to the ratio that was injected (FIG. 3B). Transduced CD200R-9aas-CD28Cys$^+$ TCR$_{gag}$ T cells exhibited reduced CD62L expression 3 days post-transfer to tumor-bearing mice, suggesting an effector T cell phenotype (FIG. 3C). By day 15, transduced and control T cells exhibited similar phenotypes, including a lack of exhaustion markers (FIG. 3D). Similar to the in vitro findings, T cells that expressed CD200R-9aas-CD28Cys displayed increased accumulation in response to tumor stimulation in vivo. Furthermore, they exhibited protein expression patterns consistent with an effector T cell phenotype for at least 3 days following transfer to tumor-bearing mice.

Example 5

Adoptive Immunotherapy with CD200R-CD28$^+$ T Cells Exhibits Greater Activity in Therapy of Disseminated Leukemia Adoptive immunotherapy with T cells transduced with CD200R-CD28 mediated increased therapeutic activity in the preclinical mouse model of disseminated leukemia.

Figure 4A:
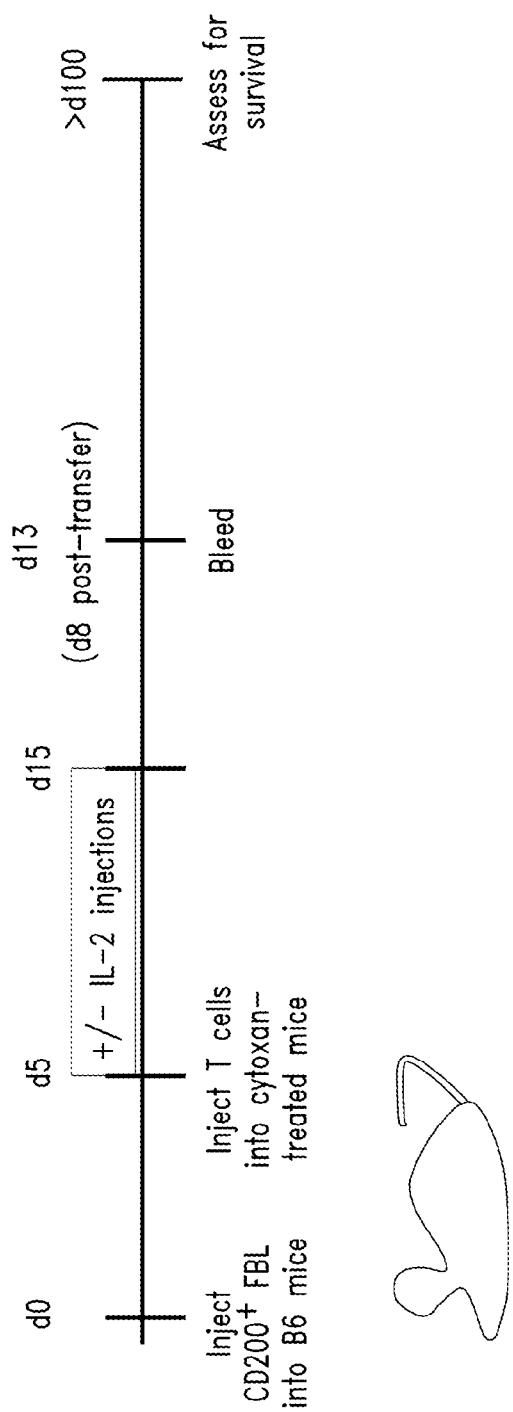
FIGS. 4A to 4D show that adoptive immunotherapy with CD200R-CD28-transduced T cells can eradicate disseminated leukemia. (A) Experiment schematic. C57BL/6 mice were injected with 4×10$^6$ CD200$^+$ FBL cells. Five days later, CD200R-CD28tm, CD200R-CD28Cys, CD200R-9aas-CD28Cys, or eGFP TCR$_{gag}$ T cells were injected i.p. into Cy-treated FBL-bearing mice at 10$^5$ cells/mouse. IL-2 was administered every 2 days (2×10$^4$ U/dose) in a cohort of mice as indicated. (B) Representative example of expression of cell surface proteins in CD200R-CD28tm transduced T cells and non-transduced T cells on day of injection with IL-2, as determined by flow cytometry. (C) Survival of mice treated in the presence of IL-2 injections. (D) Survival of mice treated in the absence of IL-2 injections. Transfer of CD200R-9aas-CD28Cys TCR$_{gag}$ T cells significantly improved survival in the absence of IL-2 injections (P<0.05, log-rank Mantel-Cox test).
Figure 4B:
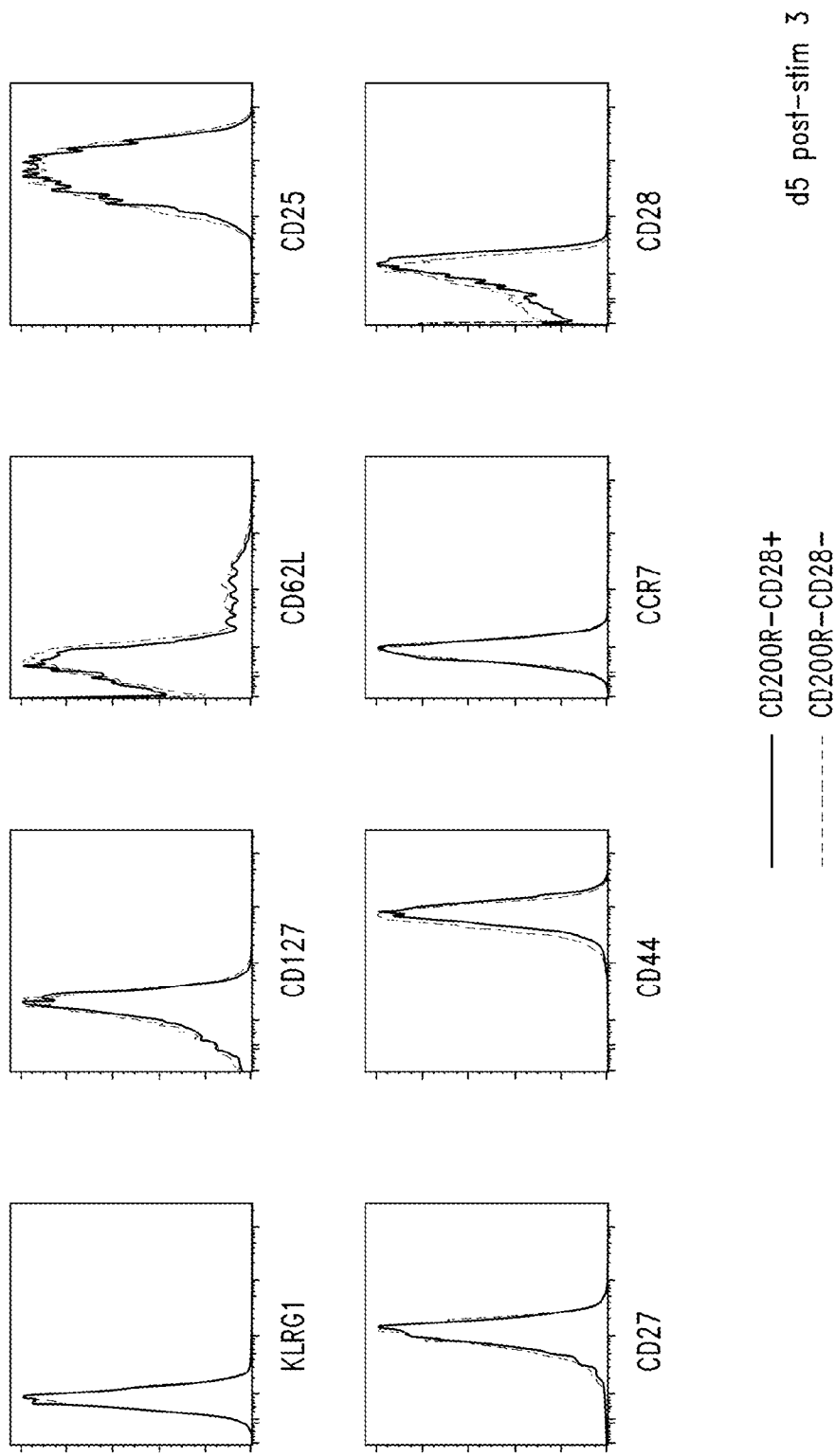

Mice were injected with a lethal dose of CD200$^+$ FBL leukemia and five days later, cohorts of Cy-treated mice received additional therapy with $10^5$ T cells (FIG. 4A). The contribution of the CD28 cysteine bond to efficacy mediated by the CD200R-CD28 construct was assessed by comparing T cells transduced with CD200R-CD28tm, CD200R-9aas-CD28Cys, and GFP control constructs as shown in FIG. 1A. IL-2 was administered for 10 days as an additional therapeutic reagent to a cohort of mice to promote the activity of the T cells (Stromnes et al., J. Clin. Invest. 120: 3722-34, 2010). Before injection, T cells were assessed for various surface proteins by flow cytometry. Transduced and control TCR$_{gag}$ T cells displayed similar phenotypes, indicating that transduction did not alter the phenotype of the cells prior to injection (FIG. 4B).

Figure 4C:
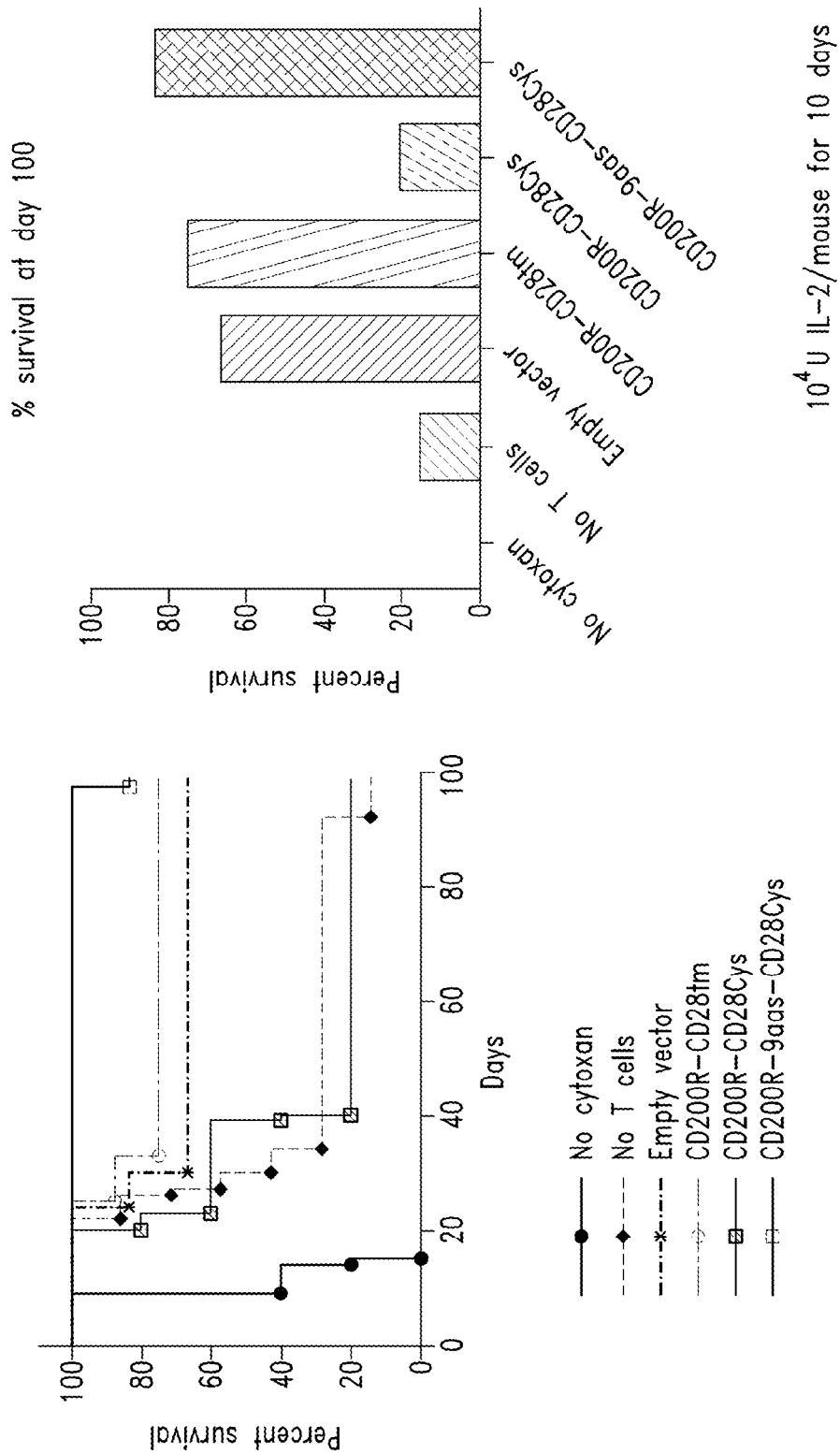
Figure 4D:
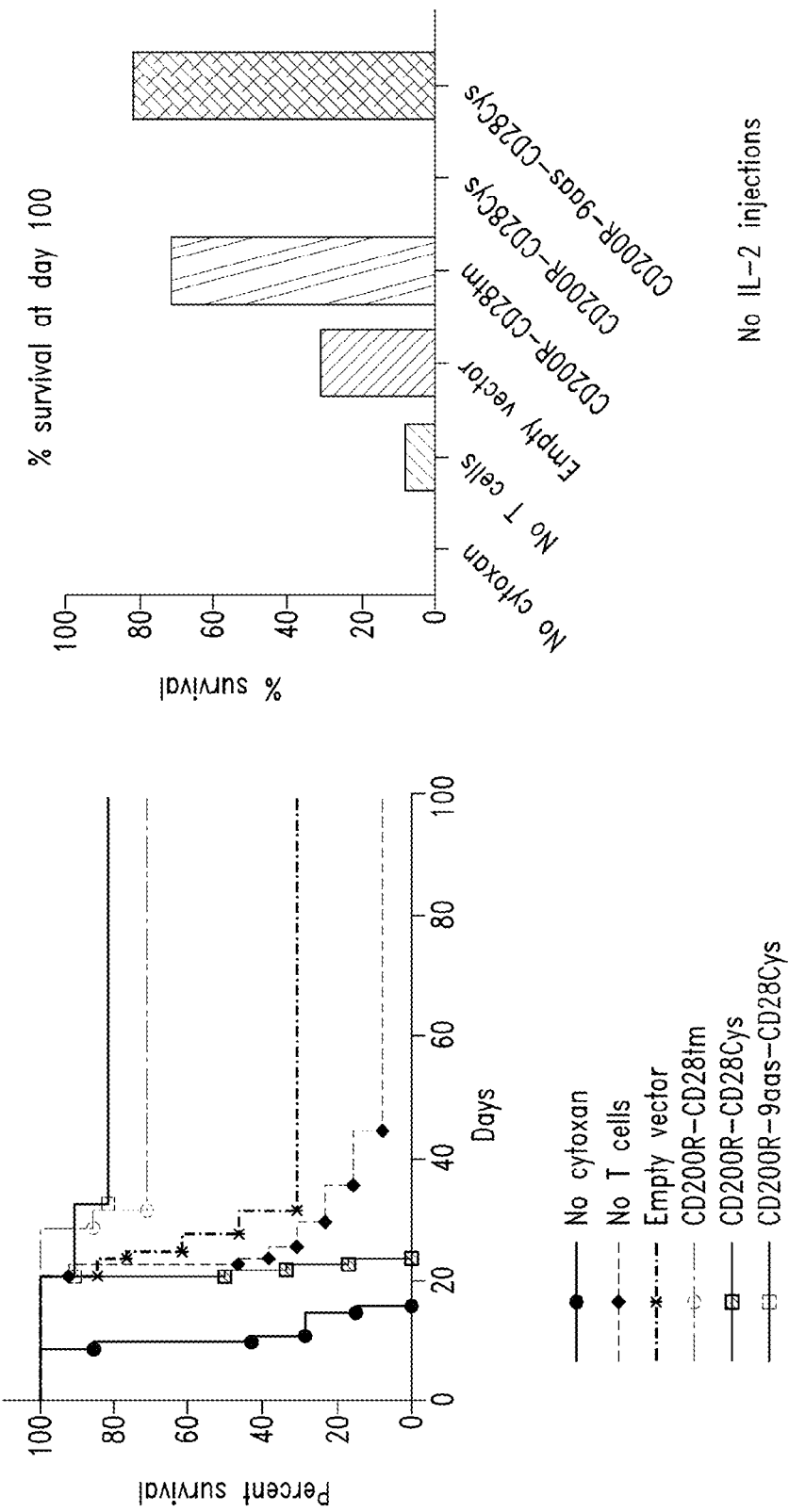

In the small cohort of mice that received IL-2 injections, T cells improved survival but a significant difference in the survival of mice that received the different groups of T cells could not be detected (FIG. 4C). However, in the cohort of mice that did not receive IL-2 injections, there was a significant improvement in the survival of mice that received T cells transduced with CD200R-CD28 constructs appropriately sized to fit within the immunological synapse (FIG. 4D). The majority of the mice not receiving T cells, receiving T cells transduced with the GFP control vector or T cells transduced with the largest ectodomain (CD200R-CD28Cys IFP) did not survive beyond day 30 (FIGS. 4C and 4D, black solid, dashed, and orange lines, respectively). In contrast, 71% of mice that received CD200R-CD28tm$^+$ T cells and 83% of mice that received CD200R-9aas-CD28Cys$^+$ T cells survived more than 100 days post-therapy (FIGS. 4C and 4D, green and red lines, respectively). These data suggest that transduction of T cells with CD200R-CD28 constructs that span a distance similar to a distance between membranes in an immunological synapse provides sufficient costimulation to overcome the dependence of T cell immunotherapy on injection of exogenous IL-2. Furthermore, although there were differences in proliferation and accumulation between the CD200Rtm-CD28 and CD200R-9aas-CD28Cys constructs tested in mice that did not receive injections of exogenous IL-2, both IFPs effectively enhanced T cell immunotherapy to significantly improve the clinical outcome from otherwise progressive leukemia.

Example 6

Figure 5A:
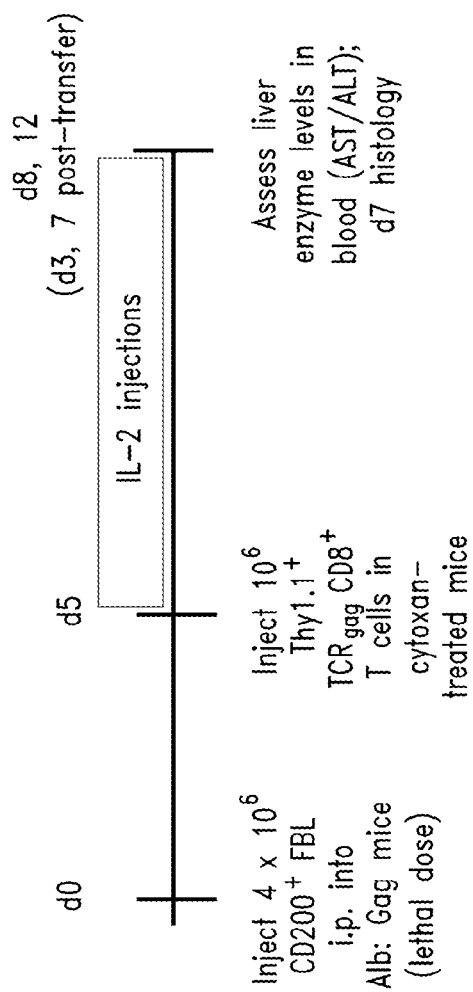
FIGS. 5A to 5C show that T cells expressing CD200R-9aas-CD28Cys do not induce detectable autoimmune liver damage or infiltrate normal tissues. (A) Experiment schematic. Cyclophosphamide-treated Alb/Gag mice were injected with 4×10$^6$ CD200$^+$ FBL cells. Five days later, CD200R-9aas-CD28Cys, and eGFP TCR$_{gag}$ T cells were injected i.p. into the cyclophosphamide-treated FBL-bearing mice at 10$^5$ cells/mouse. IL-2 was administered every 2 days (2×10$^4$ U/dose) in a cohort of mice as indicated. Three and 7 days post-transfer, liver damage was assessed by quantification of serum levels of liver enzymes aspartate aminotransferase (AST) and alanine aminotransferase (ALT). (B) AST and ALT levels measured at 3 and 7 days post-transfer for mice receiving no T cells, control T cells expressing GFP, or T cells expressing CD200R-9aas-CD28Cys did not vary by treatment. (C) Assessment of T cell infiltration of normal tissue. Limited presence of T cells in liver tissue was observed using antibodies specific to the T cell marker CD3 (left panel), with no significant difference between recipients of CD200R-9aas-CD28Cys TCR$_{gag}$ or control TCR$_{gag}$ T cells (right panel).
Figure 5A:
Figure 5B:
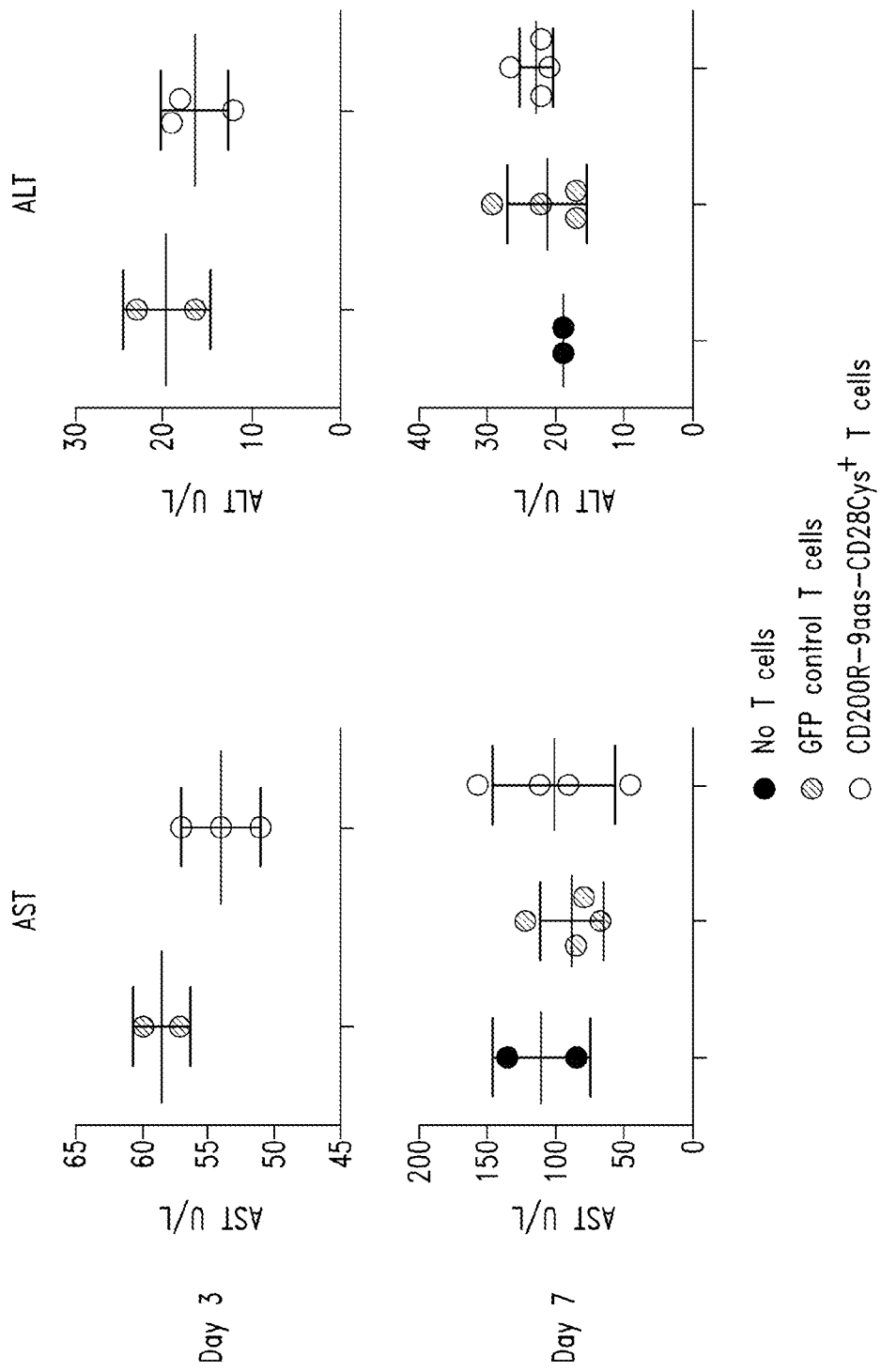

CD200R-9aas-CD28Cys$^+$ T Cells do not Cause Autoreactivity with Endogenous Tissues and do not Exhibit Infiltration of Normal Tissues In Vivo To determine if transduction of TCR$_{gag}$ T cells lowered the threshold of activation sufficiently to result in autoreactivity with endogenous tissues, autoimmune toxicity was assessed in transgenic mice engineered to express the FBL gag tumor Ag as a self-antigen in hepatocytes, under control of the albumin promoter (FIG. 5A). TCR$_{gag}$ effectors were generated in vitro and $10^6$ were transferred into cyclophosphamide-treated Alb:Gag mice with disseminated leukemia. At 3 and 7 days post-transfer, liver damage was assessed by quantification of serum levels of the liver enzymes aspartate aminotransferase (AST) and alanine aminotransferase (ALT). Adoptive therapy with control or CD200R-9aas-CD28Cys$^+$ TCR$_{gag}$ cells in mice did not affect serum levels of AST or ALT at days 3 or 7 post-transfer, indicating that CD200R-9aas-CD28Cys does not induce detectable autoimmune liver damage in Alb:Gag mice (FIG. 5B).

Figure 5C:
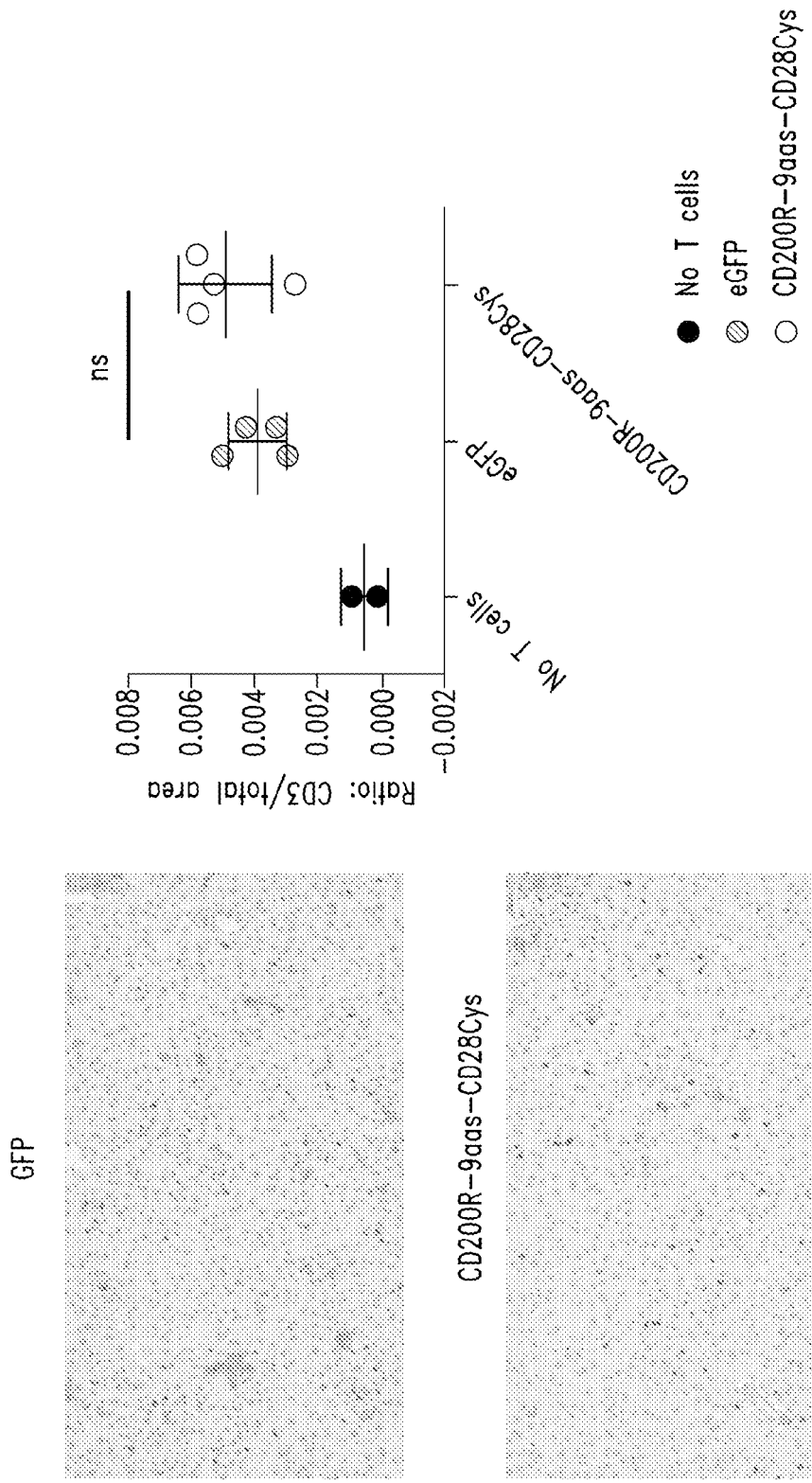

T cells transduced with IFP do not exhibit increased infiltration of normal tissues compared to control T cells. Mice were euthanized 7 days post-transfer and liver sections were stained with an antibody to the T cell marker CD3 to quantify T cell infiltration. Limited presence of T cells in liver tissue was observed, with no significant difference between recipients of CD200R-9aas-CD28Cys$^+$ or control TCR$_{gag}$, indicating no increased lymphocytic cellular infiltration as a result of IFP expression (FIG. 5C).

Example 7

Figure 6A:
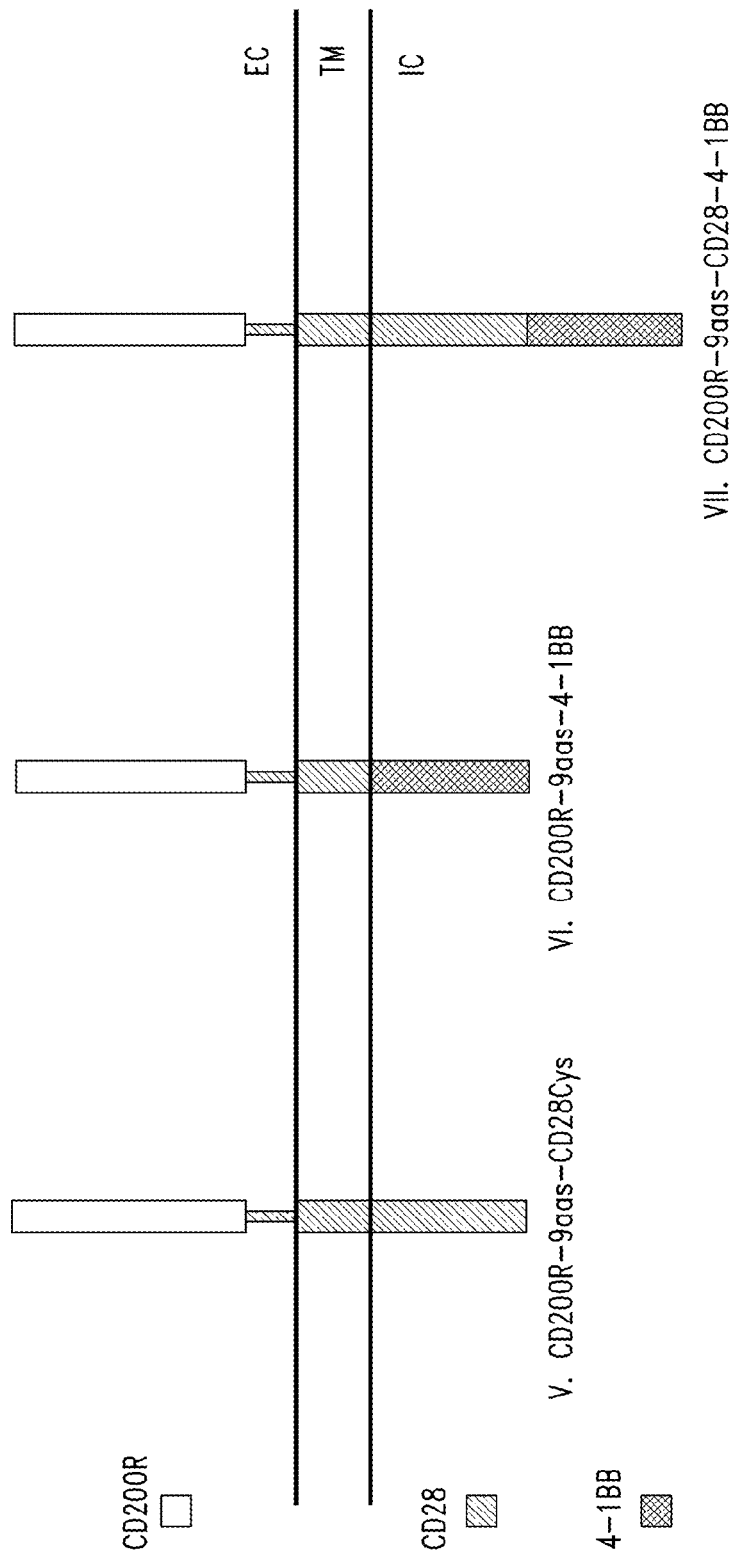
FIGS. 6A to 6D show that 4-1BB co-stimulatory signaling domains promote accumulation and effector function of transduced T cells in vitro and promote survival of tumor-bearing recipients of transduced T cell in response to CD200$^+$ tumor target cells. (A) Schematic representation of CD200R-CD28 ("V"), -4-1BB ("VI"), and -CD28-4-1BB ("VII") constructs. (B) Expansion of transduced TCR$_{gag}$ T cells relative to non-transduced TCR$_{gag}$ T cells after weekly stimulation with irradiated CD200$^+$ FBL and splenocytes. CD200R-4-1BB and CD200R-CD28-4-1BB also promote accumulation of transduced T cells in vitro. (C) CD200R-9aas-4-1BB$^+$ CD8$^+$ T cells displayed an enhanced ability to lyse CD200$^+$ FBL cells in vitro relative to controls, using a standard CFSE-based cytotoxicity assay. The percentage of FBL of the sum of FBL and control tumor cells was determined by flow cytometry. The percentage lysis was determined by dividing the percent of FBL incubated with T cells by the percent of FBL incubated without T cells. (D) CD200R-41BB-transduced T cells also promote survival relative to controls. C57BL/6 mice were injected with 4×10$^6$ CD200$^+$ FBL cells. Five days later, CD200R-9aas-CD28, CD200R-9aas-4-1BB, CD200R-9aas-CD28-4-1BB, or eGFP TCR$_{gag}$ T cells were injected i.p. into cyclophosphamide-treated FBL-bearing mice at $10^5$ cells/mouse.

4-1BB Co-Stimulatory Signaling Domain Promotes Accumulation of Transduced T Cells In Vitro Co-stimulatory receptor 4-1BB is upregulated on activated T cells, which promotes T cell survival and cytokine production (Chen and Flies, Nat. Rev. Immunol. 13: 227-242, 2013). To assess if the intracellular signaling domain of 4-1BB, with or without the intracellular signaling domain of CD28, could induce increased T cell proliferation and accumulation, IFPs using 4-1BB (CD200R-9aas-4-1BB) or combining 4-1BB with CD28 (CD200R-9aas-CD28-4-1BB) were generated (FIG. 6A) using the methods described in Example 2. TCR$_{gag}$ T cells were transduced as in Example 2, and TCR$_{gag}$ effector cells were generated in vitro as in Example 3.

Figure 6B:
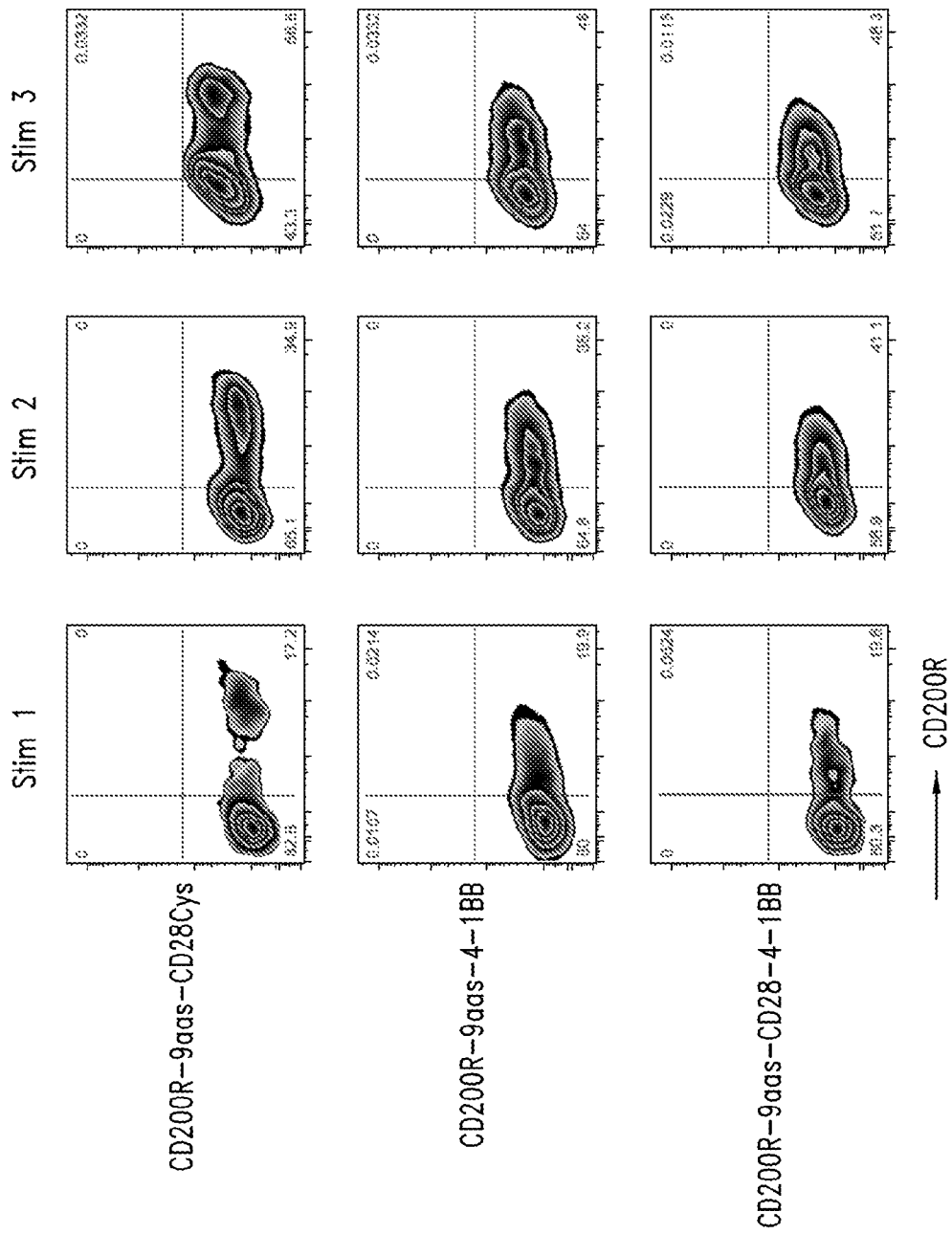

As was observed with CD200R-9aas-CD28Cys, T cells transduced with the 4-1BB constructs accumulated over multiple rounds of stimulation in vitro (FIG. 6B). These data indicate that 4-1BB IFPs also promote proliferation and survival of T cells.

Figure 6C:
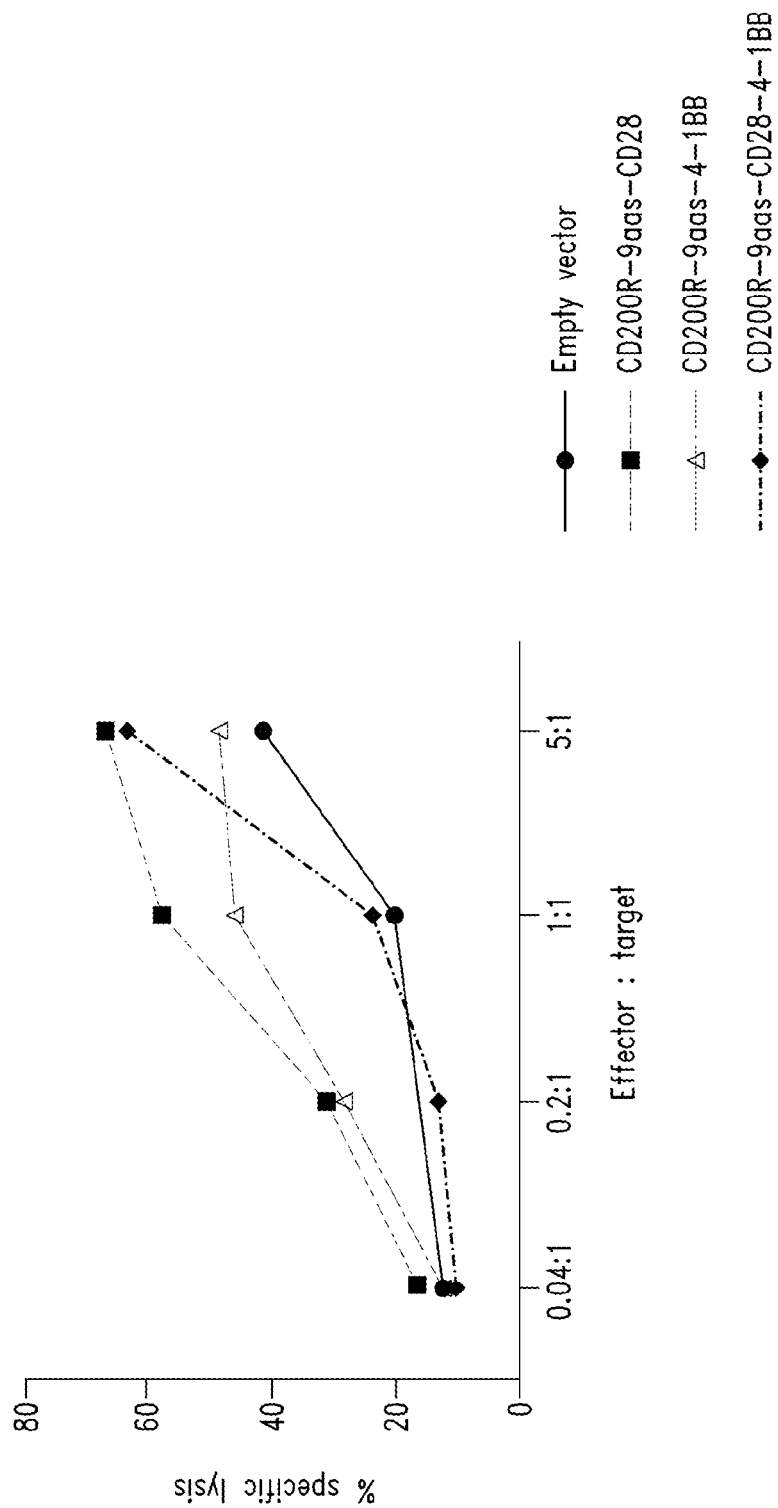
Figure 6D:
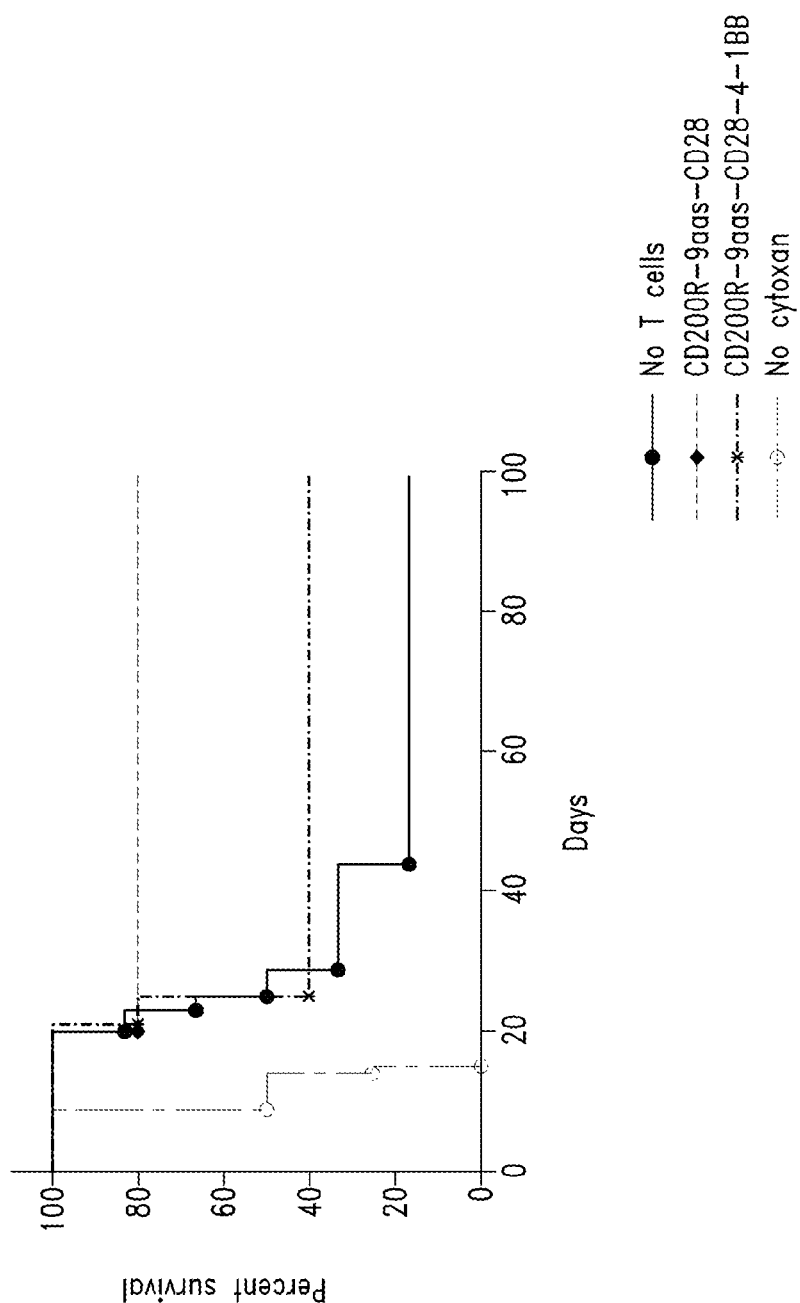

TCR$_{gag}$ T cells transduced with a CD200R-4-1BB displayed an enhanced ability to lyse FBL tumor in vitro using the CFSE-based cytotoxicity assay described in Example 3 (FIG. 6C). CD200R-41BB-transduced T cells also promote survival (FIG. 6D).

Example 8

Figure 7A:
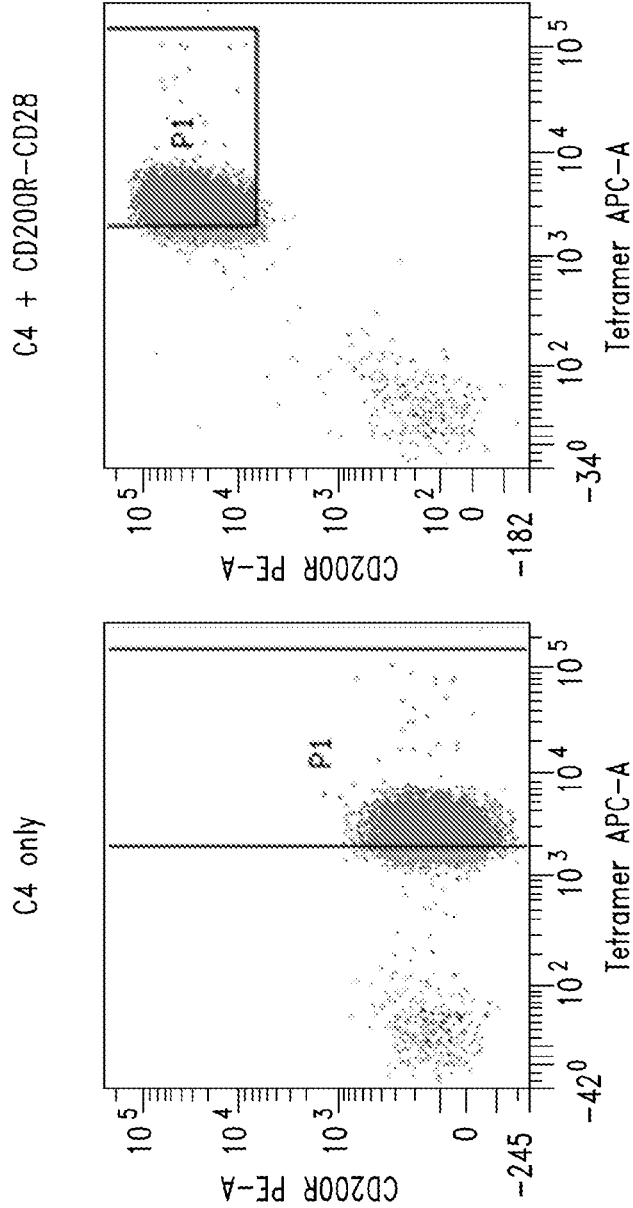
FIGS. 7A to 7D show that human primary T cells transduced to express a WT1-specific TCR and a CD200Rtm-CD28 fusion protein exhibit enhanced proliferation to target cells that express CD200 and increased cytokine production in response to tumor cells that express CD200. (A) Expression of the WT1$_{126}$-specific TCR, C4, and CD200Rtm-CD28. (B) Expression of CD200 in T2 and K562 cells. T2 cells exhibit low-level endogenous CD200 expression. (C) Proliferation of T cells as indicated by CFSE. Cells that proliferate in response to antigen show reduced CFSE fluorescence intensity. T cells transduced with both C4 and the IFP show enhanced proliferation to target cells expressing low levels of CD200 relative to T cells transduced with C4 only. (D) Cytokine production in response to exposure to CD200dim tumor cells, as measured by flow cytometry. Relative to control T cells transduced with the TCR C4 alone, T cells transduced with both C4 and the IFP CD200Rtm-CD28 show increased cytokine production.

Co-Expression of CD200Rtm-CD28 Enhances Function in WT1-Specific TCR Primary T Cells A human CD200Rtm-CD28 construct (SEQ ID NO.:1) was generated to determine if IFP expression enhanced T cell function of human primary T cells. The construct was combined with the beta and alpha chains of the HLA-A2-restricted WT1$_{126}$-specific TCR "C4" by linking the genes with P2A elements (FIG. 7A). The first P2A sequence was codon optimized to prevent genetic recombination with the second P2A sequence. To generate lentiviruses, 293 T/17 cells (3×10⁶ cells/plate) were transduced with human constructs in the pRRLSIN and the packaging vectors pMDLg/pRRE, pMD2-G, and pRSV-REV using Effectene (Qiagen). Culture media was changed on day 1 post-transfection and virus-containing supernatant collected on days 2 and 3, and aliquots frozen for future use.

The Jurkat human T cell subline, which lacks an endogenous TCR, was used to test expression of the IFP and TCRs. These Jurkat T cells were transduced by spinfection of 2×10⁶ cells with 2 ml of retroviral supernatant at 1000 g for 90 min at 32° C. Transduction of the Jurkat human T cell line with the three-gene construct resulted in high expression of the IFP and expression of the TCR at a similar MFI as T cells transduced with the TCR only (FIG. 7A).

To transduce primary human T cells, peripheral blood mononuclear cells (PBMC) were harvested from HLA-A2+ donors. CD8⁺ T cells were purified using Miltenyi magnetic beads and stimulated with Human T cell Expander CD3/CD28 Dynabeads (Life Technologies) and 50 IU/ml IL-2. Four hours following stimulation, T cells were transduced as described above for Jurkat T cells. T cells were restimulated every 10-14 days with a rapid expansion protocol (REP), as has been previously described (Ho et al., *J Immunol Methods* 310:40-52, 2006).

Figure 7B:
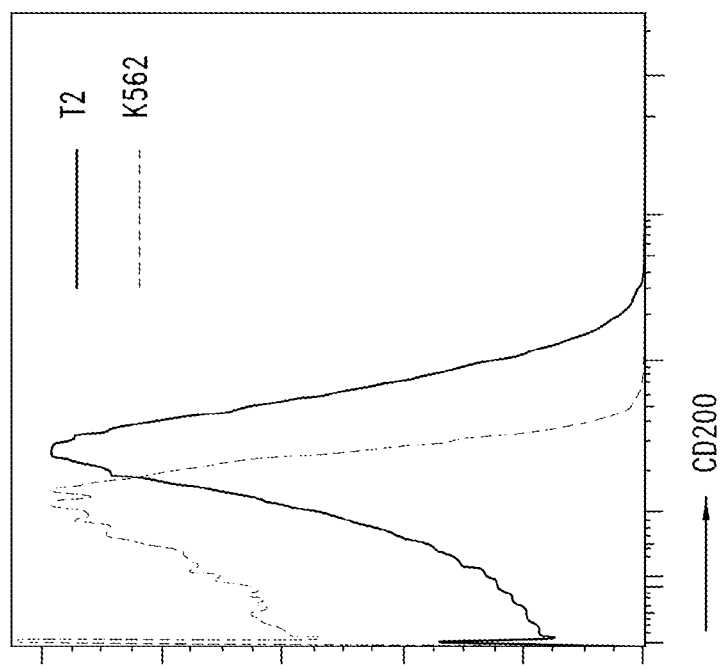

The human cell line T2 was used as an APC, because it is deficient in TAP and thus cannot present endogenous peptides, while low level MHCI expression allows presentation of exogenously loaded peptides. Expression of CD200 by the T2 cells was assessed by flow cytometry (FIG. 7B). T2 cells exhibited a low level of endogenous CD200 expression (FIG. 7B).

Figure 7C:
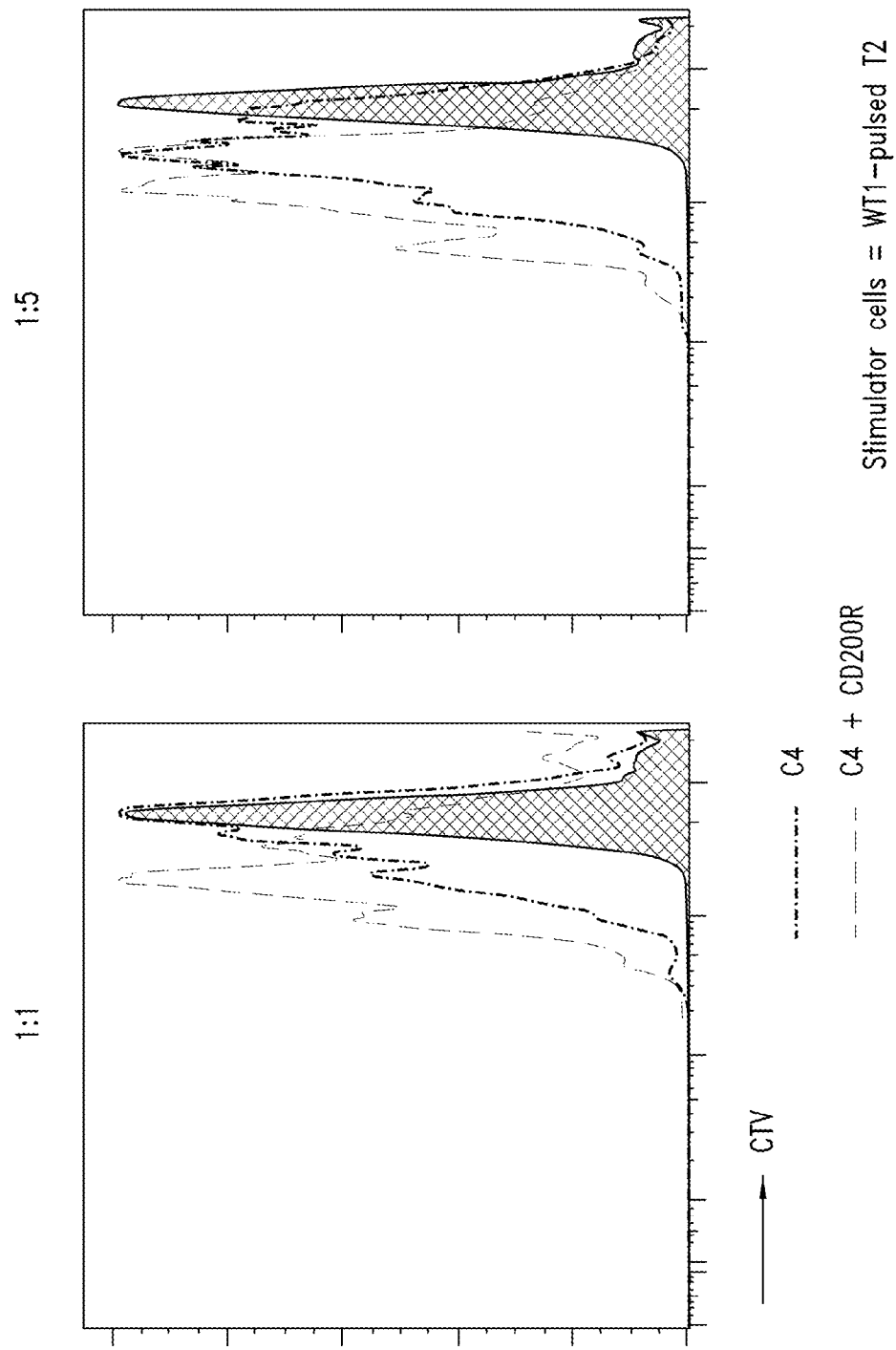
Figure 7D:
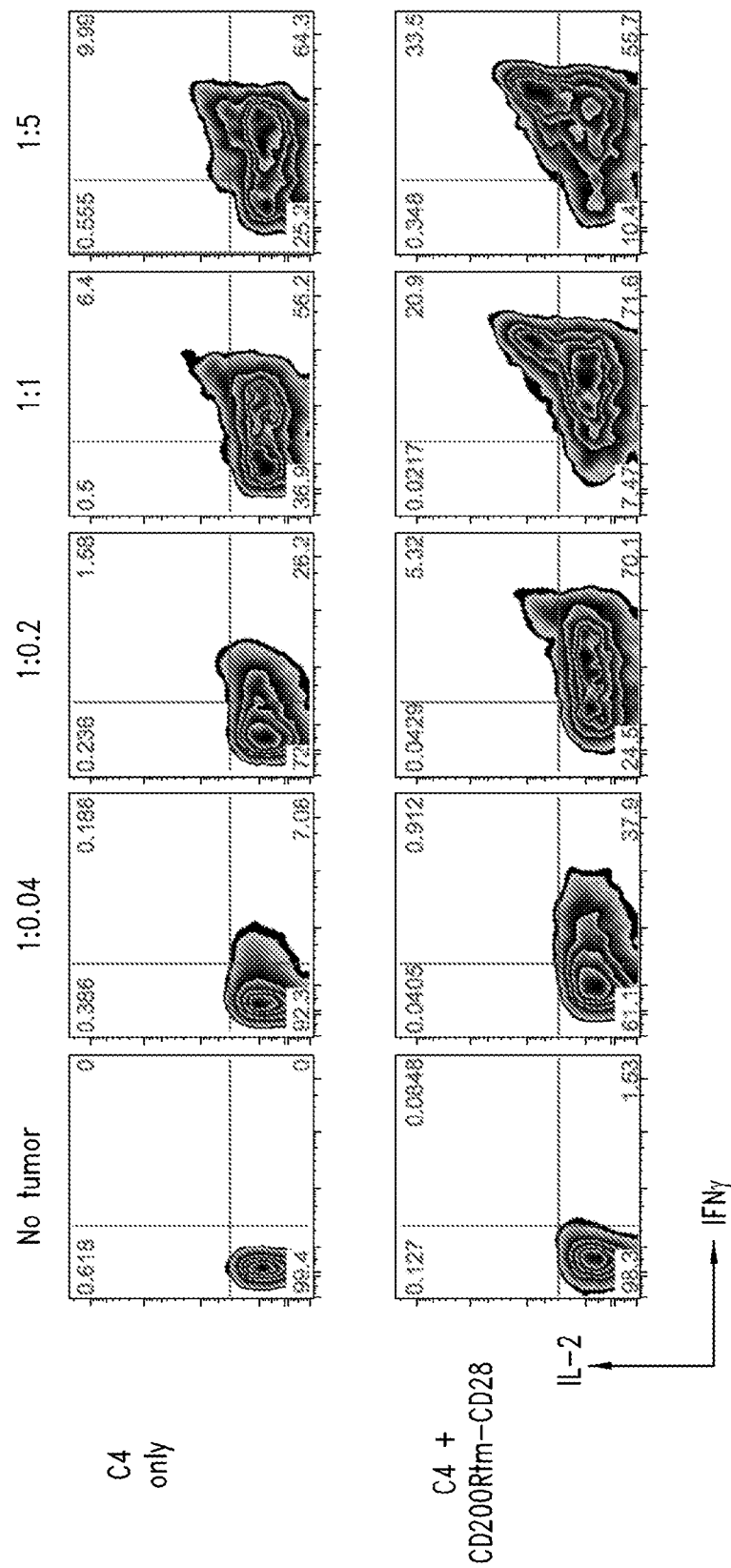

Transduced T cells were stimulated with WT1$_{126}$-pulsed T2 cells. Despite a low level of CD200 expression on the target cells, CD200Rtm-CD28-transduced T cells exhibited enhanced proliferation as compared to T cells transduced with the C4 TCR alone (FIG. 7C). In addition, stimulated CD200Rtm-CD28-transduced T cells (i.e., IFP⁺ T cells) produced increased levels of IFNγ and IL-2 compared to control T cells when exposed to CD200dim tumor cells (FIG. 7D).

Overall, these results showed that primary T cells transduced to express a human CD200Rtm-CD28 construct and the beta and alpha chains of a WT1$_{126}$-specific TCR exhibited enhanced proliferation and increased cytokine production relative to T cells transduced with the TCR construct alone.

Example 9

Figure 8A:
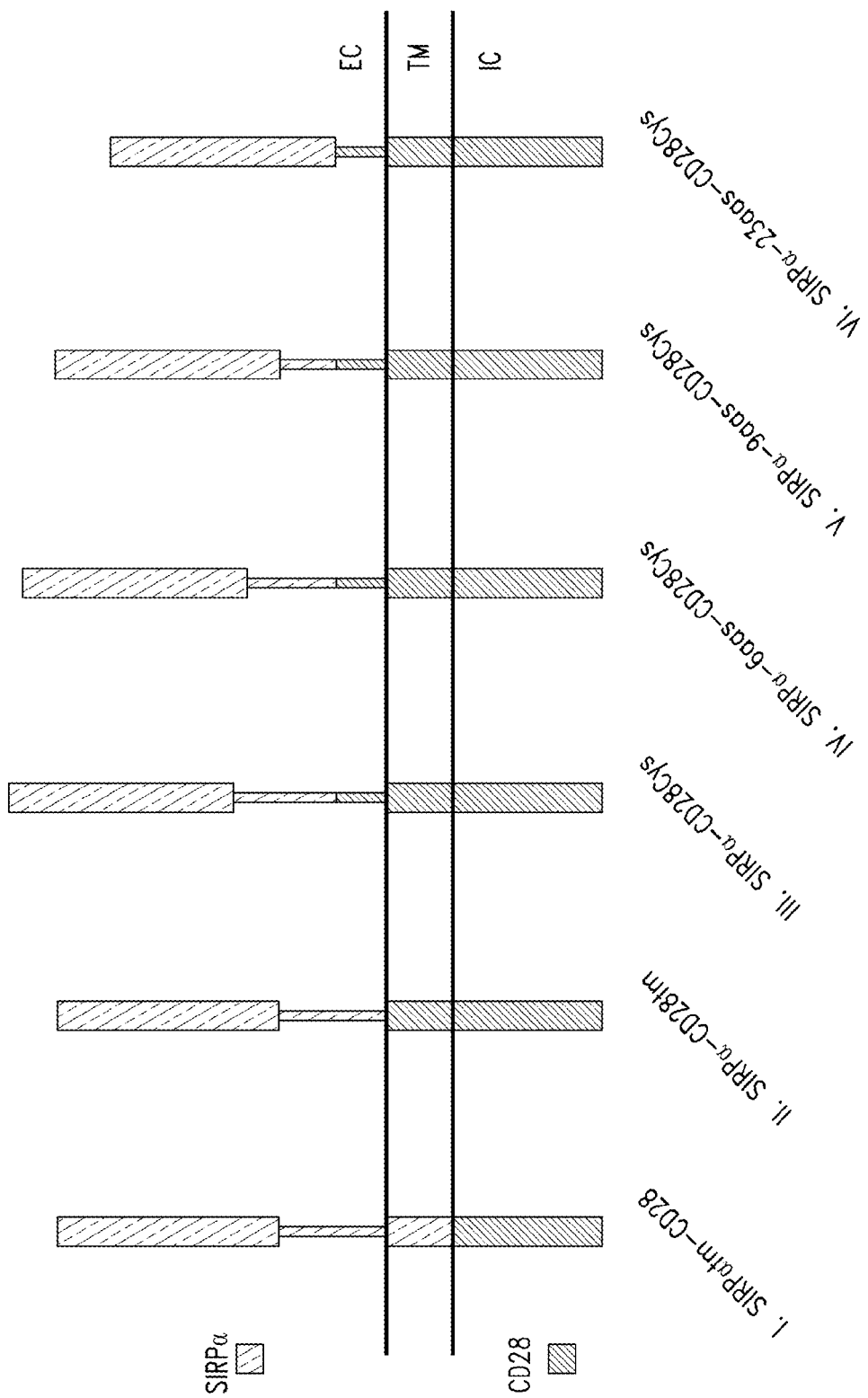
FIGS. 8A to 8E show that fusion proteins comprising SIRPα extracellular components and CD28 co-stimulatory signaling domains promote accumulation and proliferation of transduced T cells in vitro. (A) Schematic representation of exemplary SIRPα-CD28 constructs. Construct "I" contains SIRPα extracellular ("EC") and transmembrane ("TM") domains and a CD28 intracellular ("IC") signaling domain (SIRPαtm-CD28). Construct "II" contains the extracellular domain of SIRPα and the transmembrane and intracellular domains of CD28 (SIRPα-CD28tm). Constructs "III-VI" also incorporate a portion of the extracellular domain of CD28 to the transmembrane-proximal cysteine to promote multimerization and enhance CD28 signaling. To account for the extra extracellular amino acids (e.g., extra nine (9) amino acids for murine constructs, or twelve (12) amino acids for human constructs), some constructs have a truncated portion of an extracellular or intracellular domain (e.g., a SIRPα that preserves an N linked glycosylation site). Construct IV has a truncated portion of SIRPα that is truncated 6 amino acids to preserve an N linked glycosylation site. Construct V has a truncated portion of SIRPα that is truncated 9 amino acids. Construct VI has a truncated portion of SIRPα that is truncated 23 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) Expansion of transduced TCR$_{gag}$ T cells relative to non-transduced TCR$_{gag}$ T cells after weekly stimulation with irradiated SIRPα$^+$ FBL and splenocytes. SIRPα-CD28 constructs promote accumulation of transduced T cells in vitro, with SIRPα-9aas-CD28Cys exhibiting enhanced accumulation. (C) Proliferation of T cells transduced with SIRPα-CD28 constructs in a CellTrace Violet (CTV) dilution proliferation assay. T cells expressing SIRPα-CD28 constructs engineered to maintain T cell-tumor cell distance exhibited enhanced proliferation relative to nontransduced T cells. (D) CD47$^+$ tumor cells were killed after co-culture with SIRPα-CD28$^+$ T cells transduced to express SIRPαtm-CD28 or SIRPα-9aas-CD28Cys constructs. In contrast, tumor cells were not eradicated when cultured with T cells receiving empty vector, or a truncated SIRPα lacking its intracellular domain. (E) Results of an IncuCyte® assay used to quantify killing of CD47$^+$ tumor cells. CD47$^+$ FBL tumor cells were transduced with mCherry. Loss of red signal indicates killing of tumor cells. Killing of tumor cells was tested at the effector:target ratios of 10:1, 2:1, and 0.4:1. SIRPα-CD28$^+$ T cells killed CD47$^+$ tumor cells, even at the lowest effector-to-target ratio tested.

Sirpα-CD28 Fusion Protein Constructs Promote Accumulation of Transduced T Cells In Vitro Exemplary fusion proteins as described herein also include IFPs comprised of the extracellular domain of SIRPα, or portions thereof, and an intracellular signaling domain of CD28 (FIG. 8A). The hydrophobic component may be comprised of the transmembrane domain of either SIRPα or CD28, or portions thereof. In some exemplary SIRPα-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., SIRPα-CD28Cys, SIRPα-6aas-CD28Cys, SIRPα-9aas-CD28Cys, and SIRPα-9aas-CD28Cys). The extracellular component may comprise all or a portion of the extracellular domain of SIRPα. In some embodiments, the extracellular component comprises the entire extracellular domain of SIRPα. In other examples, the extracellular component comprises the first 367 amino acids (e.g., SIRPα-6aas-CD28Cys), the first 364 amino acids (e.g., SIRPα-9aas-CD28Cys), or the first 350 (SIRPα-23aas-CD28Cys) amino acids from the N-terminus of SIRPα. The size of the extracellular component may affect the ability of the fusion protein to enter the immunological synapse and co-localize with the TCR within the cSMAC to deliver a strong co-stimulatory signal. In some examples, the extracellular component comprises a truncated SIRPα, which may alter the size of the extracellular component. For example, to account for the additional extracellular amino acids of the extracellular domain of the fusion protein (e.g., an additional 9 or 12 amino acids), SIRPα-6aas-CD28 has a truncated portion of SIRPα that preserves a natural N-linked glycosylation site. In another example, SIRPα-23aas-CD28 has a truncated portion of SIRPα that lacks the entire stem region of the SIRPα extracellular domain. Additionally, a SIRPα-CD28 construct has the capacity to convert a signal initiated by the binding of SIRPα to its target into a positive (e.g., costimulatory) signal generated by the CD28 intracellular signaling domain.

IFPs using SIRPα extracellular components were generated (FIG. 8A) using the methods described in Example 2. TCR$_{gag}$ T cells were transduced as in Example 2, and TCR$_{gag}$ effector cells were generated in vitro as in Example 3. FBL cells were transduced with CD47 or mCherry with polybrene spinfection, similar to T cell transduction, and subsequently sorted to generate a homogenous population.

Figure 8B:
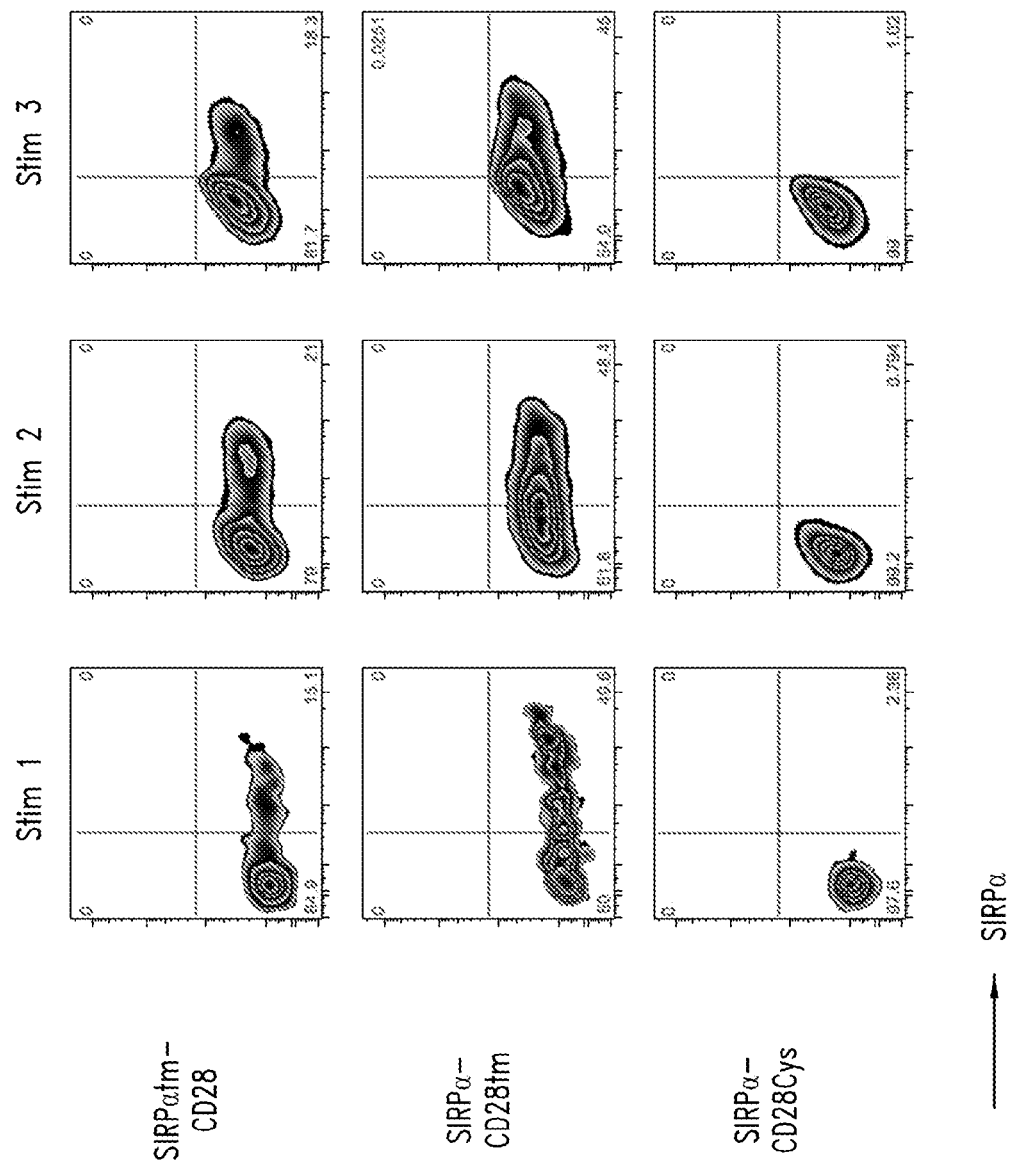
Figure 8B:
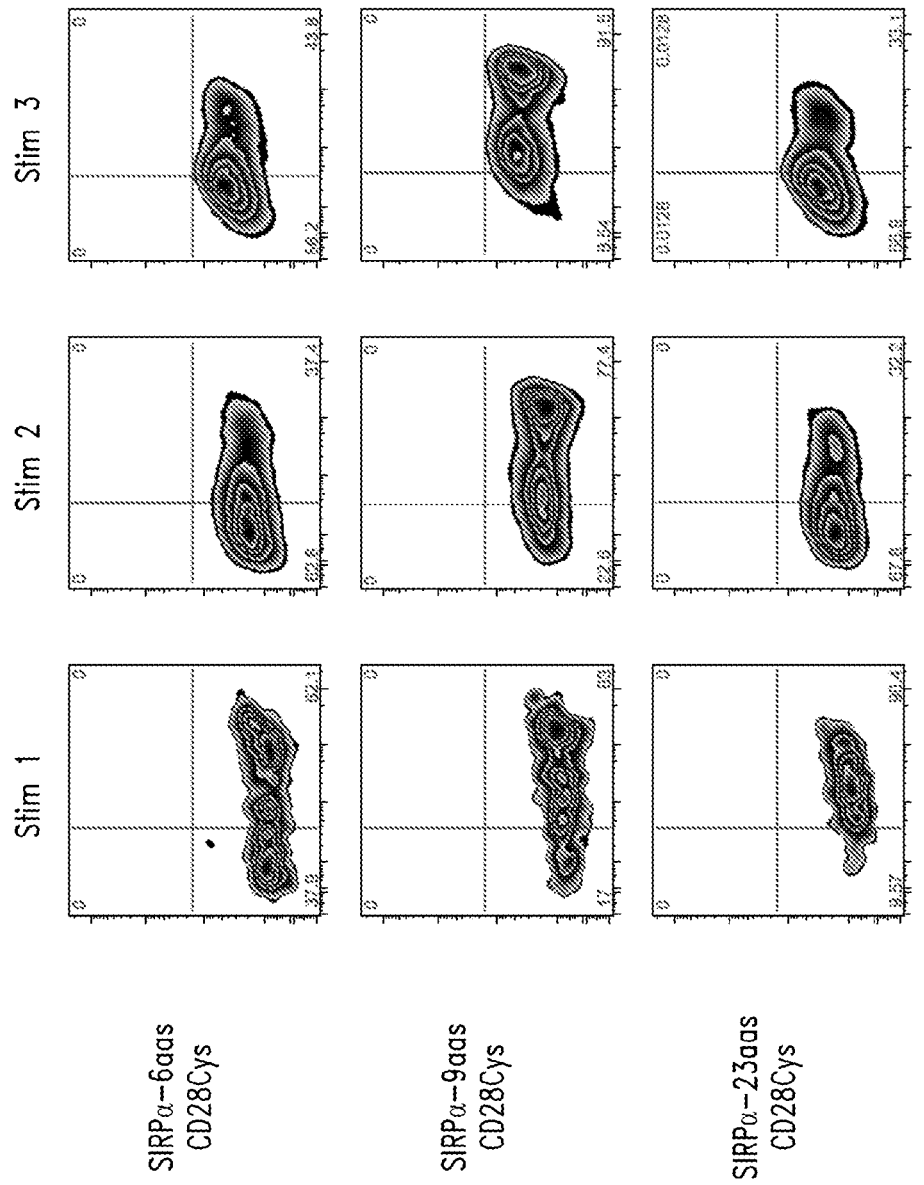

As was observed with CD200R-9aas-CD28Cys, T cells transduced with the SIRPα constructs accumulated over multiple rounds of stimulation in vitro (FIG. 8B). These data suggest that SIRPα-CD28 IFPs also promote proliferation and survival of T cells.

Figure 8C:
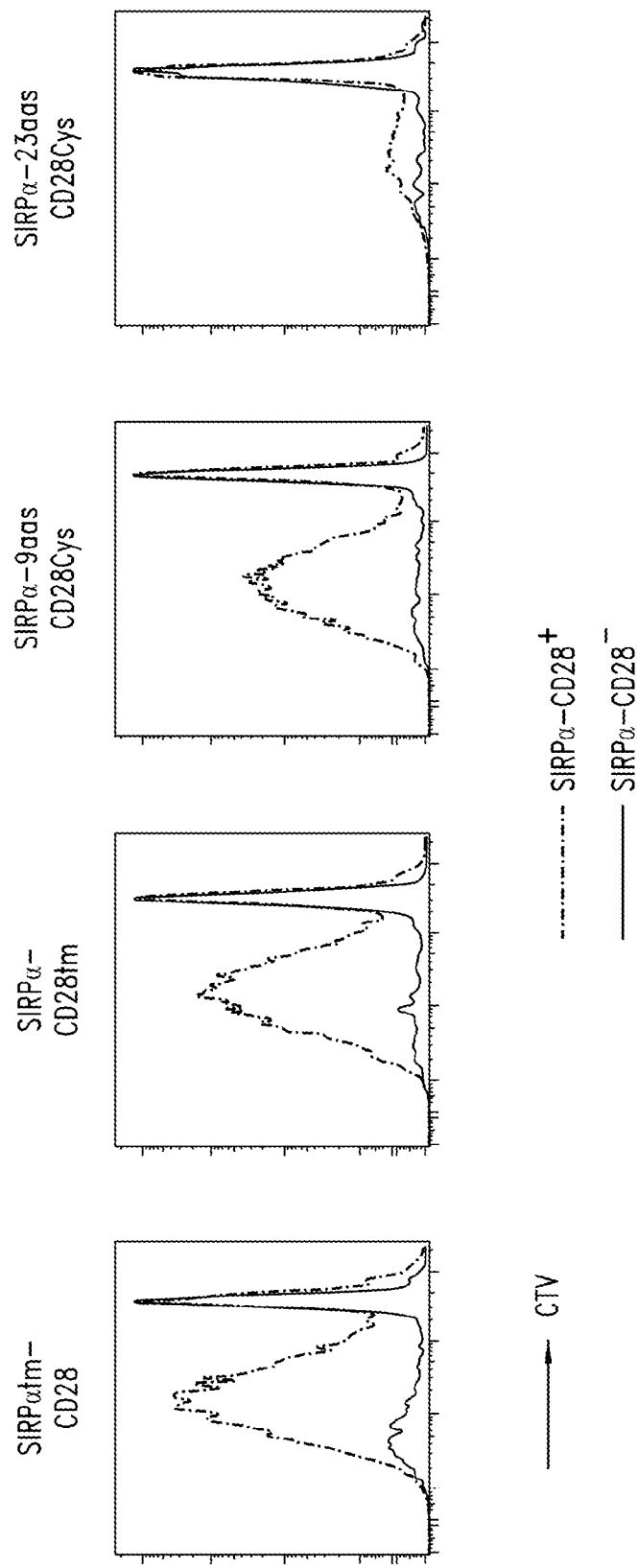
Figure 8D:
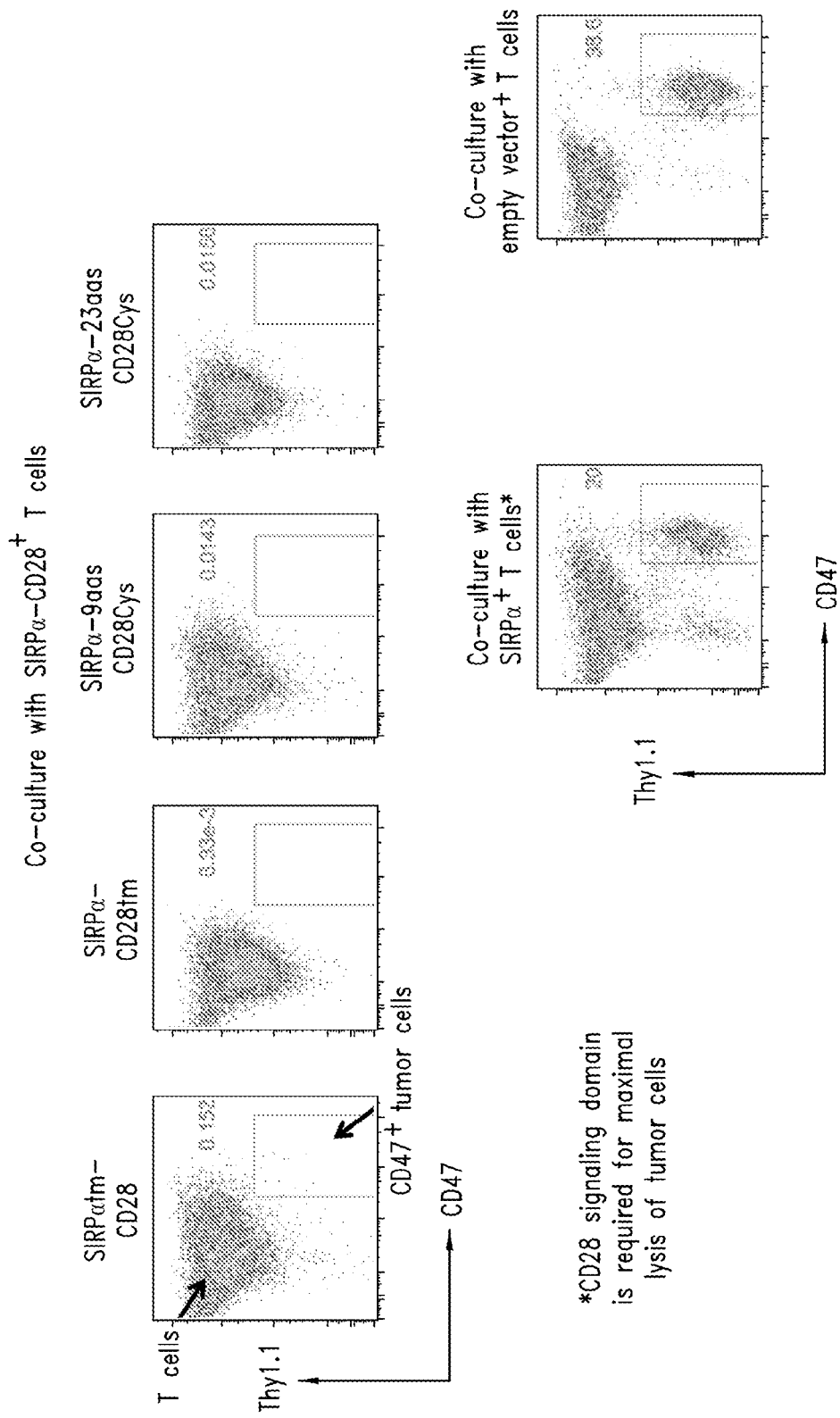
Figure 8E:
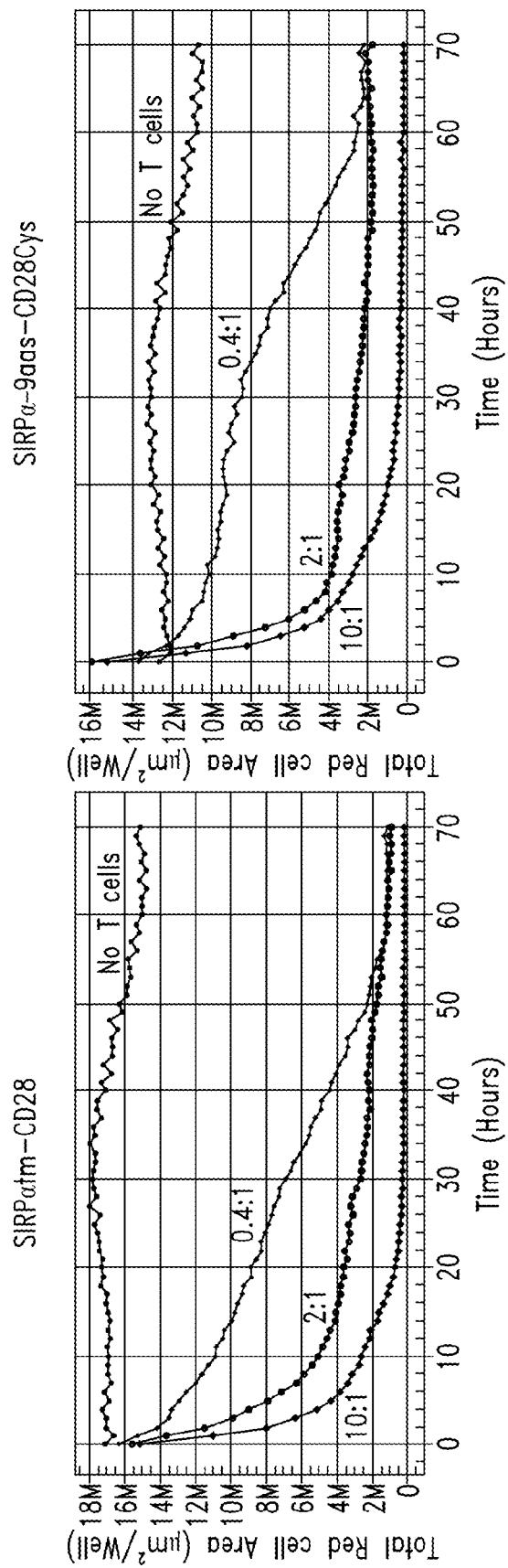

To assess T cell proliferation in vitro, a CTV Dilution Proliferation assay was performed as described in Example 2. As was observed with CD200R-9aas-CD28Cys, T cells transduced with the SIRPα constructs engineered to maintain the T cell-tumor cell synapse distance exhibited enhanced proliferation as compared to control T cells (FIG. 8C). In addition, CD47⁺ tumor cells were efficiently killed after 3 days of co-culture with SIRPα-CD28⁺ T cells but not control T cells or T cells transduced with a SIRPα construct that lacked an intracellular signaling domain (FIG. 8D). To further assess the lytic capacity of SIRPα-CD28⁺ T cells, an IncuCyte® assay was used to quantify killing of CD47⁺ FBL. A total of 10⁵ mCherry⁺ CD47⁺ FBL were co-cultured in 24-well plates with a titration of human T cells transduced with SIRPα-CD28 constructs. The plate was incubated in an IncuCyte® (Essen BioScience) inside a cell culture incubator for 70 hours. Images were captured every hour to monitor killing of tumor cells, as determined by loss of red signal. SIRPα-CD28+ T cells killed CD47+ tumor cells, even at the lowest effector-to-target ratio tested (0.4:1; FIG. 8E).

Example 10

Figure 9A:
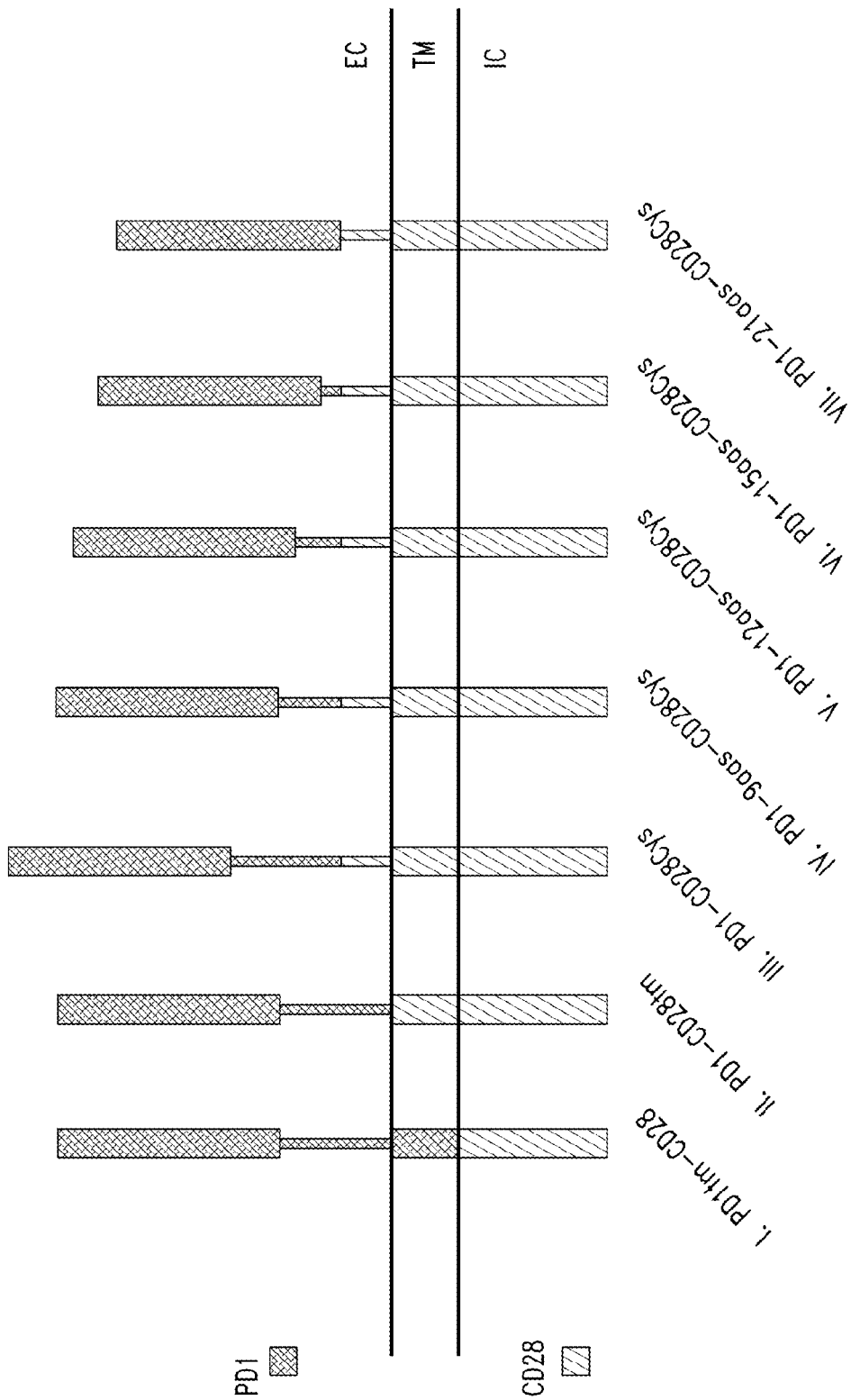
FIGS. 9A and 9B show that fusion proteins comprising PD-1 extracellular components and CD28 co-stimulatory signaling domains promote cytokine production in vitro. (A) Schematic representation of exemplary PD-1-CD28 constructs. Construct "I" contains PD-1 extracellular ("EC") and transmembrane ("TM") domains and a CD28 intracellular ("IC") signaling domain (PD1tm-CD28). Construct "II" contains the extracellular domain of PD-1 and the transmembrane and intracellular domains of CD28 (PD1-CD28tm). Constructs "III-VII" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), constructs IV-VII have a truncated portion of PD-1. Construct IV has a truncated portion of PD-1 that is truncated 9 amino acids. Construct V has a truncated portion of PD-1 that is truncated 12 amino acids. Construct VI has a truncated portion of PD-1 that is truncated 15 amino acids. Construct VII has a truncated portion of PD-1 that is truncated 21 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) PD1-CD28$^+$ T cells exhibited increased cytokine production in response to stimulation for 5 hours in the presence of Brefeldin A with FBL cells that endogenously express the PD-1 ligands, PD-L1 and PD-L2. Stimulated T cells were assessed for intracellular expression of the effector cytokines, IFNγ and TNFα, by flow cytometry.

PD-1-CD28 Fusion Protein Constructs Promote Cytokine Production in Transduced T Cells In Vitro Exemplary fusion proteins as described herein also include IFPs comprised of the extracellular domain of PD-1, or portions thereof, and an intracellular signaling domain of CD28 (FIG. 9A). The transmembrane component may be comprised of the transmembrane domain of either PD-1 or CD28, or portions thereof. In some exemplary PD1-CD28 fusion proteins, the transmembrane component comprises the transmembrane domain of CD28 and the extracellular component further comprises an extracellular portion of CD28, particularly an extracellular cysteine residue adjacent to the transmembrane component (e.g., PD1-CD28Cys, PD1-9aas-CD28Cys, and PD1-21aas-CD28Cys) to promote inter-chain dimerization. The extracellular component may comprise all or a portion of the extracellular domain of PD-1, or may be truncated (e.g., –9aas in murine constructs, –12aas or –15aas in human constructs; lacking the stem region of PD-1, –21aas) to maintain the short spatial distance between the cells to facilitate access of the liganded receptor to the immunologic synapse. Additionally, a PD1-CD28 construct has the capacity to convert what would typically be an inhibitory signal from the binding of PD1 to its target into a positive (e.g., costimulatory) signal generated by the CD28 intracellular signaling domain.

IFPs comprising PD-1 extracellular components were generated (FIG. 9A) using the methods described in Example 2. $TCR_{gag}$ T cells were transduced as in Example 2, and $TCR_{gag}$ effector cells were generated in vitro as in Example 3.

Figure 9B:
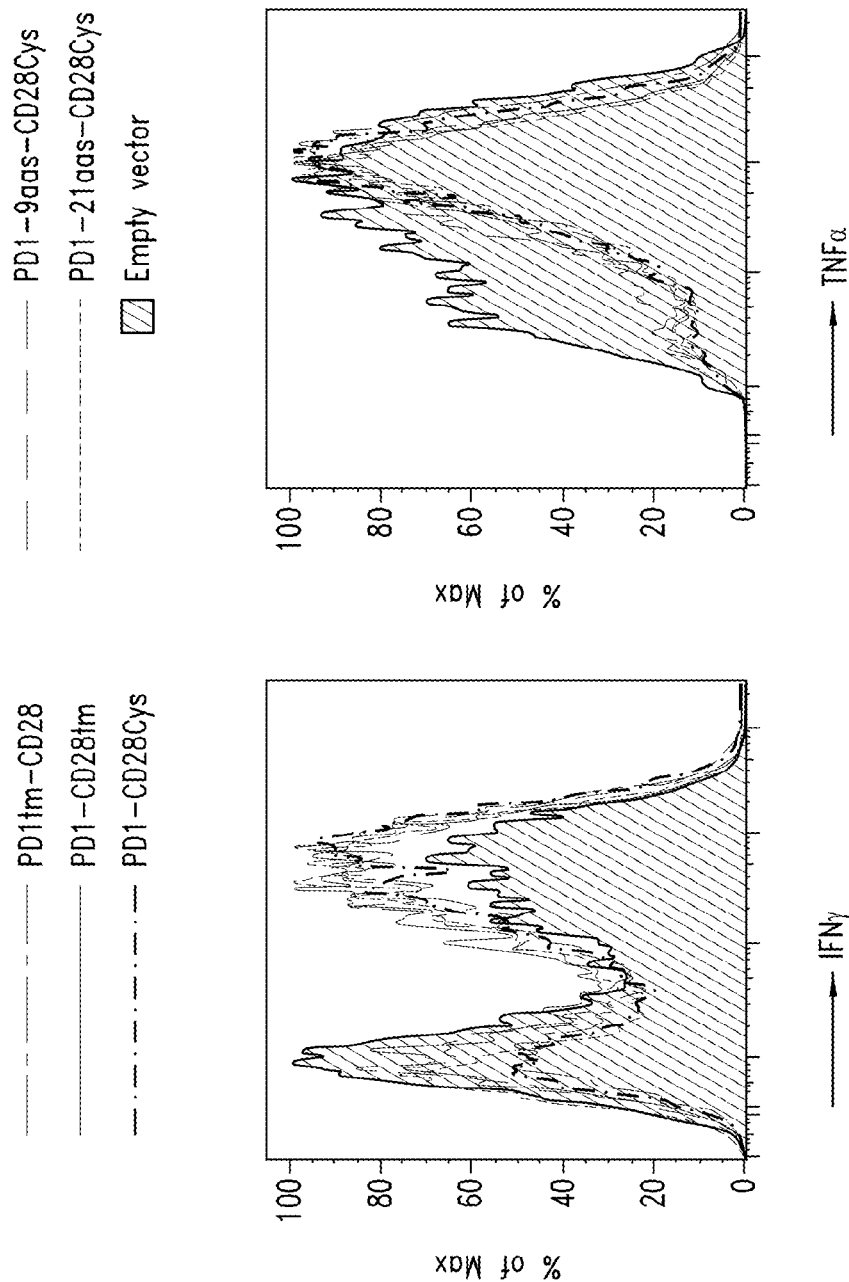

Murine PD1-CD28 IFPs were generated using constructs I-IV and VII (FIG. 9A). PD1-CD28+ T cells were restimulated in the presence of Brefeldin A (to retain produced cytokines) with FBL cells endogenously expressing the PD-1 ligands, PD-L1 and PD-L2. After 5 hours, cells were fixed and treated with the BD Cytofix/Cytoperm kit, to allow intracellular staining of the effector cytokines, IFNγ and TNFα. Transduction with each of the five PD1-CD28 constructs enhanced production of intracellular cytokines compared to control T cells (FIG. 9B).

Figure 10:
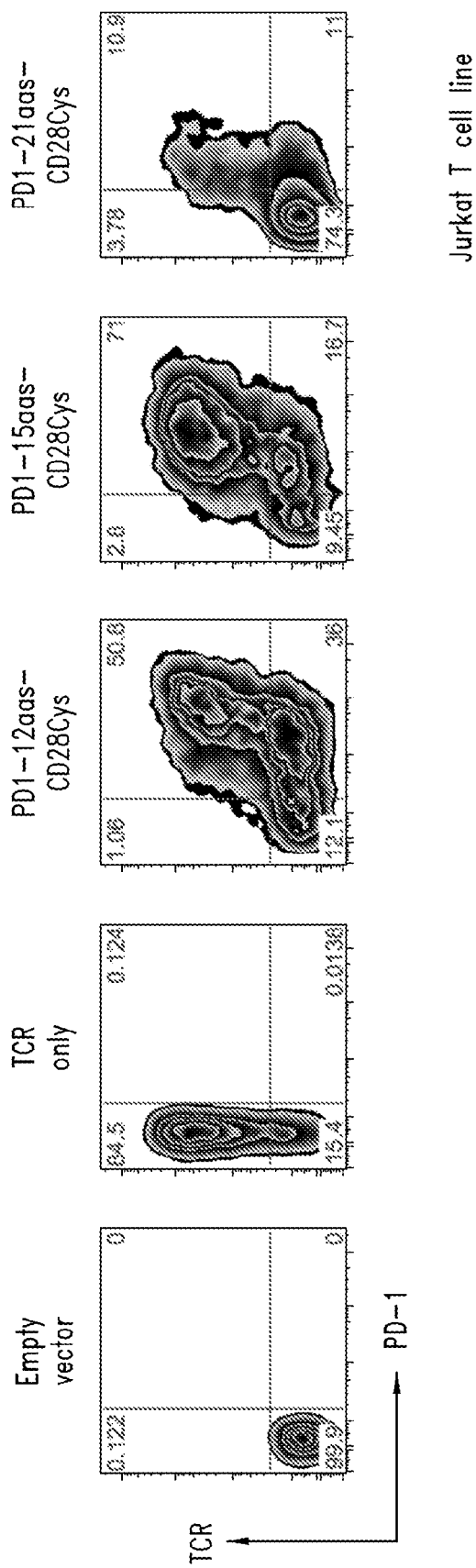
FIG. 10 shows co-expression of the TCR C4 and a PD-1 IFP (PD1-12aas-CD28Cys, PD1-15aas-CD28Cys, or PD1-21aas-CD28Cys). T cells transduced with C4 and PD1-12aas-CD28Cys or PD1-15aas-CD28Cys exhibited high transduction efficiencies and expression of both proteins.

Human PD1-CD28 IFPs were generated using constructs I-III and V-VII (FIG. 9A). Vectors containing the PD1-CD28 IFP and C4 TCR were generated as described above. Jurkat T cells were transduced as described above. T cells transduced with the TCR and PD1-12aas-CD28Cys or PD1-15aas-CD28Cys exhibited high transduction efficiencies and expression of both proteins (FIG. 10).

Example 11

Figure 11A:
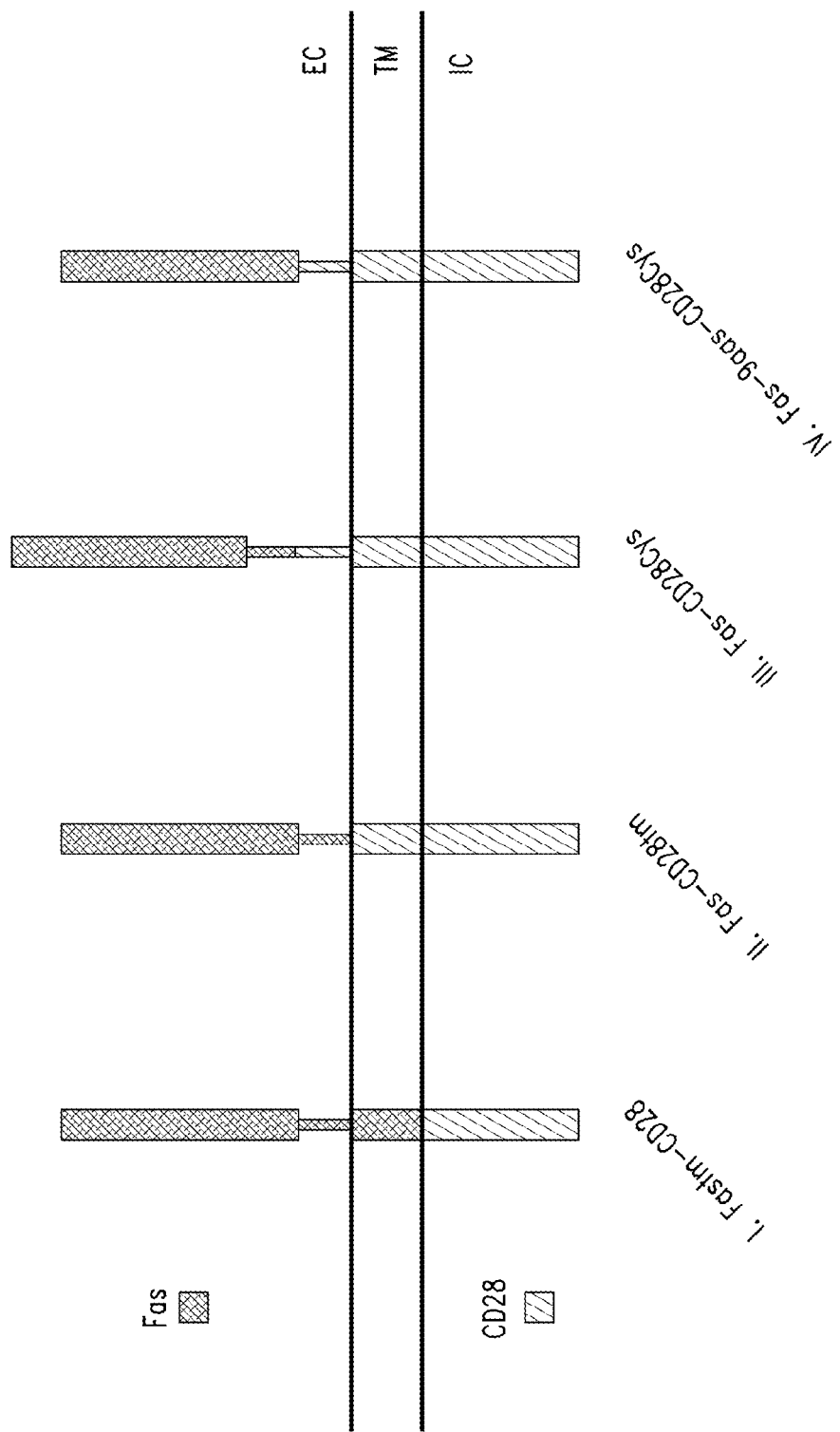
FIGS. 11A to 11C show that fusion proteins comprising Fas extracellular components and CD28 co-stimulatory signaling domains accumulate in vitro upon stimulation with irradiated FBL cells. (A) Schematic representation of exemplary Fas-CD28 constructs. Construct "I" contains Fas extracellular ("EC") and transmembrane ("TM") domains and a CD28 intracellular ("IC") signaling domain (Fastm-CD28). Construct "II" contains the extracellular domain of Fas and the transmembrane and intracellular domains of CD28 (Fas-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of Fas, wherein the Fas extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Accumulation of TCR$_{gag}$ T cells transduced with Fas constructs over multiple stimulations with irradiated FBL cells. All of the constructs promoted accumulation of T cells relative to control T cells. (C)

Fas-CD28 Fusion Protein Constructs Promote Accumulation and Enhanced Function in Transduced T Cells In Vitro Exemplary fusion proteins as described herein also include IFPs comprised of the extracellular domain of Fas, or portions thereof, and an intracellular signaling domain of CD28 (FIG. 11A). The transmembrane component may be comprised of the domain of either Fas or CD28, or portions thereof. In some exemplary Fas-CD28 fusion proteins, the transmembrane component comprises the transmembrane domain of CD28 and the extracellular component further comprises an extracellular portion of CD28, particularly an extracellular cysteine residue adjacent to the transmembrane component (e.g., Fas-CD28Cys and Fas-9aas-CD28Cys). The extracellular component may comprise all or a portion of the extracellular domain of Fas or may be truncated to preserve maintain a short spatial distance between the cells (–9aas) upon receptor-ligand interaction. Additionally, a Fas-CD28 construct has the capacity to convert a signal initiated by the binding of Fas to its target into a positive (e.g., costimulatory) signal generated by the CD28 intracellular signaling domain.

IFPs comprising Fas extracellular components were generated (FIG. 11A) using the methods described in Example 2. $TCR_{gag}$ T cells were transduced as in Example 2, and $TCR_{gag}$ effector cells were generated in vitro as in Example 3.

Figure 11B:
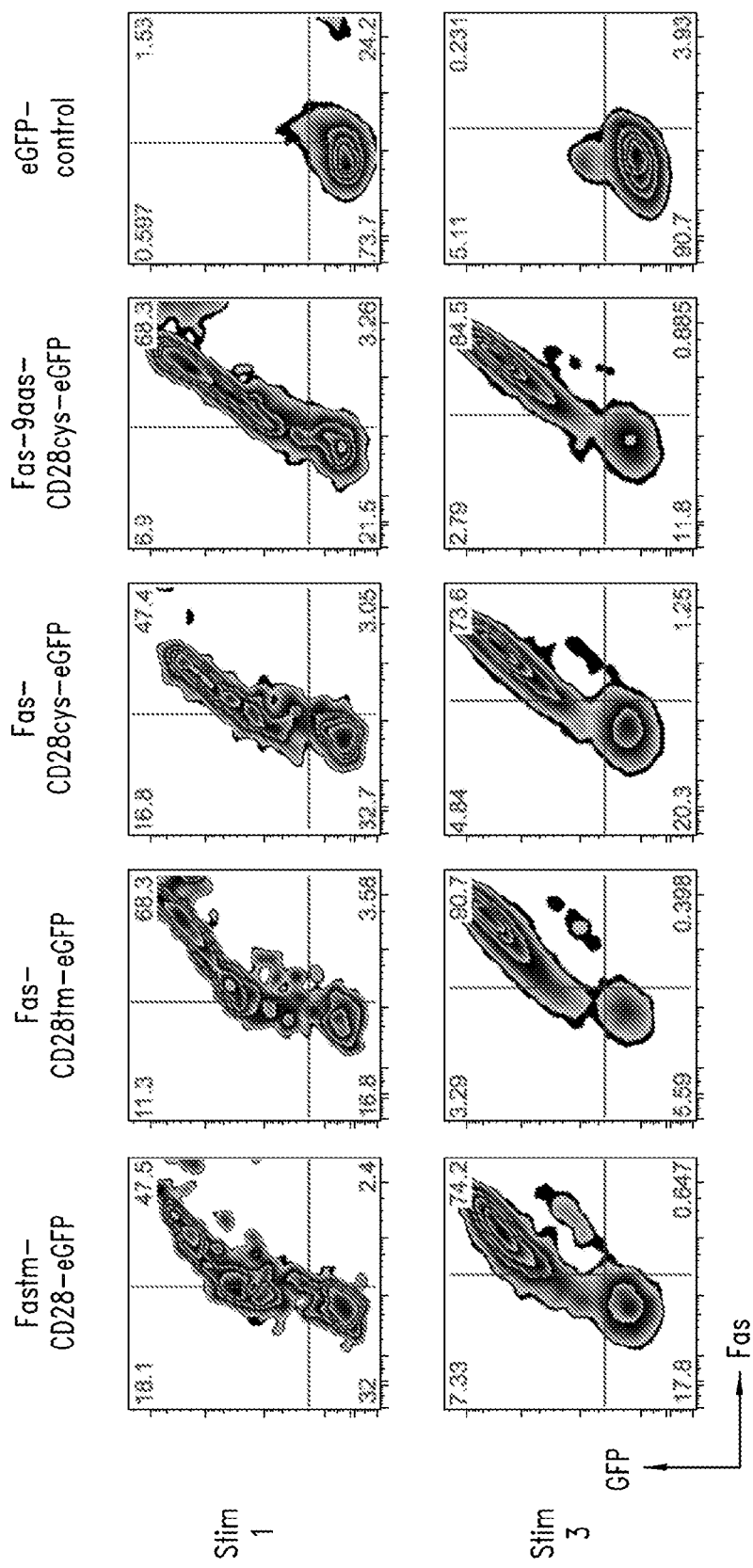
Figure 11C:
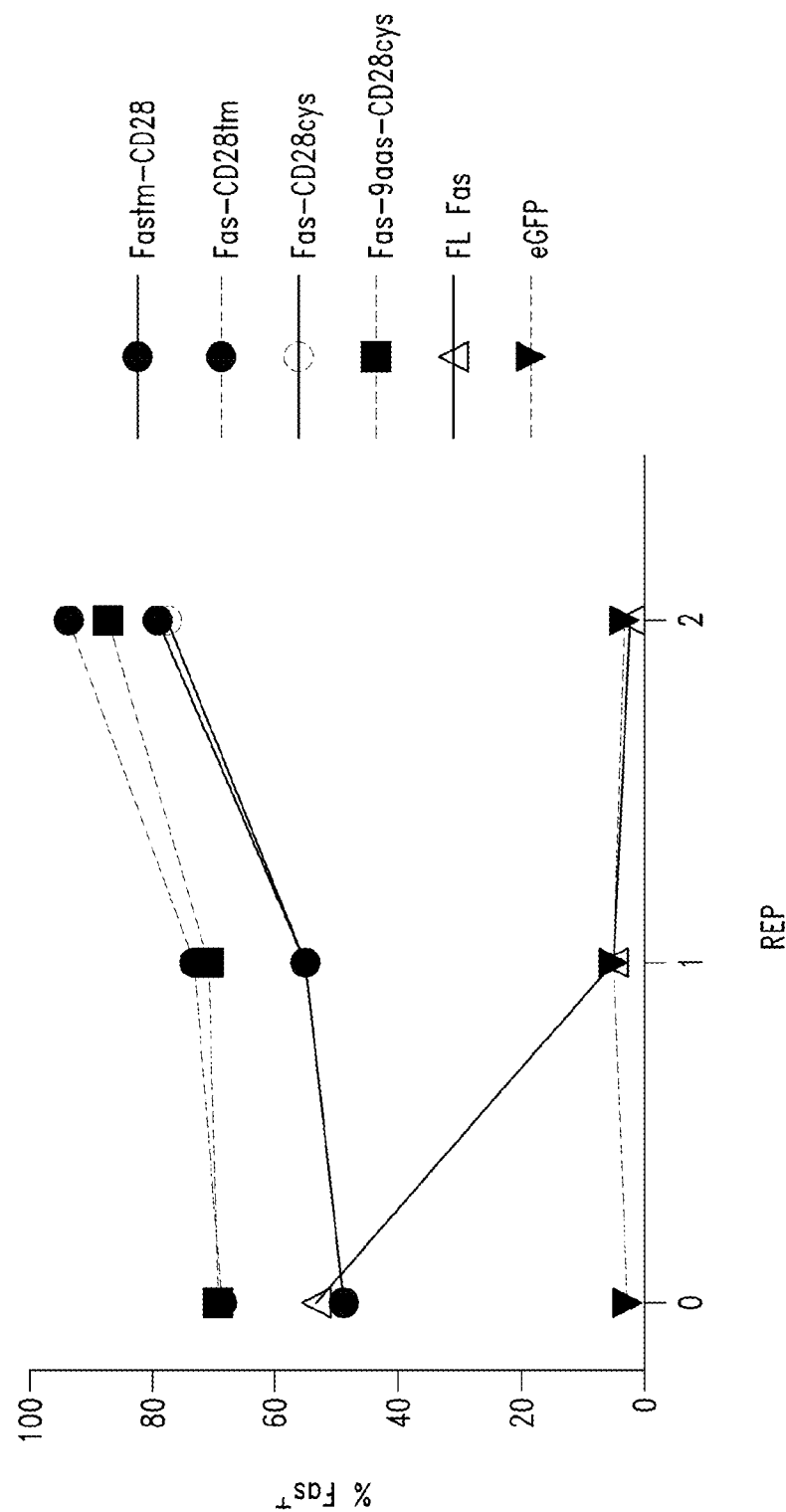

To determine if expression of the Fas-CD28 IFP results in increased accumulation of transduced cells, the proportion of transduced cells from the mixed population in the total $TCR_{gag}$ population was measured over multiple cycles of stimulation with irradiated FBL, as described in Example 3. All of the constructs promoted accumulation of transduced T cells compared to control T cells (FIG. 11B). In addition, expression of Fas-CD28 constructs but not full-length (FL) Fas promoted survival or expansion of T cells upon multiple stimulations in vitro FIG. 11C).

Example 12

LAG3-CD28 Fusion Protein Constructs

Exemplary fusion proteins as described herein also include IFPs comprised of the extracellular domain of LAG3, or portions thereof, and an intracellular signaling domain of CD28 (FIG. 12A). The transmembrane component may be comprised of the domain of either LAG3 or CD28, or portions thereof. In some exemplary LAG3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., LAG3-CD28Cys and LAG3-9aas-CD28Cys). The extracellular component may comprise all or a portion of the extracellular domain of LAG3 or may be truncated to maintain a short spatial distance between the cells (e.g., –9aas) upon receptor-ligand interaction. Additionally, a LAG3-CD28 construct has the capacity to convert what would typically be an inhibitory signal from the binding of LAG3 to its target into a positive (e.g., costimulatory) signal generated by the CD28 intracellular signaling domain.

IFPs using LAG3 extracellular components were generated (FIG. 12A) using the methods described in Example 2. T cells were transduced with LAG3-eGFP constructs as described. Five days after transduction, CD8+ T cells were analyzed for construct expression by anti-LAG3 antibody staining and flow cytometry (FIG. 12B). A vector encoding only green fluorescent protein (GFP) was used as a control. All constructs exhibited expression of LAG3 (FIG. 12B).

Example 13

TIM3-CD28 Fusion Protein Constructs

Exemplary fusion proteins as described herein also include IFPs comprised of the extracellular domain of TIM3, or portions thereof, and an intracellular signaling domain of CD28 (FIG. 13A). The transmembrane component may be comprised of the domain of either TIM3 or CD28, or portions thereof. In some exemplary TIM3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., TIM3-CD28Cys and TIM3-9aas-CD28Cys). The extracellular component may comprise all or a portion of the extracellular domain of TIM3 or may be truncated to maintain the short spatial distance between the cells (e.g., −9aas). Additionally, a TIM3-CD28 construct has the capacity to convert what would typically be an inhibitory signal from the binding of TIM3 to its target into a positive signal generated by the CD28 intracellular signaling domain.

New IFPs using TIM3 extracellular components were generated (FIG. 13A) using the methods described in Example 2. T cells were transduced with GFP-TIM3 constructs as described. Five days after transduction, CD8+ T cells were analyzed for construct expression by anti-TIM3 antibody staining and flow cytometry (FIG. 13B). A vector encoding only green fluorescent protein (GFP) was used as a control. Most constructs exhibited similar expression of TIM3 (FIG. 13B).

Example 14

CD200R-CD28 Fusion Protein Constructions can be Expressed by Primary T Cells

In a further example, exemplary fusion proteins as described herein are illustrated using schematic representations in FIG. 14A. Representative fusion proteins include IFPs comprised of the extracellular domain of CD200R or a portion thereof, and an intracellular signaling domain of CD28 or a portion thereof (FIG. 14A, constructs I-V). The hydrophobic component may be comprised of the transmembrane domain of either CD200R (FIG. 14A, construct I) or CD28 (FIG. 14A, constructs II-V), or portions thereof. In some exemplary CD200R-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., FIG. 14A construct III, CD200R-CD28Cys; construct IV, CD200R-3aas-CD28Cys; and construct V, CD200R-9aas-CD28Cys). The extracellular component may comprise all or a portion of the extracellular domain of CD200R. In some embodiments, the extracellular component comprises the entire extracellular domain of CD200R (FIG. 14A, constructs I-III). In other examples, the extracellular component comprises the first 235 amino acids (preserving an N-linked glycosylation site) (e.g., FIG. 14A, construct IV, CD200R-3aas-CD28Cys) or the first 229 amino acids (e.g., FIG. 14A, construct V, CD200R-9aas-CD28Cys) from the N-terminus of CD200R. The CD200R-CD28 constructs disclosed herein have the capacity to convert what would typically be an inhibitory signal from the binding of CD200R to its target into a positive signal generated by the CD28 intracellular signaling domain.

The size of the extracellular component, which may be manipulated by adjusting the fusion protein construct, may affect the ability of the fusion protein to enter the immunological synapse and co-localize with the TCR within the cSMAC to deliver a strong co-stimulatory signal. CD28 signaling naturally occurs in the immunological synapse, where CD28 is recruited to amplify TCR signals and lower the threshold of activation (Chen and Flies, *Nat. Rev. Immunol.* 13: 227-242, 2013; Yokosuka et al., *Immunity* 29:589-601, 2008). The spatial distance between the T cell and APC is shortest within the immunological synapse, and molecules with large ectodomains are excluded. Thus, constructs that best approximate the cell-to-cell spacing of the immunological synapse may be able to co-localize with the TCR within the immunological synapse and deliver an effective costimulatory signal. Constructs III and IV extend the CD28 transmembrane domain into the extracellular space to incorporate the membrane proximal cysteine (CD28Cys) that promotes CD28 homodimerization and enhances native CD28 signaling (Lazar-Molnar et al., *Cell Immunol.* 244: 125-129, 2006). To account for the length added by the nine amino acids of extracellular CD28 domain, the CD200R extracellular domain portion of CD200R-9aas-CD28Cys is truncated by nine amino acids, an equivalent number added by the CD28 extracellular domain. Similarly, the extracellular CD200R of CD200R-3aas-CD28Cys is truncated by 3 amino acids. The truncated extracellular CD200R is truncated from the C-terminal end, to preserve an N-linked glycosylation site. Thus, murine constructs CD200Rtm-CD28, CD200R-CD28tm, and CD200R-9aas-CD28Cys theoretically best maintain the short spatial distance between the T cell and APC needed to co-localize with the TCR in the immunological synapse.

An exemplary nucleic acid molecule encoding a CD200R-CD28 fusion protein comprises the following elements (5' to 3'): Extracellular Component (CD200R)-Multimerization Domain (CD28 Cysteine)-Hydrophobic Component (CD28 transmembrane)-Intracellular Component (CD28 intracellular). In some embodiments, a nucleic acid molecule encoding a CD200R-CD28 fusion protein comprises a nucleic acid molecule as set forth in any one of SEQ ID NOS.:47-51 or 1, 6, 7, 10, 12, 14, 15, or 183.

Nucleic acids encoding the constructs were inserted into the pMP71 retroviral vector to transduce primary mouse splenocytes stimulated with anti-CD3 and anti-CD28 antibodies. C57BL/6 (B6) mice were purchased from Jackson Laboratory. TCR$_{gag}$ transgenic mice express in CD8+ T cells a TCR transgene specific for the Friend virus gag epitope (Ohlen et al., *J. Exp. Med.* 195:1407-1418, 2002). The B6 Friend virus induced erythroleukemia (FBL) expresses the Friend virus gag epitope (peptide CCLCLTVFL (SEQ ID NO.:213)) (Teague et al., *Nat. Med.* 12:335-341, 2006). DNA constructs were ordered from Invitrogen or generated in-house by PCR. The constructs directionally TOPO-cloned into vector pENTR/D-TOPO were transferred to the retroviral vector (RV) pMP71-attR using Gateway® technology. The retroviral packaging cell line Plat-E (Cell-Bio Labs) was transduced with the RV using effectene transduction reagent (Qiagen). Viral supernatant was collected on days 2 and 3. One day prior to transfection, TCR$_{gag}$ T cells were stimulated with anti-CD3/CD28 and 100 U/mL rhIL-2. Transduction of TCR$_{gag}$ T cells was performed in 12 well plates in the presence of IL-2 and polybrene by spinfection for 90 minutes at 1000 g. Transduced cells were restimulated 7 days post stimulation in the presence of irradiated splenocytes ($5 \times 10^6$), irradiated FBL ($3 \times 10^6$), and IL-2 (IU/mL).

Five days post-transduction, CD8+ T cells were analyzed for IFP expression by flow cytometry (FIG. 14B). Fluorochrome-conjugated antibodies were purchased from eBioscience or Biolegend. Transduction efficiency ranged from 5-43%, and mean fluorescence intensity of transduced cells was similar between constructs, suggesting similar IFP expression.

Example 15

CD200R-CD28 Constructs Promote In Vitro Proliferation, Accumulation, and Effector Function of Transduced T Cells The CD200R-CD28 constructs described in Example 14 were assessed for their abilities to promote proliferation, accumulation, and effector function of $TCR_{gag}$ T cells.

In Vitro T Cell Proliferation Assay

CD28 signaling promotes proliferation and survival of T cells stimulated via the TCR (Chen and Flies, *Nat. Rev. Immunol.* 13: 227-242, 2013). To determine if CD200R-CD28 IFPs improve proliferation, naïve $CD8^+$ TCR transgenic T cells ($TCR_{gag}$ cells) specific for an epitope derived from the Friend murine leukemia virus-transformed FBL leukemia (Stromnes et al., *J Clin Invest.* 120:3722-3734, 2010), as described in Example 14, were transduced and expanded in vitro with antigen in the presence of IL-2 for 2-3 stimulation cycles to generate effector T cells and model human adoptive immunotherapy protocols. Effector T cells were labeled with CellTrace Violet (CTV), and CTV-labeled Tg T cells ($10^5$) were stimulated with either FBL, which does not naturally express CD200 ($CD200^-$ FBL) (FIG. 15A, upper panels), or an FBL line transduced to express CD200 ($CD200^+$ FBL) for 3 days and then assessed by flow cytometry (FIG. 15A, lower panels).

At a low 25:1 T cell to FBL ratio, GFP-control transduced T cells (FIG. 15A, blue lines) exhibited minimal proliferation in response to $CD200^-$ or $CD200^+$ FBL. In contrast, four of the five tested constructs (FIG. 15A, red lines) dramatically improved proliferation in response to $CD200^+$ FBL but not $CD200^-$ FBL. T cells transduced with the largest ectodomain, CD200R-CD28Cys, did not improve proliferation.

To test whether the increased proliferation delivered by the CD200R interaction with the leukemia-expressed CD200 reflected enhanced adhesion and/or decoy binding rather than costimulation, a truncated non-signaling version of the construct was generated with only CD200R extracellular and CD28 transmembrane domains ("trCD200R"; FIG. 15B). Transduced $TCR_{gag}$ T cells expressing the construct (FIG. 15C) did not exhibit enhanced proliferation to $CD200^+$ FBL (FIG. 15D), indicating a requisite role for CD28 costimulatory signals.

In Vitro T Cell Enrichment Assay

It was expected that expression of the CD200-targeted IFP would result in enrichment of $IFP^+$ T cells relative to $IFP^-$ T cells after stimulation with $CD200^+$ FBL. The proportion of transduced cells in the total $TCR_{gag}$ population after multiple cycles of stimulation with irradiated $CD200^-$ or $CD200^+$ FBL was assessed. Analysis of cell composition after 3 cycles of stimulation with either $CD200^-$ or $CD200^+$ FBL revealed no change in the fraction of GFP control-expressing $TCR_{gag}$ T cells (FIG. 15E). In contrast, IFP-expressing $TCR_{gag}$ T cells were enriched following stimulation with $CD200^+$ but not $CD200^-$ FBL (CD200R-9aas-CD28Cys, FIG. 15F). Although several constructs promoted accumulation of transduced T cells, as predicted, the construct that was sized to fit within the immunological synapse and included the dimerizing cysteine motif, CD200R-9aas-CD28Cys, produced the greatest relative increase, resulting in an average of >3-fold enrichment after 3 stimulations ($P<0.05$), in 3 separate experiments (FIG. 15G, showing fold enrichment, stimulation 3/stimulation 1, for eGFP, CD200Rtm-CD28, CD200R-CD28tm, CD200R-3aas-CD28cys, and CD200R-9aas-CD28cys-transduced T cells).

CFSE-Based Cytotoxic Assay

CD28 signaling promotes effector functions (Chen and Flies, *Nat. Rev. Immunol.* 13: 227-242, 2013). T cells transduced to express CD200R-9aas-CD28Cys were tested for increased killing of tumor target cells.

FBL and control EL4 tumors were incubated for 10 min at room temperature with 2.5 µM (hi) or 0.25 µM (lo) CFSE in PBS, respectively. Excess dye was removed by washing tumor cells in serum-containing media. A 1:1 mixture of non-specific EL4 control targets and $CD200^+$ FBL tumor cells was incubated with titrated numbers of CD200R-9aas-CD28Cys-transduced or GFP-transduced $TCR_{gag}$ effector T cells (i.e., a range of effector to target (E:T) ratios) for 5 h in 96-well, round-bottom plates at 37° C. and 5% $CO_2$. Specific FBL lysis was determined by flow cytometric analyses of the % $CFSE_{hi}$ (FBL) of total CFSE positive cells (FBL+EL4) remaining in the well.

$TCR_{gag}$ T cells transduced with CD200R-9aas-CD28Cys killed $CD200^+$ FBL cells better than control T cells, lysing >40% of $CD200^+$ FBL at a low E:T ratio (0.3:1) (FIG. 15H).

In Vitro Cytokine Production Assay

To determine if T cells transduced with the CD200R-9aas-CD28Cys IFP produced increased amounts and diversity of cytokines, which represent other functions of costimulation, polyfunctional cytokine production was assessed by flow cytometry. A higher percentage of $CD200R\ IFP^+$ T cells produced IFNγ, IL-2, and TNFα than control T cells following stimulation with $CD200^+$ FBL. A lower percentage of $CD200R\ IFP^+$ T cells were cytokine non-producing cells (27% vs 51%, FIG. 15I, blue), while a higher percentage of $CD200R\ IFP^+$ T cells were polyfunctional cells producing all 3 cytokines (22% vs 7%, FIG. 15I, purple). $CD200R\ IFP^+$ T cells stimulated with $CD200^+$ FBL had increased cytokine/cell based on mean fluorescent intensity (MFI) (FIG. 15J).

In Vitro Colocalization Assay

To more closely examine the mechanism of enhanced T cell function with IFP expression, CD200R IFP location on the T cell surface was visualized via microscopy. Localization of native CD28 to the immunological synapse after binding CD80/86 recruits signaling molecules that amplify the TCR signal (Chen and Flies, *Nat. Rev. Immunol.* 13: 227-242, 2013). To assess movement of the IFP following stimulation, FITC-conjugated cholera toxin B subunit (CTxB) was used to stain lipid rafts within the cell membrane (FIG. 15K, panel III), which are enriched at the immunological synapse (Stephan et al., *Nat Med.* 13:1440-1449, 2007), and used to define the site of immunological synapse assembly. Antibodies binding CD200 on FBL (FIG. 15K, panel II) or CD200R on the T cell (CD200R-9aas-CD28Cys, FIG. 15K, panel I) were then used to visualize these molecules in relation to the immunological synapse. CD200R IFP-transduced, in vitro expanded effector $TCR_{gag}$ cells were mixed with FBL at an E:T of 10:1 in 15 mL, then incubated at 37° C. for 20 minutes, and then loaded on a µ-Slide VI.4 chamber (Ibidi) for 15 minutes. Slides were washed with PBS and fixed with 2% paraformaldehyde for 4 minutes. Cells were then washed, stained, imaged at 60× using a Deltavision Elite Fluorescent Microscope, and analyzed using Image J (NIH).

CD200R localized with increased lipid raft staining at the region of T cell:target contact (FIGS. 15K to 15M, panel IV), suggesting that the size of the IFP can be accommodated by the immunological synapse.

LCK Phosphorylation

The tyrosine kinase, LCK, is critical for TCR signaling and recruitment of LCK to the TCR signaling complex results in phosphorylation of immunoreceptor tyrosine-based activation motif (ITAM) sequences in the CD3 complex to initiate the TCR signaling cascade (Chen and Flies, Nat. Rev. Immunol. 13: 227-242, 2013). LCK associates with CD28 via a proline motif in the CD28 signaling tail and T cell expression of CD28 is required for sustained phosphorylation of LCK residue Y394 (Holdorf et al., Nat Immunol. 3:259-264, 2002). To determine if CD200R-CD28 IFP expression provides or augments CD28 signaling, pLCK Y394 was evaluated in T cells transduced with the GFP control, the lead construct (CD200R-9aas-CD28Cys), or the ineffective construct that did not promote proliferation (CD200R-CD28Cys) (FIG. 15A). Transduced T cells were unstimulated or stimulated with PMA/ionomycin, FBL, or CD200$^+$ FBL for 10 minutes, fixed and stained for intracellular pLCK Y394, and analyzed by flow cytometry. Antibodies to phospho-LCK (Tyr394) were purchased from R&D Systems, and intracellular staining was detected via secondary labeling with anti-mouse PE from BioLegend.

The three populations of T cells achieved similar phosphorylation of LCK Y394 in response to strong stimulation (PMA/ionomycin) and CD200$^-$ FBL stimulation (FIG. 15N). T cells transduced with the GFP control or the IFP with the larger ectodomain, CD200R-CD28Cys, exhibited a similar low level of pLCK Y394 expression in response to CD200$^-$ FBL and CD200$^+$ FBL. However, when stimulated with CD200$^+$ FBL, CD200R-9aas-CD28Cys-transduced T cells exhibited sustained increased phosphorylation of LCK Y394 at 10 minutes, demonstrating that expression of CD200R-9aas-CD28cys provided a requisite function of CD28 costimulation.

Summary

Taken together, these data show that CD200R-CD28 constructs function to increase accumulation and the lytic activity of transduced T cells in response to tumor cell stimulation. Analysis of a panel CD200R-CD28 IFP constructs revealed costimulation was most effectively achieved in IFPs containing a dimerizing motif and a tumor-T cell distance that facilitates localization to the immunological synapse. T cells transduced with the such CD200R-CD28 IFPs exhibited enhanced proliferation and effector function in response to CD200$^+$ target cells in vitro.

Example 16

T Cells Transduced with CD200R-9aas-CD28Cys Exhibit Enhanced Accumulation In Vivo in Response to Recognition of FBL In adoptive T cell therapy of malignancies, tumors commonly provide limited or no costimulatory signals and rather express ligands for inhibitory receptors. In leukemia, CD200 is a commonly expressed inhibitory ligand and is associated with a poor prognosis (Tonks et al., Leukemia 21:566-568, 2007). Therefore, the ability of TCR$_{gag}$ T cells expressing CD200R-9aas-CD28Cys IFP, which appeared most effective in vitro, to proliferate and accumulate when encountering CD200$^+$ FBL leukemia in vivo was assessed.

Figure 16A:
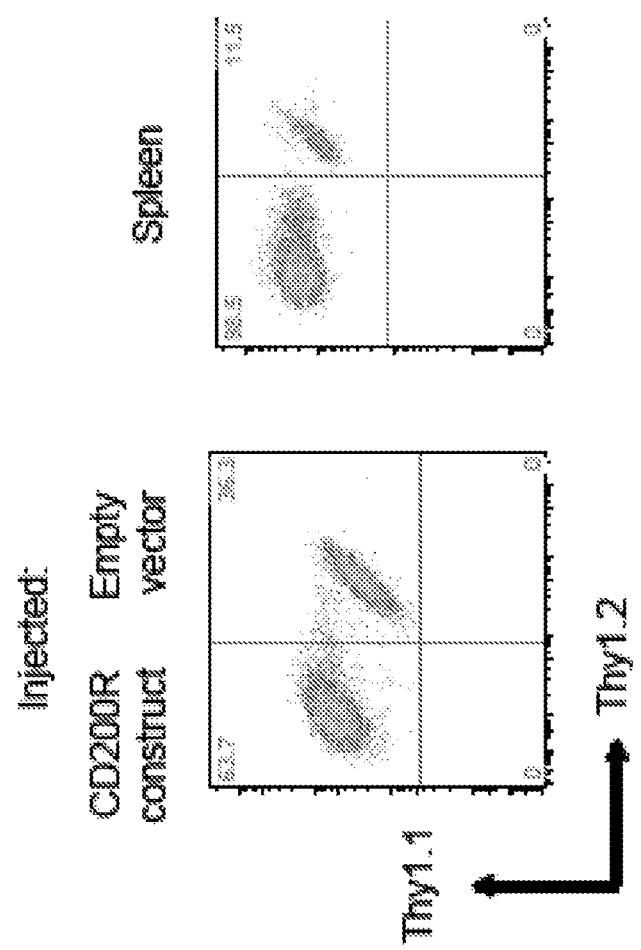
Figure 16B:
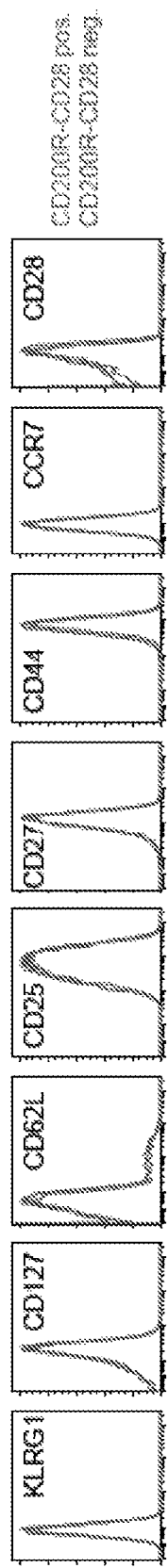

Transduced TCR$_{gag}$ T cells were generated as described in Example 15. B6 mice were injected with 4×10$^6$ live CD200$^+$ FBL leukemia intraperitoneal (i.p.) and, after allowing 5 days for the FBL to disseminate, mice received 180 mg/kg cyclophosphamide (Cy) i.p. 6 hours before transfer of the effector T cells to reduce tumor burden and induce lymphopenia similar to human adoptive immunotherapy protocols. To assess short-term proliferation and accumulation, 2×10$^6$ IFP-transduced Thy1.1$^+$ T cells were co-injected with an equal number of congenically distinct GFP-control-transduced Thy1.1$^+$×Thy1.2$^+$ T cells into tumor-bearing mice so that each mouse could serve as an internal control (FIG. 16A). Both T cell populations were generated in vitro and expanded with three stimulation cycles by identical methods, and appeared phenotypically similar on the day of injection, 5 days after the third stimulation (FIG. 16B). IL-2 was administered every 2 days (2×10$^4$ U/dose). On day 8 post-T cell transfer, mice were euthanized and spleens and inguinal lymph nodes harvested.

For some studies, CD8$^+$ T cells were isolated by negative selection using the EasySep™ Mouse CD8$^+$ T Cell Enrichment Kit (STEMCELL). Mice were regularly monitored for increasing tumor burden and euthanized if evidence of tumor progression predicted mortality would occur within 24-48 hours.

Figure 16C:
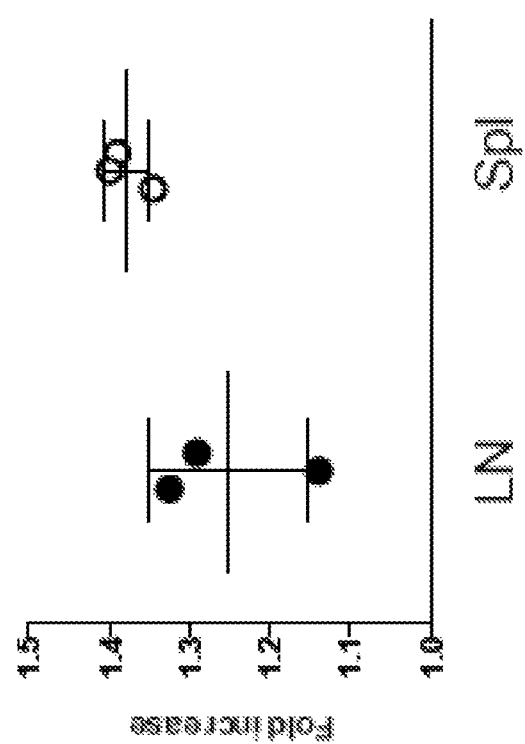
Figure 16D:
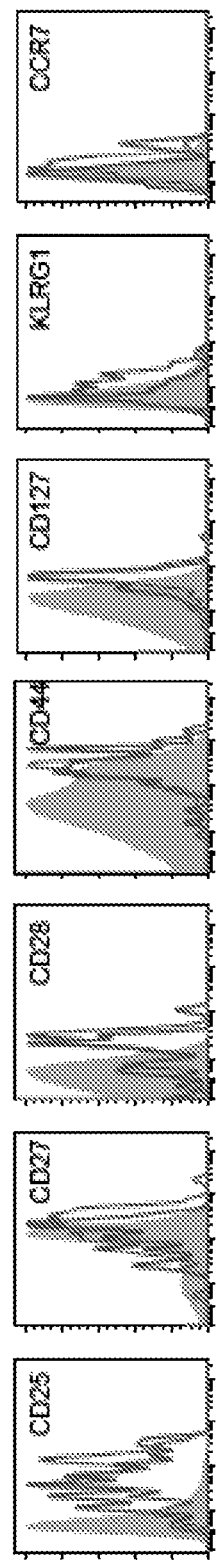
Figure 16E:
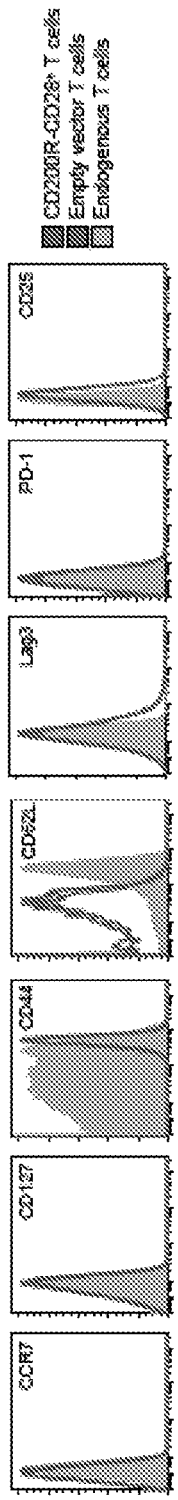

IFP-expressing T cells were 1.2- to 1.4-fold enriched in both spleen and lymph nodes compared to control cells (FIG. 16C). To assess possible phenotypic differences acquired by the transferred T cells, cohorts of mice were euthanized at early (d3) and late (d15) time points to identify effector, memory, and exhaustion markers. T cells were isolated from the spleen by untouched CD8$^+$ T cell enrichment and assessed by flow cytometry. Transduced CD200R-9aas-CD28Cys$^+$ TCR$_{gag}$ and control T cells expressed similar surface molecules consistent with an effector T cell phenotype at 3 days post-transfer (FIG. 16D). By day 15, the persisting IFP$^+$ and control T cells again appeared similar phenotypically, and did not express exhaustion markers PD-1 or Lag-3 (FIG. 16E), suggesting both cell types likely remained functional during this period.

In summary, in an in vivo study of adoptive therapy of disseminated leukemia, CD200R-CD28 transduced leukemia-specific T cells eradicated otherwise lethal disease more efficiently than wild type cells, and bypassed the requirement for IL-2 administration to sustain in vivo activity.

Example 17

Adoptive Immunotherapy with CD200R-CD28$^+$ T Cells Exhibits Greater Activity in Therapy of Disseminated Leukemia Whether the costimulation provided to cells expressing CD200R-9aas-CD28Cys IFP results in enhanced therapeutic T cell activity was evaluated in a preclinical mouse model of disseminated leukemia, which requires a T cell response lasting >25 days to achieve leukemia eradication (Cheever et al., J Immunol. 125:711-714, 1980). B6 mice were injected with a lethal dose (4×10$^6$) of CD200$^+$ FBL leukemia cells i.p., as previously described (Stromnes et al., J Clin Invest. 120:3722-3734, 2010). Five days later, cohorts of mice received 180 mg/kg cyclophosphamide (Cy) i.p. and received 10$^5$ TCR$_{gag}$ effector T cells 6 hours later, to allow for metabolism of the drug (Cheever et al., 1980). The TCR$_{gag}$ T cells were previously stimulated 1-3× in vitro. The efficacy of therapy with T cells transduced with CD200R-9aas-CD28Cys was compared to T cells expressing a GFP control (FIGS. 17A, 17B). This approach was initially tested with a small cohort of mice that received IL-2 for 10 days following T cell transfer to enhance and sustain T cell activity (Stromnes et al., J Clin Invest. 120:3722-3734, 2010) (FIG. 17A).

With IL-2 injections, immunotherapy using the control T cells cured 67% of mice and CD200R-9aas-CD28Cys$^+$ T cells cured 100% of mice, which did not achieve statistical significance (FIG. 17A). Subsequent studies were conducted with a larger cohort and with the IL-2 injections omitted. In these studies, only 40% of mice treated with T cells transduced with the GFP control vector survived beyond day 30

(FIG. 17B, blue line). By contrast, 89% of mice that received CD200R-9aas-CD28Cys+ T cells survived 100 days post-transfer of FBL (FIG. 17B, red line, P<0.05). These results indicate that an IFP with a CD200R providing a costimulatory signal not only enhances T cell immunotherapy of progressive leukemia, but can largely bypass the requirement for administration of IL-2.

Example 18

Co-Expression of CD200Rtm-CD28 Enhances Function in WT1-Specific TCR Primary T Cells Adoptive therapy with engineered T cells has shown promising clinical benefit, particularly in acute lymphocytic leukemia with T cells expressing a chimeric antigen receptor (CAR) specific for the cell surface protein CD19 (Turtle et al., *J Clin Invest.* 126:2123-2138, 2016; Kalos et al., *Sci Transl Med.* 3:95ra73, 2011). T cells can alternatively be transduced to express a tumor-specific T cell receptor (TCR), which greatly expands the breadth of target antigens by including intracellular proteins such as transcription factors that often drive the oncogenic phenotype. CD8+ T cells specific for WT1, a transcription factor over-expressed in many malignancies (Yang et al., *Leukemia* 21:868-876, 2007; Qi et al., *Sci Rep.* 5:8924, 2015), exhibit anti-leukemic activity after transfer to patients (Chapuis et al., *Sci Transl Med.* 5:174ra127, 2013), and there are ongoing trials with CD8+ T cells transduced with a high affinity WT1-specific TCR in patients with leukemia, lung cancer, or mesothelioma (clinicaltrials.gov NCT01640301, NCT02408016). T cell activation with associated proliferation and survival requires a costimulatory signal concurrent with triggering the antigen receptor (Chen et al., *Nat Rev Immunol.* 13:227-242, 2013). Unlike CARs, which include a costimulatory domain in the chimeric signaling protein, cells with introduced TCRs require independent triggering of a costimulatory receptor. However, tumor cells generally not only express few if any ligands for costimulatory receptors, but commonly upregulate inhibitory receptor ligands that can interfere with costimulation and block T cell activation (Driessens et al., *Immunol Rev.* 229:126-144, 2009).

Strategies to overcome inhibitory signaling and increase costimulatory/activation signaling are thus being actively pursued to promote T cell anti-tumor activity (Mellman et al., *Nature* 480:480-489, 2011).

Acute myeloid leukemia (AML) has a 5-year survival rate of 26% with current therapies (Society AC, Cancer Facts & Figures 2016. Atlanta: American Cancer Society, 2016). As T cells naturally traffic to hematopoietic sites where AML localizes, T cell therapy has significant potential for treating this disease but overexpression of inhibitory molecules by AML cells represents a substantive barrier to success (Geiger & Rubnitz, *Discov Med.* 19:275-284, 2015). The type-1 membrane protein CD200, a member of the immunoglobulin superfamily, binds to the T cell inhibitory receptor CD200R (Hatherley et al., *Structure* 21:820-832, 2013), and increased CD200 expression is observed in AML and other malignancies, including multiple myeloma, ovarian, and prostate cancers (Siva et al., *Cancer Immunol Immunother.* 57:987-996, 2008; Stumpfova et al., *Cancer Res.* 70:2962-2972, 2010; Kawasaki et al., *Trends Immunol.* 29:464-468, 2008). Importantly for targeted therapy, increased CD200 expression has been reported in cancer stem cells (CSCs) and leukemia stem cells (LSCs), a small population of cells that initiate and maintain disease with a high proliferative capacity and resistance to radiation and chemotherapy (Snauwaert et al., *Oncoimmunology* 2:e22943, 2013; Tonks et al., *Leukemia* 21:566-568, 2007; Ho et al., 58th ASH Annual Meeting, San Diego, C A, 2016; Kawasaki et al., *Biochem Biophys Res Commun.* 364:778-782, 2007). CD200R signaling inhibits T cell function (Coles et al., *Leukemia* 26:2148-2151, 2012; Kretz-Rommel et al., *The Journal of Immunology* 178:5595-5605, 2007) as well as other immune cells, including natural killer (NK) cells (Coles et al., *Leukemia* 25:792-799, 2011), and high levels of CD200 expression have been linked with poor outcomes in AML patients (Tonks et al., *Leukemia* 21:566-568, 2007).

Synthetic biology affords the opportunity to engineer T cells not just with tumor-reactive receptors but also molecules that abrogate negative signals and replace them with activating signals. To both overcome inhibitory CD200R signaling associated with AML and concurrently provide missing costimulatory signals to CD8+ T cells, immunomodulatory fusion proteins (IFPs) were designed consisting of the CD200R ectodomain fused to an intracellular T cell costimulatory signaling domain so that the IFP could take advantage of leukemia cells expressing CD200 by binding this inhibitory ligand but generating a costimulatory signal. An fusion protein comprising a PD-1 ectodomain has been shown capable of providing costimulatory signals (Prosser et al., *Mol Immunol.* 51:263-272, 2012), but principles for designing molecules to generate or even optimize costimulatory signals have not been defined.

Therapy with TCR-transduced T cells was investigated in an AML clinical trial (registered at clinicaltrials.org as NCT01640301). All clinical investigations were conducted according to the Declaration of Helsinki principles. Protocol 2498 was approved by the Fred Hutchinson Cancer Research Center (FHCRC) Institutional Review Board (IRB) and the U.S. Food and Drug Administration (FDA). AML patients were treated with TCR-transduced T cells. Peripheral blasts were obtained from 4 patients who progressed/relapsed after T cell therapy. The AML maintenance subpopulation, LSCs, reside within the CD45$^{dim}$CD34+ CD38⁻ population of leukemic blasts (Bachas et al., *Leukemia* 26:1313-1320, 2012; Ho et al., 58th ASH Annual Meeting, San Diego, C A, 2016) and CD200 expression was compared with CD34+ cells obtained from mobilized leukaphereses from 3 healthy donors used to generate the T cells for infusion. Although CD200 expression was not detected on the normal CD34+ cells, CD200 was expressed in a large fraction of the AML blasts from each of the patients tested (range 42-97%+) (FIG. 18A), consistent with previous reports (Tonks et al., *Leukemia* 21:566-568, 2007; Coles et al., *Leukemia* 29:1952-1954, 2015).

Figure 18A:
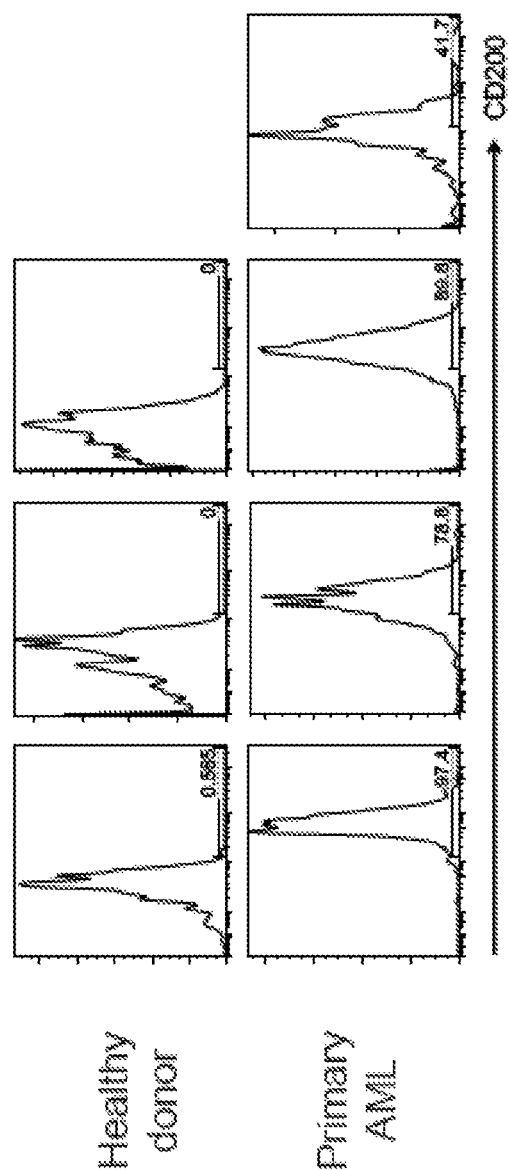
Figure 18B:
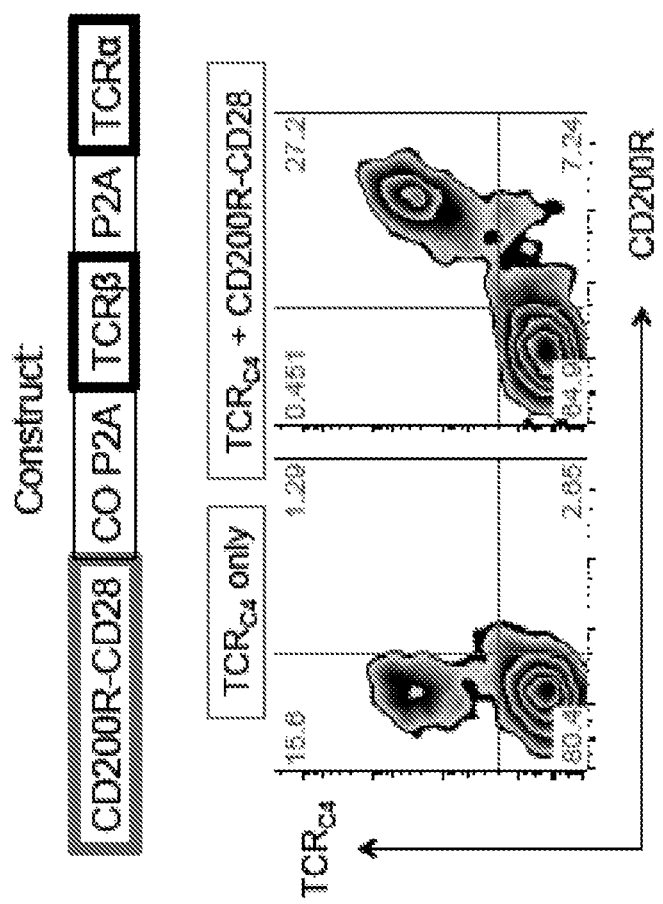

Based on the results of previous murine experiments (see Examples 14-17), human CD200Rtm-CD28 construct (SEQ ID NO.:1) was generated to maintain the spatial distance between the human T cell and tumor cell at the immunological synapse (FIG. 18B). Human primary T cells were transduced to determine if expression of this IFP could enhance function. The construct was inserted into a single lentiviral vector construct with the beta and alpha chains of the HLA-A2-restricted WT1$_{126}$-specific TCR$_{C4}$ (Stromnes et al., *Immunol Rev.* 257:145-164, 2014), which were used to transduce T cells in the clinical trial for therapy of AML, by linking each of the genes with P2A elements (FIG. 18B). The first P2A sequence was codon optimized to prevent genetic recombination with the second P2A sequence.

To generate lentiviruses, 293T/17 cells (3×10⁶ cells/plate) were transduced with human constructs in the pRRLSIN plasmid and the packaging plasmids pMDLg/pRRE, pMD2-G, and pRSV-REV using Effectene (Qiagen). Culture media was changed on day 1 post-transfection, virus-containing supernatant collected on days 2 and 3, and aliquots frozen for future use. After obtaining informed consent, peripheral blood mononuclear cells (PBMC) were harvested from normal HLA-A2+ donors. CD8+ T cells were purified using Miltenyi magnetic beads and stimulated with Human T cell Expander CD3/CD28 Dynabeads (Life Technologies) and 50 IU/mL IL-2. Four hours following stimulation, T cells were transduced by spinfection of 5-10×10$^6$ cells with 2 mL of lentiviral supernatant at 1000 g for 90 min at 32° C. T cells were restimulated every 10-14 days with a rapid expansion protocol (REP), as previously described (see Ho et al., *J. Immunol. Methods* 310:40-52, 2006).

Human primary T cells transduced to express TCR$_{C4}$ and the CD200R-CD28 fusion protein exhibited a high level of CD200R expression and equivalent levels of TCR$_{C4}$ expression relative to T cells transduced with the TCR$_{C4}$ alone (FIG. 18B).

Figure 18C:
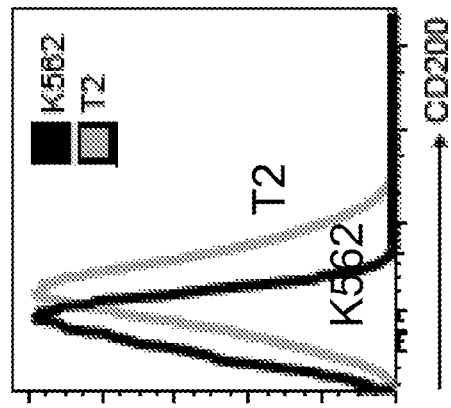
Figure 18D:
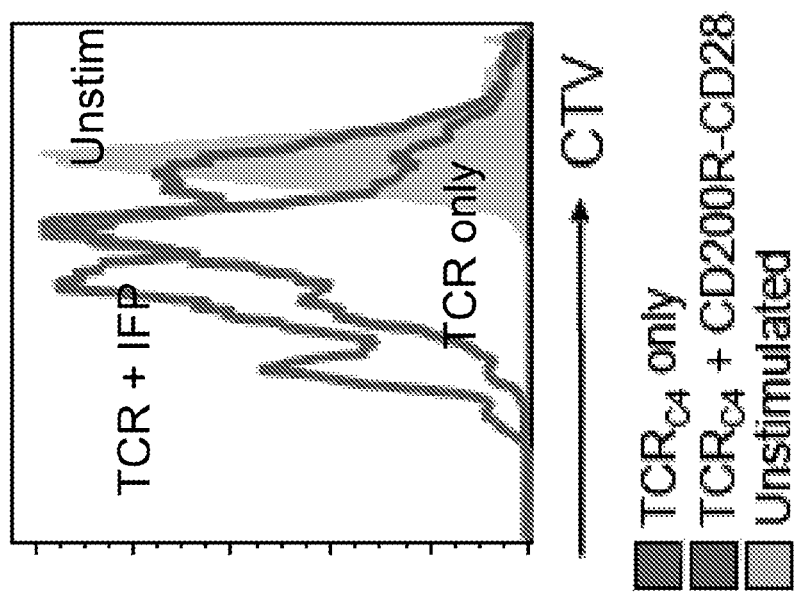
Figure 18E:
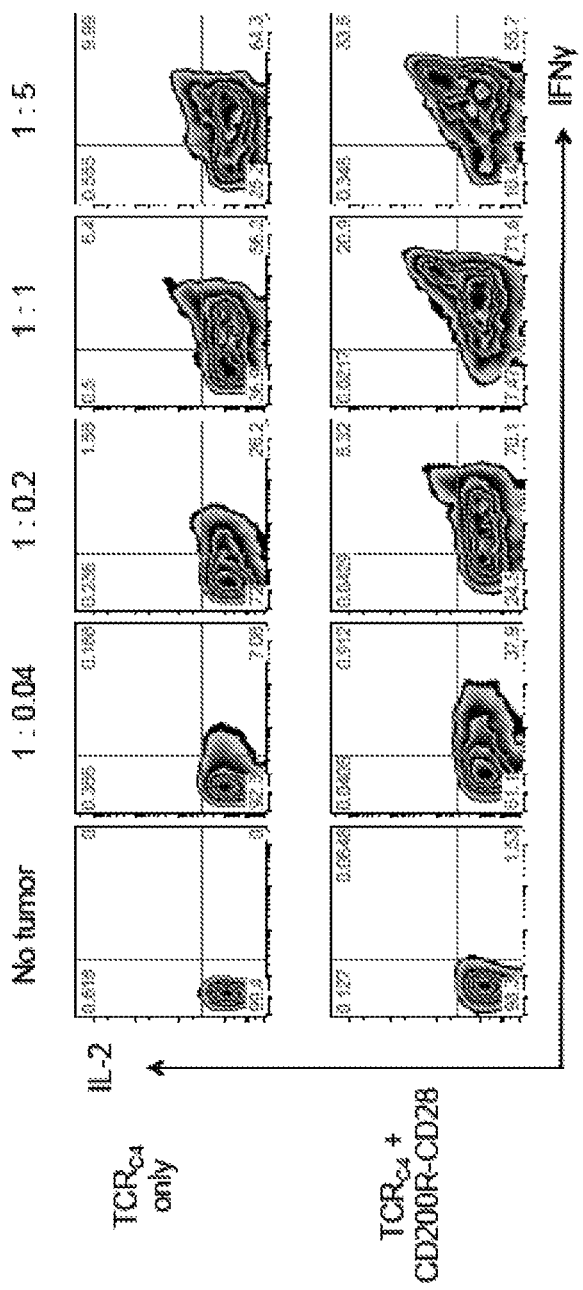

To determine if the CD200R-CD28 IFP improved the function of transduced human T cells, the cells were stimulated with peptide-pulsed T2 lymphoblastoid cells that naturally express a low level of endogenous CD200, relative to primary AML (FIG. 18A) and the CD200+ CML cell line, K562 (Coles et al., *Leukemia* 25:792-799, 2011) (FIG. 18C). In response to WT1$_{126}$-pulsed T2 cells, T cells transduced with TCR$_{C4}$ plus CD200R-CD28 IFP exhibited enhanced proliferation (FIG. 18D) and increased cytokine production, particularly at low E:T ratios (FIG. 18E), suggesting tumor cells expressing even dim CD200 expression can provide costimulation.

In summary, transduction of human primary T cells with the human IFP also increased proliferation and cytokine production in response to CD200+ leukemia cells. This study focused on generating an IFP to target the inhibitory molecule, CD200, which is frequently upregulated on cancer cells, particularly AML and LSC cells, and known to suppress T cell immune responses. In addition to AML, increased CD200 expression had been reported for other heme malignancies and solid tumors such as breast, colon, ovarian, and prostate cancers. In certain embodiments, a CD200 IFP may be used in the treatment of heme malignancies and solid tumors, including breast, colon, ovarian, and prostate cancer. These results show that genetic engineering of tumor-specific T cells with IFP containing the CD200R ectodomain can efficiently convert an inhibitory signal delivered by leukemic cells to a costimulatory one in a cell intrinsic fashion, thus obviating the requirement to globally block this inhibitory receptor with the associated risk of promoting activation of endogenous autoreactive T cells. In addition, IFPs can be used to improve sensitivity without manipulating TCRs.

Example 19

Co-Expression of CD200Rtm-CD28 or CD200R-9aas-CD28Cys with WT1-Specific TCR Enhances Function in Primary T Cells In a further example, exemplary fusion proteins as described herein are illustrated using schematic representations in FIG. 19A. Representative fusion proteins include IFPs comprised of the extracellular domain of human CD200R or a portion thereof, and an intracellular signaling domain of human CD28 or a portion thereof (FIG. 19A, constructs II-VII). The hydrophobic component may be comprised of the transmembrane domain of either human CD200R (FIG. 19A, constructs I, II, and VIII) or human CD28 (FIG. 19A, constructs III-VII), or portions thereof. In some exemplary CD200R-CD28 fusion proteins, the hydrophobic component comprises the transmembrane domain of human CD28 and the extracellular component further comprises an extracellular portion of human CD28, particularly an extracellular cysteine residue adjacent to the hydrophobic component (e.g., FIG. 19A construct IV, CD200R-CD28Cys; construct V, CD200R-9aas-CD28Cys; construct VI, CD200R-12aas-CD28Cys; and construct VII, CD200R-15aas-CD28Cys). Construct VIII comprises an extracellular domain and a transmembrane domain, but does not include an intracellular signaling domain (FIG. 19A). The extracellular component may comprise all or a portion of the extracellular domain of human CD200R. In some embodiments, the extracellular component comprises the entire extracellular domain of CD200R (FIG. 19A, constructs II-IV and VIII). In some other examples, the extracellular component comprises the first 234 amino acids (e.g., FIG. 19A, construct V, CD200R-9aas-CD28Cys), the first 231 amino acids (e.g., FIG. 19A, construct VI, CD200R-12aas-CD28Cys), or the first 228 amino acids (e.g., FIG. 19A, construct VII, CD200R-15aas-CD28Cys) from the N-terminus of CD200R. The human CD200R-CD28 constructs disclosed herein have the capacity to convert what would typically be an inhibitory signal from the binding of CD200R to its target into a positive signal generated by the CD28 intracellular signaling domain.

The size of the extracellular component, which may be manipulated by adjusting the fusion protein construct, may affect the ability of the fusion protein to enter the immunological synapse and co-localize with the TCR within the cSMAC to deliver a strong co-stimulatory signal. CD28 signaling naturally occurs in the immunological synapse, where CD28 is recruited to amplify TCR signals and lower the threshold of activation (Chen and Flies, *Nat. Rev. Immunol.* 13: 227-242, 2013; Yokosuka et al., *Immunity* 29:589-601, 2008). The spatial distance between the T cell and APC is shortest within the immunological synapse, and molecules with large ectodomains are excluded. Thus, constructs that best approximate the cell-to-cell spacing of the immunological synapse may be able to co-localize with the TCR within the immunological synapse and deliver an effective costimulatory signal. Constructs IV-VII extend the CD28 transmembrane domain into the extracellular space to incorporate the membrane proximal cysteine (CD28Cys) that promotes CD28 homodimerization and enhances native CD28 signaling (Lazar-Molnar et al., *Cell Immunol.* 244: 125-129, 2006). In some embodiments, to account for the length added by the additional amino acids of extracellular CD28 domain, the CD200R extracellular portion is truncated by an equivalent number; for example, the CD200R extracellular domain portion of CD200R-9aas-CD28Cys is truncated by nine amino acids, an equivalent number added by the CD28 extracellular domain. Similarly, the extracellular CD200R of CD200R-12aas-CD28Cys is truncated by 12 amino acids and the extracellular CD200R of CD200R-15aas-CD28Cys is truncated by 15 amino acids. In constructs V-VII, the truncated extracellular CD200R is truncated from the C-terminal end, to preserve an N-linked glycosylation site. For the representative fusion proteins illustrated in FIG. 19A, CD200Rtm-CD28, CD200R-CD28tm, and CD200R-12aas-CD28cys theoretically best maintain the short spatial distance between the T cell and APC needed to co-localize with the TCR in the immunological synapse.

All clinical investigations were conducted according to the Declaration of Helsinki principles. Protocol 2498 was approved by the Fred Hutchinson Cancer Research Center (FHCRC) Institutional Review Board (IRB) and the U.S.

Food and Drug Administration (FDA). The trial was registered at clinicaltrials.org as NCT01640301.

To generate lentiviruses, 293T/17 cells (3×10⁶ cells/plate) were transduced with human constructs (FIG. 19B) in the pRRLSIN plasmid and the packaging plasmids pMDLg/pRRE, pMD2-G, and pRSV-REV using Effectene (Qiagen). Culture media was changed on day 1 post-transfection, virus-containing supernatant collected on days 2 and 3, and aliquots frozen for future use.

Human CD200R-CD28 IFP constructs were generated that theoretically maintained the spatial distance between the T cell and tumor cell at the immunological synapse (FIG. 19B). The construct was inserted into a single lentiviral vector construct with the beta and alpha chains of the HLA-A2-restricted WT1$_{126}$-specific TCR$_{C4}$ (Stromnes et al., *Immunol Rev.* 257:145-164, 2014), which were used to transduce T cells in the clinical trial for therapy of AML, by linking each of the genes with P2A elements The first P2A sequence was codon optimized to prevent genetic recombination with the second P2A sequence.

After obtaining informed consent, peripheral blood mononuclear cells (PBMC) were harvested from normal HLA-A2⁺ donors. CD8⁺ T cells were purified using Miltenyi magnetic beads and stimulated with Human T cell Expander CD3/CD28 Dynabeads (Life Technologies) and 50 IU/mL IL-2. Four hours following stimulation, T cells were transduced by spinfection of 5-10×10⁶ cells with 2 mL of lentiviral supernatant at 1000 g for 90 min at 32° C. T cells were restimulated every 10-14 days with a rapid expansion protocol (REP), as has been previously described (Ho et al., *J Immunol Methods* 310:40-52, 2006).

Transduced CD8⁺ T cells were analyzed for IFP expression by flow cytometry (FIG. 19C). The results show that, when transduced with constructs encoding an IFP and a WT1-specific TCR, primary human T cells co-expressed the CD200R-CD28 IFPs and WT1-specific TCRs.

Example 20

T Cells Expressing CD200-Targeted IFPs are Enriched Relative to IFP⁻ T Cells after Stimulation with Cd200⁺ Cells To test whether expression of a CD200-targeted IFP would result in enrichment of IFP⁺ T cells relative to IFP⁻ T cells after stimulation with CD200⁺ cells, the relative proportion of CD200R⁺ cells was measured before and after stimulation with CD200⁺ LCL cells.

Figure 20A:
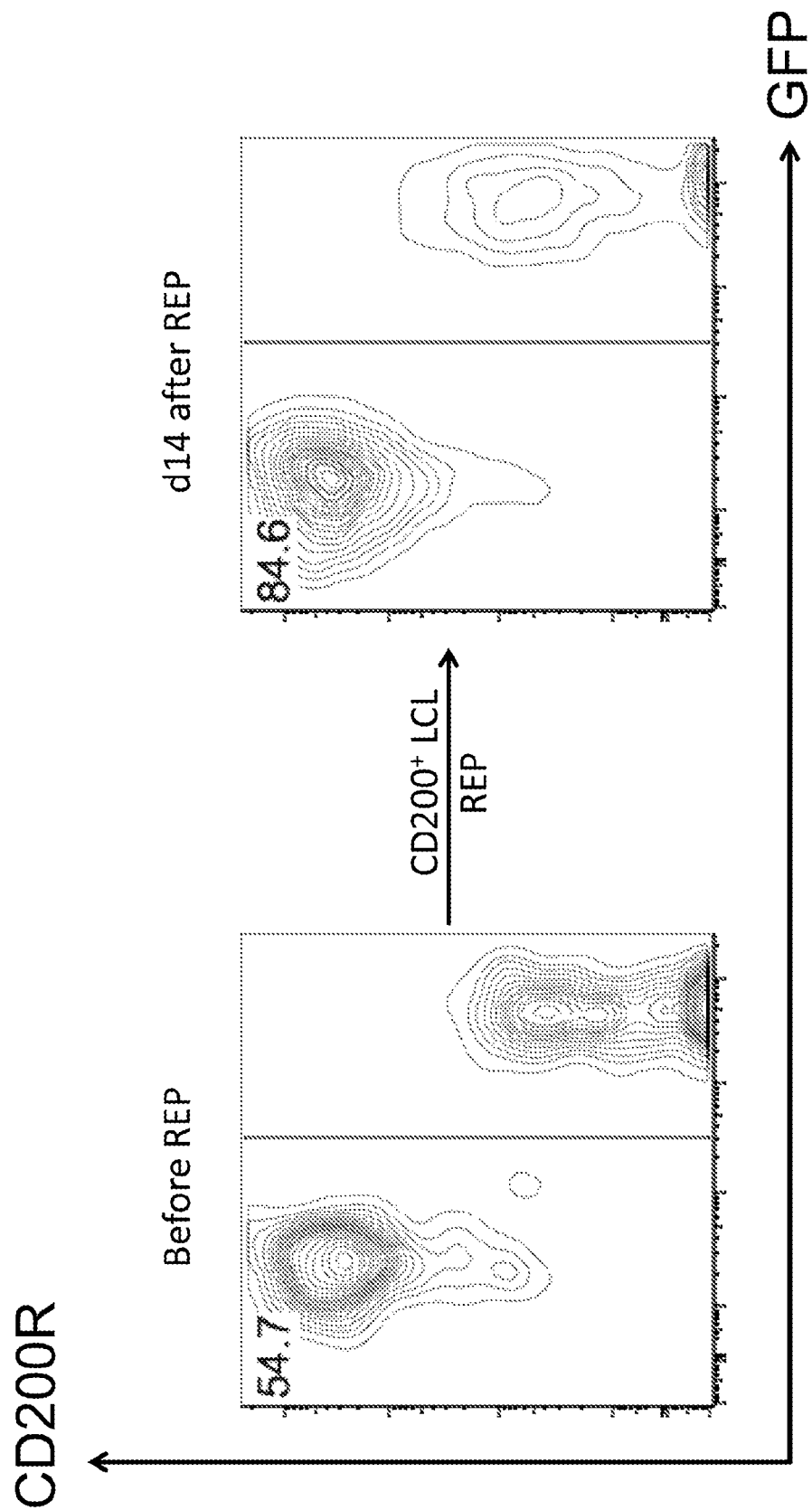

As shown in FIG. 20A, expression of the IFP CD200R-CD28tm (construct III in FIG. 19A) results in enrichment of IFP⁺ T cells (CD200R⁺) relative to IFP⁻ T cells (CD200R⁻) after restimulation with CD200-transduced LCL.

Figure 20B:
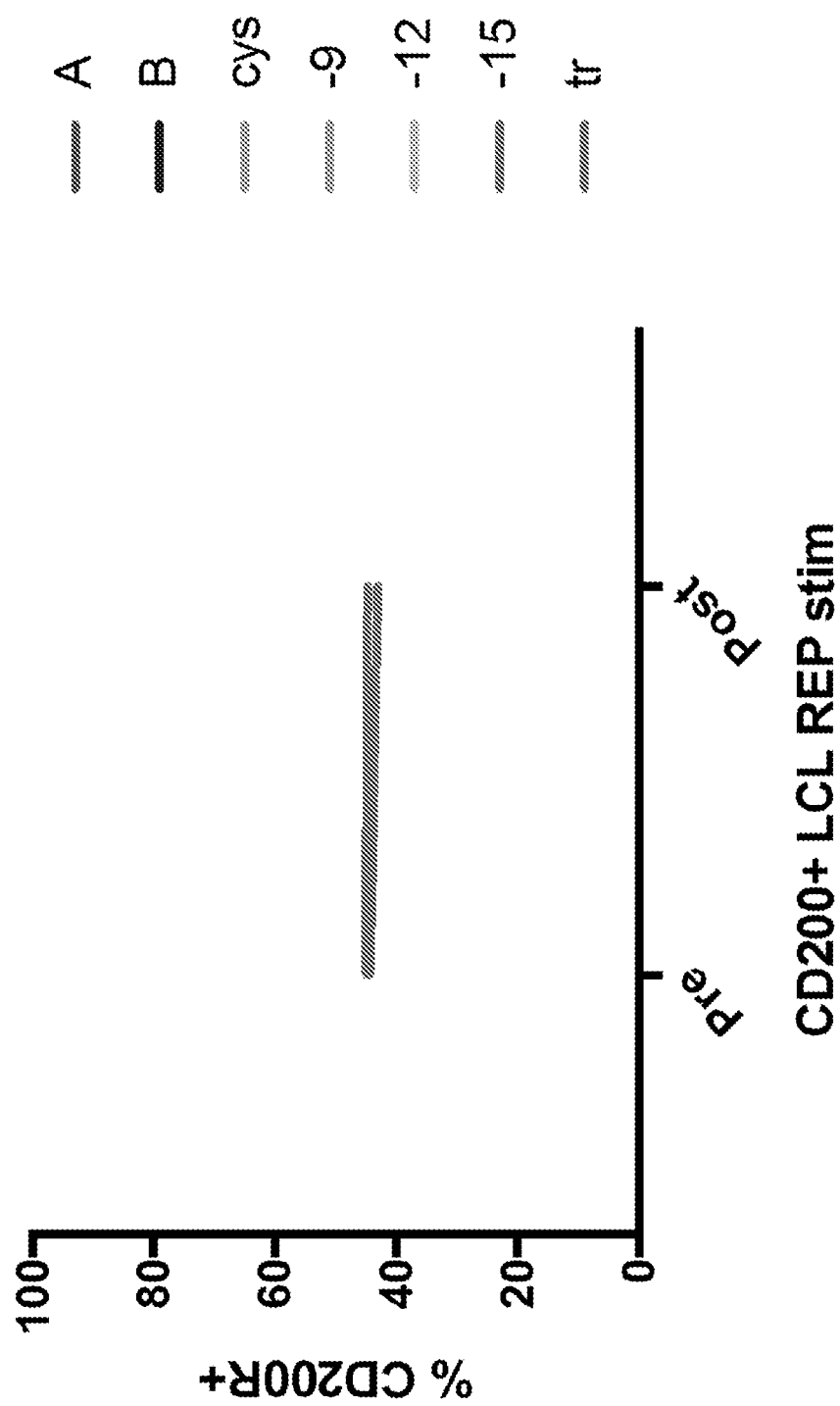
Figure 20C:
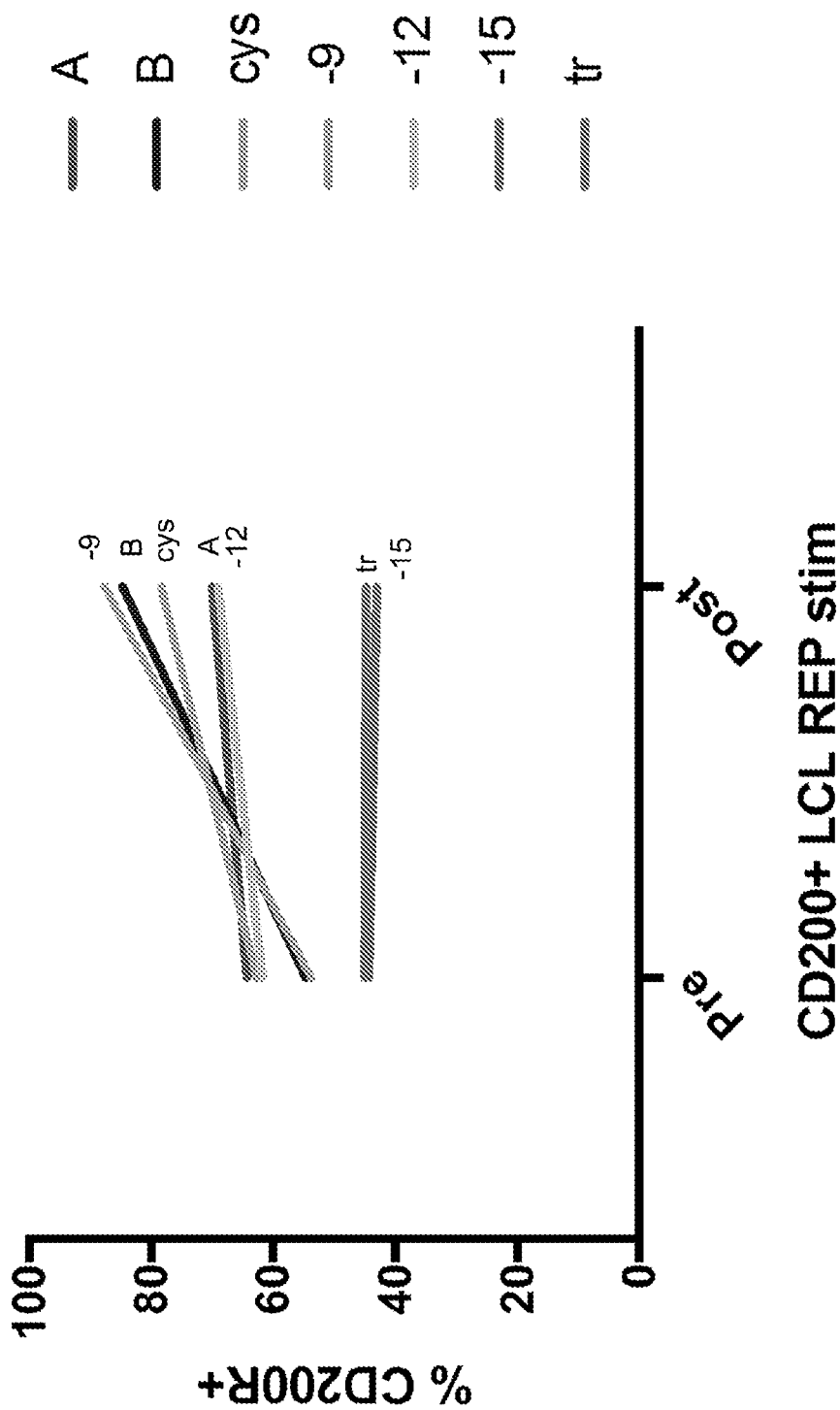
Figure 20D:
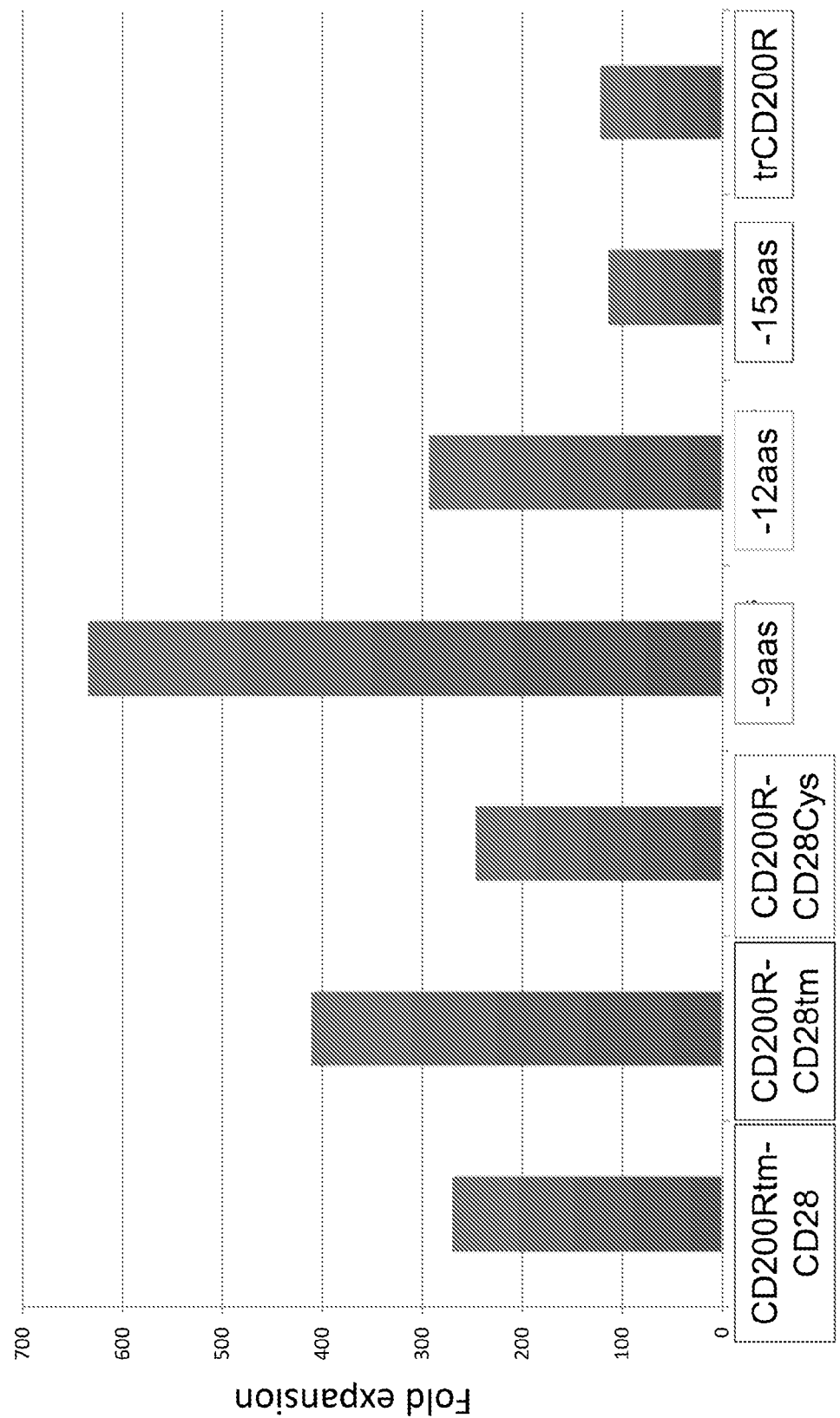

T cells transduced with trCD200R (construct VIII in FIG. 19A) and CD200R-15aas-CD28Cys (construct VII FIG. 19A) were not enriched, suggesting lack of costimulation (FIGS. 20B and 20C). T cells expressing several other constructs, however, increase in ratio after CD200⁺ LCL REP, especially CD200R-CD28tm (construct III in FIG. 19A) and CD200R-9aas-CD28Cys (construct V in FIG. 19A) (FIGS. 20C and 20D).

Example 21

Figure 21A:
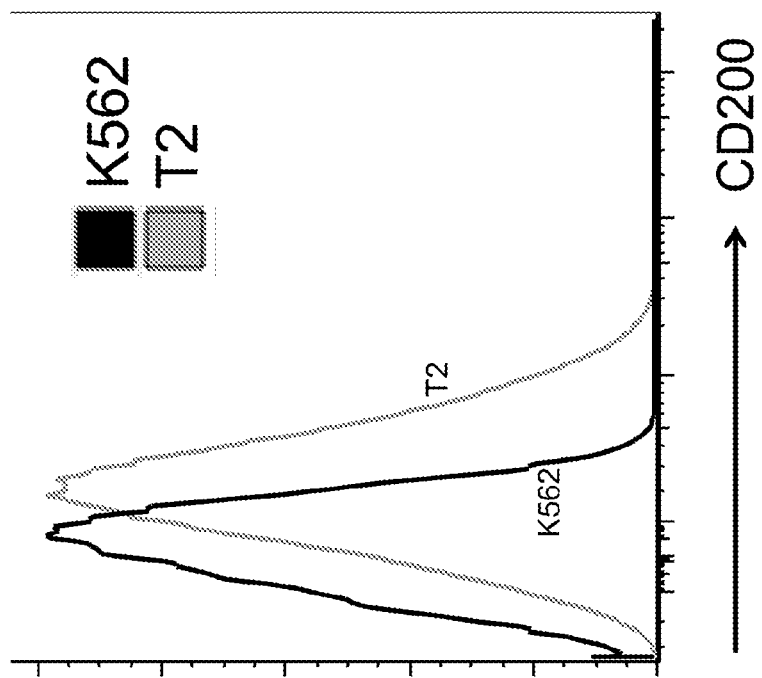
Figure 21B:
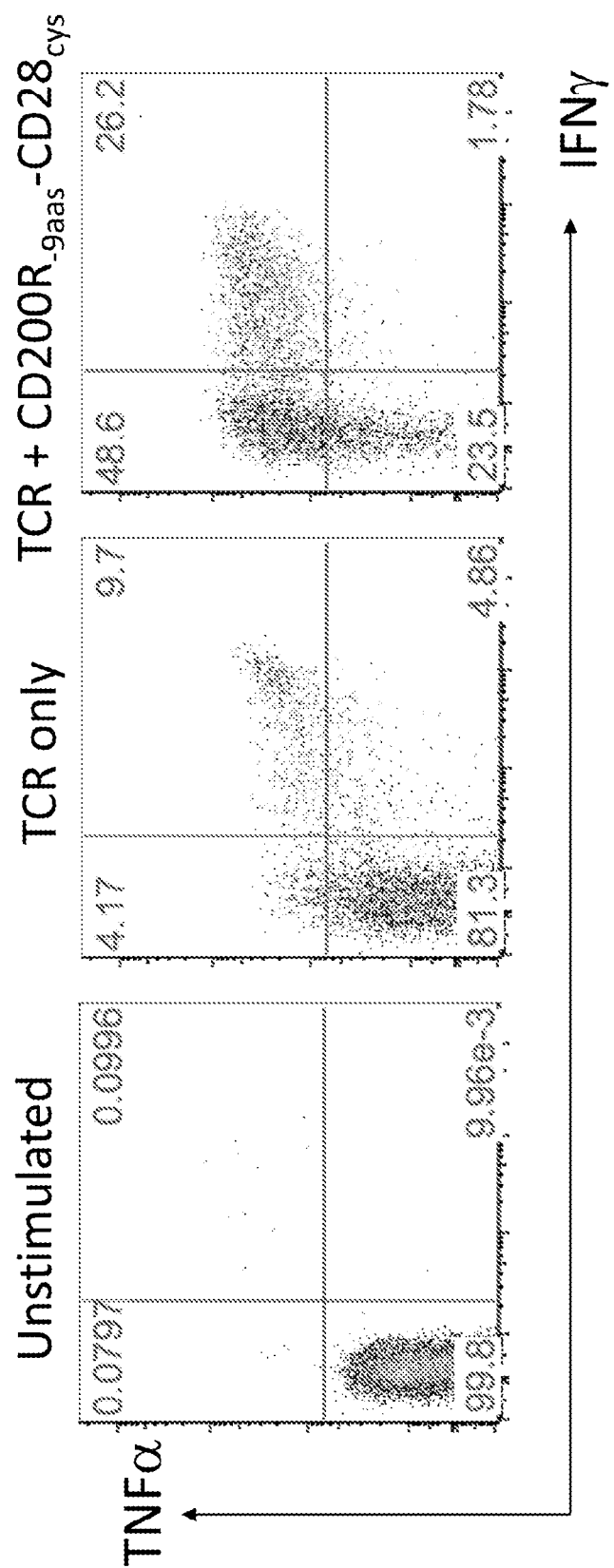

Human T Cells Expressing CD200R-CD28Tm and CD200R-9aas-CD28Cys IFP Exhibit Greater Effector Function Human T cells expressing the CD200-targeted IFP CD200R-9aas-CD28Cys, had increased cytokine production relative to IFP⁻ cells. The TAP-deficient tumor cell line, T2, expresses endogenous CD200 (FIG. 21A). CD200R-9aas-CD28Cys expression enhanced cytokine production to peptide-pulsed T2 cells (pulsed with 1 ug/mL WT$_{1-126}$), relative to unstimulated cells and stimulated cells expressing a TCR but not the IFP (FIG. 21B).

Figure 21C:
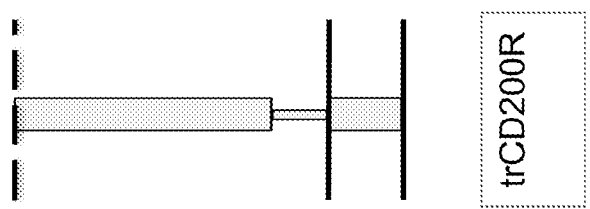
Figure 21D:
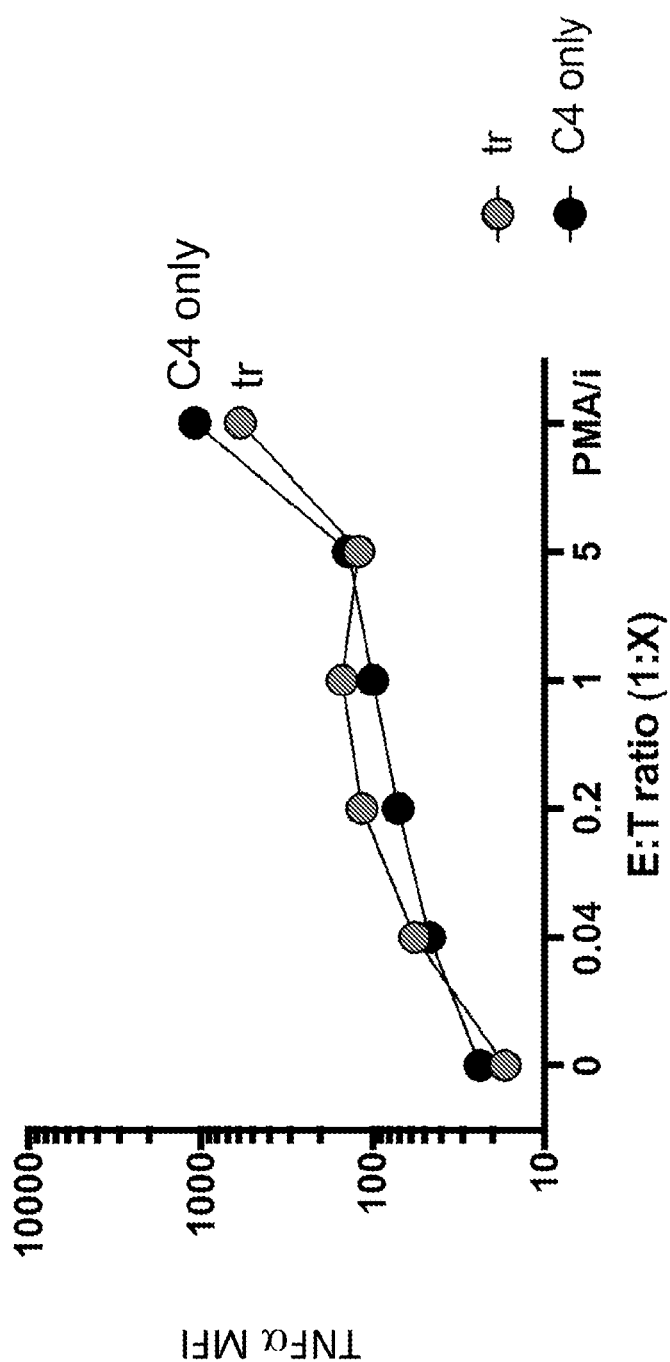

To test whether the increased effector function associated with CD200R-9aas-CD28Cys expression reflected enhanced adhesion and/or decoy binding rather than costimulation, a truncated non-signaling version of the construct was generated with only CD200R extracellular and CD28 transmembrane domains ("trCD200R"; FIG. 19A, construct VIII; FIG. 21C). Transduced T cells expressing the construct did not exhibit enhanced cytokine production relative to cells expressing TCR$_{C4}$ alone (FIG. 21D), indicating that CD200R-9aas-CD28Cys provides costimulatory signals.

Figure 21E:
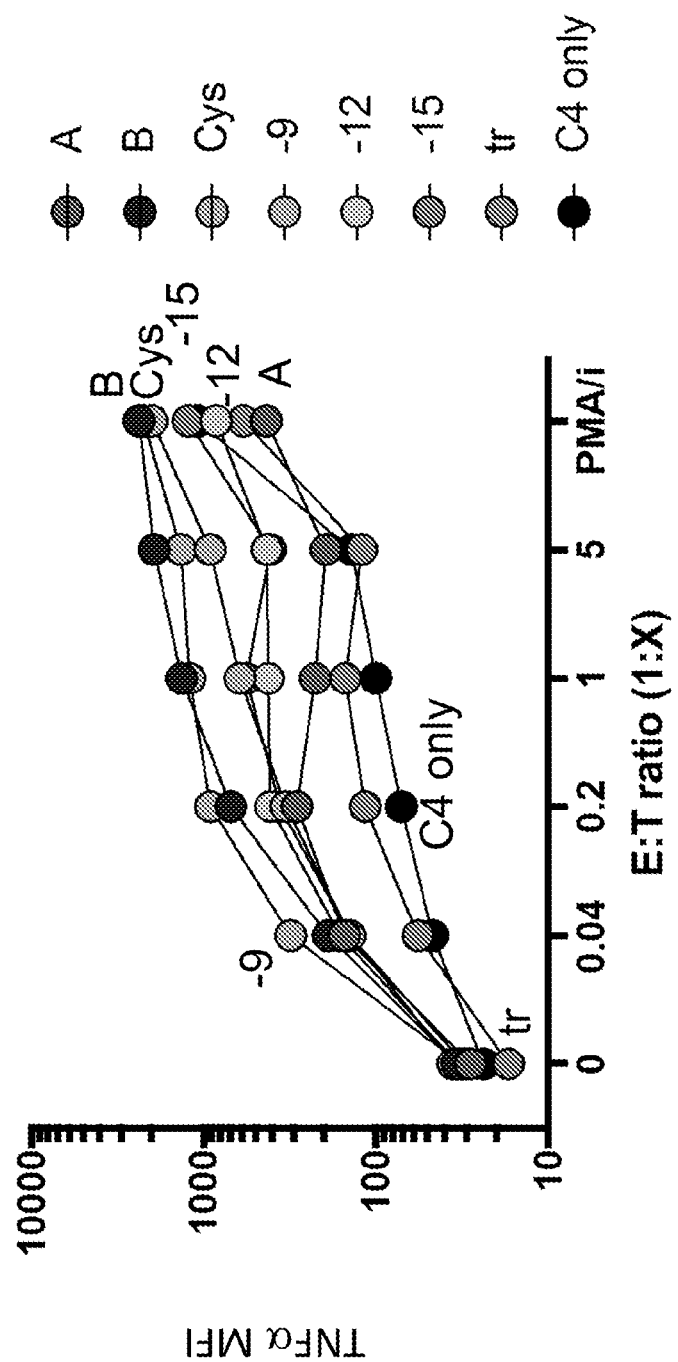
Figure 21F:
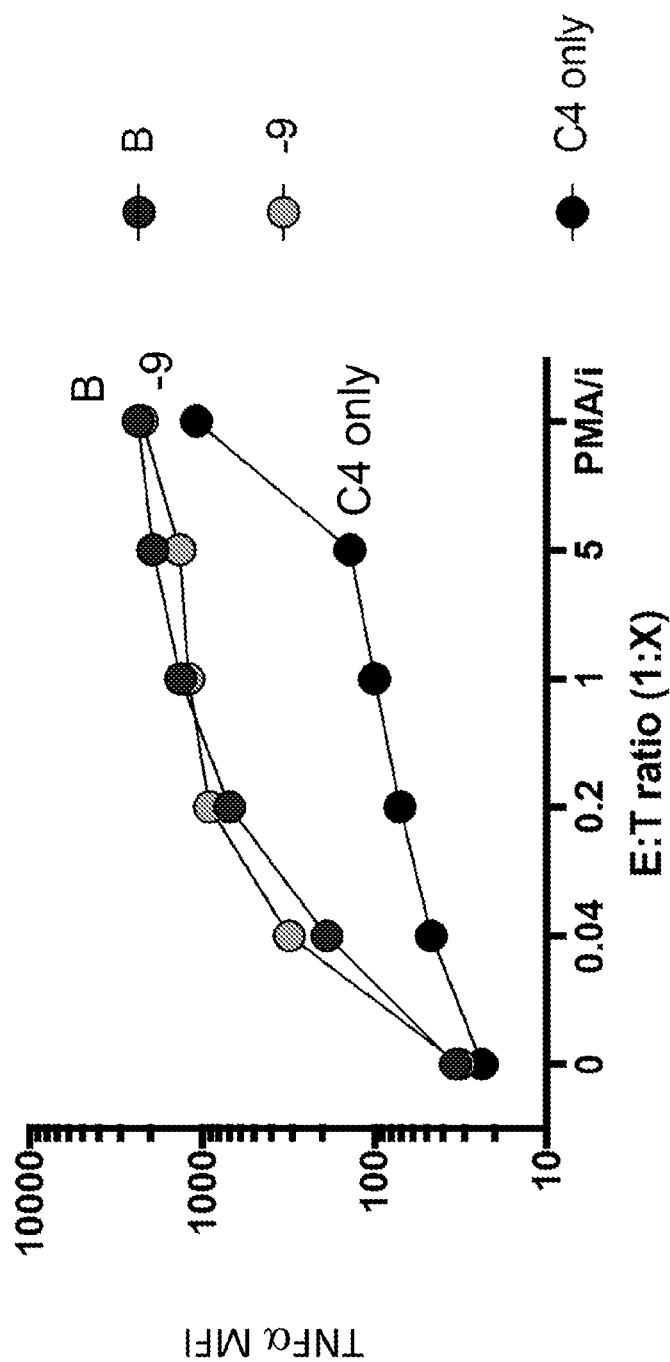
Figure 21G:
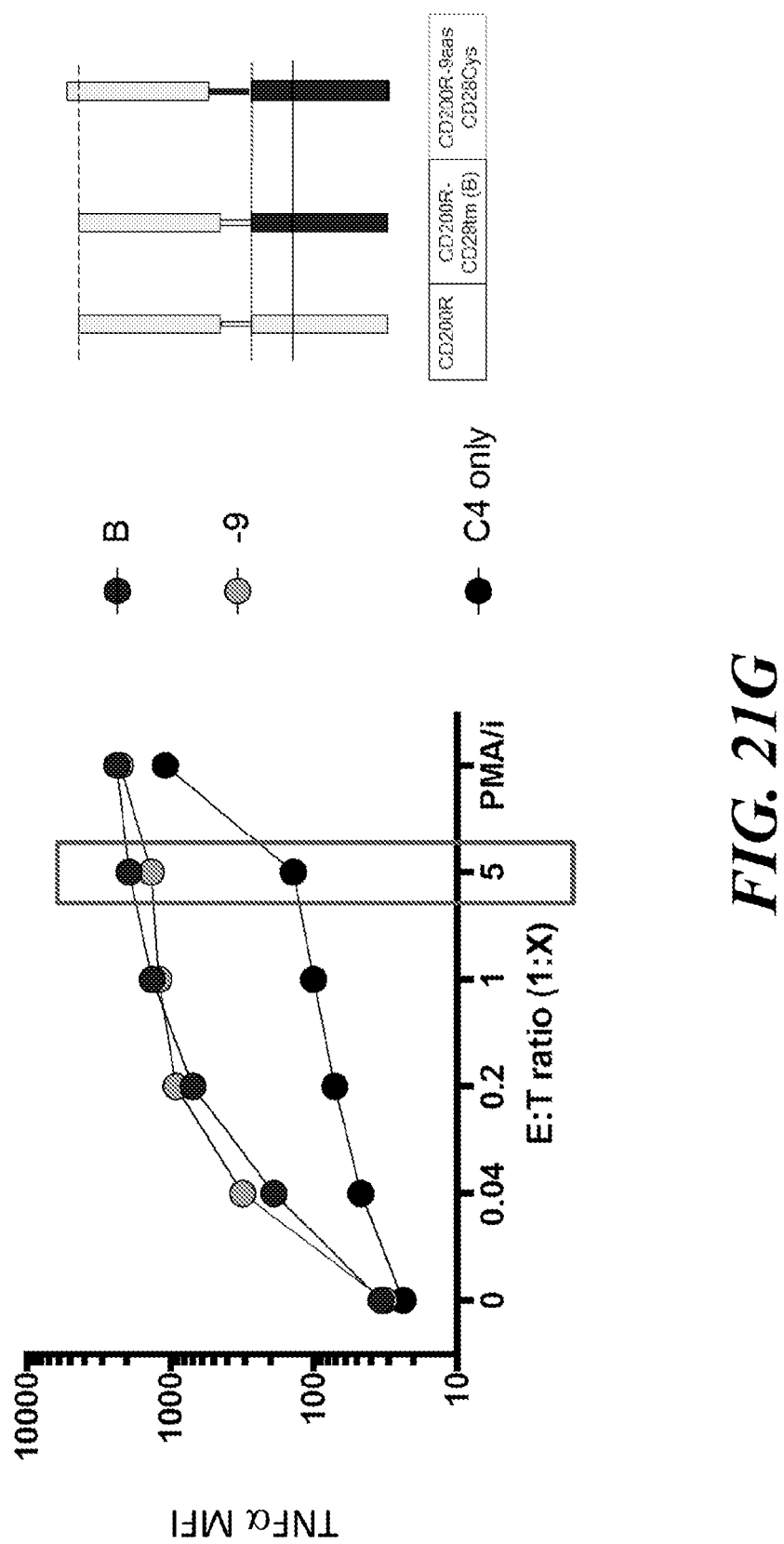
Figure 21H:
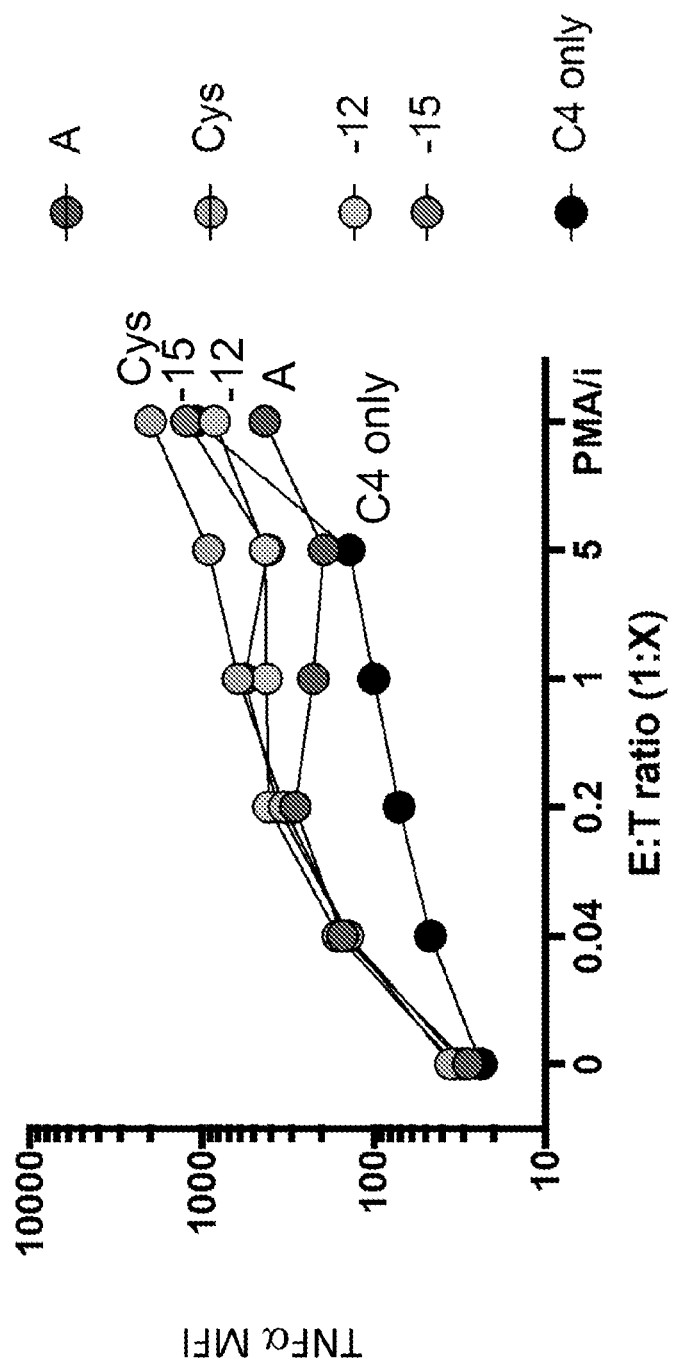
Figure 21I:
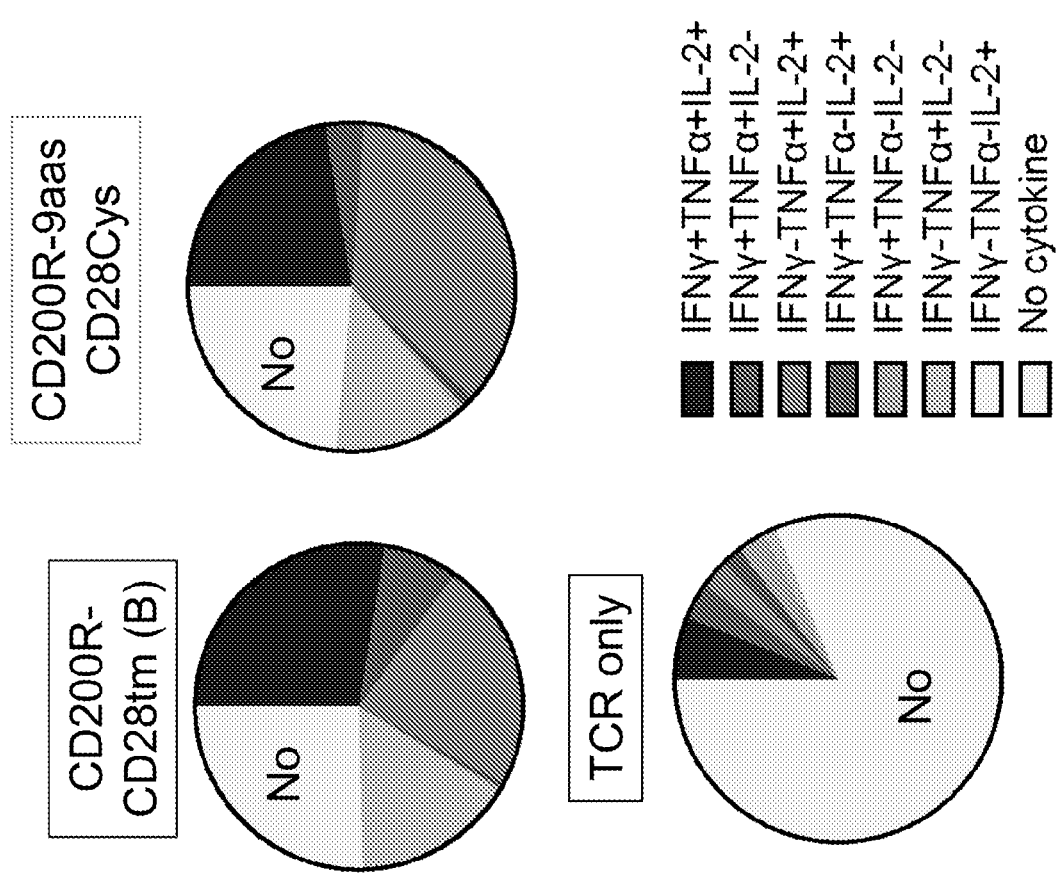

The ability of other CD200R-targeted constructs to increase cytokine production is shown in FIG. 21E. CD200R-CD28tm (FIGS. 21F and 21G, labeled "B") and CD200R-9aas-CD28Cys (FIGS. 21F and 21G, labeled "-9") notably improved cytokine production. CD200-targeted IFPs exhibited increased and polyfunctional cytokine production (FIG. 21I).

Figure 21J:
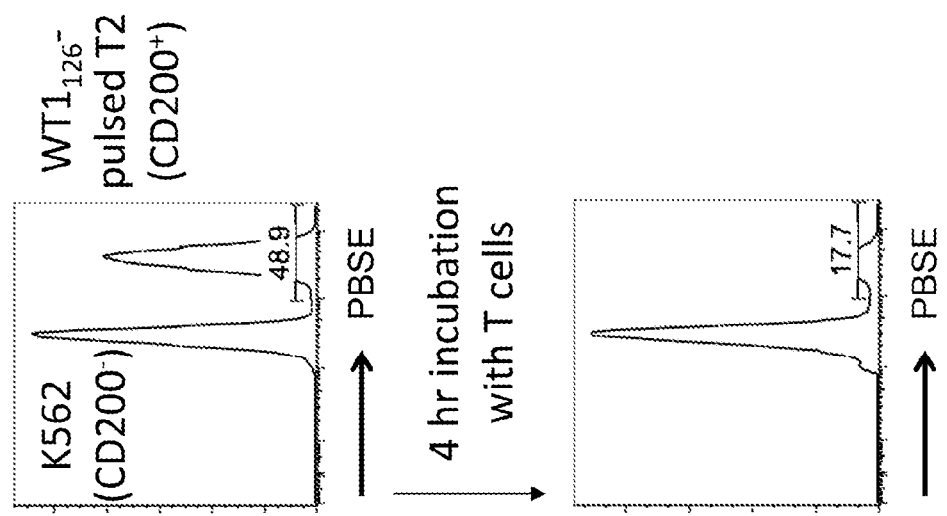
Figure 21K:
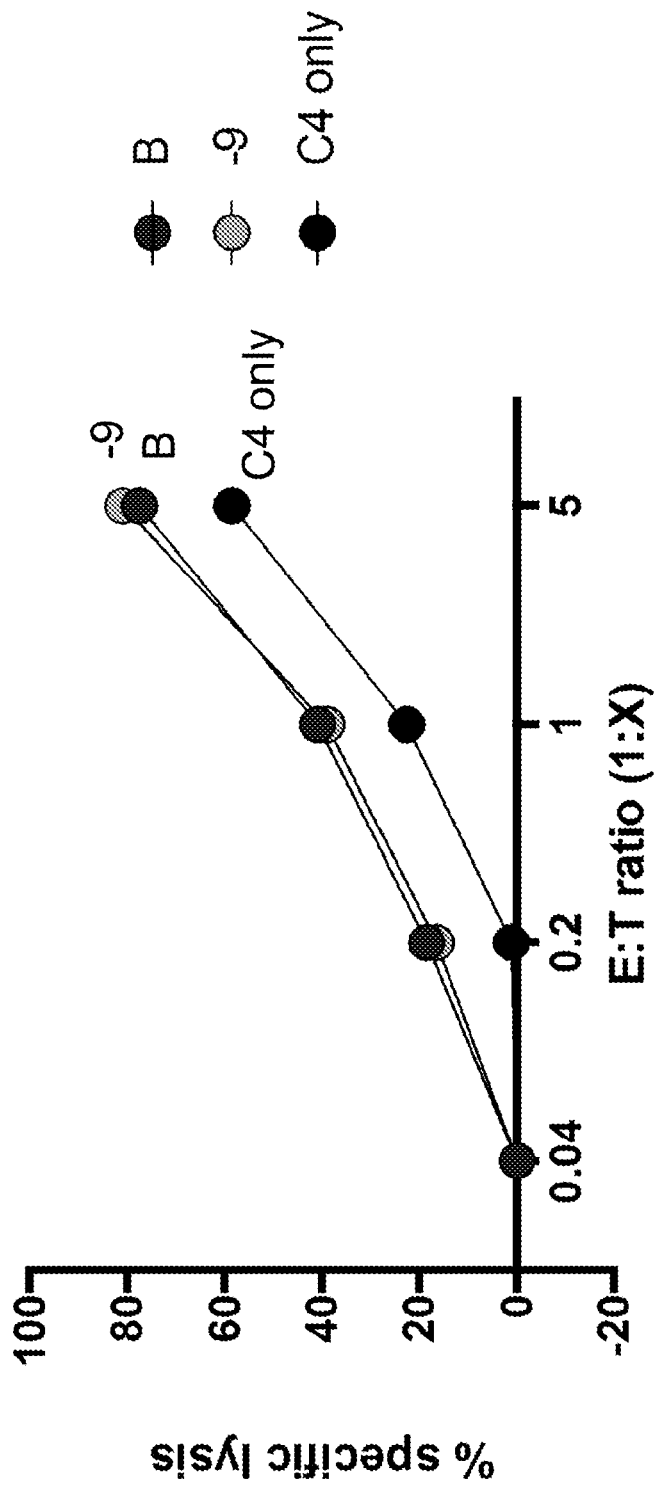

Effector function was also assessed in a flow cytometry-based cytotoxicity assay similar to that described in Example 15 (FIG. 21J). T cells transduced with CD200R-CD28 constructs lysed targets more effectively than control T cells (FIG. 21K, CD200R-CD28tm, labeled "B", and CD200R-9aas-CD28Cys, labeled "-9").

Example 22

In Vivo Testing of FAS IFPs

Fas-CD28 constructs were designed as in Example 11 and tested in an in vivo mouse model of leukemia (FIG. 22A). C57BL/6 mice were inoculated intraperitoneally with 4×10⁶ tumor cells (day 0) and treated with cyclophosphamide, and subsequently provided with (1) no additional treatment, (2) adoptive transfer of 10⁶ GFP-transduced TCR$_{gag}$ transgenic CD8⁺ T cells (day 5), or (3) adoptive transfer of 10⁶ Fas-CD28-transduced TCR$_{gag}$ transgenic CD8⁺ T cells (day 5). In vivo bioluminescence imaging of firefly luciferase⁺ FBL tumors was used to measure leukemia in the mice at various time points.

T cells transduced with Fas IFP tended to eradicate disease quicker (FIG. 22B) and provide protection over time (FIGS. 22B, 22C).

Example 23

Fas-4-1BB Fusion Protein Constructs

Figure 23A:
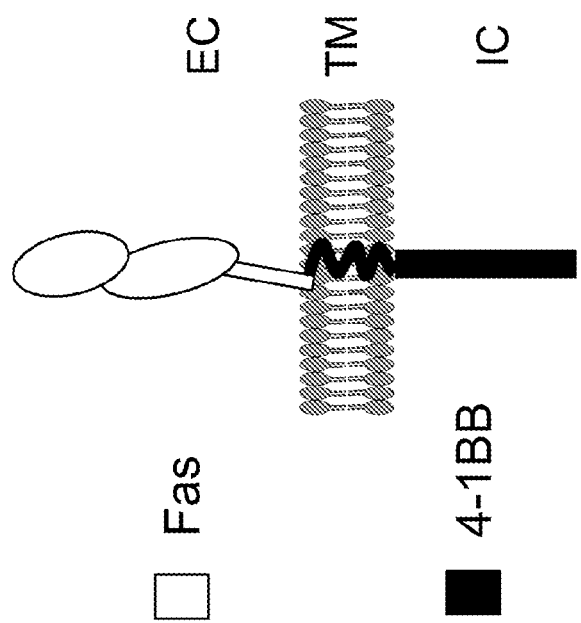

Exemplary fusion proteins as described herein also include IFPs comprised of the extracellular domain of Fas, or portions thereof, and an intracellular signaling domain of 4-1BB. The extracellular component may comprise all or a portion of the extracellular domain of Fas. In some embodiments, the transmembrane component may be comprised of the domain of Fas, 4-1BB, or CD28, or portions thereof. In some exemplary Fas-4-1BB fusion proteins, the transmembrane component comprises the transmembrane domain of CD28 and the extracellular component further comprises an extracellular portion of CD28, particularly an extracellular cysteine residue adjacent to the transmembrane component (e.g., Fas-CD28Cys-4-1BBic and Fas-9aas-CD28Cys-4-1BBic). The extracellular component may comprise all or a portion of the extracellular domain of Fas or may be truncated to preserve maintain a short spatial distance between the cells (~9aas) upon receptor-ligand interaction. In some other exemplary Fas-4-1BB fusion proteins, the transmembrane component comprises the transmembrane domain of 4-1BB (e.g., Fas-4-1BBtm; FIG. 23A). Additionally, a Fas-4-1BB construct has the capacity to convert a signal initiated by the binding of Fas to its target into a positive (e.g., costimulatory) signal generated by the 4-1BB intracellular signaling domain.

Figure 23B:
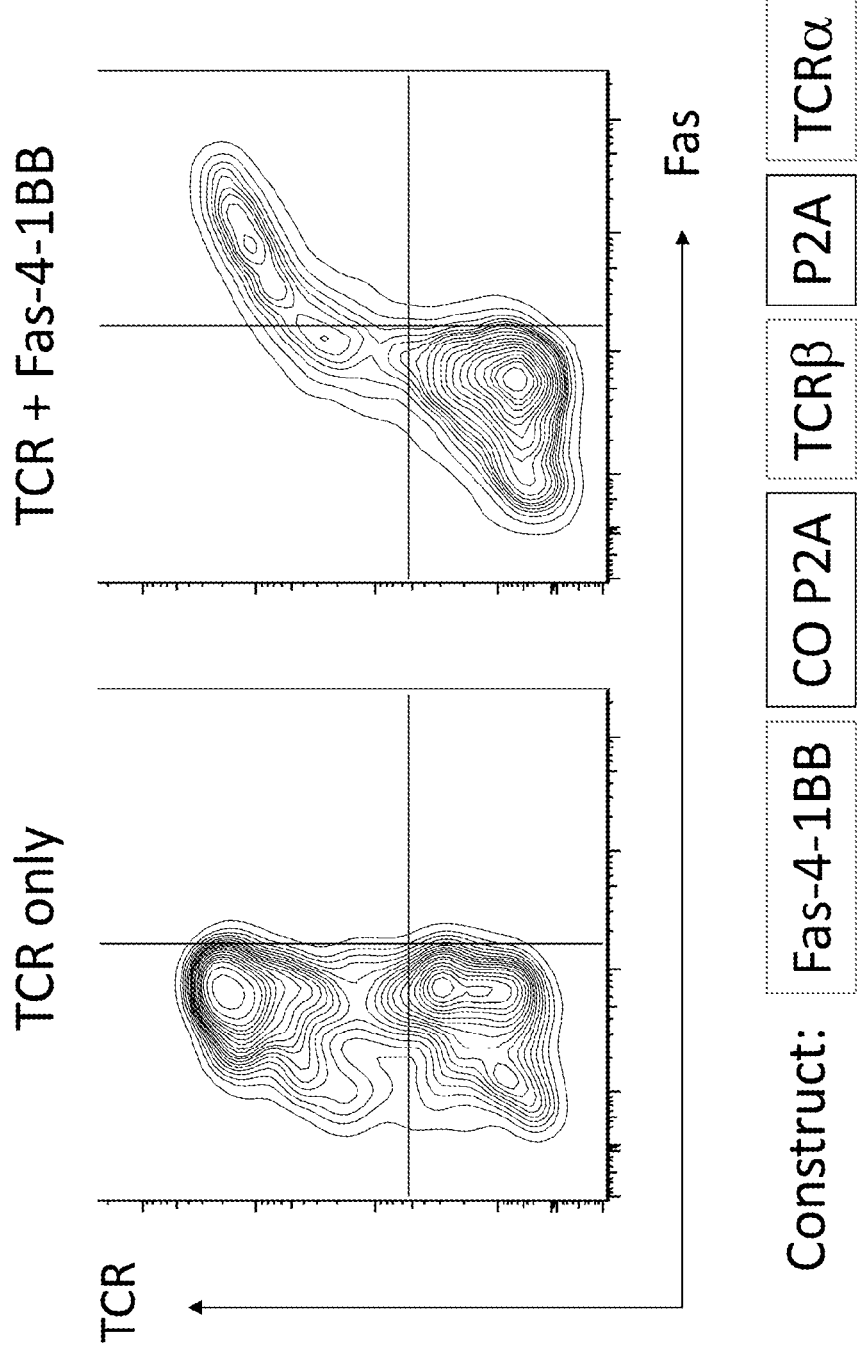

Fas-4-1BB IFP and a transgenic TCR can be co-expressed in transduced murine T cells. IFPs comprising a Fas extracellular component were generated using the general methods described in Example 2. P14 T cells were transduced to co-express the Fas-4-1BBtm IFP and a transgenic TCR ($TCR_{gag}$, specific for an epitope derived from the Friend murine leukemia virus-transformed FBL leukemia (Stromnes et al., *J Clin Invest.* 120:3722-3734, 2010)). Retroviral supernatant was generated by transfection of Plat-E cells with DNA constructs encoding either $TCR_{gag}$ alone, or $TCR_{gag}$ and Fas-4-1BBtm. Naïve P14 T cells were stimulated with anti-CD3 and anti-CD28, then transduced for 2 days with retroviral supernatant. Five days post-stimulation, transduced T cells were stained with specific antibodies to the TCR and to Fas, and analyzed by flow cytometry. P14 T cells transduced with constructs encoding $TCR_{gag}$ and Fas-4-1BBtm expressed similar levels of TCR, and also expressed high levels of the Fas-4-1BBtm IFP construct (FIG. 23B).

Figure 23C:
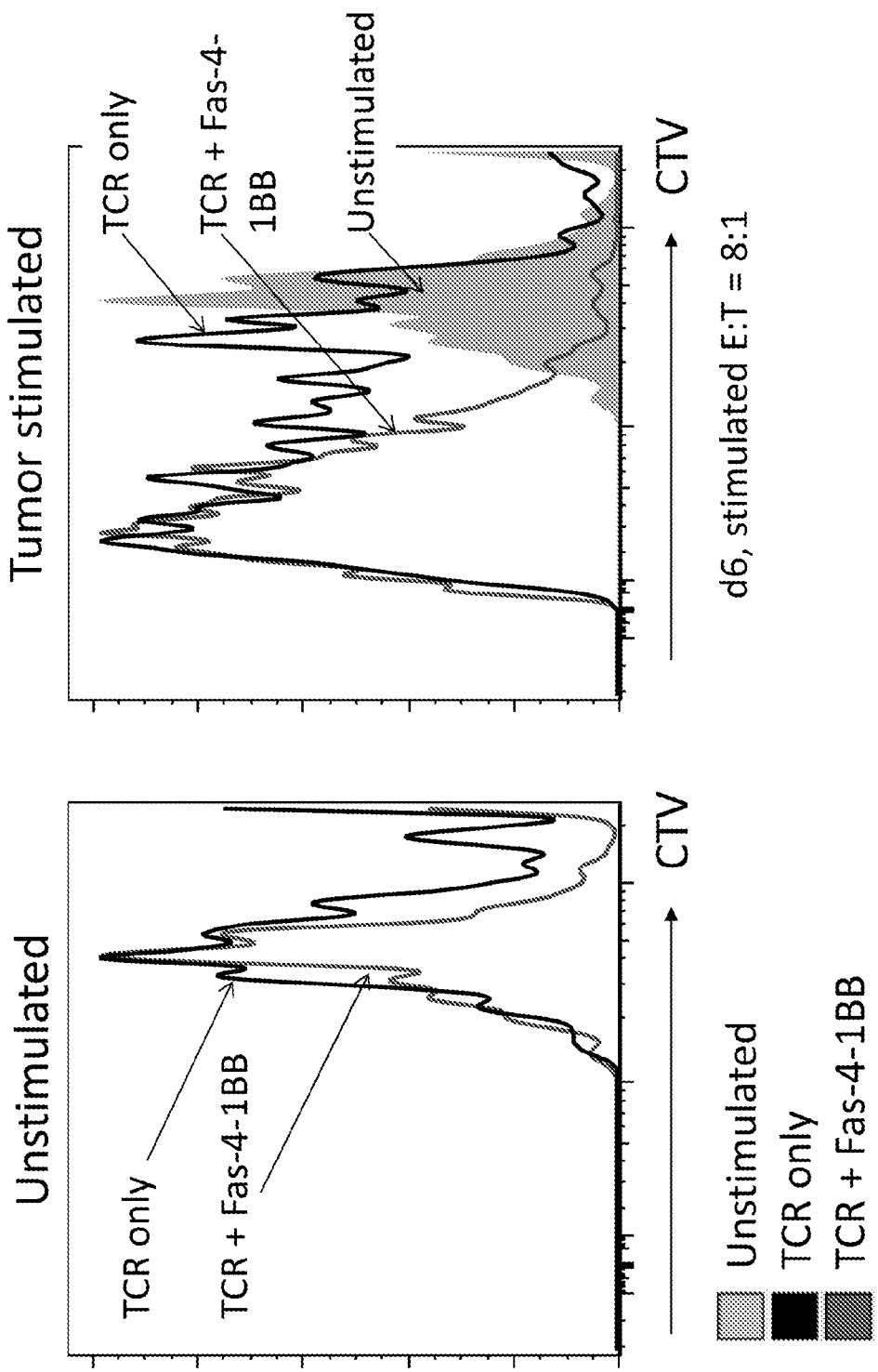

Fas-4-1BB$^+$ T cells were found to exhibit enhanced proliferation in vitro. Transduced P14 T cells were stained with CellTrace Violet (CTV) proliferation dye and stimulated with FBL tumor cells for 6 days at an effector-to-target (E:T) ratio of 8:1. T cells were then harvested and analyzed by flow cytometry. Without stimulation, T cells transduced with the $TCR_{gag}$ only exhibited a lack of proliferation, as did T cells transduced with both $TCR_{gag}$ and Fas-4-1BBtm (TCR+Fas-4-1BBtm) (FIG. 23C, left). With an E:T of 8:1, some TCR-only T cells exhibited proliferation; however, all TCR+Fas-4-1BB$^+$ T cells exhibited robust proliferation, supporting increased stimulation and proliferative capacity (FIG. 23C, right).

Figure 23D:
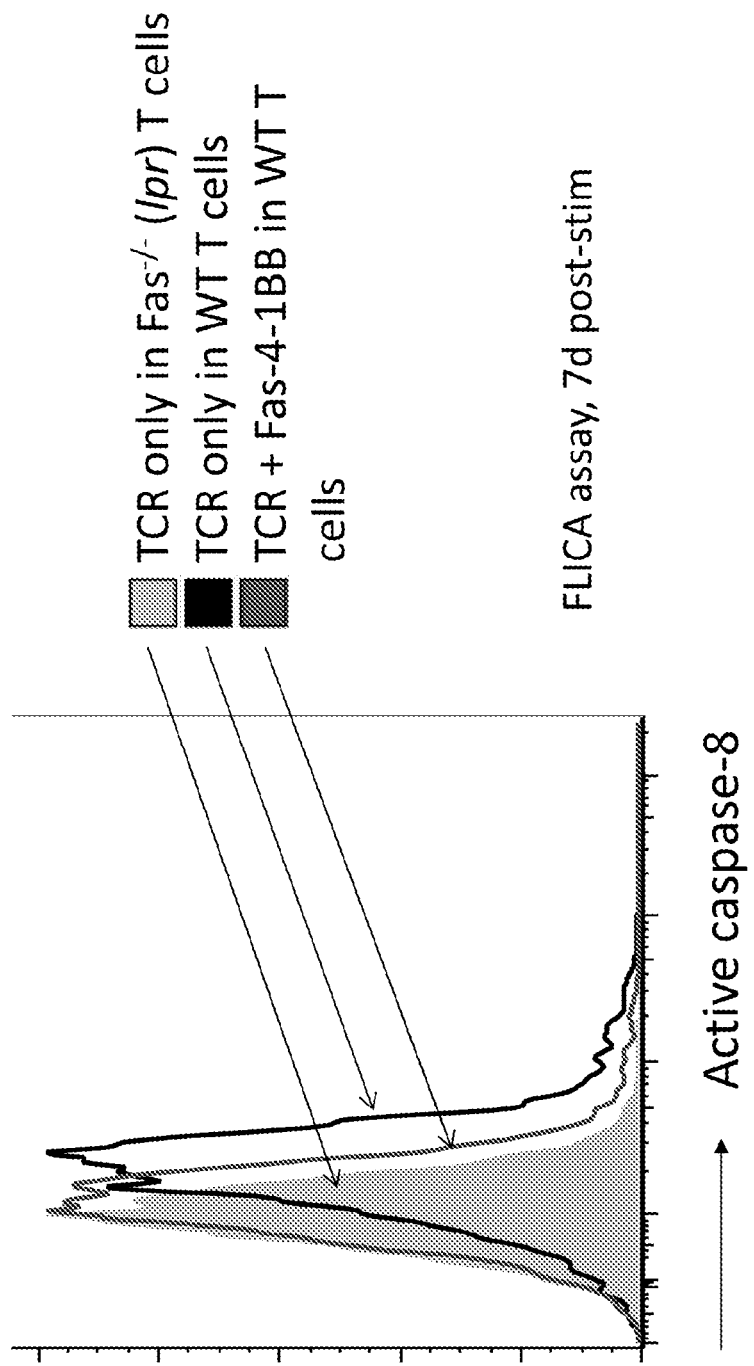

Additionally, Fas-4-1BB$^+$ T cells exhibited reduced cell death Fas pathway signaling, indicating that binding of the Fas extracellular domain did not result in activation of the Fas signaling pathway, as expected for the IFP wherein the Fas intracellular domain was replaced with a 4-1BB intracellular domain. Cell death Fas signaling pathway activity in (i) T cells expressing transgenic $TCR_{gag}$ but lacking Fas expression; (ii) wild-type T cells expressing transgenic $TCR_{gag}$; and (iii) T cells expressing transgenic $TCR_{gag}$ and Fas-4-1BBtm is shown in FIG. 23D. P14 T cells were stimulated and transduced with $TCR_{gag}$ or $TCR_{gag}$+Fas-4-1BB IFP. Seven days later, T cells were stained for active caspase-8 expression using the fluorescent inhibitor of caspases (FLICA) methodology, as a measure of cell death by the Fas pathway. Fas-deficient T cells (grey) exhibited no active caspase-8 expression, whereas TCR-transduced T cells exhibited elevated expression. TCR+Fas-4-1BB T cells had less active caspase-8 expression relative to TCR-only T cells, indicating less cell death by the Fas pathway (FIG. 23D).

Overall, these data indicate that Fas-4-1BBtm fusion proteins are able to convert negative/cell death signaling associated with binding of Fas into positive co-stimulatory signals.

Example 24

Fas-4-1bb Fusion Proteins Enhance Control of Tumor Growth and Improve Survival in an ID8 Ovarian Cancer Model T cells transduced with Fas-4-1BBtm controlled tumor growth and promoted survival in an ID8 model of ovarian cancer.

The ID8 model is a transplantable murine model of ovarian cancer (Walton et al., *Cancer Res* 76: 6118-29, 2016). An IncuCyte® assay used to quantify killing of ID8 ovarian tumor cells. Murine transduced T cells (TCR or TCR+4-1BB) were co-incubated with red fluorescent ID8 ovarian tumor cells for two days and ID8 cell growth was quantified by IncuCyte® analysis. Loss of red signal indicates killing of tumor cells. TCR+Fas-4-1BB T cells exhibited increased control of ID8 tumor cell growth, relative to TCR-only T cells, as indicated by less red signal (FIG. 24A).

Additionally, mice treated T cells transduced with anti-mesothelin TCR+Fas-4-1BBtm had increased survival relative to mice treated with T cells transduced with anti-mesothelin TCR only. In the ID8 murine ovarian cancer model, 5e6 ID8 tumor cells were implanted and allowed to disseminate for 6 weeks. Following cyclophosphamide treatment, mice received $10^7$ T cells and 50e7 mesothelin-pulsed splenocytes, followed by IL-2 injections for 10 days. Mice were treated every two weeks until euthanized according to IACUC-approved endpoint criteria. Survival was improved with T cells transduced with TCR+Fas-4-1BBtm relative to TCR-only T cells (FIG. 24B).

Example 25

T Cells Expressing Fas-4-1bb Fusion Proteins Exhibit T Cell Persistence and Improve Survival in a KPC Mouse Model of Pancreatic Cancer It has previously been shown that immunotherapy with TCR-T cells targeting mesothelin can significantly prolong survival in the murine pancreatic KPC tumor model. In this study, the KPC model was used to determine whether immunotherapy with T cells expressing Fas-4-1BB fusion proteins can improve survival.

The autochthonous KPC pancreatic cancer model was used to model human disease (Lee et al., *Curr. Protoc. Pharmacol.* 73:14.39.1-14.39.20, 2016). In patients, >90% of pancreatic ductal adenoma (PDA) cases exhibit activating mutations in KRAS and >75% have mutations in p53. The KPC model uses a pancreas-specific Cre recombinase ("C") to create mutations in Kras ("K") and p53 ("P") in the pancreatic epithelium. The KPC model (i) reproduces many of the key features of the immune microenvironment observed in human PDA including a robust inflammatory reaction and exclusion of effector T cells, (ii) is the most extensively studied genetic model of PDA for evaluation of immunotherapy, and (iii) it has reproduced clinical observations seen in PDA patients treated with several immune oncology drugs including CD40 agonists and anti-PDL1 antibodies. The model has also been useful in screening drugs as a predictor of therapeutic efficacy in patients.

Figure 25A:
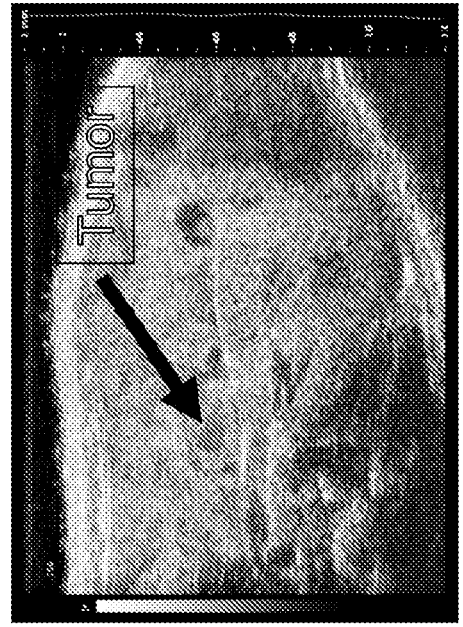
Figure 25A:
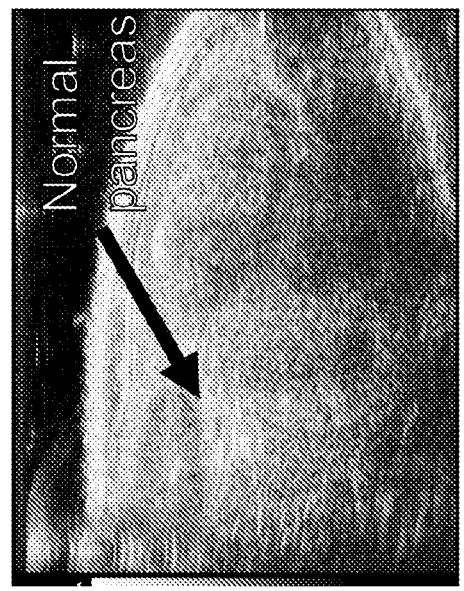
Figure 25B:
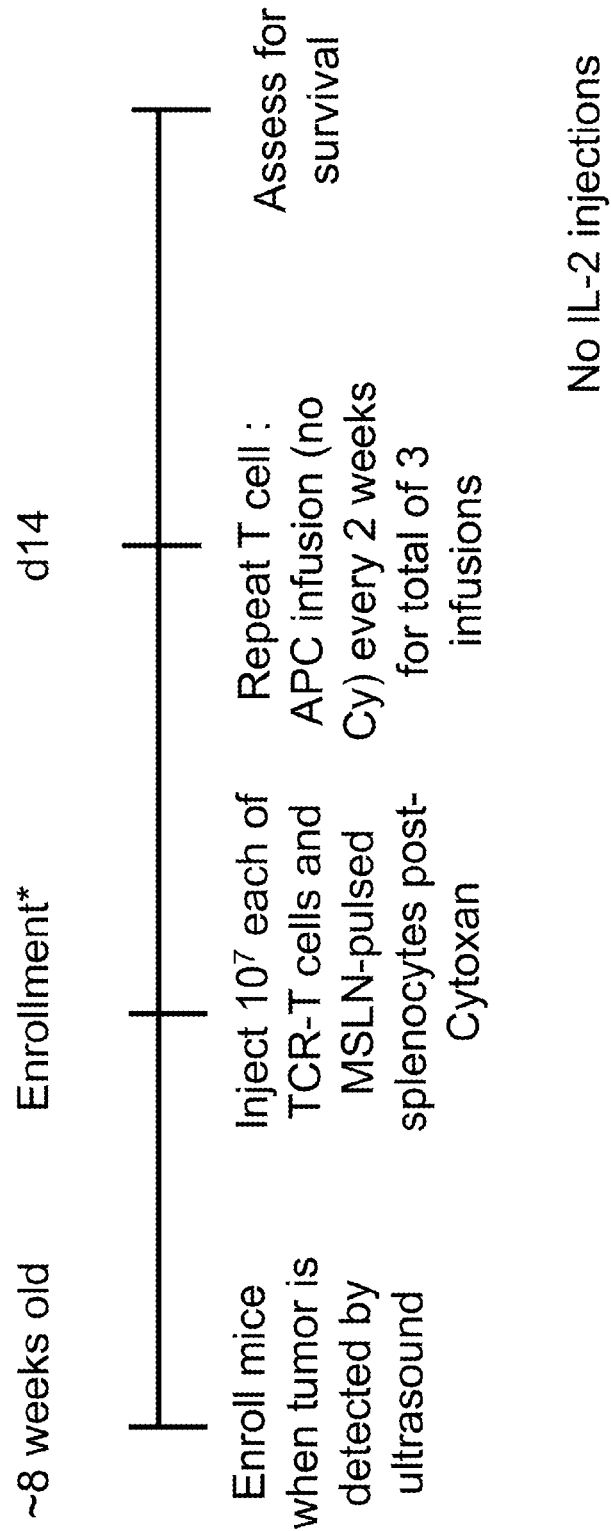

KPC mice were screened by ultrasound to determine when tumors arise, and were enrolled in the study when a tumor was detected, at approximately 8 weeks of age. FIG. 25A shows an ultrasound image of a healthy mouse with normal pancreas and a pancreatic tumor in an "enrolled" mouse (a KPC genetically engineered mouse). Mice were randomly assigned to treatment groups. Mice were treated with cyclophosphamide, and those receiving TCR-T cells were injected with 10⁷ each of mesothelin-specific-T cells (transduced with anti-mesothelin TCR cells or with anti-mesothelin TCR+Fas-4-1BBtm) and mesothelin peptide-pulsed splenocytes post-cyclophosphamide. Beginning 14 days post-enrollment, the T cell/APC infusion (but without cyclophosphamide) was repeated every 2 weeks for a total of 3 infusions, without IL-2 injections. Mice that survived 28 days after the final T cell infusion were bled and the persistence of transferred T cells was assessed by detection of congenically marked T cells using flow cytometry. At the end of the study, the mice were assessed for survival and euthanized according to IACUC-approved endpoint criteria. A summary of the experimental design used in this example is shown in FIG. 25B.

Figure 25C:
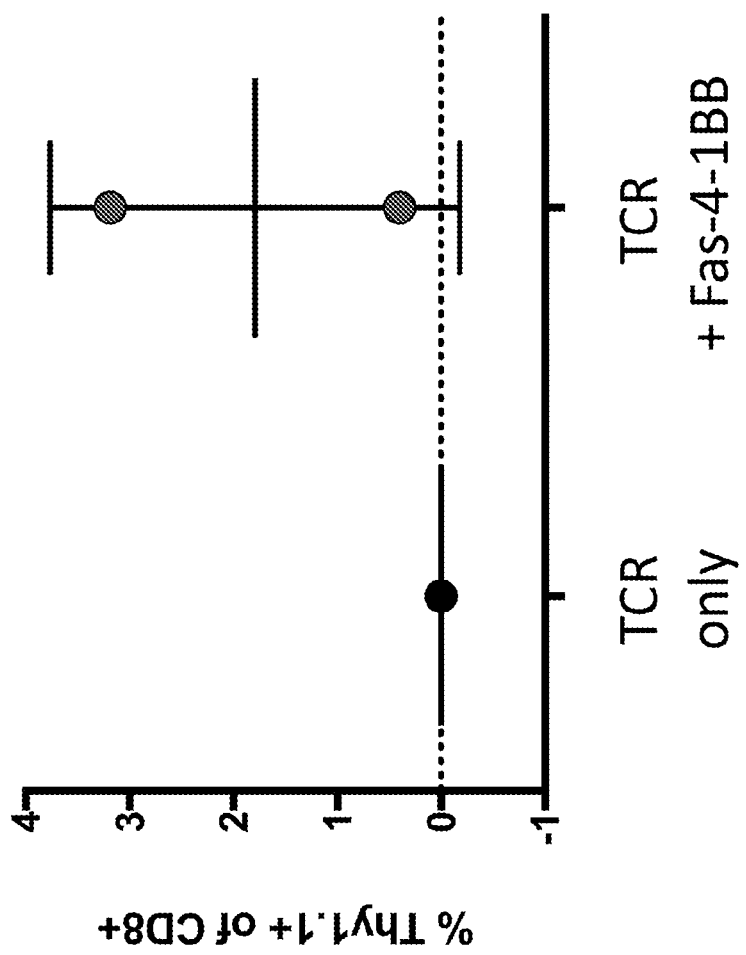
Figure 25D:
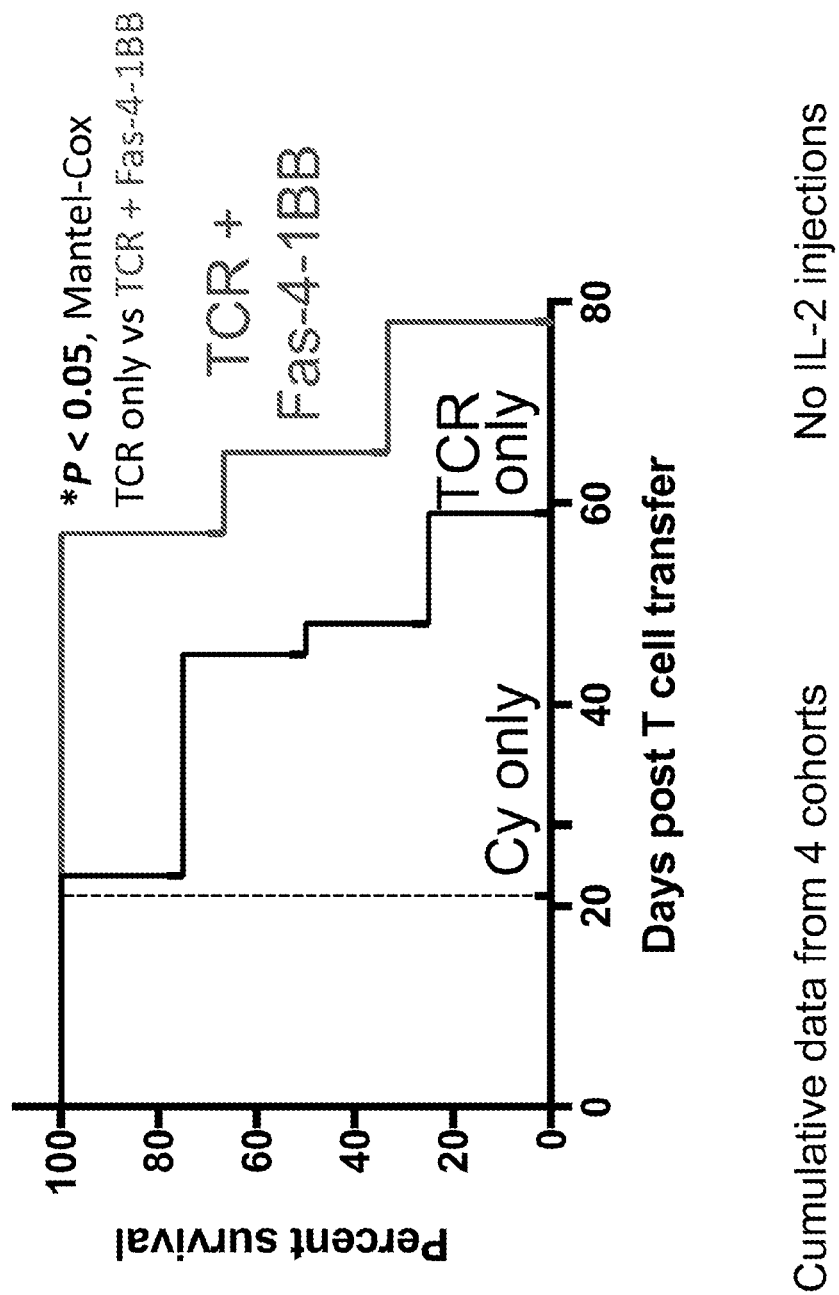

Fas-4-1BB⁺ T cells exhibited greater persistence in the blood 28 days after the third T cell infusion (FIG. 25C). All of the mice (100%) that received Fas-4-1BB⁺ T cells exhibited T cell persistence whereas TCR-only T cells did not persist (FIG. 25C). Survival of mice treated with mesothelin-specific TCR and Fas-4-1BB⁺ T cells was significantly improved over mesothelin-specific TCR only T cell immunotherapy (Mantel-Cox test, P<0.05; FIG. 25D).

Example 26

Fas-4-1BB Expression Enhances Adoptive Immunotherapy in a Mouse Model of AML

As was shown in Example 24 for solid tumors, treatment with Fas-4-1BB⁺ T cells improves survival in liquid tumors. In the murine AML model (Teague et al., *Nature Medicine* 12: 335-341, 2006; Oda et al., *Blood* 130: 2410-2419, 2017), FBL cells were injected and allowed to disseminate for 5 days. On day 5, mice were treated with cyclophosphamide with or without 10⁶ T cells. Survival was improved with T cells transduced with TCR+Fas-4-1BBtm relative to TCR-only T cells (FIG. 26).

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification or listed in the Application Data Sheet, including but not limited to U.S. Provisional Patent Application. No. 62/128,979 filed Mar. 5, 2015, U.S. Provisional Patent Application No. 62/473,282 filed Mar. 17, 2017, U.S. Provisional Patent Application No. 62/629,663 filed Feb. 12, 2018, International Application No. PCT/US2016/021064 filed Mar. 4, 2016, and International Application No. PCT/US2018/022998 filed Mar. 16, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
Sequence total quantity: 213
SEQ ID NO: 1            moltype = DNA  length = 915
FEATURE                 Location/Qualifiers
misc_feature            1..915
                        note = huCD200Rtm-CD28 construct
source                  1..915
                        mol_type = other DNA
                        organism = synthetic construct
SEQUENCE: 1
atgctgtgcc cttggagaac cgccaacctg ggcctgctgc tgatcctgac catcttcctg   60
gtggccgcca gcagcagcct gtgcatggac gagaagcaga tcacccagaa ctacagcaag  120
gtgctggccg aagtgaacac cagctggccc gtgaagatgg ccaccaacgc cgtgctgtgc  180
tgccctccta tcgccctgcg gaacctgatc atcatcacct gggagatcat cctgcgggc   240
cagcccagct gtaccaaggc ctaccggaaa gagacaaacg agacaaaaga aacaaactgc  300
accgacgagc ggatcacatg ggtgtccaga cccgaccaga acagcgacct gcagatcaga  360
cccgtggcca tcacccacga cggctactac cggtgcatca tggtcacccc cgatggcaac  420
ttccaccggg gataccatct gcaggtgctc gtgaccccccg aagtgaccct gttccagaac  480
cggaacagaa ccgccgtgtg caaggccgtg gccggaaaac ctgccgccca gatctcttgg  540
atccccgagg gcgattgcgc caccaagcag gaatactggt ccaacggcac cgtgaccgtg  600
aagtccacct gtcactggga ggtgcacaac gtgtccaccg tgacatgcca cgtgtcccac  660
ctgaccggca acaagagcct gtacatcgag ctgctgcctg tgcctggcgc caagaagtcc  720
gccaagctgt acatccccta catcatcctg acaatcatca ttctgaccat cgtgggcttc  780
atctggctgc tgcgcagcaa gcggagcaga ggcggccaca gcgactacat gaacatgacc  840
cctagacggc ctggccccac cagaaagcac taccagccct acgcccctcc ccgggacttt  900
gccgcctaca gaagc                                                    915

SEQ ID NO: 2            moltype = DNA  length = 728
FEATURE                 Location/Qualifiers
misc_feature            1..728
                        note = huCD200R entire extracellular domain
source                  1..728
                        mol_type = other DNA
                        organism = synthetic construct
SEQUENCE: 2
tgctgtgccc ttggagaacc gccaacctgg gcctgctgct gatcctgacc atcttcctgg   60
tggccgccag cagcagcctg tgcatggacg agaagcagat cacccagaac tacagcaagg  120
```

```
tgctggccga agtgaacacc agctggcccg tgaagatggc caccaacgcc gtgctgtgct    180
gccctcctat cgccctgcgg aacctgatca tcatcacctg ggagatcatc ctgcggggcc    240
agcccagctg taccaaggcc taccggaaag agacaaacga dacaaaagaa acaaactgca    300
ccgacgagcg gatcacatgg gtgtccagac ccgaccagaa cagcgacctg cagatcgac    360
ccgtggccat cacccacgac ggctactacc ggtgcatcat ggtcacccc gatggcaact    420
tccaccgggg ataccatctg caggtgctct gacccccga agtgaccctg ttccagaacc    480
ggaacagaac cgccgtgtgc aaggccgtgg ccggaaaacc tgccgcccag atctcttgga    540
tccccgaggg cgattgcgcc accaagcagg aatactggtc caacggcacc gtgaccgtga    600
agtccacctg tcactgggag gtgcacaacg tgtccaccgt gacatgccac gtgtcccacc    660
tgaccggcaa caagagcctg tacatcgagc tgctgcctgt gcctggcgcc aagaagtccg    720
ccaagctg                                                             728

SEQ ID NO: 3              moltype = DNA   length = 63
FEATURE                   Location/Qualifiers
misc_feature              1..63
                          note = huCD200R transmembrane domain
source                    1..63
                          mol_type = other DNA
                          organism = synthetic construct
SEQUENCE: 3
tacatcccct acatcatcct gacaatcatc attctgacca tcgtgggctt catctggctg    60
ctg                                                                   63

SEQ ID NO: 4              moltype = DNA   length = 81
FEATURE                   Location/Qualifiers
misc_feature              1..81
                          note = CD28 transmembrane domain
source                    1..81
                          mol_type = other DNA
                          organism = synthetic construct
SEQUENCE: 4
ttctgggtgc tggtggtggt cggaggcgtg ctggcctgct acagcctgct ggtcaccgtg    60
gccttcatca tcttttgggt c                                               81

SEQ ID NO: 5              moltype = DNA   length = 123
FEATURE                   Location/Qualifiers
misc_feature              1..123
                          note = CD28 intracellular domain
source                    1..123
                          mol_type = other DNA
                          organism = synthetic construct
SEQUENCE: 5
cgcagcaagc ggagcagagg cggccacagc gactacatga acatgacccc tagacggcct    60
ggccccacca gaaagcacta ccagccctac gcccctcccc gggactttgc cgcctacaga    120
agc                                                                   123

SEQ ID NO: 6              moltype = DNA   length = 933
FEATURE                   Location/Qualifiers
misc_feature              1..933
                          note = huCD200R-CD28tm construct
source                    1..933
                          mol_type = other DNA
                          organism = synthetic construct
SEQUENCE: 6
atgctgtgcc cttggagaac cgccaacctg ggcctgctgc tgatcctgac catcttcctg    60
gtggccgcca gcagcagcct gtgcatggac gagaagcaga tcacccagaa ctacagcaag    120
gtgctggccg aagtgaacac cagctggccc gtgaagatgg ccaccaacgc cgtgctgtgc    180
tgccctccta tcgccctgcg gaacctgatc atcatcacct gggagatcat cctgcggggc    240
cagcccagct gtaccaaggc ctaccggaaa gagacaaacg agacaaaaga aacaaactgc    300
accgacgagc ggatcacatg ggtgtccaga cccgaccaga cagcgacct gcagatcaga    360
cccgtggcca tcacccacga cggctactac cggtgcatca tggtcacccc cgatggcaac    420
ttccaccggg gataccatct gcaggtgctc tgacccccg aagtgaccct gttccagaac    480
cggaacagaa ccgccgtgtg caaggccgtg gccggaaaac ctgccgccca gatctcttgg    540
atccccgagg gcgattgcgc caccaagcag gaatactggt ccaacggcac cgtgaccgtg    600
aagtccacct gtcactggga ggtgcacaac gtgtccaccg tgacatgcca cgtgtcccac    660
ctgaccggca acaagagcct gtacatcgag ctgctgcctg tgcctggcgc caagaagtcc    720
gccaagctgt ctgggtgctg gtggtggtc ggaggcgtgc tggcctgcta cagcctgctg    780
gtcaccgtgg ccttcatcat cttttgggtc cgcagcaagc ggagcagagg cggccacagc    840
gactacatga acatgacccc tagacggcct ggccccacca gaaagcacta ccagccctac    900
gcccctcccc gggactttgc cgcctacaga agc                                  933

SEQ ID NO: 7              moltype = DNA   length = 942
FEATURE                   Location/Qualifiers
misc_feature              1..942
                          note = huCD200R-9aas-CD28Cys construct
source                    1..942
                          mol_type = other DNA
                          organism = synthetic construct
SEQUENCE: 7
```

```
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga acagcgacct gcagatcaga   360
cccgtggcca tcacccacga cggctactac cggtgcatca tggtcacccc cgatggcaac   420
ttccaccggg gataccatct gcaggtgctc gtgaccccg aagtgaccct gttccagaac    480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtacatcgag ctgctgcctg tgtgtcccag ccctctgttt    720
cccggcccta gcaagccttt ctgggtgctg gtggtggtcg gaggcgtgct ggcctgctac   780
agcctgctgg tcaccgtggc cttcatcatc ttttgggtc gcagcaagcg gagcagaggc   840
ggccacagcg actacatgaa catgaccccc tagacggcctg gccccaccag aaagcactac   900
cagcccctacg ccccctccccg ggactttgcc gcctacagaa gc                    942

SEQ ID NO: 8         moltype = DNA  length = 702
FEATURE              Location/Qualifiers
misc_feature         1..702
                     note = huCD200R-9aas portion of extracellular domain
source               1..702
                     mol_type = other DNA
                     organism = synthetic construct
SEQUENCE: 8
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga acagcgacct gcagatcaga   360
cccgtggcca tcacccacga cggctactac cggtgcatca tggtcacccc cgatggcaac   420
ttccaccggg gataccatct gcaggtgctc gtgaccccg aagtgaccct gttccagaac    480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca acaagagcct gtacatcgag ctgctgcctg tg                      702

SEQ ID NO: 9         moltype = DNA  length = 36
FEATURE              Location/Qualifiers
misc_feature         1..36
                     note = CD28Cys multimerization domain
source               1..36
                     mol_type = other DNA
                     organism = synthetic construct
SEQUENCE: 9
tgtcccagcc ctctgtttcc cggccctagc aagcct                              36

SEQ ID NO: 10        moltype = DNA  length = 933
FEATURE              Location/Qualifiers
misc_feature         1..933
                     note = huCD200R-12aas-CD28Cys construct
source               1..933
                     mol_type = other DNA
                     organism = synthetic construct
SEQUENCE: 10
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga acagcgacct gcagatcaga   360
cccgtggcca tcacccacga cggctactac cggtgcatca tggtcacccc cgatggcaac   420
ttccaccggg gataccatct gcaggtgctc gtgaccccg aagtgaccct gttccagaac    480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca acaagagcct gtacatcgag ctgtgtccca gccctctgtt tcccggccct   720
agcaagcctt tctgggtgct ggtggtggtc ggaggcgtgc tggcctgcta cagcctgctg   780
gtcaccgtgg ccttcatcat cttttgggtc gcagcaagcg ggagcagagg cggccacagc   840
gactacatga acatgacccc tagacggcct ggccccacca gaaagcacta ccagccctac   900
gccccctccc gggactttgc cgcctacaga agc                                933

SEQ ID NO: 11        moltype = DNA  length = 693
FEATURE              Location/Qualifiers
misc_feature         1..693
                     note = huCD200R-12aas portion of extracellular domain
source               1..693
                     mol_type = other DNA
```

```
                      organism = synthetic construct
SEQUENCE: 11
atgctgtgcc cttggagaac cgccaacctg ggcctgctgc tgatcctgac catcttcctg   60
gtggccgcca gcagcagcct gtgcatggac gagaagcaga tcacccagaa ctacagcaag  120
gtgctggccg aagtgaacac cagctggccc gtgaagatgg ccaccaacgc cgtgctgtgc  180
tgccctccta tcgccctgcg gaacctgatc atcatcacct gggagatcat cctgcggggc  240
cagcccagct gtaccaaggc ctaccggaaa gagacaaacg agacaaaaga aacaaactgc  300
accgacgagc ggatcacatg ggtgtccaga cccgaccaga cagcgacct gcagatcaga   360
cccgtggcca tcacccacga cggctactac cggtgcatca tggtcacccc cgatggcaac  420
ttccaccggg gataccatct gcaggtgctc gtgacccccg aagtgaccct gttccagaac  480
cggaacagaa ccgccgtgtg caaggccgtg gccggaaaac ctgccgccca gatctcttgg  540
atccccgagg gcgattgcgc caccaagcag gaatactggt ccaacggcac cgtgaccgtg  600
aagtccacct gtcactggga ggtgcacaac gtgtccaccg tgacatgcca cgtgtcccac  660
ctgaccggca acaagagcct gtacatcgag ctg                               693

SEQ ID NO: 12          moltype = DNA   length = 945
FEATURE                Location/Qualifiers
misc_feature           1..945
                       note = huCD200R-9aas-CD28Cys tm-41BBic construct
source                 1..945
                       mol_type = other DNA
                       organism = synthetic construct
SEQUENCE: 12
atgctgtgcc cttggagaac cgccaacctg ggcctgctgc tgatcctgac catcttcctg   60
gtggccgcca gcagcagcct gtgcatggac gagaagcaga tcacccagaa ctacagcaag  120
gtgctggccg aagtgaacac cagctggccc gtgaagatgg ccaccaacgc cgtgctgtgc  180
tgccctccta tcgccctgcg gaacctgatc atcatcacct gggagatcat cctgcggggc  240
cagcccagct gtaccaaggc ctaccggaaa gagacaaacg agacaaaaga aacaaactgc  300
accgacgagc ggatcacatg ggtgtccaga cccgaccaga cagcgacct gcagatcaga   360
cccgtggcca tcacccacga cggctactac cggtgcatca tggtcacccc cgatggcaac  420
ttccaccggg gataccatct gcaggtgctc gtgacccccg aagtgaccct gttccagaac  480
cggaacagaa ccgccgtgtg caaggccgtg gccggaaaac ctgccgccca gatctcttgg  540
atccccgagg gcgattgcgc caccaagcag gaatactggt ccaacggcac cgtgaccgtg  600
aagtccacct gtcactggga ggtgcacaac gtgtccaccg tgacatgcca cgtgtcccac  660
ctgaccggca acaagagcct gtacatcgag ctgtgtccag ccctctgttt              720
cccggcccta gcaagccttt ctgggtgctg tggtggtcg gaggcgtgct ggcctgctac   780
agcctgctgg tcaccgtggc cttcatcatc tttgggtca agcggggcag aaagaagctg   840
ctgtacatct tcaagcagcc tttcatgcgg cccgtgcaga ccacccagga agaggacggc  900
tgctcctgca gattccccga ggaagaagaa ggcggctgcg agctg                  945

SEQ ID NO: 13          moltype = DNA   length = 126
FEATURE                Location/Qualifiers
misc_feature           1..126
                       note = 4-1BB intracellular component
source                 1..126
                       mol_type = other DNA
                       organism = synthetic construct
SEQUENCE: 13
aagcggggca gaaagaagct gctgtacatc ttcaagcagc ctttcatgcg gcccgtgcag   60
accacccagg aagaggacgg ctgctcctgc agattccccg aggaagaaga aggcggctgc  120
gagctg                                                             126

SEQ ID NO: 14          moltype = DNA   length = 936
FEATURE                Location/Qualifiers
misc_feature           1..936
                       note = huCD200R-12aas-CD28Cys tm-41BBic construct
source                 1..936
                       mol_type = other DNA
                       organism = synthetic construct
SEQUENCE: 14
atgctgtgcc cttggagaac cgccaacctg ggcctgctgc tgatcctgac catcttcctg   60
gtggccgcca gcagcagcct gtgcatggac gagaagcaga tcacccagaa ctacagcaag  120
gtgctggccg aagtgaacac cagctggccc gtgaagatgg ccaccaacgc cgtgctgtgc  180
tgccctccta tcgccctgcg gaacctgatc atcatcacct gggagatcat cctgcggggc  240
cagcccagct gtaccaaggc ctaccggaaa gagacaaacg agacaaaaga aacaaactgc  300
accgacgagc ggatcacatg ggtgtccaga cccgaccaga cagcgacct gcagatcaga   360
cccgtggcca tcacccacga cggctactac cggtgcatca tggtcacccc cgatggcaac  420
ttccaccggg gataccatct gcaggtgctc gtgacccccg aagtgaccct gttccagaac  480
cggaacagaa ccgccgtgtg caaggccgtg gccggaaaac ctgccgccca gatctcttgg  540
atccccgagg gcgattgcgc caccaagcag gaatactggt ccaacggcac cgtgaccgtg  600
aagtccacct gtcactggga ggtgcacaac gtgtccaccg tgacatgcca cgtgtcccac  660
ctgaccggca acaagagcct gtacatcgag ctgtgtccca gccctctgtt tcccggccct  720
agcaagcctt tctgggtgct ggtggtggtc ggaggcgtgc tggcctgcta cagcctgctg  780
gtcaccgtgg ccttcatcat cttcgggtcc aaggggggca gaaagaagct gctgtacatc  840
ttcaagcagc ctttcatgcg gcccgtgcag accacccagg aagaggacgg ctgctcctgc  900
agattccccg aggaagaaga aggcggctgc gagctg                            936

SEQ ID NO: 15          moltype = DNA   length = 1059
FEATURE                Location/Qualifiers
```

| misc_feature | 1..1059 |
| | note = huCD200R-12aas-CD28Cys tm ic-41BBic construct |
| source | 1..1059 |
| | mol_type = other DNA |
| | organism = synthetic construct |

SEQUENCE: 15

```
atgctgtgcc cttggagaac cgccaacctg ggcctgctgc tgatcctgac catcttcctg   60
gtggccgcca gcagcagcct gtgcatggac gagaagcaga tcacccagaa ctacagcaag  120
gtgctggccg aagtgaacac cagctggccc gtgaagatgg ccaccaacgc cgtgctgtgc  180
tgccctccta tcgccctgcg gaacctgatc atcatcacct gggagatcat cctgcggggc  240
cagcccagct gtaccaaggc ctaccggaaa gagacaaacg agacaaaaga aacaaactgc  300
accgacgagc ggatcacatg ggtgtccaga cccgaccaga cagcgacct gcagatcaga  360
cccgtggcca tcacccacga cggctactac cggtgcatca tggtcacccc cgatggcaac  420
ttccaccggg gataccatct gcaggtgctc gtgaccccg aagtgaccct gttccagaac  480
cggaacagaa ccgccgtgtg caaggccgtg gccggaaaac ctgccgccca gatctcttgg  540
atccccgagg gcgattgcgc caccaagcag gaatactggt ccaacggcac cgtgaccgtg  600
aagtccacct gtcactggga ggtgcacaac gtgtccaccg tgcatgcca cgtgtcccac  660
ctgaccggca acaagagcct gtacatcgag ctgtgtccca gccctctgtt tcccgtccct  720
agcaagcctt tctgggtgct ggtggtggtc ggaggcgtgc tggcctgcta cagcctgctg  780
gtcaccgtgg ccttcatcat cttttgggtc cgcagcaagc ggagcagagg cggccacagc  840
gactacatga acatgacccc tagacggcct ggccccacca gaaagcacta ccagccctac  900
gcccctccc gggactttgc cgcctacaga gcaagcgggg cagaaagaa gctgctgtac  960
atcttcaagc agccttttcat gcggcccgtg cagaccacc aggaagagga cggctgctcc 1020
tgcagattcc ccgaggaaga agaaggcggc tgcgagctg                       1059
```

SEQ ID NO: 16   moltype = DNA   length = 1305
FEATURE         Location/Qualifiers
misc_feature    1..1305
                note = huSIRPalphatm-CD28 construct
source          1..1305
                mol_type = other DNA
                organism = synthetic construct

SEQUENCE: 16

```
atggaacctg ccggacctgc tcctggcaga ctgggacctc tgctgtgtct gctgctggcc   60
gcctcttgtg cttggagcgg agtggctggc gaagaggaac tgcaagtgat ccagcccgac  120
aagagcgtgc tggtggccgc tggcgaaacc gccaccctga tgtacagc accagcctg  180
atccccgtgg cccccatcca gtggtttaga ggcgctggcc ctggcagaga gctgatctac  240
aaccagaaag agggccactt ccccagagtg accaccgtgt ccgacctgac caagcggaac  300
aacatggact tcagcatccg gatcggcaac atcaccctg ccgatgccgg cacctactac  360
tgcgtgaagt ccggaagggg cagccccgac gacgtggaat caaaagcgg agccggcacc  420
gagctgagcg tgcgggctaa accttctgcc ctgtggtgt ctggacctgc cgccagagct  480
acacctcagc acaccgtgtc ttttacctgc gagagccacg gcttcagccc cagagacatc  540
accctggtca ggttcaagaa cggcaacgag ctgtccgact tccagaccaa cgtggaccct  600
gtgggcgaga gcgtgtccta cagcatccac agcaccgcca aggtggtgct gacccgcgaa  660
gatgtgcaca gccaagtgat ctgcgaggtg gcccacgtga cactgcaggg cgatcctctg  720
agaggaaccg ccaacctgtc cgagacaatc agagtgcccc ccaccctgga agtgacccag  780
cagcctgtgc gggccgagaa ccaagtgaac gtgacctgcc aagtgcggaa gttctacccc  840
cagcggctgc agctgacctg gctggaaaac ggcaatgtgt cccggaccga cagccagc  900
accgtgaccg agaacaagga tgccacctac aattggatga ctggctgct cgtgaacgtg  960
tccgccaccc gggacgatgt gaagctgaca tgccaggtgg aacacgacgg ccagcctgcc 1020
gtgtccaaga gccacgatct gaaggtgtca gcccatccca aagagcaggg ctccaacaca 1080
gccgccgaga caccggcag caacgagcgg aacatctaca tcgtcgtggg cgtcgtgtgc 1140
accctgctgg tggcactgct gatggccgct ctgtaccctcg tgcgcagcaa gcggagcaga 1200
ggcggccaca cgactacat gaacatgacc cctagacggc ctggccccac cagaaagcac 1260
taccagcct acgccctcc cgggactttt gccgcctaca gaagc                1305
```

SEQ ID NO: 17   moltype = DNA   length = 1119
FEATURE         Location/Qualifiers
misc_feature    1..1119
                note = huSIRP alpha entire extracellular domain
source          1..1119
                mol_type = other DNA
                organism = synthetic construct

SEQUENCE: 17

```
atggaacctg ccggacctgc tcctggcaga ctgggacctc tgctgtgtct gctgctggcc   60
gcctcttgtg cttggagcgg agtggctggc gaagaggaac tgcaagtgat ccagcccgac  120
aagagcgtgc tggtggccgc tggcgaaacc gccaccctga tgtacagc accagcctg  180
atccccgtgg cccccatcca gtggtttaga ggcgctggcc ctggcagaga gctgatctac  240
aaccagaaag agggccactt ccccagagtg accaccgtgt ccgacctgac caagcggaac  300
aacatggact tcagcatccg gatcggcaac atcaccctg ccgatgccgg cacctactac  360
tgcgtgaagt ccggaagggg cagccccgac gacgtggaat caaaagcgg agccggcacc  420
gagctgagcg tgcgggctaa accttctgcc ctgtggtgt ctggacctgc cgccagagct  480
acacctcagc acaccgtgtc ttttacctgc gagagccacg gcttcagccc cagagacatc  540
accctggtca ggttcaagaa cggcaacgag ctgtccgact tccagaccaa cgtggaccct  600
gtgggcgaga gcgtgtccta cagcatccac agcaccgcca aggtggtgct gacccgcgaa  660
gatgtgcaca gccaagtgat ctgcgaggtg gcccacgtga cactgcaggg cgatcctctg  720
agaggaaccg ccaacctgtc cgagacaatc agagtgcccc ccaccctgga agtgacccag  780
cagcctgtgc gggccgagaa ccaagtgaac gtgacctgcc aagtgcggaa gttctacccc  840
cagcggctgc agctgacctg gctggaaaac ggcaatgtgt cccggaccga cagccagc  900
```

```
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca aagagcaggg ctccaacaca   1080
gccgccgaga acaccggcag caacgagcgg aacatctac                          1119

SEQ ID NO: 18          moltype = DNA   length = 63
FEATURE                Location/Qualifiers
misc_feature           1..63
                       note = huSIRP alpha transmembrane domain
source                 1..63
                       mol_type = other DNA
                       organism = synthetic construct
SEQUENCE: 18
atcgtcgtgg gcgtcgtgtg caccctgctg gtggcactgc tgatggccgc tctgtacctc     60
gtg                                                                   63

SEQ ID NO: 19          moltype = DNA   length = 1323
FEATURE                Location/Qualifiers
misc_feature           1..1323
                       note = huSIRP alpha-CD28tm construct
source                 1..1323
                       mol_type = other DNA
                       organism = synthetic construct
SEQUENCE: 19
atggaacctg ccggacctgc tcctggcaga ctgggacctc tgctgtgtct gctgctggcc     60
gcctcttgtg cttggagcgg agtggctggc gaagaggaac tgcaagtgat ccagcccgac    120
aagagcgtgc tggtggccgc tggcgaaacc gccaccctga gatgtacagc caccagcctg    180
atccccgtgg gccccatcca gtggtttaga ggcgctggcc ctggcagaga gctgatctac    240
aaccagaaag agggccactt ccccagagtg accaccgtgt ccgacctgac caagcggaac    300
aacatggact tcagcatccg gatcggcaac atcactacc cgatgccgg cacctactac      360
tgcgtgaagt tccggaaggg cagccccgac gacgtggaat caaaagcgg agccggcacc    420
gagctgagcg tgcgggctaa accttctgcc cctgtggtgt ctggacctgc cgccagagct    480
acacctcagc acaccgtgtc ttttacctgc gagagccacg gcttcagccc cagagacatc    540
accctgaagt ggttcaagaa cggcaacgag ctgtccgact tccagaccaa cgtgaccct    600
gtgggcgaga gcgtgtccta cagcatccac agcaccgcca aggtggtgct gaccccgcgaa   660
gatgtgcaca gccaagtgat ctgcgaggtg gcccacgtga cactgcaggg cgatcctctg    720
agaggaaccg ccaacctgtc cgagacaatc agagtgcccc ccacccgtgga agtgaccag    780
cagcctgtgc gggccgagaa ccaagtgaac gtgacctgcc aagtgcggaa gttctacccc    840
cagcggctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca aagagcaggg ctccaacaca   1080
gccgccgaga acaccggcag caacgagcgg aacatctact ctgggtgtc ggtggtgtc    1140
ggaggcgtgc tggcctgcta cagcctgctg gtcaccgtgg ccttcatcat cttttgggtc   1200
cgcagcaagc ggagcagagg cggccacagc gactacatga acatgacccc tagacggcct   1260
ggccccacca gaaagcacta ccagcccac gcccctcccc gggactttgc cgcctacaga    1320
agc                                                                  1323

SEQ ID NO: 20          moltype = DNA   length = 1323
FEATURE                Location/Qualifiers
misc_feature           1..1323
                       note = huSIRP alpha 12aas-CD28Cys construct
source                 1..1323
                       mol_type = other DNA
                       organism = synthetic construct
SEQUENCE: 20
atggaacctg ccggacctgc tcctggcaga ctgggacctc tgctgtgtct gctgctggcc     60
gcctcttgtg cttggagcgg agtggctggc gaagaggaac tgcaagtgat ccagcccgac    120
aagagcgtgc tggtggccgc tggcgaaacc gccaccctga gatgtacagc caccagcctg    180
atccccgtgg gccccatcca gtggtttaga ggcgctggcc ctggcagaga gctgatctac    240
aaccagaaag agggccactt ccccagagtg accaccgtgt ccgacctgac caagcggaac    300
aacatggact tcagcatccg gatcggcaac atcaccctg ccgatgccgg cacctactac     360
tgcgtgaagt tccggaaggg cagccccgac gacgtggaat caaaagcgg agccggcacc    420
gagctgagcg tgcgggctaa accttctgcc cctgtggtgt ctggacctgc cgccagagct    480
acacctcagc acaccgtgtc ttttacctgc gagagccacg gcttcagccc cagagacatc    540
accctgaagt ggttcaagaa cggcaacgag ctgtccgact tccagaccaa cgtgaccct    600
gtgggcgaga gcgtgtccta cagcatccac agcaccgcca aggtggtgct gaccccgcgaa   660
gatgtgcaca gccaagtgat ctgcgaggtg gcccacgtga cactgcaggg cgatcctctg    720
agaggaaccg ccaacctgtc cgagacaatc agagtgcccc ccacccgtgga agtgaccag    780
cagcctgtgc gggccgagaa ccaagtgaac gtgacctgcc aagtgcggaa gttctacccc    840
cagcggctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca aagagcaggg ctccaacaca   1080
gcctgtccca gccctctgtt tcccggccct agcaagcctt tctgggtgct ggtggtggtc   1140
ggaggcgtgc tggcctgcta cagcctgctg gtcaccgtgg ccttcatcat cttttgggtc   1200
cgcagcaagc ggagcagagg cggccacagc gactacatga acatgacccc tagacggcct   1260
ggccccacca gaaagcacta ccagcccac gcccctcccc gggactttgc cgcctacaga    1320
agc                                                                  1323
```

```
SEQ ID NO: 21            moltype = DNA  length = 1083
FEATURE                  Location/Qualifiers
misc_feature             1..1083
                         note = huSIRP alpha 12aas portion of extracellular domain
source                   1..1083
                         mol_type = other DNA
                         organism = synthetic construct
SEQUENCE: 21
atggaacctg ccggacctgc tcctggcaga ctgggacctc tgctgtgtct gctgctggcc   60
gcctcttgtg cttggagcgg agtggctggc gaagaggaac tgcaagtgat ccagcccgac   120
aagagcgtgc tggtggccgc tggcgaaacc gccaccctga gatgtacagc caccagcctg   180
atcccgtgg gccccatcca gtggtttaga ggcgctggcc ctggcagaga gctgatctac   240
aaccagaaag agggccactt ccccagagtg accaccgtgt ccgacctgac caagcggaac   300
aacatggact tcagcatccg gatcggcaac atcacccctg ccgatgccgg cacctactac   360
tgcgtgaagt tccggaaggg cagccccgac gacgtgaat tcaaaagcgg agccggcacc   420
gagctgagcg tgcgggctaa accttctgcc cctgtggtgt ctggacctgc cgccagagct   480
acacctcagc acaccgtgtc ttttacctgc gagagccacg gcttcagccc cagagacatc   540
accctgaagt ggttcaagaa cggcaacgag ctgtccgact tccagaccaa cgtggaccct   600
gtgggcgaga gcgtgtccta cagcatccac agcaccgcca aggtggtgct gacccgcgaa   660
gatgtgcaca gccaagtgat ctgcgaggtg cccacgtga cactgcaggg cgatcctctg   720
agaggaaccg ccaacctgtc cgagacaatc agagtgcccc ccaccctgga agtgacccag   780
cagcctgtgc gggccgagaa ccaagtgaac gtgacctgcc aagtgcggaa gttctacccc   840
cagcggctgc agctgacctg gctggaaaac ggcaatgtgt cccggaccga dacagccagc   900
accgtgaccg agaacaagga tggcacctac aattggatga gctggctgct cgtgaacgtg   960
tccgcccacc gggacgatgt gaagctgaca tgccaggtgg aacacgacgg ccagcctgcc  1020
gtgtccaaga gccacgatct gaaggtgtca gcccatccca aagagcaggg ctccaacaca  1080
gcc                                                                1083

SEQ ID NO: 22            moltype = DNA  length = 1326
FEATURE                  Location/Qualifiers
misc_feature             1..1326
                         note = huSIRP alpha-12aas-CD28Cys tm-41BBic construct
source                   1..1326
                         mol_type = other DNA
                         organism = synthetic construct
SEQUENCE: 22
atggaacctg ccggacctgc tcctggcaga ctgggacctc tgctgtgtct gctgctggcc   60
gcctcttgtg cttggagcgg agtggctggc gaagaggaac tgcaagtgat ccagcccgac   120
aagagcgtgc tggtggccgc tggcgaaacc gccaccctga gatgtacagc caccagcctg   180
atcccgtgg gccccatcca gtggtttaga ggcgctggcc ctggcagaga gctgatctac   240
aaccagaaag agggccactt ccccagagtg accaccgtgt ccgacctgac caagcggaac   300
aacatggact tcagcatccg gatcggcaac atcacccctg ccgatgccgg cacctactac   360
tgcgtgaagt tccggaaggg cagccccgac gacgtgaat tcaaaagcgg agccggcacc   420
gagctgagcg tgcgggctaa accttctgcc cctgtggtgt ctggacctgc cgccagagct   480
acacctcagc acaccgtgtc ttttacctgc gagagccacg gcttcagccc cagagacatc   540
accctgaagt ggttcaagaa cggcaacgag ctgtccgact tccagaccaa cgtggaccct   600
gtgggcgaga gcgtgtccta cagcatccac agcaccgcca aggtggtgct gacccgcgaa   660
gatgtgcaca gccaagtgat ctgcgaggtg cccacgtga cactgcaggg cgatcctctg   720
agaggaaccg ccaacctgtc cgagacaatc agagtgcccc ccaccctgga agtgacccag   780
cagcctgtgc gggccgagaa ccaagtgaac gtgacctgcc aagtgcggaa gttctacccc   840
cagcggctgc agctgacctg gctggaaaac ggcaatgtgt cccggaccga dacagccagc   900
accgtgaccg agaacaagga tggcacctac aattggatga gctggctgct cgtgaacgtg   960
tccgcccacc gggacgatgt gaagctgaca tgccaggtgg aacacgacgg ccagcctgcc  1020
gtgtccaaga gccacgatct gaaggtgtca gcccatccca aagagcaggg ctccaacaca  1080
gcctgtccca gccctctgtt tcccggccct agcaagcctt tctgggtgct ggtggtggtc  1140
ggaggcgtgc tggcctgcta cagcctgctg gtcaccgtgg ccttcatcat ctttttgggtc  1200
aagcggggca gaaagaagct gctgtacatc ttcaagcagc cttttcatcgc gcccgtgcag  1260
accaccccagg aagaggacgg ctgctcctgc agattccccg aggaagaaga aggcggctgc  1320
gagctg                                                             1326

SEQ ID NO: 23            moltype = DNA  length = 1449
FEATURE                  Location/Qualifiers
misc_feature             1..1449
                         note = huSIRP alpha-12aas-CD28Cys tm ic-41BBic construct
source                   1..1449
                         mol_type = other DNA
                         organism = synthetic construct
SEQUENCE: 23
atggaacctg ccggacctgc tcctggcaga ctgggacctc tgctgtgtct gctgctggcc   60
gcctcttgtg cttggagcgg agtggctggc gaagaggaac tgcaagtgat ccagcccgac   120
aagagcgtgc tggtggccgc tggcgaaacc gccaccctga gatgtacagc caccagcctg   180
atcccgtgg gccccatcca gtggtttaga ggcgctggcc ctggcagaga gctgatctac   240
aaccagaaag agggccactt ccccagagtg accaccgtgt ccgacctgac caagcggaac   300
aacatggact tcagcatccg gatcggcaac atcacccctg ccgatgccgg cacctactac   360
tgcgtgaagt tccggaaggg cagccccgac gacgtgaat tcaaaagcgg agccggcacc   420
gagctgagcg tgcgggctaa accttctgcc cctgtggtgt ctggacctgc cgccagagct   480
acacctcagc acaccgtgtc ttttacctgc gagagccacg gcttcagccc cagagacatc   540
accctgaagt ggttcaagaa cggcaacgag ctgtccgact tccagaccaa cgtggaccct   600
```

```
                                     -continued
gtgggcgaga gcgtgtccta cagcatccac agcaccgcca aggtggtgct gaccccgcgaa    660
gatgtgcaca gccaagtgat ctgcgaggtg gcccacgtga cactgcaggg cgatcctctg    720
agaggaaccg ccaacctgtc cgagacaatc agagtgcccc ccaccctgga agtgacccag    780
cagcctgtgc gggccgagaa ccaagtgaac gtgacctgcc aagtgcggaa gttctacccc    840
cagccgctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca agagcagggc tccaacaca    1080
gcctgtccca gccctctgtt tcccggccct agcaagcctt tctgggtgct ggtggtggtc    1140
ggaggcgtgc tggcctgcta cagcctgctg gtcaccgtgg ccttcatcat cttttgggtc   1200
cgcagcaagc ggagcagagg cggccacagc gactacatga acatgacccc tagacgcct    1260
ggccccacca gaaagcacta ccagccctac gcccctcccc gggactttgc cgcctacaga   1320
agcaagcggg gcagaaagaa gctgctgtac atcttcaagc agcctttcat gcggcccgtg   1380
cagaccaccc aggaagagga cggctgctcc tgcagattcc ccgaggaaga agaaggcggc   1440
tgcgagctg                                                           1449

SEQ ID NO: 24              moltype = AA   length = 305
FEATURE                    Location/Qualifiers
REGION                     1..305
                           note = huCD200Rtm-CD28 protein
source                     1..305
                           mol_type = protein
                           organism = synthetic construct
SEQUENCE: 24
MLCPWRTANL GLLLILTIFL VAASSSLCMD EKQITQNYSK VLAEVNTSWP VKMATNAVLC     60
CPPIALRNLI IITWEIILRG QPSCTKAYRK ETNETKETNC TDERITWVSR PDQNSDLQIR    120
PVAITHDGYY RCIMVTPDGN FHRGYHLQVL VTPEVTLFQN RNRTAVCKAV AGKPAAQISW    180
IPEGDCATKQ EYWSNGTVTV KSTCHWEVHN VSTVTCHVSH LTGNKSLYIE LLPVPGAKKS    240
AKLYIPYIIL TIIILTIVGF IWLLRSKRSR GGHSDYMNMT PRRPGPTRKH YQPYAPPRDF    300
AAYRS                                                                305

SEQ ID NO: 25              moltype = AA   length = 243
FEATURE                    Location/Qualifiers
REGION                     1..243
                           note = huCD200R entire extracellular domain
source                     1..243
                           mol_type = protein
                           organism = synthetic construct
SEQUENCE: 25
MLCPWRTANL GLLLILTIFL VAASSSLCMD EKQITQNYSK VLAEVNTSWP VKMATNAVLC     60
CPPIALRNLI IITWEIILRG QPSCTKAYRK ETNETKETNC TDERITWVSR PDQNSDLQIR    120
PVAITHDGYY RCIMVTPDGN FHRGYHLQVL VTPEVTLFQN RNRTAVCKAV AGKPAAQISW    180
IPEGDCATKQ EYWSNGTVTV KSTCHWEVHN VSTVTCHVSH LTGNKSLYIE LLPVPGAKKS    240
AKL                                                                  243

SEQ ID NO: 26              moltype = AA   length = 21
FEATURE                    Location/Qualifiers
REGION                     1..21
                           note = huCD200R transmembrane domain
source                     1..21
                           mol_type = protein
                           organism = synthetic construct
SEQUENCE: 26
YIPYIILTII ILTIVGFIWL L                                               21

SEQ ID NO: 27              moltype = AA   length = 27
FEATURE                    Location/Qualifiers
REGION                     1..27
                           note = CD28 transmembrane domain protein
source                     1..27
                           mol_type = protein
                           organism = synthetic construct
SEQUENCE: 27
FWVLVVVGGV LACYSLLVTV AFIIFWV                                         27

SEQ ID NO: 28              moltype = AA   length = 41
FEATURE                    Location/Qualifiers
REGION                     1..41
                           note = CD28 intracellular domain protein
source                     1..41
                           mol_type = protein
                           organism = synthetic construct
SEQUENCE: 28
RSKRSRGGHS DYMNMTPRRP GPTRKHYQPY APPRDFAAYR S                         41

SEQ ID NO: 29              moltype = AA   length = 311
FEATURE                    Location/Qualifiers
REGION                     1..311
                           note = huCD200R-CD28tm protein
```

```
                        source              1..311
                                            mol_type = protein
                                            organism = synthetic construct
SEQUENCE: 29
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPVPGAKKS   240
AKLFWVLVVV GGVLACYSLL VTVAFIIFWV RSKRSRGGHS DYMNMTPRRP GPTRKHYQPY   300
APPRDFAAYR S                                                       311

SEQ ID NO: 30           moltype = AA  length = 314
FEATURE                 Location/Qualifiers
REGION                  1..314
                        note = huCD200R-9aas-CD28Cys protein
source                  1..314
                        mol_type = protein
                        organism = synthetic construct
SEQUENCE: 30
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPVCPSPLF   240
PGPSKPFWVL VVVGGVLACY SLLVTVAFII FWVRSKRSRG GHSDYMNMTP RRPGPTRKHY   300
QPYAPPRDFA AYRS                                                    314

SEQ ID NO: 31           moltype = AA  length = 234
FEATURE                 Location/Qualifiers
REGION                  1..234
                        note = huCD200R-9aas protein
source                  1..234
                        mol_type = protein
                        organism = synthetic construct
SEQUENCE: 31
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPV        234

SEQ ID NO: 32           moltype = AA  length = 12
FEATURE                 Location/Qualifiers
REGION                  1..12
                        note = CD28Cys (extracellular portion) protein
source                  1..12
                        mol_type = protein
                        organism = synthetic construct
SEQUENCE: 32
CPSPLFPGPS KP                                                       12

SEQ ID NO: 33           moltype = AA  length = 311
FEATURE                 Location/Qualifiers
REGION                  1..311
                        note = huCD200R-12aas-CD28Cys protein
source                  1..311
                        mol_type = protein
                        organism = synthetic construct
SEQUENCE: 33
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LCPSPLFPGP   240
SKPFWVLVVV GGVLACYSLL VTVAFIIFWV RSKRSRGGHS DYMNMTPRRP GPTRKHYQPY   300
APPRDFAAYR S                                                       311

SEQ ID NO: 34           moltype = AA  length = 231
FEATURE                 Location/Qualifiers
REGION                  1..231
                        note = huCD200R-12aas protein
source                  1..231
                        mol_type = protein
                        organism = synthetic construct
SEQUENCE: 34
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE L            231

SEQ ID NO: 35           moltype = AA  length = 315
FEATURE                 Location/Qualifiers
```

```
REGION                       1..315
                             note = huCD200R-9aas-CD28Cys tm-41BBic protein
source                       1..315
                             mol_type = protein
                             organism = synthetic construct
SEQUENCE: 35
MLCPWRTANL GLLLILTIFL VAASSSLCMD EKQITQNYSK VLAEVNTSWP VKMATNAVLC    60
CPPPIALRNLI IITWEIILRG QPSCTKAYRK ETNETKETNC TDERITWVSR PDQNSDLQIR  120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPVCPSPLF   240
PGPSKPFWVL VVVGGVLACY SLLVTVAFII FWVKRGRKKL LYIFKQPFMR PVQTTQEEDG   300
CSCRFPEEEE GGCEL                                                   315

SEQ ID NO: 36             moltype = AA    length = 42
FEATURE                   Location/Qualifiers
REGION                    1..42
                          note = 4-1BB intracellular component protein
source                    1..42
                          mol_type = protein
                          organism = synthetic construct
SEQUENCE: 36
KRGRKKLLYI FKQPFMRPVQ TTQEEDGCSC RFPEEEEGGC EL                     42

SEQ ID NO: 37             moltype = AA    length = 312
FEATURE                   Location/Qualifiers
REGION                    1..312
                          note = huCD200R-12aas-CD28Cys tm-41BBic protein
source                    1..312
                          mol_type = protein
                          organism = synthetic construct
SEQUENCE: 37
MLCPWRTANL GLLLILTIFL VAASSSLCMD EKQITQNYSK VLAEVNTSWP VKMATNAVLC    60
CPPPIALRNLI IITWEIILRG QPSCTKAYRK ETNETKETNC TDERITWVSR PDQNSDLQIR  120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LCPSPLFPGP   240
SKPFWVLVVV GGVLACYSLL VTVAFIIFWV KRGRKKLLYI FKQPFMRPVQ TTQEEDGCSC   300
RFPEEEEGGC EL                                                      312

SEQ ID NO: 38             moltype = AA    length = 353
FEATURE                   Location/Qualifiers
REGION                    1..353
                          note = huCD200R-12aas-CD28Cys tm ic-41BBic protein
source                    1..353
                          mol_type = protein
                          organism = synthetic construct
SEQUENCE: 38
MLCPWRTANL GLLLILTIFL VAASSSLCMD EKQITQNYSK VLAEVNTSWP VKMATNAVLC    60
CPPPIALRNLI IITWEIILRG QPSCTKAYRK ETNETKETNC TDERITWVSR PDQNSDLQIR  120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LCPSPLFPGP   240
SKPFWVLVVV GGVLACYSLL VTVAFIIFWV RSKRSRGGHS DYMNMTPRRP GPTRKHYQPY   300
APPRDFAAYR SKRGRKKLLY IFKQPFMRPV QTTQEEDGCS CRFPEEEEGG CEL          353

SEQ ID NO: 39             moltype = AA    length = 435
FEATURE                   Location/Qualifiers
REGION                    1..435
                          note = huSIRP alpha tm-CD28 protein
source                    1..435
                          mol_type = protein
                          organism = synthetic construct
SEQUENCE: 39
MEPAGPAPGR LGPLLCLLLA ASCAWSGVAG EEELQVIQPD KSVLVAAGET ATLRCTATSL    60
IPVGPIQWFR GAGPGRELIY NQKEGHFPRV TTVSDLTKRN NMDFSIRIGN ITPADAGTTY   120
CVKFRKGSPD DVEFKSGAGT ELSVRAKPSA PVVSGPAARA TPQHTVSFTC ESHGFSPRDI   180
TLKWFKNGNE LSDFQTNVDP VGESVSYSIH STAKVVLTRE DVHSQVICEV AHVTLQGDPL   240
RGTANLSETI RVPPTLEVTQ QPVRAENQVN VTCQVRKFYP QRLQLTWLEN GNVSRTETAS   300
TVTENKDGTY NWMSWLLVNV SAHRDDVKLT CQVEHDGQPA VSKSHDLKVS AHPKEQGSNT   360
AAENTGSNER NIYIVGVVC TLLVALLMAA LYLVRSKRSR GGHSDYMNMT PRRPGPTRKH    420
YQPYAPPRDF AAYRS                                                   435

SEQ ID NO: 40             moltype = AA    length = 373
FEATURE                   Location/Qualifiers
REGION                    1..373
                          note = huSIRP alpha entire extracellular domain protein
source                    1..373
                          mol_type = protein
                          organism = synthetic construct
SEQUENCE: 40
MEPAGPAPGR LGPLLCLLLA ASCAWSGVAG EEELQVIQPD KSVLVAAGET ATLRCTATSL    60
```

```
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
AAENTGSNER NIY                                                      373

SEQ ID NO: 41           moltype = AA  length = 21
FEATURE                 Location/Qualifiers
REGION                  1..21
                        note = huSIRP alpha transmembrane domain protein
source                  1..21
                        mol_type = protein
                        organism = synthetic construct
SEQUENCE: 41
IVVGVVCTLL VALLMAALYL V                                              21

SEQ ID NO: 42           moltype = AA  length = 441
FEATURE                 Location/Qualifiers
REGION                  1..441
                        note = huSIRP alpha -CD28tm protein
source                  1..441
                        mol_type = protein
                        organism = synthetic construct
SEQUENCE: 42
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
AAENTGSNER NIYFWVLVVV GGVLACYSLL VTVAFIIFWV RSKRSRGGHS DYMNMTPRRP    420
GPTRKHYQPY APPRDFAAYR S                                             441

SEQ ID NO: 43           moltype = AA  length = 441
FEATURE                 Location/Qualifiers
REGION                  1..441
                        note = huSIRP alpha-12aas-CD28Cys protein
source                  1..441
                        mol_type = protein
                        organism = synthetic construct
SEQUENCE: 43
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
ACPSPLFPGP SKPFWVLVVV GGVLACYSLL VTVAFIIFWV RSKRSRGGHS DYMNMTPRRP    420
GPTRKHYQPY APPRDFAAYR S                                             441

SEQ ID NO: 44           moltype = AA  length = 361
FEATURE                 Location/Qualifiers
REGION                  1..361
                        note = huSIRP alpha-12aas protein
source                  1..361
                        mol_type = protein
                        organism = synthetic construct
SEQUENCE: 44
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
RGTANLSETI RVPPTLEVTQ QPVRAENQVN VTCQVRKFYP QRLQLTWLEN GNVSRTETAS    300
TVTENKDGTY NWMSWLLVNV SAHRDDVKLT CQVEHDGQPA VSKSHDLKVS AHPKEQGSNT    360
A                                                                   361

SEQ ID NO: 45           moltype = AA  length = 442
FEATURE                 Location/Qualifiers
REGION                  1..442
                        note = huSIRP alpha-12aas-CD28Cys tm-41BBic protein
source                  1..442
                        mol_type = protein
                        organism = synthetic construct
SEQUENCE: 45
MEPAGPAPGR LGPLLCLLLA ASCAWSGVAG EEELQVIQPD KSVLVAAGET ATLRCTATSL     60
IPVGPIQWFR GAGPGRELIY NQKEGHFPRV TTVSDLTKRN NMDFSIRIGN ITPADAGTYY    120
CVKFRKGSPD DVEFKSGAGT ELSVRAKPSA PVVSGPAARA TPQHTVSFTC ESHGFSPRDI    180
TLKWFKNGNE LSDFQTNVDP VGESVSYSIH STAKVVLTRE DVHSQVICEV AHVTLQGDPL    240
```

```
RGTANLSETI RVPPTLEVTQ QPVRAENQVN VTCQVRKFYP QRLQLTWLEN GNVSRTETAS   300
TVTENKDGTY NWMSWLLVNV SAHRDDVKLT CQVEHDGQPA VSKSHDLKVS AHPKEQGSNT   360
ACPSPLFPGP SKPFWVLVVV GGVLACYSLL VTVAFIIFWV KRGRKKLLYI FKQPFMRPVQ   420
TTQEEDGCSC RFPEEEEGGC EL                                           442

SEQ ID NO: 46           moltype = AA  length = 483
FEATURE                 Location/Qualifiers
REGION                  1..483
                        note = huSIRP alpha-12aas-CD28Cys tm ic-41BBic protein
source                  1..483
                        mol_type = protein
                        organism = synthetic construct
SEQUENCE: 46
MEPAGPAPGR LGPLLCLLLA ASCAWSGVAG EELQVIQPD  KSVLVAAGET ATLRCTATSL    60
IPVGPIQWFR GAGPGRELIY NQKEGHFPRV TTVSDLTKRN NMDFSIRIGN ITPADAGTYY   120
CVKFRKGSPD DVEFKSGAGT ELSVRAKPSA PVVSGPAARA TPQHTVSFTC ESHGFSPRDI   180
TLKWFKNGNE LSDFQTNVDP VGESVSYSIH STAKVVLTRE DVHSQVICEV AHVTLQGDPL   240
RGTANLSETI RVPPTLEVTQ QPVRAENQVN VTCQVRKFYP QRLQLTWLEN GNVSRTETAS   300
TVTENKDGTY NWMSWLLVNV SAHRDDVKLT CQVEHDGQPA VSKSHDLKVS AHPKEQGSNT   360
ACPSPLFPGP SKPFWVLVVV GGVLACYSLL VTVAFIIFWV RSKRSRGGHS DYMNMTPRRP   420
GPTRKHYQPY APPRDFAAYR SKRGRKKLLY IFKQPFMRPV QTTQEEDGCS CRFPEEEEGG   480
CEL                                                                483

SEQ ID NO: 47           moltype = DNA  length = 900
FEATURE                 Location/Qualifiers
misc_feature            1..900
                        note = muCD200Rtm-CD28
source                  1..900
                        mol_type = other DNA
                        organism = synthetic construct
SEQUENCE: 47
atgttctgct tctggcggac aagcgccctg gccgtgctgc tgatctgggg agtgtttgtg    60
gccggcagca gctgcaccga caagaaccag accacccaga caacagcag  cagcccctg   120
acccaagtga acaccaccgt gtccgtgcag atcggccctg caagcctgct gtgctgtttc   180
agcatccctc tgaccaaggc tgtgctgatc acctggatca tcaagctgag aggcctgccc   240
agctgcacaa tcgcctacaa ggtggacacc aagaccaacg agacaagctg cctgggcaga   300
aacatcacct gggccagcac cccagaccac agccctgagc tgcagatcag cgccgtgaca   360
ctgcagcacg agggcaccta cacatgcgag acagtgaccc ccgagggcaa cttcgagaag   420
aactacgatc tgcaggtgct ggtgccccccc gaagtgacct acttcccga  gaagaataga   480
agcgccgtgt gcgaggccat ggctggcaaa cctgccgccc agatcttg   gagccctgac   540
ggcgactgtg tgaccaccag cgagagccac agcaacggca cagtgaccgt gcggagcacc   600
tgtcactggg agcagaacaa cgtgtccgac gtgtcctgca tcgtgtccca cctgaccggc   660
aaccagagcc tgagcatcga gctgagcaga ggcgaaaacc agtccctgag gccctacatc   720
ccttacatca tccccagcat catcatcctg atcatcatcg gctgcatctg cctgctgaac   780
agcagaagaa acagaggcgg ccagagcgac tacatgaaca tgacccccag aaggcctggc   840
ctgaccagaa agccctacca gccttacgcc ctgccagag  acttcgccgc ctacagacct   900

SEQ ID NO: 48           moltype = DNA  length = 918
FEATURE                 Location/Qualifiers
misc_feature            1..918
                        note = muCD200R-CD28tm
source                  1..918
                        mol_type = other DNA
                        organism = synthetic construct
SEQUENCE: 48
atgttctgct tctggcggac aagcgccctg gccgtgctgc tgatctgggg agtgtttgtg    60
gccggcagca gctgcaccga caagaaccag accacccaga caacagcag  cagcccctg   120
acccaagtga acaccaccgt gtccgtgcag atcggcacca aggccctgct gtgctgtttc   180
agcatccctc tgaccaaggc tgtgctgatc acctggatca tcaagctgag aggcctgccc   240
agctgcacaa tcgcctacaa ggtggacacc aagaccaacg agacaagctg cctgggcaga   300
aacatcacct gggccagcac cccagaccac agccctgagc tgcagatcag cgccgtgaca   360
ctgcagcacg agggcaccta cacatgcgag acagtgaccc ccgagggcaa cttcgagaag   420
aactacgatc tgcaggtgct ggtgccccccc gaagtgacct acttcccga  gaagaataga   480
agcgccgtgt gcgaggccat ggctggcaaa cctgccgccc agatcttg   gagccctgac   540
ggcgactgtg tgaccaccag cgagagccac agcaacggca cagtgaccgt gcggagcacc   600
tgtcactggg agcagaacaa cgtgtccgac gtgtcctgca tcgtgtccca cctgaccggc   660
aaccagagcc tgagcatcga gctgagcaga ggcgaaaacc agtccctgag gcccttctgg   720
gccctggtgg tggtggccgg cgtgctgttt tgttacggcc tgctcgtgac cgtggccctg   780
tgcgtgatct ggaccaacag cagaagaaac agaggcggcc agagcgacta catgaacatg   840
acccccagaa ggcctggcct gaccagaaag ccctaccagc cttacgcccc tgccagagac   900
ttcgccgcct acagacct                                                918

SEQ ID NO: 49           moltype = DNA  length = 945
FEATURE                 Location/Qualifiers
misc_feature            1..945
                        note = muCD200R-CD28Cys
source                  1..945
                        mol_type = other DNA
                        organism = synthetic construct
```

```
SEQUENCE: 49
atgttctgct tctggcggac aagcgccctg gccgtgctgc tgatctgggg agtgtttgtg   60
gccggcagca gctgcaccga caagaaccag accacccaga acaacagcag cagccccctg  120
acccaagtga acaccaccgt gtccgtgcag atcggcacca aggccctgct gtgctgtttc  180
agcatccctc tgaccaaggc tgtgctgatc acctggatca tcaagctgag aggcctgccc  240
agctgcacaa tcgcctacaa ggtggacacc aagaccaacg agacaagctg cctgggcaga  300
aacatcacct gggccagcac cccagaccac agccctgagc tgcagatcag cgccgtgaca  360
ctgcagcacg agggcaccta cacatgcgag acagtgaccc ccgagggcaa cttcgagaag  420
aactacgatc tgcaggtgct ggtgccccc gaagtgacct acttccccga gaagaataga  480
agcgccgtgt gcgaggccat ggctggcaaa cctgccgcc agatctcttg gagccctgac  540
ggcgactgtg tgaccaccag cgagagccac agcaacggca cagtgaccgt gcggagcacc  600
tgtcactggg agcagaacaa cgtgtccgac gtgtcctgca tcgtgtccca cctgaccggc  660
aaccagagcc tgagcatcga gctgagcaga ggcggaaacc agtccctgag gccctgccac  720
acccagagcc gccccaagct gttctgggcc ctggtggtga tggccggcgt gctgttttgt  780
tacggcctgc tcgtgaccgt ggccctgtgc gtgatctgga ccaacagcag aagaaacaga  840
ggcggccaga gcgactacat gaacatgacc ccagaaggc ctggcctgac cagaaagccc  900
taccagcctt acgccctgc cagagacttc gccgcctaca gacct                   945

SEQ ID NO: 50           moltype = DNA  length = 936
FEATURE                 Location/Qualifiers
misc_feature            1..936
                        note = muCD200R-3aas-CD28Cys
source                  1..936
                        mol_type = other DNA
                        organism = synthetic construct
SEQUENCE: 50
atgttctgct tctggcggac aagcgccctg gccgtgctgc tgatctgggg agtgtttgtg   60
gccggcagca gctgcaccga caagaaccag accacccaga acaacagcag cagccccctg  120
acccaagtga acaccaccgt gtccgtgcag atcggcacca aggccctgct gtgctgtttc  180
agcatccctc tgaccaaggc tgtgctgatc acctggatca tcaagctgag aggcctgccc  240
agctgcacaa tcgcctacaa ggtggacacc aagaccaacg agacaagctg cctgggcaga  300
aacatcacct gggccagcac cccagaccac agccctgagc tgcagatcag cgccgtgaca  360
ctgcagcacg agggcaccta cacatgcgag acagtgaccc ccgagggcaa cttcgagaag  420
aactacgatc tgcaggtgct ggtgccccc gaagtgacct acttccccga gaagaataga  480
agcgccgtgt gcgaggccat ggctggcaaa cctgccgcc agatctcttg gagccctgac  540
ggcgactgtg tgaccaccag cgagagccac agcaacggca cagtgaccgt gcggagcacc  600
tgtcactggg agcagaacaa cgtgtccgac gtgtcctgca tcgtgtccca cctgaccggc  660
aaccagagcc tgagcatcga gctgagcaga ggcggaaacc agtcctgcca cacccagagc  720
agcccaagc tgttctgggc cctggtggtg gtggccggcg tgctgttttg ttacggcctg  780
ctcgtgaccg tggccctgtg cgtgatctgg accaacagca gaagaaacag aggcggccag  840
agcgactaca tgaacatgac cccagaaggc ctggcctga ccagaaagcc ctaccagcct  900
tacgcccctg ccagagactt cgccgcctac agacct                            936

SEQ ID NO: 51           moltype = DNA  length = 918
FEATURE                 Location/Qualifiers
misc_feature            1..918
                        note = muCD200R-9aas-CD28Cys
source                  1..918
                        mol_type = other DNA
                        organism = synthetic construct
SEQUENCE: 51
atgttctgct tctggcggac aagcgccctg gccgtgctgc tgatctgggg agtgtttgtg   60
gccggcagca gctgcaccga caagaaccag accacccaga acaacagcag cagccccctg  120
acccaagtga acaccaccgt gtccgtgcag atcggcacca aggccctgct gtgctgtttc  180
agcatccctc tgaccaaggc tgtgctgatc acctggatca tcaagctgag aggcctgccc  240
agctgcacaa tcgcctacaa ggtggacacc aagaccaacg agacaagctg cctgggcaga  300
aacatcacct gggccagcac cccagaccac agccctgagc tgcagatcag cgccgtgaca  360
ctgcagcacg agggcaccta cacatgcgag acagtgaccc ccgagggcaa cttcgagaag  420
aactacgatc tgcaggtgct ggtgccccc gaagtgacct acttccccga gaagaataga  480
agcgccgtgt gcgaggccat ggctggcaaa cctgccgcc agatctcttg gagccctgac  540
ggcgactgtg tgaccaccag cgagagccac agcaacggca cagtgaccgt gcggagcacc  600
tgtcactggg agcagaacaa cgtgtccgac gtgtcctgca tcgtgtccca cctgaccggc  660
aaccagagcc tgagcatcga gctgagctgc acacccagag cagcccaa gctgttctgg  720
gccctggtgg tggtggccgg cgtgctgttt tgttacggcc tgctcgtgac cgtggccctg  780
tgcgtgatct ggaccaacag cagaagaaac agaggcggcc agagcgacta catgaacatg  840
accccagaa ggcctggcct gaccagaaag ccctaccagc cttacgcccc tgccagagac  900
ttcgccgcct acagacct                                                918

SEQ ID NO: 52           moltype = DNA  length = 939
FEATURE                 Location/Qualifiers
misc_feature            1..939
                        note = muCD200R-9aas-CD28Cys tm-41BBic
source                  1..939
                        mol_type = other DNA
                        organism = synthetic construct
SEQUENCE: 52
atgttctgct tctggcggac aagcgccctg gccgtgctgc tgatctgggg agtgtttgtg   60
gccggcagca gctgcaccga caagaaccag accacccaga acaacagcag cagccccctg  120
acccaagtga acaccaccgt gtccgtgcag atcggcacca aggccctgct gtgctgtttc  180
```

```
agcatccctc tgaccaaggc tgtgctgatc acctggatca tcaagctgag aggcctgccc    240
agctgcacaa tcgcctacaa ggtgacacc  aagaccaacg agacaagctg cctgggcaga    300
aacatcacct gggccagcac cccagaccac agccctgagc tgcagatcag cgccgtgaca    360
ctgcagcacg agggcaccta cacatgcgag acagtgaccc ccgagggcaa cttcgagaag    420
aactacgatc tgcaggtgct ggtgcccccc gaagtgacac acttccccga gaagaataga    480
agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagctgc cacacccaga gcagccccaa gctgttctgg    720
gccctggtgg tggtggccgg cgtgctgttt tgttacggcg tgctcgtgac cgtggccctg    780
tgcgtgatct ggaccagcgt gctgaagtgg atcagaaaga agttcccccca tcttcaag     840
cagcccttca gaaaaccac  cggcgctgcc caggaagagg acgcctgcag ctgtagatgc    900
cctcaggaag aagaaggcgg cggaggcggc tacgagctg                           939

SEQ ID NO: 53         moltype = DNA  length = 1062
FEATURE               Location/Qualifiers
misc_feature          1..1062
                      note = muCD200R-9aas-CD28Cys tm ic-41BBic
source                1..1062
                      mol_type = other DNA
                      organism = synthetic construct
SEQUENCE: 53
atgttctgct tctggcggac aagcgccctg gccgtgctgc tgatctgggg agtgtttgtg    60
gccggcagca gctgcaccga caagaaccag accaccagga caacagcag  cagccccctg    120
acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtgacacc  aagaccaacg agacaagctg cctgggcaga    300
aacatcacct gggccagcac cccagaccac agccctgagc tgcagatcag cgccgtgaca    360
ctgcagcacg agggcaccta cacatgcgag acagtgaccc ccgagggcaa cttcgagaag    420
aactacgatc tgcaggtgct ggtgcccccc gaagtgacac acttccccga gaagaataga    480
agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagctgc cacacccaga gcagccccaa gctgttctgg    720
gccctggtgg tggtggccgg cgtgctgttt tgttacggcg tgctcgtgac cgtggccctg    780
tgcgtgatct ggaccaacag cagaagaaac agaggcggcc agagcgacta catgaacatg    840
accccccagaa ggcctggcct gaccagaaag ccctaccagc cttacgcccc tgccagagac    900
ttcgccgcct acagacctag cgtgctgaag tggatcagaa agaagttccc ccacatcttc    960
aagcagcccct tcaagaaaac caccggcgct gcccaggaag aggacgcctg cagctgtaga   1020
tgccctcagg aagaagaagg cggcggaggc ggctacgagc tg                       1062

SEQ ID NO: 54         moltype = DNA  length = 1305
FEATURE               Location/Qualifiers
misc_feature          1..1305
                      note = muSIRP alpha tm-CD28
source                1..1305
                      mol_type = other DNA
                      organism = synthetic construct
SEQUENCE: 54
atggaacctg ctggacctgc ccctggcaga ctgggacctc tgctgctgtg cctgctgctg    60
agcgccagct gtttctgtac cggcgccacc ggcaaagtgac tgaaagtgac ccagcccgag    120
aagtccgtgt ctgtgccgc  tggcgacagc accgtgctga actgtaccct gaccagcctg    180
ctgcccgtgg gccccatcag atggtataga ggcgtgggcc ctagcagact gctgatctac    240
agcttcgctg gcgagtacgt gcccagaatc agaaacgtgt ccgacaccac caagcggaac    300
aacatggact tcagcatcag gatcatgcaa ctgaccctcc ccgacgccgg catctactac    360
tgcgtgaagt tccagaaggg cagcagcgag cccgacaccg agattcagtc tggcggcgga    420
accgaggtgt acgtgctggc taagcccagc cctcctgagg tgtccggccc tgctgataga    480
ggcatccccg accagaaagt gaacttcaca tgcaagagcc acggcttcag ccccagaaac    540
atcaccctga agtggttcaa ggacggccag gaactgcacc cctggaaac  caccgtgaac    600
cccagcggca agaacgtgtc ctacaacatc agctccaccg tgcgggtggt gctgaacagc    660
atggacgtga acagcaaagt gatctgcgag gtgcccaca  tcacactgga cagaagcccc    720
ctgagaggaa tcgccaacct gagcaacttc atcagagtgt ccccaaccgt gaaagtgaca    780
cagcagagcc ccaccagcat gaaccaagtg aacctgacct gcagagccga gagattctac    840
cccgagatgc tgcagctgat ctggctggaa aacggcaacg tgtccagaaa cgacacccgg    900
aagaacctga caaagaacac cgacggcacc tacaactaca cctccctgtt tctcgtgaac    960
tcctccgccc accgcgagga cgtggtgttc acgtgccaag tgaagcacga ccagcagccc    1020
gccatcacca gaaccacac  agtgctgggc ttcgcccaca gcagcgacca gggcagcatg    1080
cagaccttcc ccgacaacaa cgccaccccac aactggacag tgttcatcgg cgtgggcgtg    1140
gcctgtgctc tgctggtggt gctgctgatg gccgccctgt ataacagcag aagaaacaga    1200
ggcggccaga gcgactacat gaacatgacc cccagaaggc ctggcctgac cagaaagccc    1260
taccagcctt acgcccctgc cagagacttc gccgcctaca gacct                    1305

SEQ ID NO: 55         moltype = DNA  length = 1323
FEATURE               Location/Qualifiers
misc_feature          1..1323
                      note = muSIRP alpha-CD28tm
source                1..1323
                      mol_type = other DNA
                      organism = synthetic construct
```

```
SEQUENCE: 55
atggaacctg ctggacctgc ccctggcaga ctgggacctc tgctgctgtg cctgctgctg    60
agcgccagct gtttctgtac cggcgccacc ggcaaagaac tgaaagtgac ccagcccgag   120
aagtccgtgt ctgtggccgc tggcgacagc accgtgctga actgtaccct gaccagcctg   180
ctgcccgtgg gccccatcag atggtataga ggcgtgggcc ctagcagact gctgatctac   240
agcttcgctg gcgagtacgt gcccagaatc agaaacgtgt ccgacaccac caagcggaac   300
aacatggact tcagcatcag gatcagcaac gtgacccctg ccgacgccgg catctactac   360
tgcgtgaagt tccagaaggg cagcagcgag cccgacaccg agattcagtc tggcggcgga   420
accgaggtgt acgtgctggc taagcccagc cctcctgagg tgtccggccc tgctgataga   480
ggcatccccg accagaaagt gaacttcaca tgcaagagcc acggcttcag ccccagaaac   540
atcaccctga gtggttcaa ggacggccag gaactgcacc cctggaaac caccgtgaac   600
cccagcggca gaacgtgtc ctacaacatc agctccaccg tgcgggtggt gctgaacagc   660
atggacgtga acagcaaagt gatctgcgag gtggcccaca tcacactgga cagaagcccc   720
ctgagaggaa tcgccaacct gagcaacttc atcagagtgt cccccaaccgt gaaagtgaca   780
cagcagagcc ccaccagcat gaaccaagtg aacctgacct gcagagccga gagattctac   840
cccgaggacc tgcagctgat ctggctggaa acggcaacg tgtccagaaa cgacaccccc   900
aagaacctga caaagaacac cgacggcacc tacaactaca cctccctgtt tctcgtgaac   960
tcctccgccc accgcgagga cgtggtgttc acgtgccaag tgaagcacga ccagcagccc  1020
gccatcacca gaaaccacac agtgctgggc ttcgcccaca gcagcgacca gggcagcatg  1080
cagaccttcc ccgacaacaa cgccacccac aactggaact ctgggccct ggtggtggtg  1140
gccggcgtgc tgttttgtta cggcctgctc gtgaccgtgg ccctgtgcgt gatctggacc  1200
aacagcagaa gaaacagagg cggccagagc gactacatga acatgacccc cagaaggcct  1260
ggcctgacca gaaagcccta ccagccttac gcccctgcca gagacttcgc cgcctacaga  1320
cct                                                                1323

SEQ ID NO: 56          moltype = DNA  length = 1350
FEATURE                Location/Qualifiers
misc_feature           1..1350
                       note = muSIRP alpha-CD28cys
source                 1..1350
                       mol_type = other DNA
                       organism = synthetic construct
SEQUENCE: 56
atggaacctg ctggacctgc ccctggcaga ctgggacctc tgctgctgtg cctgctgctg    60
agcgccagct gtttctgtac cggcgccacc ggcaaagaac tgaaagtgac ccagcccgag   120
aagtccgtgt ctgtggccgc tggcgacagc accgtgctga actgtaccct gaccagcctg   180
ctgcccgtgg gccccatcag atggtataga ggcgtgggcc ctagcagact gctgatctac   240
agcttcgctg gcgagtacgt gcccagaatc agaaacgtgt ccgacaccac caagcggaac   300
aacatggact tcagcatcag gatcagcaac gtgacccctg ccgacgccgg catctactac   360
tgcgtgaagt tccagaaggg cagcagcgag cccgacaccg agattcagtc tggcggcgga   420
accgaggtgt acgtgctggc taagcccagc cctcctgagg tgtccggccc tgctgataga   480
ggcatccccg accagaaagt gaacttcaca tgcaagagcc acggcttcag ccccagaaac   540
atcaccctga gtggttcaa ggacggccag gaactgcacc cctggaaac caccgtgaac   600
cccagcggca gaacgtgtc ctacaacatc agctccaccg tgcgggtggt gctgaacagc   660
atggacgtga acagcaaagt gatctgcgag gtggcccaca tcacactgga cagaagcccc   720
ctgagaggaa tcgccaacct gagcaacttc atcagagtgt cccccaaccgt gaaagtgaca   780
cagcagagcc ccaccagcat gaaccaagtg aacctgacct gcagagccga gagattctac   840
cccgaggacc tgcagctgat ctggctggaa acggcaacg tgtccagaaa cgacaccccc   900
aagaacctga caaagaacac cgacggcacc tacaactaca cctccctgtt tctcgtgaac   960
tcctccgccc accgcgagga cgtggtgttc acgtgccaag tgaagcacga ccagcagccc  1020
gccatcacca gaaaccacac agtgctgggc ttcgcccaca gcagcgacca gggcagcatg  1080
cagaccttcc ccgacaacaa cgccacccac aactggaact gccacaccca gagcagcccc  1140
aagctgttct gggctctggt ggtggtggcc ggcgtgctgt ttgttacgg cctgctcgtg  1200
accgtggccc tgtgcgtgat ctggaccaac agcagaagaa acagaggcgg ccagagcgac  1260
tacatgaaca tgacccccag aaggcctggc ctgacccgga gccttacca gccttacgcc  1320
cctgccagag acttcgccgc ctacagacct                                   1350

SEQ ID NO: 57          moltype = DNA  length = 1332
FEATURE                Location/Qualifiers
misc_feature           1..1332
                       note = muSIRP alpha -6aas-CD28cys
source                 1..1332
                       mol_type = other DNA
                       organism = synthetic construct
SEQUENCE: 57
atggaacctg ctggacctgc ccctggcaga ctgggacctc tgctgctgtg cctgctgctg    60
agcgccagct gtttctgtac cggcgccacc ggcaaagaac tgaaagtgac ccagcccgag   120
aagtccgtgt ctgtggccgc tggcgacagc accgtgctga actgtaccct gaccagcctg   180
ctgcccgtgg gccccatcag atggtataga ggcgtgggcc ctagcagact gctgatctac   240
agcttcgctg gcgagtacgt gcccagaatc agaaacgtgt ccgacaccac caagcggaac   300
aacatggact tcagcatcag gatcagcaac gtgacccctg ccgacgccgg catctactac   360
tgcgtgaagt tccagaaggg cagcagcgag cccgacaccg agattcagtc tggcggcgga   420
accgaggtgt acgtgctggc taagcccagc cctcctgagg tgtccggccc tgctgataga   480
ggcatccccg accagaaagt gaacttcaca tgcaagagcc acggcttcag ccccagaaac   540
atcaccctga gtggttcaa ggacggccag gaactgcacc cctggaaac caccgtgaac   600
cccagcggca gaacgtgtc ctacaacatc agctccaccg tgcgggtggt gctgaacagc   660
atggacgtga acagcaaagt gatctgcgag gtggcccaca tcacactgga cagaagcccc   720
ctgagaggaa tcgccaacct gagcaacttc atcagagtgt cccccaaccgt gaaagtgaca   780
cagcagagcc ccaccagcat gaaccaagtg aacctgacct gcagagccga gagattctac   840
```

```
cccgaggacc tgcagctgat ctggctggaa aacggcaacg tgtccagaaa cgacaccccc   900
aagaacctga caaagaacac cgacggcacc tacaactaca cctccctgtt tctcgtgaac   960
tcctccgccc accgcgagga cgtggtgttc acgtgccaag tgaagcacga ccagcagccc  1020
gccatcacca gaaaccacac agtgctgggc ttcgcccaca gcagcgacca gggcagcatg  1080
cagaccttcc ccgacaacaa ctgccacacc cagagcagcc ccaagctgtt ctgggctctg  1140
gtggtggtgg ccggcgtgct gttttgttac ggcctgctcg tgaccgtggc cctgtgcgt   1200
atctggacca acagcagaag aaacagaggc ggccagagcg actacatgaa catgaccccc  1260
agaaggcctg gcctgacccg gaagccttac cagccttacg cccctgccag agacttcgcc  1320
gcctacagac ct                                                      1332
```

| SEQ ID NO: 58 | moltype = DNA   length = 1323 |
|---|---|
| FEATURE | Location/Qualifiers |
| misc_feature | 1..1323 |
| | note = muSIRP alpha -9aas-CD28cys |
| source | 1..1323 |
| | mol_type = other DNA |
| | organism = synthetic construct |

```
SEQUENCE: 58
atggaacctg ctggacctgc ccctggcaga ctgggacctc tgctgctgtg cctgctgctg    60
agcgccagct gtttctgtac cggcgccacc ggcaaagaac tgaaagtgac ccagcccgag   120
aagtccgtgt ctgtggccgc tggcgacagc accgtgctga actgtaccct gaccagcctg   180
ctgcccgtgg gccccatcag atggtataga ggcgtgggcc ctagcagact gctgatctac   240
agcttcgctg gcgagtacgt gcccagaatc agaaacgtgt ccgacaccac caagcggaac   300
aacatggact tcagcatcag gatcagcaac gtgacccctg ccgacgccgg catctactac   360
tgcgtgaagt tccagaaggg cagcagcgag cccgacaccg agattcagtc tggcggcgga   420
accgaggtgt acgtgctggc taagcccagc cctcctgagg tgtccggccc tgctgataga   480
ggcatccccg accagaaagt gaacttcaca tgcaagagcc acggcttcag ccccagaaac   540
atcaccctga gtggttcaa  ggacggccag gaactgcacc cctggaaac  accgtgaac    600
cccagcggca gaacgtgtc  ctacaacatc agctccaccg tgcggtggt  gctgaacagc   660
atggacgtga acagcaaagt gatctgcgag gtggcccaca tcacactgga caagcccc    720
ctgagaggaa tcgccaacct gagcaacttc atcagagtgt ccccaaccgt gaaagtgaca   780
cagcagagcc ccaccagcat gaaccaagtg aacctgacct gcagagccga gagattctac   840
cccgaggacc tgcagctgat ctggctggaa aacggcaacg tgtccagaaa cgacaccccc   900
aagaacctga caaagaacac cgacggcacc tacaactaca cctccctgtt tctcgtgaac   960
tcctccgccc accgcgagga cgtggtgttc acgtgccaag tgaagcacga ccagcagccc  1020
gccatcacca gaaaccacac agtgctgggc ttcgcccaca gcagcgacca gggcagcatg  1080
cagaccttcc cctgccacac ccagagcagc ccaagctgt  tctgggctct ggtggtggtg  1140
gccggcgtgc tgttttgtta cggcctgctc gtgaccgtgg ccctgtgcgt gatctggacc  1200
aacagcagaa gaaacagagg cggccagagc gactacatga acatgacccc cagaaggcct  1260
ggcctgaccc ggaagcctta ccagccttac gcccctgcca gagacttcgc cgcctacaga  1320
cct                                                                1323
```

| SEQ ID NO: 59 | moltype = DNA   length = 1281 |
|---|---|
| FEATURE | Location/Qualifiers |
| misc_feature | 1..1281 |
| | note = muSIRP alpha-23aas-CD28cys |
| source | 1..1281 |
| | mol_type = other DNA |
| | organism = synthetic construct |

```
SEQUENCE: 59
atggaacctg ctggacctgc ccctggcaga ctgggacctc tgctgctgtg cctgctgctg    60
agcgccagct gtttctgtac cggcgccacc ggcaaagaac tgaaagtgac ccagcccgag   120
aagtccgtgt ctgtggccgc tggcgacagc accgtgctga actgtaccct gaccagcctg   180
ctgcccgtgg gccccatcag atggtataga ggcgtgggcc ctagcagact gctgatctac   240
agcttcgctg gcgagtacgt gcccagaatc agaaacgtgt ccgacaccac caagcggaac   300
aacatggact tcagcatcag gatcagcaac gtgacccctg ccgacgccgg catctactac   360
tgcgtgaagt tccagaaggg cagcagcgag cccgacaccg agattcagtc tggcggcgga   420
accgaggtgt acgtgctggc taagcccagc cctcctgagg tgtccggccc tgctgataga   480
ggcatccccg accagaaagt gaacttcaca tgcaagagcc acggcttcag ccccagaaac   540
atcaccctga gtggttcaa  ggacggccag gaactgcacc cctggaaac  accgtgaac    600
cccagcggca gaacgtgtc  ctacaacatc agctccaccg tgcggtggt  gctgaacagc   660
atggacgtga acagcaaagt gatctgcgag gtggcccaca tcacactgga cagaagcccc   720
ctgagaggaa tcgccaacct gagcaacttc atcagagtgt ccccaaccgt gaaagtgaca   780
cagcagagcc ccaccagcat gaaccaagtg aacctgacct gcagagccga gagattctac   840
cccgaggacc tgcagctgat ctggctggaa aacggcaacg tgtccagaaa cgacaccccc   900
aagaacctga caaagaacac cgacggcacc tacaactaca cctccctgtt tctcgtgaac   960
tcctccgccc accgcgagga cgtggtgttc acgtgccaag tgaagcacga ccagcagccc  1020
gccatcacca gaaaccacac agtgctgggc tgccacaccc agagcagccc aagctgttc   1080
tgggctctgg tggtggtggc cggcgtgctg ttttgttacg gcctgctcgt gaccgtggcc  1140
ctgtgcgtga tctggaccaa cagcagaaga aacagaggcg gccagagcga ctacatgaac  1200
atgacccca  aaggcctggc ctgacccgg  aagccttacc agccttacgc ccctgccaga  1260
gacttcgccg cctacagacc t                                            1281
```

| SEQ ID NO: 60 | moltype = AA   length = 137 |
|---|---|
| FEATURE | Location/Qualifiers |
| REGION | 1..137 |
| | note = huPD-1 ectodomain |
| source | 1..137 |
| | mol_type = protein |

```
                                organism = synthetic construct
SEQUENCE: 60
PPTFSPALLV VTEGDNATFT CSFSNTSESF VLNWYRMSPS NQTDKLAAFP EDRSQPGQDC    60
RFRVTQLPNG RDFHMSVVRA RRNDSGTYLC GAISLAPKAQ IKESLRAELR VTERRAEVPT   120
AHPSPSPRSA GQFQTLV                                                  137

SEQ ID NO: 61           moltype = DNA  length = 627
FEATURE                 Location/Qualifiers
misc_feature            1..627
                        note = huCD2 entire extracellular domain
source                  1..627
                        mol_type = other DNA
                        organism = synthetic construct
SEQUENCE: 61
atgagctttc catgtaaatt tgtagccagc ttccttctga ttttcaatgt tcttccaaa     60
ggtgcagtct ccaaagagat tacgaatgcc ttggaaacct ggggtgcctt gggtcaggac   120
atcaacttgg acattcctag ttttcaaatg agtgatgata ttgacgatat aaaatgggaa   180
aaaacttcag acaagaaaaa gattgcacaa ttcagaaaag agaaagagac tttcaaggaa   240
aaagatacat ataagctatt taaaaatgga actctgaaaa ttaagcatct gaagaccgat   300
gatcaggata tctacaaggt atcaatatat gatacaaaag gaaaaaatgt gttggaaaaa   360
atatttgatt tgaagattca agagagggtc tcaaaaccaa agatctcctg gacttgtatc   420
aacacaaccc tgacctgtga ggtaatgaat ggaactgacc ccgaattaaa cctgtatcaa   480
gatgggaaac atctaaaact ttctcagagg gtcatcacac acaagtggac caccagcctg   540
agtgcaaaat tcaagtgcac agcagggaac aaagtcagca aggaatccag tgtcgagcct   600
gtcagctgtc cagagaaagg tctggac                                       627

SEQ ID NO: 62           moltype = AA  length = 209
FEATURE                 Location/Qualifiers
REGION                  1..209
                        note = huCD2 entire extracellular domain
source                  1..209
                        mol_type = protein
                        organism = synthetic construct
SEQUENCE: 62
MSFPCKFVAS FLLIFNVSSK GAVSKEITNA LETWGALGQD INLDIPSFQM SDDIDDIKWE    60
KTSDKKKIAQ FRKEKETFKE KDTYKLFKNG TLKIKHLKTD DQDIYKVSIY DTKGKNVLEK   120
IFDLKIQERV SKPKISWTCI NTTLTCEVMN GTDPELNLYQ DGKHLKLSQR VITHKWTTSL   180
SAKFKCTAGN KVSKESSVEP VSCPEKGLD                                     209

SEQ ID NO: 63           moltype = DNA  length = 78
FEATURE                 Location/Qualifiers
misc_feature            1..78
                        note = huCD2 transmembrane domain
source                  1..78
                        mol_type = other DNA
                        organism = synthetic construct
SEQUENCE: 63
atctatctca tcattggcat atgtggagga ggcagcctct tgatggtctt tgtggcactg    60
ctcgttttct atatcacc                                                  78

SEQ ID NO: 64           moltype = AA  length = 26
FEATURE                 Location/Qualifiers
REGION                  1..26
                        note = huCD2 transmembrane domain
source                  1..26
                        mol_type = protein
                        organism = synthetic construct
SEQUENCE: 64
IYLIIGICGG GSLLMVFVAL LVFYIT                                         26

SEQ ID NO: 65           moltype = DNA  length = 828
FEATURE                 Location/Qualifiers
misc_feature            1..828
                        note = huCD2tm-CD28 DNA
source                  1..828
                        mol_type = other DNA
                        organism = synthetic construct
SEQUENCE: 65
atgagctttc catgtaaatt tgtagccagc ttccttctga ttttcaatgt tcttccaaa     60
ggtgcagtct ccaaagagat tacgaatgcc ttggaaacct ggggtgcctt gggtcaggac   120
atcaacttgg acattcctag ttttcaaatg agtgatgata ttgacgatat aaaatgggaa   180
aaaacttcag acaagaaaaa gattgcacaa ttcagaaaag agaaagagac tttcaaggaa   240
aaagatacat ataagctatt taaaaatgga actctgaaaa ttaagcatct gaagaccgat   300
gatcaggata tctacaaggt atcaatatat gatacaaaag gaaaaaatgt gttggaaaaa   360
atatttgatt tgaagattca agagagggtc tcaaaaccaa agatctcctg gacttgtatc   420
aacacaaccc tgacctgtga ggtaatgaat ggaactgacc ccgaattaaa cctgtatcaa   480
gatgggaaac atctaaaact ttctcagagg gtcatcacac acaagtggac caccagcctg   540
agtgcaaaat tcaagtgcac agcagggaac aaagtcagca aggaatccag tgtcgagcct   600
gtcagctgtc cagagaaagg tctggacatc tatctcatca ttggcatatg tggaggaggc   660
```

```
agcctcttga tggtctttgt ggcactgctc gttttctata tcacccgcag caagcggagc    720
agaggcggcc acagcgacta catgaacatg acccctagac ggcctggccc caccagaaag    780
cactaccagc cctacgcccc tccccgggac tttgccgcct acagaagc                 828

SEQ ID NO: 66          moltype = AA  length = 276
FEATURE                Location/Qualifiers
REGION                 1..276
                       note = huCD2tm-CD28
source                 1..276
                       mol_type = protein
                       organism = synthetic construct
SEQUENCE: 66
MSFPCKFVAS FLLIFNVSSK GAVSKEITNA LETWGALGQD INLDIPSFQM SDDIDDIKWE     60
KTSDKKKIAQ FRKEKETFKE KDTYKLFKNG TLKIKHLKTD DQDIYKVSIY DTKGKNVLEK    120
IFDLKIQERV SKPKISWTCI NTTLTCEVMN GTDPELNLYQ DGKHLKLSQR VITHKWTTSL    180
SAKFKCTAGN KVSKESSVEP VSCPEKGLDI YLIIGICGGG SLLMVFVALL VFYITRSKRS    240
RGGHSDYMNM TPRRPGPTRK HYQPYAPPRD FAAYRS                              276

SEQ ID NO: 67          moltype = DNA  length = 831
FEATURE                Location/Qualifiers
misc_feature           1..831
                       note = huCD2-CD28tm
source                 1..831
                       mol_type = other DNA
                       organism = synthetic construct
SEQUENCE: 67
atgagctttc catgtaaatt tgtagccagc ttccttctga ttttcaatgt ttcttccaaa     60
ggtgcagtct ccaaagagat tacgaatgcc ttggaaacct ggggtgcctt gggtcaggac    120
atcaacttgg acattcctag ttttcaaatg agtgatgata ttgacgatat aaaatgggaa    180
aaaacttcag acaagaaaaa gattgcacaa ttcagaaaag aaaagagac tttcaaggaa    240
aaagatacat ataagctatt taaaaatgga actctgaaaa ttaagcatct gaagaccgat    300
gatcaggata tctacaaggt atcaatatat gatacaaaag gaaaaatgt gttggaaaaa    360
atatttgatt tgaagattca agagagggtc tcaaaaccaa agatctcctg gacttgtatc    420
aacacaaccc tgacctgtga ggtaatgaat ggaactgacc ccgaattaaa cctgtatcaa    480
gatgggaaac atctaaaact ttctcagagg gtcatcacac acaagtggac caccagcctg    540
agtgcaaaat tcaagtgcac agcagggaac aaagtcagca ggaatccag tgtcgagcct    600
gtcagctgtc cagagaaagg tctggacttc tgggtgctgg tggtggtcgg aggcgtgctg    660
gcctgctaca gctgctggt caccgtggcc ttcatcatct tttgggtccg cagcaagcgg    720
agcaggggcg gccacagcga ctacatgaac atgacccca gacggcctgg ccccaccaga    780
aagcactacc agcccctacgc ccctccccgg gactttgccg cctacagaag c           831

SEQ ID NO: 68          moltype = AA  length = 277
FEATURE                Location/Qualifiers
REGION                 1..277
                       note = huCD2-CD28tm
source                 1..277
                       mol_type = protein
                       organism = synthetic construct
SEQUENCE: 68
MSFPCKFVAS FLLIFNVSSK GAVSKEITNA LETWGALGQD INLDIPSFQM SDDIDDIKWE     60
KTSDKKKIAQ FRKEKETFKE KDTYKLFKNG TLKIKHLKTD DQDIYKVSIY DTKGKNVLEK    120
IFDLKIQERV SKPKISWTCI NTTLTCEVMN GTDPELNLYQ DGKHLKLSQR VITHKWTTSL    180
SAKFKCTAGN KVSKESSVEP VSCPEKGLDF WVLVVVGGVL ACYSLLVTVA FIIFWVRSKR    240
SRGGHSDYMN MTPRRPGPTR KHYQPYAPPR DFAAYRS                             277

SEQ ID NO: 69          moltype = DNA  length = 969
FEATURE                Location/Qualifiers
misc_feature           1..969
                       note = huCD200R-CD28Cys
source                 1..969
                       mol_type = other DNA
                       organism = synthetic construct
SEQUENCE: 69
atgctgtgcc cttggagaac cgccaacctg gcctgctgc tgatcctgac catcttcctg     60
gtggccgcca gcagcagcct gtgcatggac gagaagcaga tcacccagaa ctacagcaag    120
gtgctggccg aagtgaacac cagctggccc gtgaagatgg ccaccaacgc cgtgctgtgc    180
tgccctccta tcgccctgcg gaacctgatc atcatcacct gggagatcat cctgcggggc    240
cagcccagct gtaccaaggc ctaccggaaa gagacaaacg agacaaaaga aacaaactgc    300
accgacgagc ggatcacatg ggtgtccaga cccgaccaga cagcgacct gcagatcaa    360
cccgtggcca tcacccacga cggctactac cggtgcatca tggtcacccc cgatggcaac    420
ttccaccggg gataccatct gcaggtgctc gtgaccccg aagtgaccct gttccagaac    480
cggaacagaa ccgccgtgtg caaggccgtg gccgaaaac tgccgccca gatctcttgg    540
atccccgagg gcgattgcgc caccaagcag gaatactggt ccaacggcac cgtgaccgtg    600
aagtccacct gtcactggga ggtgcacaac gtgtccaacg tgatgtccac cgtgtcccac    660
ctgaccggca caagagcct gtacatcgag ctgctgcctg cctggcgc aagaagtcc    720
gccaagctgt gtcccagccc tctgtttccc ggcctagca agcctttctg ggtgctggtg    780
gtggtcggag gcgtgctggc ctgctacagc tgctggtca ccgtggcctt catcatcttt    840
tgggtccgca gcaagcggag cagaggcggc cacagcgact acatgaacat gacccctaga    900
cggcctggcc ccaccagaaa gcactaccag ccctacgccc ctccccggga ctttgccgcc    960
```

```
tacagaagc                                                             969

SEQ ID NO: 70           moltype = AA  length = 323
FEATURE                 Location/Qualifiers
REGION                  1..323
                        note = huCD200R-CD28Cys
source                  1..323
                        mol_type = protein
                        organism = synthetic construct
SEQUENCE: 70
MLCPWRTANL GLLLILTIFL VAASSSLCMD EKQITQNYSK VLAEVNTSWP VKMATNAVLC   60
CPPIALRNLI IITWEIILRG QPSCTKAYRK ETNETKETNC TDERITWVSR PDQNSDLQIR  120
PVAITHDGYY RCIMVTPDGN FHRGYHLQVL VTPEVTLFQN RNRTAVCKAV AGKPAAQISW  180
IPEGDCATKQ EYWSNGTVTV KSTCHWEVHN VSTVTCHVSH LTGNKSLYIE LLPVPGAKKS  240
AKLCPSPLFP GPSKPFWVLV VVGGVLACYS LLVTVAFIIF WVRSKRSGG HSDYMNMTPR   300
RPGPTRKHYQ PYAPPRDFAA YRS                                          323

SEQ ID NO: 71           moltype = DNA  length = 519
FEATURE                 Location/Qualifiers
misc_feature            1..519
                        note = huFas entire extracellular domain
source                  1..519
                        mol_type = other DNA
                        organism = synthetic construct
SEQUENCE: 71
atgctgggca tctggaccct gctgcctctg gtgctgacaa gcgtggccag actgagcagc   60
aagagcgtga acgcccaagt gaccgacatc aacagcaagg gcctggaact gagaaagacc  120
gtgaccaccg tggaaaccca gaacctggaa ggcctgcacc acgacggcca gttctgccac  180
aagccttgtc ccctggcga gcggaaggcc agagactgta ctgtgaacgg cgacgagccc  240
gactgcgtgc cctgtcagga aggcaaagag tacaccgaca aggcccactt cagcagcaag  300
tgccggcggt gcagactgtg tgatgagggc cacggcctgg aagtggaaat caactgcacc  360
cggacccaga acaccaagtg cagatgcaag cccaacttct ctgcaacag caccgtgtgc   420
gagcactgcg acccctgtac caagtgcgaa acggcatca tcaaagagtg caccctgacc   480
tccaacacaa agtgcaaaga ggaaggcagc agaagcaac                         519

SEQ ID NO: 72           moltype = AA  length = 173
FEATURE                 Location/Qualifiers
REGION                  1..173
                        note = huFas entire extracellular domain
source                  1..173
                        mol_type = protein
                        organism = synthetic construct
SEQUENCE: 72
MLGIWTLLPL VLTSVARLSS KSVNAQVTDI NSKGLELRKT VTTVETQNLE GLHHDGQFCH   60
KPCPPGERKA RDCTVNGDEP DCVPCQEGKE YTDKAHFSSK CRRCRLCDEG HGLEVEINCT  120
RTQNTKCRCK PNFFCNSTVC EHCDPCTKCE HGIIKECTLT SNTKCKEEGS RSN          173

SEQ ID NO: 73           moltype = DNA  length = 498
FEATURE                 Location/Qualifiers
misc_feature            1..498
                        note = huFas extracellular domain -7aas
source                  1..498
                        mol_type = other DNA
                        organism = synthetic construct
SEQUENCE: 73
atgctgggca tctggaccct gctgcctctg gtgctgacaa gcgtggccag actgagcagc   60
aagagcgtga acgcccaagt gaccgacatc aacagcaagg gcctggaact gagaaagacc  120
gtgaccaccg tggaaaccca gaacctggaa ggcctgcacc acgacggcca gttctgccac  180
aagccttgtc ccctggcga gcggaaggcc agagactgta ctgtgaacgg cgacgagccc  240
gactgcgtgc cctgtcagga aggcaaagag tacaccgaca aggcccactt cagcagcaag  300
tgccggcggt gcagactgtg tgatgagggc cacggcctgg aagtggaaat caactgcacc  360
cggacccaga acaccaagtg cagatgcaag cccaacttct ctgcaacag caccgtgtgc   420
gagcactgcg acccctgtac caagtgcgaa acggcatca tcaaagagtg caccctgacc   480
tccaacacaa agtgcaaa                                                 498

SEQ ID NO: 74           moltype = AA  length = 166
FEATURE                 Location/Qualifiers
REGION                  1..166
                        note = huFas extracellular domain -7aas
source                  1..166
                        mol_type = protein
                        organism = synthetic construct
SEQUENCE: 74
MLGIWTLLPL VLTSVARLSS KSVNAQVTDI NSKGLELRKT VTTVETQNLE GLHHDGQFCH   60
KPCPPGERKA RDCTVNGDEP DCVPCQEGKE YTDKAHFSSK CRRCRLCDEG HGLEVEINCT  120
RTQNTKCRCK PNFFCNSTVC EHCDPCTKCE HGIIKECTLT SNTKCK                  166

SEQ ID NO: 75           moltype = DNA  length = 483
FEATURE                 Location/Qualifiers
```

```
misc_feature            1..483
                        note = huFas extracellular domain -12aas
source                  1..483
                        mol_type = other DNA
                        organism = synthetic construct
SEQUENCE: 75
atgctgggca tctggaccct gctgcctctg gtgctgacaa gcgtggccag actgagcagc    60
aagagcgtga acgcccaagt gaccgacatc aacagcaagg gcctggaact gagaaagacc   120
gtgaccaccg tggaaaccca gaacctggaa ggcctgcacc acgacggcca gttctgccac   180
aagccttgtc cccctggcga gcggaaggcc agagactgta ctgtgaacgg cgacgagccc   240
gactgcgtgc cctgtcagga aggcaaagag tacaccgaca aggcccactt cagcagcaag   300
tgccggcggt gcagactgtg tgatgagggc acggcctgg aagtgaaaat caactgcacc    360
cggacccaga acaccaagtg cagatgcaag cccaacttct tctgcaacag caccgtgtgc   420
gagcactgcg acccctgtac caagtgcgaa cacggcatca tcaaagagtg caccctgacc   480
tcc                                                                 483

SEQ ID NO: 76           moltype = AA  length = 161
FEATURE                 Location/Qualifiers
REGION                  1..161
                        note = huFas extracellular domain -12aas
source                  1..161
                        mol_type = protein
                        organism = synthetic construct
SEQUENCE: 76
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT S                       161

SEQ ID NO: 77           moltype = DNA  length = 51
FEATURE                 Location/Qualifiers
misc_feature            1..51
                        note = huFas transmembrane domain
source                  1..51
                        mol_type = other DNA
                        organism = synthetic construct
SEQUENCE: 77
ctgggctggc tgtgcctcct gctgctgccc atccctctga tcgtgtgggt c              51

SEQ ID NO: 78           moltype = AA  length = 17
FEATURE                 Location/Qualifiers
REGION                  1..17
                        note = huFas transmembrane domain
source                  1..17
                        mol_type = protein
                        organism = synthetic construct
SEQUENCE: 78
LGWLCLLLLP IPLIVWV                                                   17

SEQ ID NO: 79           moltype = DNA  length = 693
FEATURE                 Location/Qualifiers
misc_feature            1..693
                        note = huFAStm-CD28
source                  1..693
                        mol_type = other DNA
                        organism = synthetic construct
SEQUENCE: 79
atgctgggca tctggaccct gctgcctctg gtgctgacaa gcgtggccag actgagcagc    60
aagagcgtga acgcccaagt gaccgacatc aacagcaagg gcctggaact gagaaagacc   120
gtgaccaccg tggaaaccca gaacctggaa ggcctgcacc acgacggcca gttctgccac   180
aagccttgtc cccctggcga gcggaaggcc agagactgta ctgtgaacgg cgacgagccc   240
gactgcgtgc cctgtcagga aggcaaagag tacaccgaca aggcccactt cagcagcaag   300
tgccggcggt gcagactgtg tgatgagggc acggcctgg aagtgaaaat caactgcacc    360
cggacccaga acaccaagtg cagatgcaag cccaacttct tctgcaacag caccgtgtgc   420
gagcactgcg acccctgtac caagtgcgaa cacggcatca tcaaagagtg caccctgacc   480
tccaacacaa agtgcaaaga ggaaggcagc agaagcaacc tgggctggct gtgcctcctg   540
ctgctgccca tccctctgat cgtgtgggtc gcagcaagc ggagcagagg cggccacagc    600
gactacatga acatgacccc tagacggcct ggccccacca gaaagcacta ccagccctac   660
gcccctcccc gggactttgc cgcctacaga agc                                693

SEQ ID NO: 80           moltype = AA  length = 231
FEATURE                 Location/Qualifiers
REGION                  1..231
                        note = huFAStm-CD28
source                  1..231
                        mol_type = protein
                        organism = synthetic construct
SEQUENCE: 80
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
```

```
RTQNTKCRCK PNFFCNSTVC EHCDPCTKCE HGIIKECTLT SNTKCKEEGS RSNLGWLCLL      180
LLPIPLIVWV RSKRSRGGHS DYMNMTPRRP GPTRKHYQPY APPRDFAAYR S               231

SEQ ID NO: 81           moltype = DNA   length = 723
FEATURE                 Location/Qualifiers
misc_feature            1..723
                        note = huFAS-CD28tm
source                  1..723
                        mol_type = other DNA
                        organism = synthetic construct
SEQUENCE: 81
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc      240
gactgcgtgc cctgtcagga aggcaaagag tacaccgaca aggcccactt cagcagcaag     300
tgccggcggt gcagactgtg tgatgagggc acggcctgg aagtggaaat caactgcacc      360
cggacccaga acaccaagtg cagatgcaag cccaacttct ctgcaacag caccgtgtgc      420
gagcactgcg accctgtac caagtgcaaa cacggcatca tcaaagagtg cacccctgacc    480
tccaacacaa agtgcaaaga ggaaggcagc agaagcaact ctgggtgct ggtggtggtc      540
ggaggcgtgc tggcctgcta cagcctgctg gtcaccgtgg ccttcatcat ctttgggtc      600
cgcagcaagc ggagcagagg cggccacagc gactacatga acatgacccc tagacggcct    660
ggccccacca gaaagcacta ccagcctac gcccctcccc gggactttgc cgcctacaga     720
agc                                                                    723

SEQ ID NO: 82           moltype = AA   length = 241
FEATURE                 Location/Qualifiers
REGION                  1..241
                        note = huFAS-CD28tm
source                  1..241
                        mol_type = protein
                        organism = synthetic construct
SEQUENCE: 82
MLGIWTLLPL VLTSVARLSS KSVNAQVTDI NSKGLELRKT VTTVETQNLE GLHHDGQFCH      60
KPCPPGERKA RDCTVNGDEP DCVPCQEGKE YTDKAHFSSK CRRCRLCDEG HGLEVEINCT     120
RTQNTKCRCK PNFFCNSTVC EHCDPCTKCE HGIIKECTLT SNTKCKEEGS RSNFWVLVVV     180
GGVLACYSLL VTVAFIIFWV RSKRSRGGHS DYMNMTPRRP GPTRKHYQPY APPRDFAAYR     240
S                                                                      241

SEQ ID NO: 83           moltype = DNA   length = 759
FEATURE                 Location/Qualifiers
misc_feature            1..759
                        note = huFAS-CD28Cys
source                  1..759
                        mol_type = other DNA
                        organism = synthetic construct
SEQUENCE: 83
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc      240
gactgcgtgc cctgtcagga aggcaaagag tacaccgaca aggcccactt cagcagcaag     300
tgccggcggt gcagactgtg tgatgagggc acggcctgg aagtggaaat caactgcacc      360
cggacccaga acaccaagtg cagatgcaag cccaacttct ctgcaacag caccgtgtgc      420
gagcactgcg accctgtac caagtgcaaa cacggcatca tcaaagagtg cacccctgacc    480
tccaacacaa agtgcaaaga ggaaggcagc agaagcaact gtcccagccc tctgtttccc     540
ggccctagca agccttttctg ggtgctggtg gtggtcggag gcgtgctggc ctgctacagc    600
ctgctggtca ccgtggcctt catcatcttt gggtccgca gcaagcggag cagaggcggc      660
cacagcgact acatgaacat gacccctaga cggcctggcc caccagaaa gcactaccag     720
ccctacgccc ctccccggga ctttgccgcc tacagaagc                             759

SEQ ID NO: 84           moltype = AA   length = 253
FEATURE                 Location/Qualifiers
REGION                  1..253
                        note = huFAS-CD28Cys
source                  1..253
                        mol_type = protein
                        organism = synthetic construct
SEQUENCE: 84
MLGIWTLLPL VLTSVARLSS KSVNAQVTDI NSKGLELRKT VTTVETQNLE GLHHDGQFCH      60
KPCPPGERKA RDCTVNGDEP DCVPCQEGKE YTDKAHFSSK CRRCRLCDEG HGLEVEINCT     120
RTQNTKCRCK PNFFCNSTVC EHCDPCTKCE HGIIKECTLT SNTKCKEEGS RSNCPSPLFP     180
GPSKPFWVLV VVGGVLACYS LLVTVAFIIF WVRSKRSRGG HSDYMNMTPR RPGPTRKHYQ     240
PYAPPRDFAA YRS                                                         253

SEQ ID NO: 85           moltype = DNA   length = 738
FEATURE                 Location/Qualifiers
misc_feature            1..738
                        note = huFAS-7aas-CD28Cys
```

```
source                      1..738
                            mol_type = other DNA
                            organism = synthetic construct
SEQUENCE: 85
atgctgggca tctggaccct gctgcctctg gtgctgacaa gcgtggccag actgagcagc   60
aagagcgtga acgcccaagt gaccgacatc aacagcaagg gcctggaact gagaaagacc  120
gtgaccaccg tggaaaccca gaacctggaa ggcctgcacc acgacggcca gttctgccac  180
aagccttgtc ccctggcga gcggaaggcc agagactgta ctgtgaacgg cgacgagccc   240
gactgcgtgc cctgtcagga aggcaaagag tacaccgaca aggcccactt cagcagcaag  300
tgccggcggt gcagactgtg tgatgagggc cacggcctgg aagtggaaat caactgcacc  360
cggacccaga acaccaagtg cagatgcaag cccaacttct tctgcaacag caccgtgtgc  420
gagcactgcg acccctgtac caagtgcgaa cacggcatca tcaaagagtg caccctgacc  480
tccaacacaa agtgcaaatg tcccagccct ctgtttcccg gccctagcaa gccttttctgg  540
gtgctggtgg tggtcggagg cgtgctggcc tgctacagcc tgctggtcac cgtggccttc  600
atcatctttt gggtccgcag caagcggagc agaggcggcc acagcgacta catgaacatg  660
acccctagac ggcctggccc caccagaaag cactaccagc cctacgcccc tccccgggac  720
tttgccgcct acagaagc                                                738

SEQ ID NO: 86               moltype = AA  length = 246
FEATURE                     Location/Qualifiers
REGION                      1..246
                            note = huFAS-7aas-CD28Cys
source                      1..246
                            mol_type = protein
                            organism = synthetic construct
SEQUENCE: 86
MLGIWTLLPL VLTSVARLSS KSVNAQVTDI NSKGLELRKT VTTVETQNLE GLHHDGQFCH   60
KPCPPGERKA RDCTVNGDEP DCVPCQEGKE YTDKAHFSSK CRRCRLCDEG HGLEVEINCT  120
RTQNTKCRCK PNFFCNSTVC EHCDPCTKCE HGIIKECTLT SNTKCKCPSP LFPGPSKPFW  180
VLVVVGGVLA CYSLLVTVAF IIFWVRSKRS RGGHSDYMNM TPRRPGPTRK HYQPYAPPRD  240
FAAYRS                                                             246

SEQ ID NO: 87               moltype = DNA  length = 723
FEATURE                     Location/Qualifiers
misc_feature                1..723
                            note = FAS-12aas-CD28Cys
source                      1..723
                            mol_type = other DNA
                            organism = synthetic construct
SEQUENCE: 87
atgctgggca tctggaccct gctgcctctg gtgctgacaa gcgtggccag actgagcagc   60
aagagcgtga acgcccaagt gaccgacatc aacagcaagg gcctggaact gagaaagacc  120
gtgaccaccg tggaaaccca gaacctggaa ggcctgcacc acgacggcca gttctgccac  180
aagccttgtc ccctggcga gcggaaggcc agagactgta ctgtgaacgg cgacgagccc   240
gactgcgtgc cctgtcagga aggcaaagag tacaccgaca aggcccactt cagcagcaag  300
tgccggcggt gcagactgtg tgatgagggc cacggcctgg aagtggaaat caactgcacc  360
cggacccaga acaccaagtg cagatgcaag cccaacttct tctgcaacag caccgtgtgc  420
gagcactgcg acccctgtac caagtgcgaa cacggcatca tcaaagagtg caccctgacc  480
tcctgtccca gccctctgtt tcccggccct agcaagcctt tctgggtgct ggtggtggtc  540
ggaggcgtgc tggcctgcta cagcctgctg gtcaccgtgg ccttcatcat cttttgggtc  600
cgcagcaagc ggagcagagg cggccacagc gactacatga acatgacccc tagacggcct  660
ggccccacca gaaagcacta ccagccctac gcccctcccg ggactttgcc gcctacaga   720
agc                                                                723

SEQ ID NO: 88               moltype = AA  length = 241
FEATURE                     Location/Qualifiers
REGION                      1..241
                            note = FAS-12aas-CD28Cys
source                      1..241
                            mol_type = protein
                            organism = synthetic construct
SEQUENCE: 88
MLGIWTLLPL VLTSVARLSS KSVNAQVTDI NSKGLELRKT VTTVETQNLE GLHHDGQFCH   60
KPCPPGERKA RDCTVNGDEP DCVPCQEGKE YTDKAHFSSK CRRCRLCDEG HGLEVEINCT  120
RTQNTKCRCK PNFFCNSTVC EHCDPCTKCE HGIIKECTLT SCPSPLFPGP SKPFWVLVVV  180
GGVLACYSLL VTVAFIIFWV RSKRSRGGHS DYMNMTPRRP GPTRKHYQPY APPRDFAAYR  240
S                                                                  241

SEQ ID NO: 89               moltype = DNA  length = 510
FEATURE                     Location/Qualifiers
misc_feature                1..510
                            note = huPD1 entire extracellular domain 2
source                      1..510
                            mol_type = other DNA
                            organism = synthetic construct
SEQUENCE: 89
atgcagatcc ctcaggcccc ttggcctgtc gtgtgggctg tgctgcagct gggatggcgg   60
cctggctggt ttctggacag ccccgacaga ccctggaacc ccctacatt ttcccctgcc   120
ctgctggtcg tgaccgaggg cgacaatgcc accttcacct gtagcttcag caacaccagc  180
```

```
gagagcttcg tgctgaactg gtacagaatg agccccagca accagaccga caagctggcc    240
gccttccccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccaccctag cccatctcca    480
agacctgccg gccagttcca gacactggtc                                     510
```

```
SEQ ID NO: 90              moltype = AA   length = 170
FEATURE                    Location/Qualifiers
REGION                     1..170
                           note = huPD1 entire extracellular domain 2
source                     1..170
                           mol_type = protein
                           organism = synthetic construct
SEQUENCE: 90
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAHPSPSP RPAGQFQTLV              170
```

```
SEQ ID NO: 91              moltype = DNA   length = 474
FEATURE                    Location/Qualifiers
misc_feature               1..474
                           note = huPD1 2 -12aas
source                     1..474
                           mol_type = other DNA
                           organism = synthetic construct
SEQUENCE: 91
atgcagatcc ctcaggcccc cttggcctgt cgtgtgggctg tgctgcagct gggatggcgg    60
cctggctggt ttctggacag ccccgacaga ccctggaacc cccctacatt ttccctgca     120
ctgctggtcg tgaccgaggg cgacaatgcc accttcacct gtagcttcag caacaccagc    180
gagagcttcg tgctgaactg gtacagaatg agccccagca accagaccga caagctggcc    240
gccttccccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccaccctag ccca          474
```

```
SEQ ID NO: 92              moltype = AA   length = 158
FEATURE                    Location/Qualifiers
REGION                     1..158
                           note = huPD1 2 -12aas
source                     1..158
                           mol_type = protein
                           organism = synthetic construct
SEQUENCE: 92
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAHPSP                            158
```

```
SEQ ID NO: 93              moltype = DNA   length = 465
FEATURE                    Location/Qualifiers
misc_feature               1..465
                           note = huPD1 2 -15aas
source                     1..465
                           mol_type = other DNA
                           organism = synthetic construct
SEQUENCE: 93
atgcagatcc ctcaggcccc cttggcctgt cgtgtgggctg tgctgcagct gggatggcgg    60
cctggctggt ttctggacag ccccgacaga ccctggaacc cccctacatt ttccctgca     120
ctgctggtcg tgaccgaggg cgacaatgcc accttcacct gtagcttcag caacaccagc    180
gagagcttcg tgctgaactg gtacagaatg agccccagca accagaccga caagctggcc    240
gccttccccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccac                    465
```

```
SEQ ID NO: 94              moltype = AA   length = 155
FEATURE                    Location/Qualifiers
REGION                     1..155
                           note = huPD1 2 -15aas
source                     1..155
                           mol_type = protein
                           organism = synthetic construct
SEQUENCE: 94
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAH                               155
```

```
SEQ ID NO: 95              moltype = DNA   length = 447
FEATURE                    Location/Qualifiers
```

```
misc_feature            1..447
                        note = huPD1 2 -21aas
source                  1..447
                        mol_type = other DNA
                        organism = synthetic construct
SEQUENCE: 95
atgcagatcc ctcaggcccc ttggcctgtc gtgtgggctg tgctgcagct gggatggcgg    60
cctggctggt ttctggacag ccccgacaga ccctggaacc cccctacatt ttcccctgcc   120
ctgctggtcg tgaccgaggg cgacaatgcc accttcacct gtagcttcag caacaccagc   180
gagagcttcg tgctgaactg gtacagaatg agcccccagc accagaccga caagctggcc   240
gccttccccg aggatagatc tcagcccggc caggactgcc ggttcagagt gacccagctg   300
cccaacggcc gggacttcca catgtctgtc gtgcgggcca gacggaacga cagcggcaca   360
tatctgtgcg gcgccatcag cctggccccc aaggcccaga tcaaagagag cctgagagcc   420
gagctgagag tgaccgagag aagggcc                                      447

SEQ ID NO: 96          moltype = AA  length = 149
FEATURE                Location/Qualifiers
REGION                 1..149
                       note = huPD1 2 -21aas
source                 1..149
                       mol_type = protein
                       organism = synthetic construct
SEQUENCE: 96
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRA                                    149

SEQ ID NO: 97          moltype = DNA  length = 750
FEATURE                Location/Qualifiers
misc_feature           1..750
                       note = huPD1-CD28Cys
source                 1..750
                       mol_type = other DNA
                       organism = synthetic construct
SEQUENCE: 97
atgcagatcc ctcaggcccc ttggcctgtc gtgtgggctg tgctgcagct gggatggcgg    60
cctggctggt ttctggacag ccccgacaga ccctggaacc cccctacatt ttcccctgcc   120
ctgctggtcg tgaccgaggg cgacaatgcc accttcacct gtagcttcag caacaccagc   180
gagagcttcg tgctgaactg gtacagaatg agcccccagc accagaccga caagctggcc   240
gccttccccg aggatagatc tcagcccggc caggactgcc ggttcagagt gacccagctg   300
cccaacggcc gggacttcca catgtctgtc gtgcgggcca gacggaacga cagcggcaca   360
tatctgtgcg gcgccatcag cctggccccc aaggcccaga tcaaagagag cctgagagcc   420
gagctgagag tgaccgagag aagggccgaa gtgcctaccg cccaccctag cccatctcca   480
agacctgccg gccagttcca gacactggtc tgtcccagcc ctctgtttcc cggccctagc   540
aagccttttct gggtgctggt ggtggtcgga ggcgtgctgg cctgctacag cctgctggtc   600
accgtggcct tcatcatctt tgggtccgc agcaagcgga gcagaggcgg ccacagcgac   660
tacatgaaca tgacccctag acggcctggc cccaccagaa agcactacca gcctacgcc   720
cctcccgg actttgccgc ctacagaagc                                      750

SEQ ID NO: 98          moltype = AA  length = 250
FEATURE                Location/Qualifiers
REGION                 1..250
                       note = huPD1-CD28Cys
source                 1..250
                       mol_type = protein
                       organism = synthetic construct
SEQUENCE: 98
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV CPSPLFPGPS   180
KPFWVLVVVG GVLACYSLLV TVAFIIFWVR SKRSRGGHSD YMNMTPRRPG PTRKHYQPYA   240
PPRDFAAYRS                                                         250

SEQ ID NO: 99          moltype = DNA  length = 714
FEATURE                Location/Qualifiers
misc_feature           1..714
                       note = huPD1-12aas-CD28Cys
source                 1..714
                       mol_type = other DNA
                       organism = synthetic construct
SEQUENCE: 99
atgcagatcc ctcaggcccc ttggcctgtc gtgtgggctg tgctgcagct gggatggcgg    60
cctggctggt ttctggacag ccccgacaga ccctggaacc cccctacatt ttcccctgcc   120
ctgctggtcg tgaccgaggg cgacaatgcc accttcacct gtagcttcag caacaccagc   180
gagagcttcg tgctgaactg gtacagaatg agcccccagc accagaccga caagctggcc   240
gccttccccg aggatagatc tcagcccggc caggactgcc ggttcagagt gacccagctg   300
cccaacggcc gggacttcca catgtctgtc gtgcgggcca gacggaacga cagcggcaca   360
tatctgtgcg gcgccatcag cctggccccc aaggcccaga tcaaagagag cctgagagcc   420
gagctgagag tgaccgagag aagggccgaa gtgcctaccg cccaccctag cccatgtccc   480
```

-continued

```
agccctctgt tcccggccc tagcaagcct ttctgggtgc tggtggtggt cggaggcgtg    540
ctggcctgct acagcctgct ggtcaccgtg gccttcatca tcttttgggt ccgcagcaag    600
cggagcagag gcggccacag cgactacatg aacatgaccc ctagacggcc tggccccacc    660
agaaagcact accagcccta cgcccctccc cgggactttg ccgcctacag aagc          714

SEQ ID NO: 100             moltype = AA   length = 238
FEATURE                    Location/Qualifiers
REGION                     1..238
                           note = huPD1-12aas-CD28Cys
source                     1..238
                           mol_type = protein
                           organism = synthetic construct
SEQUENCE: 100
MQIPQAPWPV VWAVLQLGWR PGWFLDSPDR PWNPPTFSPA LLVVTEGDNA TFTCSFSNTS     60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAHPSPCP SPLFPGPSKP FWVLVVVGGV    180
LACYSLLVTV AFIIFWVRSK RSRGGHSDYM NMTPRRPGPT RKHYQPYAPP RDFAAYRS      238

SEQ ID NO: 101             moltype = DNA   length = 705
FEATURE                    Location/Qualifiers
misc_feature               1..705
                           note = huPD1-15aas-CD28Cys
source                     1..705
                           mol_type = other DNA
                           organism = synthetic construct
SEQUENCE: 101
atgcagatcc ctcaggcccc ttggcctgtc gtgtgggctg tgctgcagct gggatggcgg     60
cctggctggt ttctggacag ccccgacaga ccctggaacc ccctacatt ttcccctgcc    120
ctgctggtcg tgaccgaggg cgacaatgcc accttcacct gtagcttcag caacaccagc    180
gagagcttcg tgctgaactg gtacagaatg agcccccagca accagaccga caagctggcc    240
gccttcccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccactgtcc cagccctctg    480
tttcccggcc ctagcaagcc tttctgggtg ctggtggtgg tcggaggcgt gctggcctgc    540
tacagcctgc tggtcaccgt ggccttcatc atcttttggg tccgcagcaa gcggagcaga    600
ggcggccaca gcgactacat gaacatgacc cctagacggc ctggcccac cagaaagcac    660
taccagcccta cgcccctcc ccgggacttt gccgcctaca gaagc                    705

SEQ ID NO: 102             moltype = AA   length = 235
FEATURE                    Location/Qualifiers
REGION                     1..235
                           note = huPD1-15aas-CD28Cys
source                     1..235
                           mol_type = protein
                           organism = synthetic construct
SEQUENCE: 102
MQIPQAPWPV VWAVLQLGWR PGWFLDSPDR PWNPPTFSPA LLVVTEGDNA TFTCSFSNTS     60
ESFVLNWYRM SPSNQTDKLA AFPEDRSQPG QDCRFRVTQL PNGRDFHMSV VRARRNDSGT    120
YLCGAISLAP KAQIKESLRA ELRVTERRAE VPTAHCPSPL FPGPSKPFWV LVVVGGVLAC    180
YSLLVTVAFI IFWVRSKRSR GGHSDYMNMT PRRPGPTRKH YQPYAPPRDF AAYRS         235

SEQ ID NO: 103             moltype = DNA   length = 687
FEATURE                    Location/Qualifiers
misc_feature               1..687
                           note = huPD1-21aas-CD28Cys
source                     1..687
                           mol_type = other DNA
                           organism = synthetic construct
SEQUENCE: 103
atgcagatcc ctcaggcccc ttggcctgtc gtgtgggctg tgctgcagct gggatggcgg     60
cctggctggt ttctggacag ccccgacaga ccctggaacc ccctacatt ttcccctgcc    120
ctgctggtcg tgaccgaggg cgacaatgcc accttcacct gtagcttcag caacaccagc    180
gagagcttcg tgctgaactg gtacagaatg agcccccagca accagaccga caagctggcc    240
gccttcccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggcctgt cccagccctc tgtttcccgg cctagcaag    480
ccttttctggg tgctggtggt ggtcggaggc gtgctggcct gctacagcct gctggtcacc    540
gtggccttca tcatcttttg ggtccgcagc aagcggagca gaggcggcca cagcgactac    600
atgaacatga cccctagacg gcctggcccc accagaaagc actaccagcc ctacgcccct    660
ccccgggact ttgccgccta cagaagc                                         687

SEQ ID NO: 104             moltype = AA   length = 229
FEATURE                    Location/Qualifiers
REGION                     1..229
                           note = huPD1-21aas-CD28Cys
source                     1..229
                           mol_type = protein
```

```
                       organism = synthetic construct
SEQUENCE: 104
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAC PSPLFPGPSK PFWVLVVVGG VLACYSLLVT   180
VAFIIFWVRS KRSRGGHSDY MNMTPRRPGP TRKHYQPYAP PRDFAAYRS              229

SEQ ID NO: 105          moltype = DNA   length = 810
FEATURE                 Location/Qualifiers
misc_feature            1..810
                        note = muCD2tm-CD28
source                  1..810
                        mol_type = other DNA
                        organism = synthetic construct
SEQUENCE: 105
atgaagtgca agttcctggg ctcattcttc ctgctgttca gcctgagcgg caagggcgcc    60
gactgcagag acaacgagac aatctggggc gtgctgggcc acggcatcac cctgaacatc   120
cccaacttcc agatgaccga cgacatcgac gaagtgcgct gggtgcgaag aggcacactg   180
gtggccgagt tcaagagaaa gaagcccca ttcctgatca gcgagacata cgaggtgctg    240
gccaacggca gcctgaagat caagaaaccc atgatgagaa acgacagcgg cacctacaac   300
gtgatggtgt acggcaccaa cggcatgacc agactggaaa aggacctgga cgtgcggatc   360
ctggaaaggg tgtccaagcc catgatccac tgggagtgcc caacaccac cctgacctgt    420
gctgtgctgc agggcaccga cttcgagctg aagctgtacc agggcgagac actgctgaac   480
tccctgccccc agaaaaacat gagctaccag tggaccaacc tgaacgcccc cttcaagtgc   540
gaggccatca cccccgtgtc caagaaagc aagatggaag tcgtgaactg ccccgagaag    600
ggcctgagct tctacgtgac agtgggcgtg ggagctggcg gactgctgct ggtgctgctg   660
gtggccctgt tcatcttctg catctgcaac agcagacgac acagaggcgg ccagagcgac   720
tacatgaaca tgacccccag aaggcctggc ctgaccagaa agccctacca gccttacgcc   780
cctgccagag acttcgccgc ctacagacct                                    810

SEQ ID NO: 106          moltype = AA   length = 270
FEATURE                 Location/Qualifiers
REGION                  1..270
                        note = muCD2tm-CD28
source                  1..270
                        mol_type = protein
                        organism = synthetic construct
SEQUENCE: 106
MKCKFLGSFF LLFSLSGKGA DCRDNETIWG VLGHGITLNI PNFQMTDDID EVRWVRRGTL    60
VAEFKRKKPP FLISETYEVL ANGSLKIKKP MMRNDSGTYN VMVYGTNGMT RLEKDLDVRI   120
LERVSKPMIH WECPNTTLTC AVLQGTDFEL KLYQGETLLN SLPQKNMSYQ WTNLNAPFKC   180
EAINPVSKES KMEVVNCPEK GLSFYVTVGV GAGGLLLVLL VALFIFCICN SRRNRGGQSD   240
YMNMTPRRPG LTRKPYQPYA PARDFAAYRP                                    270

SEQ ID NO: 107          moltype = DNA   length = 813
FEATURE                 Location/Qualifiers
misc_feature            1..813
                        note = muCD2-CD28tm
source                  1..813
                        mol_type = other DNA
                        organism = synthetic construct
SEQUENCE: 107
atgaagtgca agttcctggg ctcattcttc ctgctgttca gcctgagcgg caagggcgcc    60
gactgcagag acaacgagac aatctggggc gtgctgggcc acggcatcac cctgaacatc   120
cccaacttcc agatgaccga cgacatcgac gaagtgcgct gggtgcgaag aggcacactg   180
gtggccgagt tcaagagaaa gaagcccca ttcctgatca gcgagacata cgaggtgctg    240
gccaacggca gcctgaagat caagaaaccc atgatgagaa acgacagcgg cacctacaac   300
gtgatggtgt acggcaccaa cggcatgacc agactggaaa aggacctgga cgtgcggatc   360
ctggaaaggg tgtccaagcc catgatccac tgggagtgcc caacaccac cctgacctgt    420
gctgtgctgc agggcaccga cttcgagctg aagctgtacc agggcgagac actgctgaac   480
tccctgccccc agaaaaacat gagctaccag tggaccaacc tgaacgcccc cttcaagtgc   540
gaggccatca cccccgtgtc caagaaagc aagatggaag tcgtgaactg ccccgagaag    600
ggcctgagct tctgggccct ggtggtggtg gccggcgtgc tgttttgtta cggcctgctc   660
gtgaccgtgg ccctgtgtgt gatctggacc aacagcagaa gaaacagagg cggccagagc   720
gactacatga acatgacccc cagaaggcct ggcctgacca gaaagcccta ccagccttac   780
gcccctgcca gagacttcgc cgcctacaga ccc                                813

SEQ ID NO: 108          moltype = AA   length = 271
FEATURE                 Location/Qualifiers
REGION                  1..271
                        note = muCD2-CD28tm
source                  1..271
                        mol_type = protein
                        organism = synthetic construct
SEQUENCE: 108
MKCKFLGSFF LLFSLSGKGA DCRDNETIWG VLGHGITLNI PNFQMTDDID EVRWVRRGTL    60
VAEFKRKKPP FLISETYEVL ANGSLKIKKP MMRNDSGTYN VMVYGTNGMT RLEKDLDVRI   120
LERVSKPMIH WECPNTTLTC AVLQGTDFEL KLYQGETLLN SLPQKNMSYQ WTNLNAPFKC   180
EAINPVSKES KMEVVNCPEK GLSFWALVVV AGVLFCYGLL VTVALCVIWT NSRRNRGGQS   240
```

DYMNMTPRRP GLTRKPYQPY APARDFAAYR P                                            271

```
SEQ ID NO: 109          moltype = DNA   length = 840
FEATURE                 Location/Qualifiers
misc_feature            1..840
                        note = muCD2-CD28Cys
source                  1..840
                        mol_type = other DNA
                        organism = synthetic construct
SEQUENCE: 109
atgaagtgca agttcctggg ctcattcttc ctgctgttca gcctgagcgg caagggcgcc    60
gactgcagag acaacgagac aatctggggc gtgctgggcc acggcatcac cctgaacatc   120
cccaacttcc agatgaccga cgacatcgac gaagtgcgct gggtgcgaag aggcacactg   180
gtggccgagt tcaagagaaa gaagcccccca ttcctgatca gcgagacata cgaggtgctg   240
gccaacggca gcctgaagat caagaaaccc atgatgagaa acgacagcgg cacctacaac   300
gtgatggtgt acggcaccaa cggcatgacc agactgaaaa aggacctgga cgtgcggatc   360
ctggaaaggg tgtccaagcc catgatccac tgggagtgcc caacaccac cctgacctgt    420
gctgtgctgc agggcaccga cttcgagctg aagctgtacc agggcgagac actgctgaac   480
tccctgcccc agaaaaacat gagctaccag tggaccaacc tgaacgcccc cttcaagtgc   540
gaggccatca cccccgtgtc caagaaaagc aagatgaag tcgtgaactg ccccgagaag    600
ggcctgagct gccacaccca gagcagcccc aagctgttct gggccctggt ggtggtggcc   660
ggcgtgctgt tttgttacgg cctgctcgtg accgtggccc tgtgcgtgat ctggaccagc   720
agcagaagaa acagaggcgg ccagagcgac tacatgaaca tgaccccag aaggcctggc    780
ctgaccagaa agccctacca gccttacgcc cctgccagag acttcgccgc ctacagacct   840

SEQ ID NO: 110          moltype = AA   length = 280
FEATURE                 Location/Qualifiers
REGION                  1..280
                        note = muCD2-CD28Cys
source                  1..280
                        mol_type = protein
                        organism = synthetic construct
SEQUENCE: 110
MKCKFLGSFF LLFSLSGKGA DCRDNETIWG VLGHGITLNI PNFQMTDDID EVRWVRRGTL    60
VAEFKRKKPP FLISETYEVL ANGSLKIKKP MMRNDSGTYN VMVYGTNGMT RLEKDLDVRI   120
LERVSKPMIH WECPNTTLTC AVLQGTDFEL KLYQGETLLN SLPQKNMSYQ WTNLNAPFKC   180
EAINPVSKES KMEVVNCPEK GLSCHTQSSP KLFWALVVVA GVLFCYGLLV TVALCVIWTN   240
SRRNRGGQSD YMNMTPRRPG LTRKPYQPYA PARDFAAYRP                         280

SEQ ID NO: 111          moltype = DNA   length = 861
FEATURE                 Location/Qualifiers
misc_feature            1..861
                        note = muCD2-CD28Cys-41BBic
source                  1..861
                        mol_type = other DNA
                        organism = synthetic construct
SEQUENCE: 111
atgaagtgca agttcctggg ctcattcttc ctgctgttca gcctgagcgg caagggcgcc    60
gactgcagag acaacgagac aatctggggc gtgctgggcc acggcatcac cctgaacatc   120
cccaacttcc agatgaccga cgacatcgac gaagtgcgct gggtgcgaag aggcacactg   180
gtggccgagt tcaagagaaa gaagcccccca ttcctgatca gcgagacata cgaggtgctg   240
gccaacggca gcctgaagat caagaaaccc atgatgagaa acgacagcgg cacctacaac   300
gtgatggtgt acggcaccaa cggcatgacc agactgaaaa aggacctgga cgtgcggatc   360
ctggaaaggg tgtccaagcc catgatccac tgggagtgcc caacaccac cctgacctgt    420
gctgtgctgc agggcaccga cttcgagctg aagctgtacc agggcgagac actgctgaac   480
tccctgcccc agaaaaacat gagctaccag tggaccaacc tgaacgcccc cttcaagtgc   540
gaggccatca cccccgtgtc caagaaaagc aagatgaag tcgtgaactg ccccgagaag    600
ggcctgagct gccacaccca gagcagcccc aagctgttct gggccctggt ggtggtggcc   660
ggcgtgctgt tttgttacgg cctgctcgtg accgtggccc tgtgcgtgat ctggaccagc   720
gtgctgaagt ggatcagaaa gaagttcccc cacatcttca agcagccctt caagaaaacc   780
accggcgctg cccaggaaga ggacgcctgc agctgtagat gccctcagga agaagaaggc   840
ggcggaggcg gctacgagct g                                             861

SEQ ID NO: 112          moltype = AA   length = 287
FEATURE                 Location/Qualifiers
REGION                  1..287
                        note = muCD2-CD28Cys-41BBic
source                  1..287
                        mol_type = protein
                        organism = synthetic construct
SEQUENCE: 112
MKCKFLGSFF LLFSLSGKGA DCRDNETIWG VLGHGITLNI PNFQMTDDID EVRWVRRGTL    60
VAEFKRKKPP FLISETYEVL ANGSLKIKKP MMRNDSGTYN VMVYGTNGMT RLEKDLDVRI   120
LERVSKPMIH WECPNTTLTC AVLQGTDFEL KLYQGETLLN SLPQKNMSYQ WTNLNAPFKC   180
EAINPVSKES KMEVVNCPEK GLSCHTQSSP KLFWALVVVA GVLFCYGLLV TVALCVIWTS   240
VLKWIRKKFP HIFKQPFKKT TGAAQEEDAC SCRCPQEEEG GGGGYEL                 287

SEQ ID NO: 113          moltype = DNA   length = 1080
FEATURE                 Location/Qualifiers
```

| | | |
|---|---|---|
| misc_feature | 1..1080 | |
| | note = muCD200R-3aas-CD28Cys tm ic-41BB | |
| source | 1..1080 | |
| | mol_type = other DNA | |
| | organism = synthetic construct | |

SEQUENCE: 113
```
atgttctgct tctggcggac aagcgccctg gccgtgctgc tgatctgggg agtgtttgtg    60
gccggcagca gctgcaccga caagaaccag accacccaga caacagcag cagcccctg    120
acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtggacacc aagaccaacg agaagctg cctgggcaga    300
aacatcacct gggccagcac cccagaccac agccctgagc tgcagatcag cgccgtgaca    360
ctgcagcacg agggcaccta cacatgcgag acagtgaccc cgagggcaa cttcgagaag    420
aactacgatc tgcaggtgct ggtgcccccc gaagtgacct acttcccga gaagaataga    480
agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagcaga ggcggaaacc agtcctgcca caccccagag    720
agccccaagc tgttctgggc cctggtggtg gtggccggcg tgctgttttg ttacggcctg    780
ctcgtgaccg tggccctgtg cgtgatctgg accaacagca agaaaacag aggcggccag    840
agcgactaca tgaacatgac ccccagaagg cctggcctga ccagaaagcc ctaccagcct    900
tacgccccctg ccagagactt cgccgcctac agacctgcgt tctgaagtg gatcagaaag    960
aagttccccc acatcttcaa gcagcccttc aagaaaacca ccggcgctgc ccaggaagag    1020
gacgcctgca gctgtagatg ccctcaggaa gaagaaggcg gcgcgaggcgg ctacgagctg    1080
```

| | | |
|---|---|---|
| SEQ ID NO: 114 | moltype = AA length = 360 | |
| FEATURE | Location/Qualifiers | |
| REGION | 1..360 | |
| | note = muCD200R-3aas-CD28Cys tm ic-41BB | |
| source | 1..360 | |
| | mol_type = protein | |
| | organism = synthetic construct | |

SEQUENCE: 114
```
MFCFWRTSAL AVLLIWGVFV AGSSCTDKNQ TTQNNSSSPL TQVNTTVSVQ IGTKALLCCF    60
SIPLTKAVLI TWIIKLRGLP SCTIAYKVDT KTNETSCLGR NITWASTPDH SPELQISAVT    120
LQHEGTYTCE TVTPEGNFEK NYDLQVLVPP EVTYFPEKNR SAVCEAMAGK PAAQISWSPD    180
GDCVTTSESH SNGTVTVRST CHWEQNNVSD VSCIVSHLTG NQSLSIELSR GGNQSCHTQS    240
SPKLFWALVV VAGVLFCYGL LVTVALCVIW TNSRRNRGGQ SDYMNMTPRR PGLTRKPYQP    300
YAPARDFAAY RPSVLKWIRK KFPHIFKQPF KKTTGAAQEE DACSCRCPQE EEGGGGGYEL    360
```

| | | |
|---|---|---|
| SEQ ID NO: 115 | moltype = DNA length = 966 | |
| FEATURE | Location/Qualifiers | |
| misc_feature | 1..966 | |
| | note = muCD200R-CD28Cys tm ic-41BB | |
| source | 1..966 | |
| | mol_type = other DNA | |
| | organism = synthetic construct | |

SEQUENCE: 115
```
atgttctgct tctggcggac aagcgccctg gccgtgctgc tgatctgggg agtgtttgtg    60
gccggcagca gctgcaccga caagaaccag accacccaga caacagcag cagcccctg    120
acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtggacacc aagaccaacg agaagctg cctgggcaga    300
aacatcacct gggccagcac cccagaccac agccctgagc tgcagatcag cgccgtgaca    360
ctgcagcacg agggcaccta cacatgcgag acagtgaccc cgagggcaa cttcgagaag    420
aactacgatc tgcaggtgct ggtgcccccc gaagtgacct acttcccga gaagaataga    480
agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagcaga ggcggaaacc agtccctgcca gccctgcccag    720
acccagagca gccccaagct gttctgggcc ctggtggtgg tggccggcgt gctgttttgt    780
tacggcctgc tcgtgaccgt ggccctgtgc gtgatctgga ccagcgtgct gaagtggatc    840
agaaagaagt tcccccacat cttcaagcag cccttcaaga aaccaccgg cgctgcccag    900
gaagaggacg cctgcagctg tagatgccct caggaagaag aaggcggcgg aggcggctac    960
gagctg    966
```

| | | |
|---|---|---|
| SEQ ID NO: 116 | moltype = AA length = 322 | |
| FEATURE | Location/Qualifiers | |
| REGION | 1..322 | |
| | note = muCD200R-CD28Cys tm ic-41BB | |
| source | 1..322 | |
| | mol_type = protein | |
| | organism = synthetic construct | |

SEQUENCE: 116
```
MFCFWRTSAL AVLLIWGVFV AGSSCTDKNQ TTQNNSSSPL TQVNTTVSVQ IGTKALLCCF    60
SIPLTKAVLI TWIIKLRGLP SCTIAYKVDT KTNETSCLGR NITWASTPDH SPELQISAVT    120
LQHEGTYTCE TVTPEGNFEK NYDLQVLVPP EVTYFPEKNR SAVCEAMAGK PAAQISWSPD    180
GDCVTTSESH SNGTVTVRST CHWEQNNVSD VSCIVSHLTG NQSLSIELSR GGNQSLRPCH    240
TQSSPKLFWA LVVVAGVLFC YGLLVTVALC VIWTSVLKWI RKKFPHIFKQ PFKKTTGAAQ    300
```

EEDACSCRCP QEEEGGGGGY EL                                                        322

SEQ ID NO: 117              moltype = DNA   length = 681
FEATURE                     Location/Qualifiers
misc_feature                1..681
                            note = muFas tm-CD28
source                      1..681
                            mol_type = other DNA
                            organism = synthetic construct
SEQUENCE: 117
atgctgtgga tctgggccgt gctgcctctg gtgctggctg gatcacagct gagagtgcac  60
acccagggca ccaacagcat cagcgagagc ctgaagctga agaagagt gcgcgagaca   120
gacaagaact gcagcgaggg cctgtaccag ggcggacccc tctgctgtca gccttgccag  180
cccggcaaga aaaggtgga agattgcaag atgaacggcg caccccctac ctgcgcccct  240
tgtacagagg gcaaagagta catggacaag aaccactacg ccgacaagtg cagacggtgc  300
accctgtgcg acgaggaaca cggcctggaa gtggaaacaa actgcaccct gacccagaac  360
accaagtgca agtgcaaacc cgacttctac tgcgacagcc ccggctgcga gcactgcgtc  420
agatgtgcct cttgcgagca cggcacccctg gaaccttgta ccgccaccag caacaccaac  480
tgccggaagc agagccccag aaacagactg tggctgctga ccatcctggt gctgctgatc  540
ccctggtgt tcatctacaa cagcagaaga aacagaggcg gccagagcga ctacatgaac  600
atgacccca gaaggcctgg cctgaccaga aagcctacc agccttacgc ccctgccaga  660
gacttcgccg cctacagacc t                                            681

SEQ ID NO: 118              moltype = AA   length = 227
FEATURE                     Location/Qualifiers
REGION                      1..227
                            note = muFas tm-CD28
source                      1..227
                            mol_type = protein
                            organism = synthetic construct
SEQUENCE: 118
MLWIWAVLPL VLAGSQLRVH TQGTNSISES LKLRRRVRET DKNCSEGLYQ GGPFCCQPCQ  60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN CRKQSPRNRL WLLTILVLLI  180
PLVFIYNSRR NRGGQSDYMN MTPRRPGLTR KPYQPYAPAR DFAAYRP              227

SEQ ID NO: 119              moltype = DNA   length = 711
FEATURE                     Location/Qualifiers
misc_feature                1..711
                            note = muFas-CD28tm
source                      1..711
                            mol_type = other DNA
                            organism = synthetic construct
SEQUENCE: 119
atgctgtgga tctgggccgt gctgcctctg gtgctggctg gatcacagct gagagtgcac  60
acccagggca ccaacagcat cagcgagagc ctgaagctga agaagagt gcgcgagaca   120
gacaagaact gcagcgaggg cctgtaccag ggcggacccc tctgctgtca gccttgccag  180
cccggcaaga aaaggtgga agattgcaag atgaacggcg caccccctac ctgcgcccct  240
tgtacagagg gcaaagagta catggacaag aaccactacg ccgacaagtg cagacggtgc  300
accctgtgcg acgaggaaca cggcctggaa gtggaaacaa actgcaccct gacccagaac  360
accaagtgca agtgcaaacc cgacttctac tgcgacagcc ccggctgcga gcactgcgtc  420
agatgtgcct cttgcgagca cggcacccctg gaaccttgta ccgccaccag caacaccaac  480
tgccggaagc agagccccag aaacagattc tgggccctgg tggtggtggc cggcgtgctg  540
ttttgttacg gcctgctcgt gaccgtggcc ctgtgcgtga tctggaccaa cagcagaaga  600
aacagaggcg gccagagcga ctacatgaac atgacccca gaaggcctgg cctgaccaga  660
aagcctacc agccttacgc ccctgccaga gacttcgccg cctacagacc t            711

SEQ ID NO: 120              moltype = AA   length = 237
FEATURE                     Location/Qualifiers
REGION                      1..237
                            note = muFas-CD28tm
source                      1..237
                            mol_type = protein
                            organism = synthetic construct
SEQUENCE: 120
MLWIWAVLPL VLAGSQLRVH TQGTNSISES LKLRRRVRET DKNCSEGLYQ GGPFCCQPCQ  60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN CRKQSPRNRF WALVVVAGVL  180
FCYGLLVTVA LCVIWTNSRR NRGGQSDYMN MTPRRPGLTR KPYQPYAPAR DFAAYRP    237

SEQ ID NO: 121              moltype = DNA   length = 738
FEATURE                     Location/Qualifiers
misc_feature                1..738
                            note = muFas-CD28Cys
source                      1..738
                            mol_type = other DNA
                            organism = synthetic construct
SEQUENCE: 121
atgctgtgga tctgggccgt gctgcctctg gtgctggctg gatcacagct gagagtgcac  60

```
acccagggca ccaacagcat cagcgagagc ctgaagctga aagaagagt gcgcgagaca   120
gacaagaact gcagcgaggg cctgtaccag ggcggaccct tctgctgtca gccttgccag   180
cccggcaaga aaaggtgga agattgcaag atgaacggcg gcaccccac ctgcgcccct   240
tgtacagagg gcaaagagta catggacaag aaccactacg ccgacaagtg cagacggtgc   300
accctgtgcg acgaggaaca cggcctggaa gtggaaacaa actgcaccct gacccagaac   360
accaagtgca agtgcaaacc cgacttctac tgcgacagcc ccggctgcga gcactgcgtc   420
agatgtgcct cttgcgagca cggcaccctg aaccttgta ccgccaccag caacaccaac   480
tgccggaagc agagccccag aaacagatgc cacacccaga gcagcccaa gctgttctgg   540
gccctggtgg tggtggccgg cgtgctgttt tgttacggcc tgctcgtgac cgtggccctg   600
tgcgtgatct ggaccaacag cagaagaaac agaggcggcc agagcgacta catgaacatg   660
acccccagaa ggcctggcct gaccagaaag ccctaccagc cttacgcccc tgccagagac   720
ttcgccgcct acagacct                                                 738

SEQ ID NO: 122            moltype = AA   length = 246
FEATURE                   Location/Qualifiers
REGION                    1..246
                          note = muFas-CD28Cys
source                    1..246
                          mol_type = protein
                          organism = synthetic construct
SEQUENCE: 122
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN   120
TKCKCKPDFY CDSPGCEHCV RCASCEHGTL EPCTATSNTN CRKQSPRNRC HTQSSPKLFW   180
ALVVVAGVLF CYGLLVTVAL CVIWTNSRRN RGGQSDYMNM TPRRPGLTRK PYQPYAPARD   240
FAAYRP                                                              246

SEQ ID NO: 123            moltype = DNA  length = 711
FEATURE                   Location/Qualifiers
misc_feature              1..711
                          note = muFas-9aas-CD28Cys
source                    1..711
                          mol_type = other DNA
                          organism = synthetic construct
SEQUENCE: 123
atgctgtgga tctgggccgt gctgcctctg gtgctggctg atcacagct gagagtgcac   60
acccagggca ccaacagcat cagcgagagc ctgaagctga aagaagagt gcgcgagaca   120
gacaagaact gcagcgaggg cctgtaccag ggcggaccct tctgctgtca gccttgccag   180
cccggcaaga aaaggtgga agattgcaag atgaacggcg gcaccccac ctgcgcccct   240
tgtacagagg gcaaagagta catggacaag aaccactacg ccgacaagtg cagacggtgc   300
accctgtgcg acgaggaaca cggcctggaa gtggaaacaa actgcaccct gacccagaac   360
accaagtgca agtgcaaacc cgacttctac tgcgacagcc ccggctgcga gcactgcgtc   420
agatgtgcct cttgcgagca cggcaccctg aaccttgta ccgccaccag caacaccaac   480
tgccacaccc agagcagccc caagctgttc tgggccctgg tggtggtggc cggcgtgctg   540
ttttgttacg gcctgctcgt gaccgtggcc ctgtgcgtga tctggaccaa cagcagaaga   600
aacagaggcg gccagagcga ctacatgaac atgaccccca gaaggcctgg cctgaccaga   660
aagcccctacc agccttacgc ccctgccaga cttcgccgcc ctacagacc t             711

SEQ ID NO: 124            moltype = AA   length = 237
FEATURE                   Location/Qualifiers
REGION                    1..237
                          note = muFas-9aas-CD28Cys
source                    1..237
                          mol_type = protein
                          organism = synthetic construct
SEQUENCE: 124
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN   120
TKCKCKPDFY CDSPGCEHCV RCASCEHGTL EPCTATSNTN CHTQSSPKLF WALVVVAGVL   180
FCYGLLVTVA LCVIWTNSRR NRGGQSDYMN MTPRRPGLTR KPYQPYAPAR DFAAYRP      237

SEQ ID NO: 125            moltype = DNA  length = 693
FEATURE                   Location/Qualifiers
misc_feature              1..693
                          note = muPD1tm-CD28
source                    1..693
                          mol_type = other DNA
                          organism = synthetic construct
SEQUENCE: 125
atgtgggtgc acaggtgcc ctggtctttc acctgggctg tgctgcagct gagctggcag   60
tctggctggc tgctggaagt gcctaacggc ccttggagaa gcctgacctt ctaccccgct   120
tggctgaccg tgtctgaggg cgccaacgcc accttcacct gtagcctgag caattggagc   180
gaggacctga tgctgaactg aacagactg agccccagca accagaccga agaagcaggcc   240
gccttgtca acggcctgtc tcagctgtg caggacgcca gattccagat catccagctg   300
cccaacagac acgacttcca catgaacatc ctggacacca agaaaacga cagcggcatc   360
tacctgtgcg gcgccatcag cctgcacccc aaggccaaga tcgaggaatc tcctggcgcc   420
gagctggtcg tgaccgagag aatcctggaa acctccacca gatacccccag ccccagccct   480
aagcccgagg gcagatttca gggcatggtc atcggcatca gcgtagccct cgtgggcatc   540
ccagtgttgc tgctgctggc ctgggccctg aacagcagaa gaaacagagg cggccagagc   600
```

```
gactacatga acatgacccc cagaaggcct ggcctgacca gaaagcccta ccagccttac    660
gcccctgcca gagacttcgc cgcctacaga cct                                 693

SEQ ID NO: 126          moltype = AA  length = 231
FEATURE                 Location/Qualifiers
REGION                  1..231
                        note = muPD1tm-CD28
source                  1..231
                        mol_type = protein
                        organism = synthetic construct
SEQUENCE: 126
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI    120
YLCGAISLHP KAKIEESPGA ELVVTERILE TSTRYPSPSP KPEGRFQGMV IGIMSALVGI    180
PVLLLLAWAL NSRRNRGGQS DYMNMTPRRP GLTRKPYQPY APARDFAAYR P             231

SEQ ID NO: 127          moltype = DNA  length = 711
FEATURE                 Location/Qualifiers
misc_feature            1..711
                        note = muPD1-CD28tm
source                  1..711
                        mol_type = other DNA
                        organism = synthetic construct
SEQUENCE: 127
atgtgggtgc gacaggtgcc ctggtctttc acctgggctg tgctgcagct gagctggcag    60
tctggctggc tgctggaagt gcctaacggc ccttggagaa gcctgacctt ctacccagct    120
tggctgaccg tgtctgaggg cgccaacgcc accttcacct gtagcctgag caattggagc    180
gaggacctga tgctgaactg aacagactg agccccagca accagaccga aagcaggcc     240
gccttctgca acggcctgtc tcagcctgtg caggacgcca gattccagat catccagctg    300
cccaacagac acgacttcca catgaacatc ctggacacca agaaaacga cagcggcatc    360
tacctgtgcg gcgccatcag cctgcacccc aaggccaaga tcgaggaatc tcctggcgc    420
gagctggtcg tgaccgagag aatcctggaa acctccacca gataccccag ccccagccct    480
aagcccgagg gcagatttca gggcatgttc tgggcctgg tggtggtggc cggcgtgctg     540
tttttgttacg gcctgctcgt gaccgtggcc ctgtgcgtga tctggaccaa cagcagaaga    600
aacagaggcg gccagagcga ctacatgaac atgacccca aaggcctgg cctgaccaga    660
aagcccacc agccttacgc ccctgccaga gacttcgcc cctacagacc t              711

SEQ ID NO: 128          moltype = AA  length = 237
FEATURE                 Location/Qualifiers
REGION                  1..237
                        note = muPD1-CD28tm
source                  1..237
                        mol_type = protein
                        organism = synthetic construct
SEQUENCE: 128
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI    120
YLCGAISLHP KAKIEESPGA ELVVTERILE TSTRYPSPSP KPEGRFQGMF WALVVVAGVL    180
FCYGLLVTVA LCVIWTNSRR NRGGQSDYMN MTPRRPGLTR KPYQPYAPAR DFAAYRP      237

SEQ ID NO: 129          moltype = DNA  length = 738
FEATURE                 Location/Qualifiers
misc_feature            1..738
                        note = muPD1-CD28Cys
source                  1..738
                        mol_type = other DNA
                        organism = synthetic construct
SEQUENCE: 129
atgtgggtgc gacaggtgcc ctggtctttc acctgggctg tgctgcagct gagctggcag    60
tctggctggc tgctggaagt gcctaacggc ccttggagaa gcctgacctt ctacccagct    120
tggctgaccg tgtctgaggg cgccaacgcc accttcacct gtagcctgag caattggagc    180
gaggacctga tgctgaactg aacagactg agccccagca accagaccga aagcaggcc     240
gccttctgca acggcctgtc tcagcctgtg caggacgcca gattccagat catccagctg    300
cccaacagac acgacttcca catgaacatc ctggacacca agaaaacga cagcggcatc    360
tacctgtgcg gcgccatcag cctgcacccc aaggccaaga tcgaggaatc tcctggcgc    420
gagctggtcg tgaccgagag aatcctggaa acctccacca gataccccag ccccagccct    480
aagcccgagg gcagatttca gggcatgtgc cacacccaga gcagcccaa gctgttctgg    540
gctctggtgg tggtggccgg cgtgctgttt tgttacggcc tgctcgtgac cgtggccctg    600
tgcgtgatct ggaccaacag cagacgaac agaggcggc agagcgacta catgaatatg     660
acccccagaa ggcctggcct gaccagaaag ccctaccagc cttacgcccc tgccagagac    720
ttcgccgcct acagacct                                                  738

SEQ ID NO: 130          moltype = AA  length = 246
FEATURE                 Location/Qualifiers
REGION                  1..246
                        note = muPD1-CD28Cys
source                  1..246
                        mol_type = protein
                        organism = synthetic construct
```

```
SEQUENCE: 130
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERILE TSTRYPSPSP KPEGRFQGMC HTQSSPKLFW   180
ALVVVAGVLF CYGLLVTVAL CVIWTNSRRN RGGQSDYMNM TPRRPGLTRK PYQPYAPARD   240
FAAYRP                                                              246

SEQ ID NO: 131          moltype = DNA   length = 711
FEATURE                 Location/Qualifiers
misc_feature            1..711
                        note = muPD1-9aas-CD28Cys
source                  1..711
                        mol_type = other DNA
                        organism = synthetic construct
SEQUENCE: 131
atgtgggtgc gacaggtgcc ctggtctttc acctgggctg tgctgcagct gagctggcag    60
tctggctggc tgctggaagt gcctaacggc ccttggagaa gcctgacctt ctaccccgct   120
tggctgaccg tgtctgaggg cgccaacgcc accttcacct gtagcctgag caattggagc   180
gaggacctga tgctgaactg gaacagactg agcccccagc accagaccga gaagcaggcc   240
gccttctgca acggcctgtc tcagcctgtg caggacgcca gattccagat catccagctg   300
cccaacgaca cgacttcca catgaacatc ctggacacca agagaaacga cagcggcatc   360
tacctgtgcg gcgccatcag cctgcacccc aaggccaaga tcgaggaatc tcctggcgc    420
gagctggtcg tgaccgagag aatcctggaa acctccacca gataccccag ccccagccct   480
tgccacaccc agagcagccc caagctgttc tgggctctgg tggtggtggc cggcgtgctg   540
ttttgttacg gcctgctcgt gaccgtggcc ctgtgcgtga tctggaccaa cagcagacgg   600
aacagaggcg gccagagcga ctacatgaat atgacccccca gaaggcctgg cctgaccaga   660
aagcccctacc agccttacgc ccctgccaga cttcgccg cctacagacc t             711

SEQ ID NO: 132          moltype = AA   length = 237
FEATURE                 Location/Qualifiers
REGION                  1..237
                        note = muPD1-9aas-CD28Cys
source                  1..237
                        mol_type = protein
                        organism = synthetic construct
SEQUENCE: 132
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERILE TSTRYPSPSP CHTQSSPKLF WALVVVAGVL   180
FCYGLLVTVA LCVIWTNSRR NRGGQSDYMN MTPRRPGLTR KPYQPYAPAR DFAAYRP      237

SEQ ID NO: 133          moltype = DNA   length = 675
FEATURE                 Location/Qualifiers
misc_feature            1..675
                        note = muPD1-21aas-CD28Cys
source                  1..675
                        mol_type = other DNA
                        organism = synthetic construct
SEQUENCE: 133
atgtgggtgc gacaggtgcc ctggtctttc acctgggctg tgctgcagct gagctggcag    60
tctggctggc tgctggaagt gcctaacggc ccttggagaa gcctgacctt ctaccccgct   120
tggctgaccg tgtctgaggg cgccaacgcc accttcacct gtagcctgag caattggagc   180
gaggacctga tgctgaactg gaacagactg agcccccagc accagaccga gaagcaggcc   240
gccttctgca acggcctgtc tcagcctgtg caggacgcca gattccagat catccagctg   300
cccaacgac acgacttcca catgaacatc ctggacacca agagaaacga cagcggcatc   360
tacctgtgcg gcgccatcag cctgcacccc aaggccaaga tcgaggaatc tcctggcgc    420
gagctggtcg tgaccgagag aatcctgcca cccagagca gccccaagct gttctgggct   480
ctggtggtgt tggccggcgt gctgtttttgt tacggcctgc tcgtgaccgt ggccctgtgc   540
gtgatctgga ccaacagcag acggaacaga ggcggccaga gcgactacat gaatatgacc   600
cccagaaggc ctggcctgac cagaaagccc taccagcctt acgcccctgc cagagacttc   660
gccgcctaca gacct                                                    675

SEQ ID NO: 134          moltype = AA   length = 225
FEATURE                 Location/Qualifiers
REGION                  1..225
                        note = muPD1-21aas-CD28Cys
source                  1..225
                        mol_type = protein
                        organism = synthetic construct
SEQUENCE: 134
MWVRQVPWSF TWAVLQLSWQ SGWLLEVPNG PWRSLTFYPA WLTVSEGANA TFTCSLSNWS    60
EDLMLNWNRL SPSNQTEKQA AFCNGLSQPV QDARFQIIQL PNRHDFHMNI LDTRRNDSGI   120
YLCGAISLHP KAKIEESPGA ELVVTERICH TQSSPKLFWA LVVVAGVLFC YGLLVTVALC   180
VIWTNSRRNR GGQSDYMNMT PRRPGLTRKP YQPYAPARDF AAYRP                   225

SEQ ID NO: 135          moltype = DNA   length = 1512
FEATURE                 Location/Qualifiers
misc_feature            1..1512
                        note = muLag3tm-CD28
```

```
source                  1..1512
                        mol_type = other DNA
                        organism = synthetic construct
SEQUENCE: 135
atgagagagg acctgctgct gggctttctg ctgctgggac tgctgtggga ggcccctgtg    60
gtgtcatctg gccctggcaa agaactgccc gtcgtgtggg ctcaggaagg cgctcctgtg   120
catctgccct gcagcctgaa gtcccccaac ctggacccca acttcctgag aagaggcggc   180
gtgatctggc agcaccagcc tgattctggc agcccacac ctatccctgc cctggatctg   240
caccagggca tgcctagccc tagacagcct gcccctggca gatacaccgt gctgtctgtg   300
gctcctggcg gcctgagaag tggcagacag cctctgcacc ctcacgtgca gctggaagag   360
aggggactgc agaggggcga cttcagcctg tggctgaggc ctgccctgag aacagatgcc   420
ggcgagtacc acgctaccgt gcggctgcct aacagagccc tgagctgctc cctgagactg   480
agagtgggcc aggccagcat gatcgcctct ccatctggcg tgctgaagct gagcgactgg   540
gtgctgctga actgcagctt ctccagaccc gacagaccc tgtccgtgca ctggttccag   600
ggacagaaca gagtgcccgt gtacaacagc cccagacact tcctggccga cattcctg   660
ctgctgcccc aggtgtcccc tctggactct ggcacatggg gctgcgtgct gacatacagg   720
gacggcttca acgtgtccat cacctacaac ctgaaggtgc tgggcctgga accgtggct   780
cctctgacag tgtacgccgc cgagggcagc agagtggaac tgccttgtca tctgccaccc   840
ggcgtgggca ccttctctct gctgatcgcc aagtggaccc ctccaggcgg aggacctgaa   900
ctgccagtgg ctggcaagag cggcaacttc accctgcacc tggaagcagt gggcctggct   960
caggccggca cctacacctg tagcatccat ctgcagggcc agcagctgaa cgccaccgtg  1020
acactggccg tgatcaccgt gaccccccaag agctttggcc tgcctggctc cagaggcaag  1080
ctgctgtgtg aagtgacccc cgccagcggc aaagaaagat cgtgtggcg gcctctgaac  1140
aacctgagca gatcctgccc aggccccgtg ctggaaatcc aggaagccag actgctggcc  1200
gagcggtggc agtgccagct gtatgaggga cagcgactgc tgggcgccac tgtgtacgct  1260
gctgagtcta gctctggcgc ccacagcgcc agaagaatca gcggcgatct gaagggcggc  1320
cacctggtgc tggtgctgat cctgggcgct ctgagcctgt tcctgctggt ggctggcgct  1380
ttcggcttta acagcagaag aaacagaggc ggcagagcg actacatgaa catgaccccc  1440
agaaggcctg gcctgaccag aaagccctac agcccttacg cccctgccag agacttcgcc  1500
gcctacgac ct                                                      1512

SEQ ID NO: 136          moltype = AA  length = 504
FEATURE                 Location/Qualifiers
REGION                  1..504
                        note = muLag3tm-CD28
source                  1..504
                        mol_type = protein
                        organism = synthetic construct
SEQUENCE: 136
MREDLLLGFL LLGLLWEAPV VSSGPGKELP VVWAQEGAPV HLPCSLKSPN LDPNFLRRGG    60
VIWQHQPDSG QPTPIPALDL HQGMPSPRQP APGRYTVLSV APGGLRSGRQ PLHPHVQLEE   120
RGLQRGDFSL WLRPALRTDA GEYHATVRLP NRALSCSLRL RVGQASMIAS PSGVLKLSDW   180
VLLNCSFSRP DRPVSVHWFQ GQNRVPVYNS PRHFLAETFL LLPQVSPLDS GTWGCVLTYR   240
DGFNVSITYN LKVLGLEPVA PLTVYAAEGS RVELPCHLPP GVGTPSLLIA KWTPPGGGPE   300
LPVAGKSGNF TLHLEAVGLA QAGTYTCSIH LQGQQLNATV TLAVITVTPK SFGLPGSRGK   360
LLCEVTPASG KERFVWRPLN NLSRSCPGPV LEIQEARLLA ERWQCQLYEG QRLLGATVYA   420
AESSSGAHSA RRISGDLKGG HLVLVLILGA LSLFLLVAGA FGFNSRRNRG GQSDYMNMTP   480
RRPGLTRKPY QPYAPARDFA AYRP                                         504

SEQ ID NO: 137          moltype = DNA  length = 1530
FEATURE                 Location/Qualifiers
misc_feature            1..1530
                        note = muLag3-CD28tm
source                  1..1530
                        mol_type = other DNA
                        organism = synthetic construct
SEQUENCE: 137
atgagagagg acctgctgct gggctttctg ctgctgggac tgctgtggga ggcccctgtg    60
gtgtcatctg gccctggcaa agaactgccc gtcgtgtggg ctcaggaagg cgctcctgtg   120
catctgccct gcagcctgaa gtcccccaac ctggacccca acttcctgag aagaggcggc   180
gtgatctggc agcaccagcc tgattctggc agcccacac ctatccctgc cctggatctg   240
caccagggca tgcctagccc tagacagcct gcccctggca gatacaccgt gctgtctgtg   300
gctcctggcg gcctgagaag tggcagacag cctctgcacc ctcacgtgca gctggaagag   360
aggggactgc agaggggcga cttcagcctg tggctgaggc ctgccctgag aacagatgcc   420
ggcgagtacc acgctaccgt gcggctgcct aacagagccc tgagctgctc cctgagactg   480
agagtgggcc aggccagcat gatcgcctct ccatctggcg tgctgaagct gagcgactgg   540
gtgctgctga actgcagctt ctccagaccc gacagaccc tgtccgtgca ctggttccag   600
ggacagaaca gagtgcccgt gtacaacagc cccagacact tcctggccga cattcctg   660
ctgctgcccc aggtgtcccc tctggactct ggcacatggg gctgcgtgct gacatacagg   720
gacggcttca acgtgtccat cacctacaac ctgaaggtgc tgggcctgga accgtggct   780
cctctgacag tgtacgccgc cgagggcagc agagtggaac tgccttgtca tctgccaccc   840
ggcgtgggca ccttctctct gctgatcgcc aagtggaccc ctccaggcgg aggacctgaa   900
ctgccagtgg ctggcaagag cggcaacttc accctgcacc tggaagcagt gggcctggct   960
caggccggca cctacacctg tagcatccat ctgcagggcc agcagctgaa cgccaccgtg  1020
acactggccg tgatcaccgt gaccccccaag agctttggcc tgcctggctc cagaggcaag  1080
ctgctgtgtg aagtgacccc cgccagcggc aaagaaagat cgtgtggcg gcctctgaac  1140
aacctgagca gatcctgccc aggccccgtg ctggaaatcc aggaagccag actgctggcc  1200
gagcggtggc agtgccagct gtatgaggga cagcgactgc tgggcgccac tgtgtacgct  1260
gctgagtcta gctctggcgc ccacagcgcc agaagaatca gcggcgatct gaagggcggc  1320
```

```
cacctgttct gggccctggt ggtggtggcc ggcgtgctgt tttgttacgg cctgctcgtg     1380
accgtggccc tgtgcgtgat ctggaccaac agcagaagaa acagaggcgg ccagagcgac     1440
tacatgaaca tgacccccag aaggcctggc ctgaccagaa agccctacca gccttacgcc     1500
cctgccagag acttcgccgc ctacagacct                                      1530

SEQ ID NO: 138          moltype = AA  length = 510
FEATURE                 Location/Qualifiers
REGION                  1..510
                        note = muLag3-CD28tm
source                  1..510
                        mol_type = protein
                        organism = synthetic construct
SEQUENCE: 138
MREDLLLGFL LLGLLWEAPV VSSGPGKELP VVWAQEGAPV HLPCSLKSPN LDPNFLRRGG      60
VIWQHQPDSG QPTPIPALDL HQGMPSPRQP APGRYTVLSV APGGLRSGRQ PLHPHVQLEE     120
RGLQRGDFSL WLRPALRTDA GEYHATVRLP NRALSCSLRL RVGQASMIAS PSGVLKLSDW     180
VLLNCSFSRP DRPVSVHWFQ GQNRVPVYNS PRHFLAETFL LLPQVSPLDS GTWGCVLTYR     240
DGFNVSITYN LKVLGLEPVA PLTVYAAEGS RVELPCHLPG GVGTPSLLIA KWTPPGGGPE     300
LPVAGKSGNF TLHLEAVGLA QAGTYTCSIH LQGQQLNATV TLAVITVTPK SFGLPGSRGK     360
LLCEVTPASG KERFVWRPLN NLSRSCPGPV LEIQEARLLA ERWQCQLYEG QRLLGATVYA     420
AESSSGAHSA RRISGDLKGG HLFWALVVVA GVLFCYGLLV TVALCVIWTN SRRNRGGQSD     480
YMNMTPRRPG LTRKPYQPYA PARDFAAYRP                                      510

SEQ ID NO: 139          moltype = DNA  length = 1557
FEATURE                 Location/Qualifiers
misc_feature            1..1557
                        note = muLag3-CD28Cys
source                  1..1557
                        mol_type = other DNA
                        organism = synthetic construct
SEQUENCE: 139
atgagagagg acctgctgct gggctttctg ctgctgggac tgctgtggga ggcccctgtg      60
gtgtcatctg ccctggcaa agaactgccc gtcgtgtggg ctcaggaagg cgctcctgtg     120
catctgccct gcagcctgaa gtcccccaac ctggaccaca acttcctgag aaggccggc     180
gtgatctggc agcaccagc tgattctggc cagccacac ctatccctgc cctggatctg     240
caccagggca tgcctagccc tagacagcct gcccctggca gataccgtg gctgtctgtg     300
gctcctggcg gcctgagaag tggcagacag cctctgcacc ctcacgtgca gctggaagag     360
aggggactgc agagggcga cttcagcctg tggctgaggc ctgccctgag aacagatgcc     420
ggcgagtacc acgctaccgt gcggctgcct aacagagcc tggctgtctc cctgagactg     480
agagtgggcc aggccagcat gatcgcctct ccatctggcg tgctgaagct gagcgactgg     540
gtgctgctga actgcagctt ctccagaccc gacagaccgt gtccgtgca ctggttccag     600
ggacagaaca gagtgcccgt gtacaacagc cccagacact cctgccga cattcctg     660
ctgctgcccc aggtgtcccc tctggactct ggacacatgg gctgcgtgct gacatacagg     720
gacggcttca acgtgtccat cacctacaac ctgaaggtgc tgggcctgga acccgtggct     780
cctctgacag tgtacgccgc cgagggcagc agagtggaac tgcccttgtca tctgccaccc     840
ggcgtgggca ccttctctct gctgatcgcc aagtggaccc ctccaggcgg aggacctgaa     900
ctgccagtgg ctggcaagag cggcaacttc acctgcacc tggaagcagt gggcctggct     960
caggccggca cctacacctg tagcatccat ctgcaggagc agcagctgaa cgccaccgtg    1020
acactggccg tgatcaccgt gaccccaag agctttggcc tgcctggctc agaggcaag    1080
ctgctgtgtg aagtgacccc cgccagcggc aaagaaagat tcgtgtggcg gcctctgaac    1140
aacctggagc gatcctgccc aggccccgtg ctggaaatcc aggaagccag actgctggct    1200
gagcggtggc agtgccagct gtatgaggga cagcgactgc tgggcgccac tgtgtacgct    1260
gctgagtcta gctctggcgc ccacagcgcc agaagaatca gcggcgatct gaagggcggc    1320
cacctgtgcc acacccagag cagccccaag ctgttctggg ccctggtggt ggtggccggc    1380
gtgctgtttt gttacggcct gctcgtgacc gtggccctgt gcgtgatcgt ggaccaacag    1440
agaagaaaca gaggcggcca gagcgactac atgaacatga ccccagaag gcctggcctg    1500
accagaaagc cctaccagcc ttacgccct gccagagact tcgccgccta cagacct     1557

SEQ ID NO: 140          moltype = AA  length = 519
FEATURE                 Location/Qualifiers
REGION                  1..519
                        note = muLag3-CD28Cys
source                  1..519
                        mol_type = protein
                        organism = synthetic construct
SEQUENCE: 140
MREDLLLGFL LLGLLWEAPV VSSGPGKELP VVWAQEGAPV HLPCSLKSPN LDPNFLRRGG      60
VIWQHQPDSG QPTPIPALDL HQGMPSPRQP APGRYTVLSV APGGLRSGRQ PLHPHVQLEE     120
RGLQRGDFSL WLRPALRTDA GEYHATVRLP NRALSCSLRL RVGQASMIAS PSGVLKLSDW     180
VLLNCSFSRP DRPVSVHWFQ GQNRVPVYNS PRHFLAETFL LLPQVSPLDS GTWGCVLTYR     240
DGFNVSITYN LKVLGLEPVA PLTVYAAEGS RVELPCHLPP GVGTPSLLIA KWTPPGGGPE     300
LPVAGKSGNF TLHLEAVGLA QAGTYTCSIH LQGQQLNATV TLAVITVTPK SFGLPGSRGK     360
LLCEVTPASG KERFVWRPLN NLSRSCPGPV LEIQEARLLA ERWQCQLYEG QRLLGATVYA     420
AESSSGAHSA RRISGDLKGG HLCHTQSSPK LFWALVVVAG VLFCYGLLVT VALCVIWTNS     480
RRNRGGQSDY MNMTPRRPGL TRKPYQPYAP ARDFAAYRP                            519

SEQ ID NO: 141          moltype = DNA  length = 1530
FEATURE                 Location/Qualifiers
misc_feature            1..1530
```

|  | note = muLag3-9aas-CD28Cys |  |
| --- | --- | --- |
| source | 1..1530 |  |
|  | mol_type = other DNA |  |
|  | organism = synthetic construct |  |

SEQUENCE: 141

```
atgagagagg acctgctgct gggctttctg ctgctgggac tgctgtggga ggcccctgtg   60
gtgtcatctg gccctggcaa agaactgccc gtcgtgtggg ctcaggaagg cgctcctgtg  120
catctgccct gcagcctgaa gtcccccaac ctggacccca acttcctgag aagaggcggc  180
gtgatctggc agcaccagcc tgattctggc cagcccacac ctatccctgc cctggatctg  240
caccagggca tgcctagccc tagacagcct gcccccgacg gatacaccgt gctgtctgtg  300
gctcctggcg gcctgagaag tggcagacag cctctgcacc ctcacgtgca gctggaagag  360
aggggactgc agaggggcga cttcagcctg tggctgaggc ctgccctgag aacagatgcc  420
ggcgagtacc acgctaccgt gcggctgcct aacagagccc tgagctgctc cctgagactg  480
agagtggcag aggccagcat gatcgcctct ccatctggcg tgctgaagct gagcgactgg  540
gtgctgctga actgcagctt ctccagaccc gacagacccg tgtccgtgca ctggttccag  600
ggacagaaca gagtgcccgt gtacaacagc cccagacact tcctggccga acattcctg  660
ctgctgcccc aggtgtcccc tctggactct ggcacatggg gctgcgtgct gacatacagg  720
gacggcttca acgtgtccat cacctacaac ctgaaggtgc tgggcctgga acccgtgcgct  780
cctctgacag tgtacgccgc cgagggcagc agagtggaac tgccttgtca tctgccaccc  840
ggcgtgggca caccttctct gctgatcgcc aagtggaccc ctccaggcgg aggacctgaa  900
ctgccagtgg ctggcaagag cggcaacttc accctgcacc tggaagcagt gggcctggct  960
caggccggca cctacacctg tagcatccat ctgcagggcc agcagctgaa cgccaccgtg 1020
acactggccg tgatcaccgt gacccccaag agctttggcc tgcctggctc cagaggcaag 1080
ctgctgtgtg aagtgacccc cgccagcggc aagaaagat cgtgtggcg gcctctgaac 1140
aacctgagca gatcctgccc aggccccgtg ctggaaatcc aggaagccag actgctggcc 1200
gagcggtggc agtgccagct gtatgaggga cagcgactgc tgggcgccac tgtgctacgct 1260
gctgagtcta gctctggcgc ccacagcgcc agaagaatct gccacaccca gagcagcccc 1320
aagctgttct gggccctggt ggtggtggcc ggcgtgctgt tttgttacgg cctgctcgtg 1380
accgtggccc tgtgcgtgat ctggaccaac agcagaagaa acagaggcgg ccagagcgac 1440
tacatgaaca tgacccccag aaggcctggc ctgaccagaa agccctacca gccttacgcc 1500
cctgccagag acttcgccgc ctacagacct                                   1530
```

| SEQ ID NO: 142 | moltype = AA length = 510 |
| --- | --- |
| FEATURE | Location/Qualifiers |
| REGION | 1..510 |
|  | note = muLag3-9aas-CD28Cys |
| source | 1..510 |
|  | mol_type = protein |
|  | organism = synthetic construct |

SEQUENCE: 142

```
MREDLLLGFL LLGLLWEAPV VSSGPGKELP VVWAQEGAPV HLPCSLKSPN LDPNFLRRGG   60
VIWQHQPDSG QPTPIPALDL HQGMPSPRQP APGRYTVLSV APGGLRSGRQ PLHPHVQLEE  120
RGLQRGDFSL WLRPALRTDA GEYHATVRLP NRALSCSLRL RVGQASMIAS PSGVLKLSDW  180
VLLNCSFSRP DRPVSVHWFQ GQNRVPVYNS PRHFLAETFL LLPQVSPLDS GTWGCVLTYR  240
DGFNVSITYN LKVLGLEPVA PLTVYAAEGS RVELPCHLPP GVGTPSLLIA KWTPPGGGPE  300
LPVAGKSGNF TLHLEAVGLA QAGTYTCSIH LQGQQLNATV TLAVITVTPK SFGLPGSRGK  360
LLCEVTPASG KERFVWRPLN NLSRSCPGPV LEIQEARLLA ERWQCQLYEG QRLLGATVYA  420
AESSSGAHSA RRICHTQSSP KLFWALVVVA GVLFCYGLLV TVALCVIWTN SRRNRGGQSD  480
YMNMTPRRPG LTRKPYQPYA PARDFAAYRP                                   510
```

| SEQ ID NO: 143 | moltype = DNA length = 765 |
| --- | --- |
| FEATURE | Location/Qualifiers |
| misc_feature | 1..765 |
|  | note = muTim3tm-CD28 |
| source | 1..765 |
|  | mol_type = other DNA |
|  | organism = synthetic construct |

SEQUENCE: 143

```
atgttcagcg gcctgaccct gaactgcgtg ctcctgctgc tgcagctgct gctggccaga   60
agcctggaaa acgcctacgt gttcgaagtg ggcaagaacg cctacctgcc ctgcagctac  120
accctgtcta cacctggcgc cctggtgcct atgtgttggg gcaagggctt ctgcccttgg  180
agccagtgca ccaacgagct gctgagaacc gacgagagaa acgtgaccta ccagaagtcc  240
agcagatacc agctgaaggg cgacctgaac aagggcgacg tgtccctgat catcaagaac  300
gtgaccctgg acgaccacgg cacctactgc tgcagaatcc agttcccgg cctgatgaac  360
gacaagaagc tggaactgaa gctggacatc aaggccgcca agtgaccc tgcccagaca  420
gcccacggcg actctacaac agccagcccc agaaccctga ccaccgagag aacggcagc  480
gagacacaga cccctcgtga cactgcacaa caacggca caagatcag cacctgggcc  540
gacagatca aggacagcgg cgagacaatc agaaccgcca tccacatcgg cgtgggcgtg  600
tccgctgac tgacacttgc tctgatcatc ggagtgctga tcaacagcag aagaaacaga  660
ggcggccaga gcgactacat gaacatgacc cccagaaggc ctggcctgac cagaaagccc  720
taccagccct tacgccctgc cagagacttc gccgcctaca gacct                  765
```

| SEQ ID NO: 144 | moltype = AA length = 255 |
| --- | --- |
| FEATURE | Location/Qualifiers |
| REGION | 1..255 |
|  | note = muTim3tm-CD28 |
| source | 1..255 |
|  | mol_type = protein |
|  | organism = synthetic construct |

```
SEQUENCE: 144
MFSGLTLNCV LLLLQLLLAR SLENAYVFEV GKNAYLPCSY TLSTPGALVP MCWGKGFCPW    60
SQCTNELLRT DERNVTYQKS SRYQLKGDLN KGDVSLIIKN VTLDDHGTYC CRIQFPGLMN   120
DKKLELKLDI KAAKVTPAQT AHGDSTTASP RTLTTERNGS ETQTLVTLHN NNGTKISTWA   180
DEIKDSGETI RTAIHIGVGV SAGLTLALII GVLINSRRNR GGQSDYMNMT PRRPGLTRKP   240
YQPYAPARDF AAYRP                                                   255

SEQ ID NO: 145          moltype = DNA   length = 783
FEATURE                 Location/Qualifiers
misc_feature            1..783
                        note = muTim3-CD28tm
source                  1..783
                        mol_type = other DNA
                        organism = synthetic construct
SEQUENCE: 145
atgttcagcg gcctgaccct gaactgcgtg ctcctgctgc tgcagctgct gctggccaga    60
agcctggaaa acgcctacgt gttcgaagtg ggcaagaacg cctacctgcc ctgcagctac   120
accctgtcta cacctggcgc cctggtgcct atgtgttggg gcaagggctt ctgcccttgg   180
agccagtgca ccaacgagct gctgagaacc gacgagagaa acgtgaccta ccagaagtcc   240
agcagatacc agctgaaggg cgacctgaac aagggcgacg tgtccctgat catcaagaac   300
gtgaccctgg acgaccacgg cacctactgc tgcagaatcc agttccccgg cctgatgaac   360
gacaagaagc tggaactgaa gctggacatc aaggccgcca aagtgacccc tgcccagaca   420
gcccacggcg actctacaac agccagcccc agaaccctga ccaccgagag gaacggcagc   480
gagacacaga ccctcgtgac actgcacaac aacaacggca ccaagatcag cacctgggcc   540
gacgagatca aggacagcgg cgagacaatc agaaccgcct tctgggccct ggtggtggtg   600
gccggcgtgc tgttttgtta cggcctgctc gtgaccgtgg ccctgtgcgt gatctggacc   660
aacagcagaa gaaacagagg cggccagagc gactacatga acatgacccc cagaaggcct   720
ggcctgacca gaaagcccta ccagccttac gcccctgcca gagacttcgc cgcctacaga   780
cct                                                                783

SEQ ID NO: 146          moltype = AA   length = 261
FEATURE                 Location/Qualifiers
REGION                  1..261
                        note = muTim3-CD28tm
source                  1..261
                        mol_type = protein
                        organism = synthetic construct
SEQUENCE: 146
MFSGLTLNCV LLLLQLLLAR SLENAYVFEV GKNAYLPCSY TLSTPGALVP MCWGKGFCPW    60
SQCTNELLRT DERNVTYQKS SRYQLKGDLN KGDVSLIIKN VTLDDHGTYC CRIQFPGLMN   120
DKKLELKLDI KAAKVTPAQT AHGDSTTASP RTLTTERNGS ETQTLVTLHN NNGTKISTWA   180
DEIKDSGETI RTAFWALVVV AGVLFCYGLL VTVALCVIWT NSRRNGGQS DYMNMTPRRP    240
GLTRKPYQPY APARDFAAYR P                                            261

SEQ ID NO: 147          moltype = DNA   length = 810
FEATURE                 Location/Qualifiers
misc_feature            1..810
                        note = muTim3-CD28Cys
source                  1..810
                        mol_type = other DNA
                        organism = synthetic construct
SEQUENCE: 147
atgttcagcg gcctgaccct gaactgcgtg ctcctgctgc tgcagctgct gctggccaga    60
agcctggaaa acgcctacgt gttcgaagtg ggcaagaacg cctacctgcc ctgcagctac   120
accctgtcta cacctggcgc cctggtgcct atgtgttggg gcaagggctt ctgcccttgg   180
agccagtgca ccaacgagct gctgagaacc gacgagagaa acgtgaccta ccagaagtcc   240
agcagatacc agctgaaggg cgacctgaac aagggcgacg tgtccctgat catcaagaac   300
gtgaccctgg acgaccacgg cacctactgc tgcagaatcc agttccccgg cctgatgaac   360
gacaagaagc tggaactgaa gctggacatc aaggccgcca aagtgacccc tgcccagaca   420
gcccacggcg actctacaac agccagcccc agaaccctga ccaccgagag gaacggcagc   480
gagacacaga ccctcgtgac actgcacaac aacaacggca ccaagatcag cacctgggcc   540
gacgagatca aggacagcgg cgagacaatc agaaccgcct gccacaccca gagcagcccc   600
aagctgttct gggccctggt ggtggtggcc ggcgtgctgt ttgttacgg cctgctcgtg   660
accgtggccc tgtgcgtgat ctggaccaac agcagaagaa acagaggcgg ccagagcgac   720
tacatgaaca tgaccccag aaggcctggc ctgaccagaa agccctacca gccttacgcc   780
cctgccagag acttcgccgc ctacagacct                                   810

SEQ ID NO: 148          moltype = AA   length = 270
FEATURE                 Location/Qualifiers
REGION                  1..270
                        note = muTim3-CD28Cys
source                  1..270
                        mol_type = protein
                        organism = synthetic construct
SEQUENCE: 148
MFSGLTLNCV LLLLQLLLAR SLENAYVFEV GKNAYLPCSY TLSTPGALVP MCWGKGFCPW    60
SQCTNELLRT DERNVTYQKS SRYQLKGDLN KGDVSLIIKN VTLDDHGTYC CRIQFPGLMN   120
DKKLELKLDI KAAKVTPAQT AHGDSTTASP RTLTTERNGS ETQTLVTLHN NNGTKISTWA   180
DEIKDSGETI RTACHTQSSP KLFWALVVVA GVLFCYGLLV TVALCVIWTN SRRNGGQSD    240
```

```
YMNMTPRRPG LTRKPYQPYA PARDFAAYRP                                         270

SEQ ID NO: 149          moltype = DNA   length = 783
FEATURE                 Location/Qualifiers
misc_feature            1..783
                        note = muTim3-9aas-CD28Cys
source                  1..783
                        mol_type = other DNA
                        organism = synthetic construct
SEQUENCE: 149
atgttcagcg gcctgaccct gaactgcgtg ctcctgctgc tgcagctgct gctggccaga     60
agcctggaaa acgcctacgt gttcgaagtg ggcaagaacg cctacctgcc ctgcagctac    120
accctgtcta cacctggcgc cctggtgcct atgtgttggg caagggcttc tgcccttgg     180
agccagtgca ccaacgagct gctgagaacc gacgagagaa acgtgaccta ccagaagtcc    240
agcagatacc agctgaaggg cgacctgaac aagggcgacg tgtccctgat catcaagaac    300
gtgaccctgg acgaccacgg cacctactgc tgcagaatcc agttccccgg cctgatgaac    360
gacaagaagc tggaactgaa gctggacatc aaggccgcca agtgaccc tgcccagaca      420
gcccacggcg actctacaac agccagcccc agaaccctga ccaccgagag gaacggcagc    480
gagacacaga ccctcgtgac actgcacaac aacaacggca ccaagatcag cacctgggcc    540
gacgagatca gtgccacac ccagagcagc ccaagctgt tctgggccct ggtggtggtg      600
gccggcgtgc tgtttgtta cggcctgctc gtgaccgtgg ccctgtgcgt gatctggacc    660
aacagcagaa gaaacagagg cggccagagc gactacatga acatgacccc cagaaggcct    720
ggcctgacca gaaagcccta ccagcttac gcccctgcca gagacttcgc cgcctacaga    780
cct                                                                 783

SEQ ID NO: 150          moltype = AA   length = 261
FEATURE                 Location/Qualifiers
REGION                  1..261
                        note = muTim3-9aas-CD28Cys
source                  1..261
                        mol_type = protein
                        organism = synthetic construct
SEQUENCE: 150
MFSGLTLNCV LLLLQLLLAR SLENAYVFEV GKNAYLPCSY TLSTPGALVP MCWGKGFCPW     60
SQCTNELLRT DERNVTYQKS SRYQLKGDLN KGDVSLIIKN VTLDDHGTYC CRIQFPGLMN    120
DKKLELKLDI KAAKVTPAQT AHGDSTTASP RTLTTERNGS ETQTLVTLHN NNGTKISTWA    180
DEIKCHTQSS PKLFWALVVV AGVLFCYGLL VTVALCVIWT NSRRNRGGQS DYMNMTPRRP    240
GLTRKPYQPY APARDFAAYR P                                             261

SEQ ID NO: 151          moltype = DNA   length = 1536
FEATURE                 Location/Qualifiers
misc_feature            1..1536
                        note = huLag3tm-CD28
source                  1..1536
                        mol_type = other DNA
                        organism = synthetic construct
SEQUENCE: 151
atgtgggaag cgcagtttct tggacttctt tttctccagc cgctgtgggt tgcgccagta     60
aagccgctcc aacccggtgc agaggttccg gtagtgtggg cgcaagaggg tgcaccagcg    120
cagctccccc gcagtccgac gattccgctg caagatttgt cactgcttag aagggcgggc    180
gtaacgtgca agcaccaacc ggatagtggc cctccggctg cagcaccagg cacccactc    240
gcccccggcc ctcatcccgc agcaccgagc agctggggtc ctagaccacg cagatataca    300
gtactctcag taggtcccgg cggcctgcgg tccggtcgct tgccccttca acctagagta    360
cagctggatg aaagaggtcg acaacggggt gatttctccc tctggttgag gcctgcacga    420
cgagcagatg ctgggagta tagggctgcc gtacacctgc gagaccgcgc acttagttgt    480
agactccggc tccggctggg acaggcctct atgacagcgt cccccctgg gtccctgcga    540
gcctctgatt gggtaatact caactgctca ttttctcggc cagatcgccc cgctagtgtt    600
cattggttcc gaaatcgcgg ccaaggtcgc gtgcctgttc gagaatctcc acaccaccat    660
ttggcggagt ctttctcttt tctgcctcag tgtctcccta tggactctgg accgtgggc    720
tgtattttga catatcggga tgggtttaac gtgagtataa tgtataatct cactgtcttg    780
ggtcttgagc cacctacgcc gctgacggta tacgcgggag ccggcagccg ggttggtctg    840
ccctgcaggc tgcctgcagg agtcgggaca aggtcattcc ttacagcaaa gtgaccccg    900
ccaggtgggg ggcccgacct ccttgtaacg ggagataatg gagatttcac tctgagactt    960
gaggatgtct ctcaagctca ggctgggact tatacatgct acattcactt gcaagaacag   1020
cagttgaatg cgacgttac cctggctatc ataacagtaa cacctaaatc tttcggtagt    1080
ccgggtagcc tgggcaaact gttgtgtgag gtaaccccg tgtcaggtca agagcggttc    1140
gtctggagct cattggacac tccctcacag cgatcctta gcggaccctg gctcgaagcc    1200
caagaagccc agctgctttc caaccatgg cagtgtcaac tctatcaggg tgagcgcctt    1260
ctcggtgcgg ctgtctactt caccgaattg tcctctccgg gagcgcaaaa agtggacgt    1320
gcccagggg ccctcccggc aggacacctt ctgctgtttt tgattttggg ggtacttagt    1380
tgctgctgc ttgtcacagg cgctttcggt tccgcagca agcggagcag aggcggccac    1440
agcgactaca tgaacatgac ccctagacgg cctggcccca ccagaaagca ctaccagccc    1500
tacgccctc cccgggactt tgccgcctac agaagc                              1536

SEQ ID NO: 152          moltype = AA   length = 512
FEATURE                 Location/Qualifiers
REGION                  1..512
                        note = huLag3tm-CD28
source                  1..512
```

```
                        mol_type = protein
                        organism = synthetic construct
SEQUENCE: 152
MWEAQFLGLL  FLQPLWVAPV  KPLQPGAEVP  VVWAQEGAPA  QLPCSPTIPL  QDLSLLRRAG   60
VTWQHQPDSG  PPAAAPGHPL  APGPHPAAPS  SWGPRPRRYT  VLSVGPGGLR  SGRLPLQPRV  120
QLDERGRQRG  DFSLWLRPAR  RADAGEYRAA  VHLRDRALSC  RLRLRLGQAS  MTASPPGSLR  180
ASDWVILNCS  FSRPDRPASV  HWFRNRGQGR  VPVRESPHHH  LAESFLFLPQ  VSPMDSGPWG  240
CILTYRDGFN  VSIMYNLTVL  GLEPPTPLTV  YAGAGSRVGL  PCRLPAGVGT  RSFLTAKWTP  300
PGGGPDLLVT  GDNGDPFTLRL EDVSQAQAGT  YTCHIHLQEQ  QLNATVTLAI  ITVTPKSFGS  360
PGSLGKLLCE  VTPVSGQERF  VWSSLDTPSQ  RSFSGPWLEA  QEAQLLSQPW  QCQLYQGERL  420
LGAAVYFTEL  SSPGAQRSGR  APGALPAGHL  LLFLILGVLS  LLLLVTGAFG  FRSKRSRGGH  480
SDYMNMTPRR  PGPTRKHYQP  YAPPRDFAAY  RS                                 512

SEQ ID NO: 153          moltype = DNA  length = 1350
FEATURE                 Location/Qualifiers
misc_feature            1..1350
                        note = huLag3 ectodomain
source                  1..1350
                        mol_type = other DNA
                        organism = synthetic construct
SEQUENCE: 153
atgtgggaag cgcagtttct tggacttctt tttctccagc cgctgtgggt tgcgccagta    60
aagccgctcc aacccggtgc agaggttccg gtagtgtggg cgcaagaggg tgcaccagcg   120
cagctcccct gcagtccgac gattccgctg caagatttgt cactgcttag aagggcgggc   180
gtaacgtggc agcaccaacc ggatagtggc cctccggctg cagcaccagg cacccactc    240
gcccccggcc ctcatcccgc agcaccgagc agctggggtc ctagaccacg cagatataca   300
gtactctcag taggtcccgg cggcctgcgg tccggtcgct tgccccttca acctagagta   360
cagctggatg aaagaggtcg acaacggggt gatttctccc tctggttgag gcctgcacga   420
cgagcagatg ctgggagta tagggctgcc gtacacctgc gagaccgcgc acttagttgt    480
agactccggc tccggctggg acaggcctct atgacagcgt cccccccctgg gtccctgcgg  540
gcctctgatt gggtaatact caactgctca ttttctcggc cagatcgccc cgctagtgtt   600
cattggttcc gaaatcgcgg ccaaggtcgc gtgcctgttc gagaatctcc acaccaccat   660
ttggcggagt cttttctttt tctgcctcag gtctccccta tggactctgg accgtggggc   720
tgtattttga catatcggga tgggtttaac gtgagtataa tgtataatct cactgtcttg   780
ggtcttgagc cacctacgcc gctgacggtg tacgcgggag ccggacagcc ggttggtctg   840
ccctgcaggc tgcctgcagg agtcgggaca aggtcattcc ttacagcaaa gtggaccccg   900
ccaggtgggg ggcccgacct ccttgtaacg ggagataatg gagattttac tctgagactt   960
gaggatgtct ctcaagctca ggctgggact tatacatgtc acattcactt gcaagaacag  1020
cagttgaatg cgacggttac cctggctatc ataacagtaa cacctaaatc tttcggtagt  1080
ccgggtagcc tgggcaaact gttgtgtgag gtaaccccg tgtcaggtca agagcggttc   1140
gtctggagct cattggacac tcccctcacag cgatcctta gcggaccctg gctcgaagcc   1200
caagaagccc agctgctttc caaccatggg cagtgtcaac tctatcaggg tgagcgcctt  1260
ctcggtgcgg ctgtctactt caccgaattg tcctctccgg gagcgcaaag aagtggacgc  1320
gccccagggg ccctcccggc aggacacctt                                   1350

SEQ ID NO: 154          moltype = AA  length = 450
FEATURE                 Location/Qualifiers
REGION                  1..450
                        note = huLag3 ectodomain
source                  1..450
                        mol_type = protein
                        organism = synthetic construct
SEQUENCE: 154
MWEAQFLGLL  FLQPLWVAPV  KPLQPGAEVP  VVWAQEGAPA  QLPCSPTIPL  QDLSLLRRAG   60
VTWQHQPDSG  PPAAAPGHPL  APGPHPAAPS  SWGPRPRRYT  VLSVGPGGLR  SGRLPLQPRV  120
QLDERGRQRG  DFSLWLRPAR  RADAGEYRAA  VHLRDRALSC  RLRLRLGQAS  MTASPPGSLR  180
ASDWVILNCS  FSRPDRPASV  HWFRNRGQGR  VPVRESPHHH  LAESFLFLPQ  VSPMDSGPWG  240
CILTYRDGFN  VSIMYNLTVL  GLEPPTPLTV  YAGAGSRVGL  PCRLPAGVGT  RSFLTAKWTP  300
PGGGPDLLVT  GDNGDPFTLRL EDVSQAQAGT  YTCHIHLQEQ  QLNATVTLAI  ITVTPKSFGS  360
PGSLGKLLCE  VTPVSGQERF  VWSSLDTPSQ  RSFSGPWLEA  QEAQLLSQPW  QCQLYQGERL  420
LGAAVYFTEL  SSPGAQRSGR  APGALPAGHL                                    450

SEQ ID NO: 155          moltype = DNA  length = 63
FEATURE                 Location/Qualifiers
misc_feature            1..63
                        note = huLag3 transmembrane domain
source                  1..63
                        mol_type = other DNA
                        organism = synthetic construct
SEQUENCE: 155
ctgctgtttt tgattttggg ggtacttagt ttgctgctgc ttgtcacagg cgctttcggt    60
ttc                                                                  63

SEQ ID NO: 156          moltype = AA  length = 21
FEATURE                 Location/Qualifiers
REGION                  1..21
                        note = huLag3 transmembrane domain
source                  1..21
                        mol_type = protein
```

```
                        organism = synthetic construct
SEQUENCE: 156
LLFLILGVLS LLLLVTGAFG F                                             21

SEQ ID NO: 157          moltype = DNA  length = 1554
FEATURE                 Location/Qualifiers
misc_feature            1..1554
                        note = huLag3-CD28tm
source                  1..1554
                        mol_type = other DNA
                        organism = synthetic construct
SEQUENCE: 157
atgtgggaag cgcagtttct tggacttctt tttctccagc cgctgtgggt tgcgccagta   60
aagccgctcc aacccggtgc agaggttccg gtagtgtggg cgcaagaggg tgcaccagcg  120
cagctcccct gcagtccgac gattccgctg caagatttgt cactgcttag aagggcgggc  180
gtaacgtggc agcaccaacc ggatagtggc cctccggctg cagcaccagg cacccactc   240
gcccccggcc ctcatcccgc agcaccgagc agctggggtc ctagaccacg cagatataca  300
gtactctcag taggtcccgg cggcctgcgg tccggtcgct tgcccttca acctagagta   360
cagctggatg aaagaggtcg acaacggggt gatttctccc tctggttgag gcctgcacga  420
cgagcagatg ctggggagta tagggctgcc gtacacctgc gagaccgcgc acttagttgt  480
agactccggc tccggctggg acaggcctct atgacagcgt ccccccctgg gtccctgcga  540
gcctctgatt gggtaatact caactgctca ttttctcggc cagatcgccc cgctagtgtt  600
cattggttcc gaaatcgcgg ccaaggtcgc gtgcctgttc gagaatctcc acaccaccat  660
ttggcggagt cttttctttt tctgcctcag gtctcccta tggactctgg accgtggggc   720
tgtattttga catatcggga tgggtttaac gtgagtataa tgtataatct cactgtcttg  780
ggtcttgagc cacctacgcc gctgacggtg tacgcgggag ccggcagccg ggttggtctg  840
ccctgcaggc tgcctgcagg agtcgggaca aggtcattcc ttacagcaaa gtggaccccg  900
ccaggtgggg ggcccgacct ccttgtaacg ggagataatg gagatttcac tctgagactt  960
gaggatgtct ctcaagctca ggctgggact tatacatgtc acattcactt gcaagaacag 1020
cagttgaatg cgacggttac cctggctatc ataacagtaa cacctaaatc tttcggtagt 1080
ccgggtagcc tgggcaaact gttgtgtgag gtaaccccg tgtcaggtca agagcggttc  1140
gtctggagct cattggacac tccctcacag cgatcctta gcggaccctg gctcgaagcc  1200
caagaagccc agctgcttc caaccatgg cagtgtcaac tctatcaggg tgagcgcctt   1260
ctcggtgcgg ctgtctactt caccgaattg tcctctccgg gagcgcaaaa agtggacgc   1320
gccccagggg ccctcccggc aggacaccttt tctgggtgtc tggtggtggt cggaggcgtg 1380
ctggcctgct acagcctgct ggtcaccgtg gccttcatca tcttttgggt ccgcagcaag 1440
cggagcagag gcgccacag cgactacatg aacatgaccc ctagacggcc tggccccacc  1500
agaaagcact accagcccta cgcccctccc cgggactttg ccgcctacag aagc         1554

SEQ ID NO: 158          moltype = AA  length = 518
FEATURE                 Location/Qualifiers
REGION                  1..518
                        note = huLag3-CD28tm
source                  1..518
                        mol_type = protein
                        organism = synthetic construct
SEQUENCE: 158
MWEAQFLGLL FLQPLWVAPV KPLQPGAEVP VVWAQEGAPA QLPCSPTIPL QDLSLLRRAG   60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDHWVILNCS FSRPDRPASV HWFRNRGQGR VPVRESPHHW LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL FWVLVVVGGV LACYSLLVTV AFIIFWVRSK  480
RSRGGHSDYM NMTPRRPGPT RKHYQPYAPP RDFAAYRS                          518

SEQ ID NO: 159          moltype = DNA  length = 1554
FEATURE                 Location/Qualifiers
misc_feature            1..1554
                        note = huLag3-12aas-CD28Cys
source                  1..1554
                        mol_type = other DNA
                        organism = synthetic construct
SEQUENCE: 159
atgtgggaag cgcagtttct tggacttctt tttctccagc cgctgtgggt tgcgccagta   60
aagccgctcc aacccggtgc agaggttccg gtagtgtggg cgcaagaggg tgcaccagcg  120
cagctcccct gcagtccgac gattccgctg caagatttgt cactgcttag aagggcgggc  180
gtaacgtggc agcaccaacc ggatagtggc cctccggctg cagcaccagg cacccactc   240
gcccccggcc ctcatcccgc agcaccgagc agctggggtc ctagaccacg cagatataca  300
gtactctcag taggtcccgg cggcctgcgg tccggtcgct tgcccttca acctagagta   360
cagctggatg aaagaggtcg acaacggggt gatttctccc tctggttgag gcctgcacga  420
cgagcagatg ctggggagta tagggctgcc gtacacctgc gagaccgcgc acttagttgt  480
agactccggc tccggctggg acaggcctct atgacagcgt ccccccctgg gtccctgcga  540
gcctctgatt gggtaatact caactgctca ttttctcggc cagatcgccc cgctagtgtt  600
cattggttcc gaaatcgcgg ccaaggtcgc gtgcctgttc gagaatctcc acaccaccat  660
ttggcggagt cttttctttt tctgcctcag gtctcccta tggactctgg accgtggggc   720
tgtattttga catatcggga tgggtttaac gtgagtataa tgtataatct cactgtcttg  780
ggtcttgagc cacctacgcc gctgacggtg tacgcgggag ccggcagccg ggttggtctg  840
```

```
ccctgcaggc tgcctgcagg agtcgggaca aggtcattcc ttacagcaaa gtggaccccg   900
ccaggtgggg ggcccgacct ccttgtaacg ggagataatg gagatttcac tctgagactt   960
gaggatgtct ctcaagctca ggctgggact tatacatgtc acattcactt gcaagaacag  1020
cagttgaatg cgacgttac cctggctatc ataacagtaa cacctaaatc tttcggtagt  1080
ccgggtagcc tgggcaaact gttgtgtgag gtaaccccg tgtcaggtca agagcggttc  1140
gtctggagct cattggacac tccctcacag cgatccttta gcggaccctg gctcgaagcc  1200
caagaagccc agctgctttc ccaaccatgg cagtgtcaac tctatcaggg tgagcgcctt  1260
ctcggtgcgg ctgtctactt caccgaattg tcctctccgg gagcgcaaag aagttgtccc  1320
agccctctgt ttcccggccc tagcaagcct ttctgggtgc tggtggtggt cggaggcgtg  1380
ctggcctgct acagcctgct ggtcaccgtg gccttcatca tctttgggt ccgcagcaag  1440
cggagcagag gcggccacag cgactacatg aacatgaccc ctagacggcc tggccccacc  1500
agaaagcact accagcccta cgcccctccc cgggactttg ccgcctacag aagc         1554

SEQ ID NO: 160           moltype = AA   length = 518
FEATURE                  Location/Qualifiers
REGION                   1..518
                         note = huLag3-12aas-CD28Cys
source                   1..518
                         mol_type = protein
                         organism = synthetic construct
SEQUENCE: 160
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCIHLQEQ QLNATVTLAI ITVTPKSFGS    360
PGSLGKLLCE VTPVSGQERF VWSSLDTPSQ RSFSGPWLEA QEAQLLSQPW QCQLYQGERL   420
LGAAVYFTEL SSPGAQRSCP SPLFPGPSKP FWVLVVVGGV LACYSLLVTV AFIIFWVRSK   480
RSRGGHSDYM NMTPRRPGPT RKHYQPYAPP RDFAAYRS                           518

SEQ ID NO: 161           moltype = DNA   length = 1314
FEATURE                  Location/Qualifiers
misc_feature             1..1314
                         note = huLag3-12aas
source                   1..1314
                         mol_type = other DNA
                         organism = synthetic construct
SEQUENCE: 161
atgtgggaag cgcagtttct tggacttctt tttctccagc cgctgtgggt tgcgccagta    60
aagccgctcc aacccggtgc agaggttccg gtagtgtggg cgcaagaggg tgcaccagcg   120
cagctcccct gcagtccgac gattccgctg caagatttgt cactgcttag aagggcgggc   180
gtaacgtggc agcaccaacc ggatagtggc cctccggcg cagcaccagg gcacccactc    240
gcccccggcc ctcatcccgc agcaccgagc agctgggtc ctagaccacg cagatatca     300
gtactctcag taggtcccgg cggcctgcgg tccgtcgct tgccccttca acctagtag     360
cagctggatg aaagaggtcg acaacggggt gatttctccc tctggttgag gcctgcacga   420
cgagcagatg ctgggagta tagggctgcc gtacaccgtc gagaccgcgc acttagttgt   480
agactccggc tccggctggg acaggcctct atgacagcgt cccccctgg gtccctgcga    540
gcctctgatt gggtaatact caactgctca ttttctcggc cagatcgccc cgctagtgtt   600
cattggttcc gaaatcgcgg ccaaggtcgc gtgcctgttc gagaatctcc acaccaccat   660
ttggcgagtt cttttctttt tctgcctcag gtctcccta tggactctgg accgtgggc    720
tgtatttga catatcggga tgggtttaac gtgagtataa tgtataatct cactgtcttg   780
ggtcttgagc caccttacgcc gctgacggtg tacgcgggag ccgcagccg ggttggctg    840
ccctgcaggc tgcctgcagg agtcgggaca aggtcattcc ttacagcaaa gtggaccccg   900
ccaggtgggg ggcccgacct ccttgtaacg ggagataatg gagatttcac tctgagactt   960
gaggatgtct ctcaagctca ggctgggact tatacatgtc acattcactt gcaagaacag  1020
cagttgaatg cgacgttac cctggctatc ataacagtaa cacctaaatc tttcggtagt  1080
ccgggtagcc tgggcaaact gttgtgtgag gtaaccccg tgtcaggtca agagcggttc  1140
gtctggagct cattggacac tccctcacag cgatccttta gcggaccctg gctcgaagcc  1200
caagaagccc agctgctttc ccaaccatgg cagtgtcaac tctatcaggg tgagcgcctt  1260
ctcggtgcgg ctgtctactt caccgaattg tcctctccgg gagcgcaaag aagt        1314

SEQ ID NO: 162           moltype = AA   length = 438
FEATURE                  Location/Qualifiers
REGION                   1..438
                         note = huLag3-12aas
source                   1..438
                         mol_type = protein
                         organism = synthetic construct
SEQUENCE: 162
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCIHLQEQ QLNATVTLAI ITVTPKSFGS    360
PGSLGKLLCE VTPVSGQERF VWSSLDTPSQ RSFSGPWLEA QEAQLLSQPW QCQLYQGERL   420
LGAAVYFTEL SSPGAQRS                                                 438
```

-continued

```
SEQ ID NO: 163          moltype = DNA   length = 1590
FEATURE                 Location/Qualifiers
misc_feature            1..1590
                        note = huLag3-CD28Cys
source                  1..1590
                        mol_type = other DNA
                        organism = synthetic construct
SEQUENCE: 163
atgtgggaag cgcagtttct tggacttctt tttctccagc cgctgtgggt tgcgccagta    60
aagccgctcc aacccggtgc agaggttccg gtagtgtggg cgcaagaggg tgcaccagcg   120
cagctcccct gcagtccgac gattccgctg caagatttgt cactgcttag aagggcgggc   180
gtaacgtggc agcaccaacc ggatagtggc cctccggctg cagcaccagg cacccactc    240
gccccggcc ctcatcccgc agcaccgagc agctggggtc ctagaccacg cagatataca    300
gtactctcag taggtcccgg cggcctgcgg tccgtcgct tgcccttca acctagagta     360
cagctggatg aaagaggtcg acaacggggt gatttctccc tctggttgag gcctgcacga    420
cgagcagatg ctggggagta tagggctgcc gtacacctgc gagaccgcgc acttagttgt    480
agactccggc tccggctggg acaggcctct atgacagcgt ccccctgg gtccctgcga     540
gcctctgatt gggtaatact caactgctca ttttctcggc cagatcgccc cgctagtgtt    600
cattggttcc gaaatcgcgg ccaaggtcgc gtgcctgttc gagaatctcc acaccaccat    660
ttggcggagt cttttctttt tctgcctcag gtctccccta tggactctgg accgtggggc    720
tgtattttga catatcggga tgggtttaac gtgagtataa tgtataatct cactgtcttg    780
ggtcttgagc cacctacgcc gctgacggtg tacgcgggaa ccggcagccg ggttggtctg    840
ccctgcaggc tgcctgcagg agtcgggaca aggtcattcc ttacagcaaa gtggaccccg    900
ccaggtgggg ggcccgacct ccttgtaacg ggagataatg gagatttcac tctgagactt    960
gaggatgtct ctcaagctca ggctgggact tatacatgtc acattcactt gcaagaacag   1020
cagttgaatg cgacggttac cctggctatc ataacagtaa cacctaaatc tttcggtagt   1080
ccgggtagcc tgggcaaact gttgtgtgag gtaaccccg tgtcaggtca agagcggttc    1140
gtctggagct cattggacac tccctcacag cgatccttta gcggaccctg gctcgaagcc   1200
caagaagccc agctgcttc caaccatgg cagtgtcaac tctatcaggg tgagcgcctt     1260
ctcggtgcgg ctgtctactt caccgaattg tcctctccgg gagcgcaaag aagtggacgc   1320
gccccagggg ccctcccggc aggacacctt tgtcccagcc ctctgtttcc cggccctagc   1380
aagcctttct gggtgctggt ggtggtcgga ggcgtgctgg cctgctacag cctgctggtc   1440
accgtggcct tcatcatctt ttgggtccgc agcaagcgga gcagaggcgg ccacagcgac   1500
tacatgaaca tgacccctag acggcctggc ccaccagaa agcactacca gccctacgcc    1560
cctcccgggg actttgccgc ctacagaagc                                   1590

SEQ ID NO: 164          moltype = AA   length = 530
FEATURE                 Location/Qualifiers
REGION                  1..530
                        note = huLag3-CD28Cys
source                  1..530
                        mol_type = protein
                        organism = synthetic construct
SEQUENCE: 164
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCHIHLQEQ QLNATVTLAI ITVTPKSFGS   360
PGSLGKLLCE VTPVSGQERF VWSSLDTPSQ RSFSGPWLEA QEAQLLSQPW QCQLYQGERL   420
LGAAVYFTEL SSPGAQRSGR APGALPAGHL CPSPLFPGPS KPFWVLVVVG GVLACYSLLV   480
TVAFIIFWVR SKRSRGGHSD YMNMTPRRPG PTRKHYQPYA PPRDFAAYRS              530

SEQ ID NO: 165          moltype = DNA   length = 792
FEATURE                 Location/Qualifiers
misc_feature            1..792
                        note = huTim3tm-CD28
source                  1..792
                        mol_type = other DNA
                        organism = synthetic construct
SEQUENCE: 165
atgttctccc atcttccctt cgactgtgtg ttgctcctc tcctcctgct tctcacccgg     60
tcaagcgaag tagagtaccg ggcggaagta ggtcagaacg catatctccc ctgtttttac   120
acacccgctg cgccgggaaa cctggttccc gtgtgttggg gaaaggggc atgcccgtt    180
ttcgagtgtg gcaacgtggt cctccggacg gatgagcgag acgtgaatta ttggacgagc   240
agatattggt tgaatggcga ttttagaaag ggtgatgtga gcttgaccat tgagaatgta   300
acgcttgctg atatcgggat atattgctgt agaattcaaa tccctggtat aatgaacgac   360
gaaaattca atctgaagct ggtaattaag ccggccaagg tgacaccgc cccgacagga    420
cagcgcgact tcacgctgc ctttccacgc atgttgacca aaggggaca tggtccagcg     480
gagacccaga cacttggtag cctccccgga ctaaacctca cacaaatatc cacgttggcg   540
aacgagctcc gagattccag gcttgcgaat gacctgaggg attctggagc taccatcaga   600
atcggtatct acataggtgc cgggatatgc gccggtctcg cacttgcctt gattttcggg   660
gcactgattc gcagcaagcg gagcagaggc ggccacagct actacatgaa catgaccct    720
agacggcctg gccccaccag aaaagcactac cagccctacg cccctcccg ggactttgcc    780
gcctacagaa gc                                                       792

SEQ ID NO: 166          moltype = AA   length = 264
FEATURE                 Location/Qualifiers
```

```
REGION                       1..264
                             note = huTim3tm-CD28
source                       1..264
                             mol_type = protein
                             organism = synthetic construct
SEQUENCE: 166
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAKVTPAPTR QRDFTAAFPR MLTTRGHPA  ETQTLGSLPD INLTQISTLA   180
NELRDSRLAN DLRDSGATIR IGIYIGAGIC AGLALALIFG ALIRSKRSRG GHSDYMNMTP   240
RRPGPTRKHY QPYAPPRDFA AYRS                                          264

SEQ ID NO: 167               moltype = DNA  length = 606
FEATURE                      Location/Qualifiers
misc_feature                 1..606
                             note = huTim3 ectodomain
source                       1..606
                             mol_type = other DNA
                             organism = synthetic construct
SEQUENCE: 167
atgttctccc atcttccctt cgactgtgtg ttgctccttc tcctcctgct tctcacccgg    60
tcaagcgaag tagagtaccg ggcggaagta ggtcagaacg catatctccc ctgtttttac   120
acacccgctg cgccgggaaa cctggttccc gtgtgttggg aaagggggc  atgccctgtt   180
ttcgagtgtg gcaacgtggt cctccggacg gatgagcgag acgtgaatta ttggacgagc   240
agatattggt tgaatggcga ttttagaaag ggtgatgtga gcttgaccat tgagaatgta   300
acgcttgctg atagcgggat atattgctgt agaattcaaa tccctggtat aatgaacgac   360
gaaaaattca atctgaagct ggtaattaag ccggccaagg tgacaccgc  ccgacacga    420
cagcgcgact tcacggctgc cttttccacg catgttgacca aaggggaca tggtccagcg   480
gagacccaga cacttggtag cctcccggac ataaacctca cacaaatatc cacgttggcg   540
aacgagctcc gagattccag gcttgcgaat gacctgaggg attctggagc taccatcaga   600
atcggt                                                              606

SEQ ID NO: 168               moltype = AA  length = 202
FEATURE                      Location/Qualifiers
REGION                       1..202
                             note = huTim3 ectodomain
source                       1..202
                             mol_type = protein
                             organism = synthetic construct
SEQUENCE: 168
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAKVTPAPTR QRDFTAAFPR MLTTRGHPA  ETQTLGSLPD INLTQISTLA   180
NELRDSRLAN DLRDSGATIR IG                                            202

SEQ ID NO: 169               moltype = DNA  length = 63
FEATURE                      Location/Qualifiers
misc_feature                 1..63
                             note = huTim3 transmembrane
source                       1..63
                             mol_type = other DNA
                             organism = synthetic construct
SEQUENCE: 169
atctacatag gtgccgggat atgcgccggt ctcgcacttg ccttgatttt cggggcactg    60
att                                                                  63

SEQ ID NO: 170               moltype = AA  length = 21
FEATURE                      Location/Qualifiers
REGION                       1..21
                             note = huTim3 transmembrane
source                       1..21
                             mol_type = protein
                             organism = synthetic construct
SEQUENCE: 170
IYIGAGICAG LALALIFGAL I                                              21

SEQ ID NO: 171               moltype = DNA  length = 810
FEATURE                      Location/Qualifiers
misc_feature                 1..810
                             note = huTim3-CD28tm
source                       1..810
                             mol_type = other DNA
                             organism = synthetic construct
SEQUENCE: 171
atgttctccc atcttccctt cgactgtgtg ttgctccttc tcctcctgct tctcacccgg    60
tcaagcgaag tagagtaccg ggcggaagta ggtcagaacg catatctccc ctgtttttac   120
acacccgctg cgccgggaaa cctggttccc gtgtgttggg aaagggggc  atgccctgtt   180
ttcgagtgtg gcaacgtggt cctccggacg gatgagcgag acgtgaatta ttggacgagc   240
agatattggt tgaatggcga ttttagaaag ggtgatgtga gcttgaccat tgagaatgta   300
```

-continued

```
acgcttgctg atagcgggat atattgctgt agaattcaaa tccctggtat aatgaacgac 360
gaaaaattca atctgaagct ggtaattaag ccggccaagg tgacacccgc ccgacacga  420
cagcgcgact tcacggctgc ctttccacgc atgttgacca caaggggaca tggtccagcg  480
gagacccaga cacttggtag cctcccggac ataaacctca cacaaatatc cacgttggcg  540
aacgagctcc gagattccag gcttgcgaat gacctggagc attctggagc taccatcaga  600
atcggtttct gggtgctggt ggtggtcgga ggcgtgctgg cctgctacag cctgctggtc  660
accgtggcct tcatcatctt tgggtccgc  agcaagcgga gcagaggcgg ccacagcgac  720
tacatgaaca tgaccccctag acggcctggc cccaccagaa agcactacca gccctacgcc  780
cctccccggg actttgccgc ctacagaagc                                    810

SEQ ID NO: 172        moltype = AA  length = 270
FEATURE               Location/Qualifiers
REGION                1..270
                      note = huTim3-CD28tm
source                1..270
                      mol_type = protein
                      organism = synthetic construct
SEQUENCE: 172
MFSHLPFDCV LLLLLLLLTR SSEVEYRAEV GQNAYLPCFY TPAAPGNLVP VCWGKGACPV   60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
NELRDSRLAN DLRDSGATIR IGFWVLVVVG GVLACYSLLV TVAFIIFWVR SKRSRGGHSD  240
YMNMTPRRPG PTRKHYQPYA PPRDFAAYRS                                    270

SEQ ID NO: 173        moltype = DNA  length = 846
FEATURE               Location/Qualifiers
misc_feature          1..846
                      note = huTim3-CD28Cys
source                1..846
                      mol_type = other DNA
                      organism = synthetic construct
SEQUENCE: 173
atgttctccc atcttccctt cgactgtgtg ttgctcctc tcctcctgct tctcacccgg    60
tcaagcgaag tagagtaccg ggcggaagta ggtcagaacg catatctccc ctgttttac  120
acacccgctg cgccgggaaa cctggttccc gtgtgttggg aaggggggc atgcctgtt  180
ttcgagtgtg caacgtggt cctccggacg gatgagcgag acgtgaatta ttggacgagc  240
agatattggt tgaatggcga ttttagaaag ggtgatgtga gcttgaccat tgagaatgta  300
acgcttgctg atagcgggat atattgctgt agaattcaaa tccctggtat aatgaacgac  360
gaaaaattca atctgaagct ggtaattaag ccggccaagg tgacacccgc ccgacacga  420
cagcgcgact tcacggctgc ctttccacgc atgttgacca caaggggaca tggtccagcg  480
gagacccaga cacttggtag cctcccggac ataaacctca cacaaatatc cacgttggcg  540
aacgagctcc gagattccag gcttgcgaat gacctgaggg attctggagc taccatcaga  600
atcggtttgtc ccagccctct gtttcccggc cctagcaagc cttctgggt gctggtgtg  660
gtcggaggcg tgctgcctg ctacagcctg ctggtcaccg tggccttcat catcttttgg  720
gtccgcagca gcggagcag aggcggccac agcgactaca tgaacatgac ccctagacgg  780
cctggcccca ccagaaagca ctaccagccc tacgccctc ccgggacttt gccgcctac  840
agaagc                                                              846

SEQ ID NO: 174        moltype = AA  length = 282
FEATURE               Location/Qualifiers
REGION                1..282
                      note = huTim3-CD28Cys
source                1..282
                      mol_type = protein
                      organism = synthetic construct
SEQUENCE: 174
MFSHLPFDCV LLLLLLLLTR SSEVEYRAEV GQNAYLPCFY TPAAPGNLVP VCWGKGACPV   60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
NELRDSRLAN DLRDSGATIR IGCPSPLFPG PSKPFWVLVV VGGVLACYSL LVTVAFIIFW  240
VRSKRSRGGH SDYMNMTPRR PGPTRKHYQP YAPPRDFAAY RS                      282

SEQ ID NO: 175        moltype = DNA  length = 810
FEATURE               Location/Qualifiers
misc_feature          1..810
                      note = huTim3-12aas-CD28Cys
source                1..810
                      mol_type = other DNA
                      organism = synthetic construct
SEQUENCE: 175
atgttctccc atcttccctt cgactgtgtg ttgctcctc tcctcctgct tctcacccgg    60
tcaagcgaag tagagtaccg ggcggaagta ggtcagaacg catatctccc ctgttttac  120
acacccgctg cgccgggaaa cctggttccc gtgtgttggg aaggggggc atgcctgtt  180
ttcgagtgtg caacgtggt cctccggacg gatgagcgag acgtgaatta ttggacgagc  240
agatattggt tgaatggcga ttttagaaag ggtgatgtga gcttgaccat tgagaatgta  300
acgcttgctg atagcgggat atattgctgt agaattcaaa tccctggtat aatgaacgac  360
gaaaaattca atctgaagct ggtaattaag ccggccaagg tgacacccgc ccgacacga  420
cagcgcgact tcacggctgc ctttccacgc atgttgacca caaggggaca tggtccagcg  480
gagacccaga cacttggtag cctcccggac ataaacctca cacaaatatc cacgttggcg  540
```

```
aacgagctcc gagattccag gcttgcgaat tgtcccagcc ctctgtttcc cggccctagc    600
aagcctttct gggtgctggt ggtggtcgga ggcgtgctgg cctgctacag cctgctggtc    660
accgtggcct tcatcatctt tttgggtccgc agcaagcgga gcagaggcgg ccacagcgac   720
tacatgaaca tgacccctag acggcctggc cccaccagaa agcactacca gccctacgcc    780
cctccccggg actttgccgc ctacagaagc                                      810

SEQ ID NO: 176         moltype = AA   length = 270
FEATURE                Location/Qualifiers
REGION                 1..270
                       note = huTim3-12aas-CD28Cys
source                 1..270
                       mol_type = protein
                       organism = synthetic construct
SEQUENCE: 176
MFSHLPFDCV LLLLLLLLTR SSEVEYRAEV GQNAYLPCFY TPAAPGNLVP VCWGKGACPV     60
FECGNVVLRT DERDVNYWTS RYWLNGDFRK GDVSLTIENV TLADSGIYCC RIQIPGIMND    120
EKFNLKLVIK PAKVTPAPTR QRDFTAAFPR MLTTRGHGPA ETQTLGSLPD INLTQISTLA    180
NELRDSRLAN CPSPLFPGPS KPFWVLVVVG GVLACYSLLV TVAFIIFWVR SKRSRGGHSD    240
YMNMTPRRPG PTRKHYQPYA PPRDFAAYRS                                     270

SEQ ID NO: 177         moltype = DNA   length = 570
FEATURE                Location/Qualifiers
misc_feature           1..570
                       note = huTim3-12aas
source                 1..570
                       mol_type = other DNA
                       organism = synthetic construct
SEQUENCE: 177
atgttctccc atcttccctt cgactgtgtg ttgctcctcc tcctcctgct ctcacccgg      60
tcaagcgaag tagagtaccg ggcggaagta ggtcagaacg catatctccc ctgtttttac   120
acacccgctg cgccgggaaa cctggttccc gtgtgttggg gaaggggggc atgccctgtt   180
ttcgagtgtg gcaacgtggt cctccggacg gatgagcgag acgtgaatta ttggacgagc   240
agatattggt tgaatggcga ttttagaaag ggtgatgtga gcttgaccat tgagaatgta   300
acgcttgctg atagcgggat atattgctgt agaattcaaa tccctggtat aatgaacgac   360
gaaaaattca atctgaagct ggtaattaag ccggccaagg tgacacccgc cccgacacga   420
cagcgcgact tcacggctgc cttttccacg atgttgacca aggggaca tggtccagcg     480
gagacccaga cacttggtag cctcccggac ataaacctca cacaaatatc cacgttggcg   540
aacgagctcc gagattccag gcttgcgaat                                    570

SEQ ID NO: 178         moltype = AA   length = 190
FEATURE                Location/Qualifiers
REGION                 1..190
                       note = huTim3-12aas
source                 1..190
                       mol_type = protein
                       organism = synthetic construct
SEQUENCE: 178
MFSHLPFDCV LLLLLLLLTR SSEVEYRAEV GQNAYLPCFY TPAAPGNLVP VCWGKGACPV     60
FECGNVVLRT DERDVNYWTS RYWLNGDFRK GDVSLTIENV TLADSGIYCC RIQIPGIMND    120
EKFNLKLVIK PAKVTPAPTR QRDFTAAFPR MLTTRGHGPA ETQTLGSLPD INLTQISTLA    180
NELRDSRLAN                                                           190

SEQ ID NO: 179         moltype = DNA   length = 792
FEATURE                Location/Qualifiers
misc_feature           1..792
                       note = Synthetic sequence hu_trCD200R
source                 1..792
                       mol_type = other DNA
                       organism = synthetic construct
SEQUENCE: 179
atgctgtgcc cttggagaac cgccaacctg gcctgctgc tgatcctgac catcttcctg      60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcctg gggagatcat cctgccgggc    240
cagcccagct gtaccaaggc ctaccggaaa gagacaaacg agacaaaaga aacaaactgc   300
accgacgagc ggatcacatg ggtgtccaga cccgaccaga cagcgacct gcagatcaga    360
cccgtggcca tcacccacga cggctactac cggtgcatca tggtcacccc cgatggcaac   420
ttccaccggg ataccatct gcaggtgctc gtgacccccg aagtgaccct gttccagaae    480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtacatcgag ctgctgcctg tgcctggcgc caagaagtcc    720
gccaagctgt acatccccta catcatcctg acaatcatca ttctgaccat cgtgggcttc   780
atctggctgc tg                                                       792

SEQ ID NO: 180         moltype = AA   length = 264
FEATURE                Location/Qualifiers
REGION                 1..264
                       note = Synthetic sequence hu_trCD200R
```

```
source                    1..264
                          mol_type = protein
                          organism = synthetic construct
SEQUENCE: 180
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPVPGAKKS   240
AKLYIPYIIL TIIILTIVGF IWLL                                         264

SEQ ID NO: 181            moltype = DNA   length = 684
FEATURE                   Location/Qualifiers
misc_feature              1..684
                          note = Synthetic sequence huCD200R-15aas portion of
                           extracellular domain
source                    1..684
                          mol_type = other DNA
                          organism = synthetic construct
SEQUENCE: 181
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga   360
cccgtggcca tcacccacga cggctactac cggtgtcatca tggtcacccc cgatggcaac   420
ttccaccggg gataccatct gcaggtgctc gtgaccccccg aagtgaccct gttccagaac   480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtac                                           684

SEQ ID NO: 182            moltype = AA    length = 228
FEATURE                   Location/Qualifiers
REGION                    1..228
                          note = Synthetic sequence huCD200R-15aas protein
source                    1..228
                          mol_type = protein
                          organism = synthetic construct
SEQUENCE: 182
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLY                228

SEQ ID NO: 183            moltype = DNA   length = 924
FEATURE                   Location/Qualifiers
misc_feature              1..924
                          note = Synthetic sequence huCD200R-15aas-CD28Cys construct
source                    1..924
                          mol_type = other DNA
                          organism = synthetic construct
SEQUENCE: 183
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga   360
cccgtggcca tcacccacga cggctactac cggtgtcatca tggtcacccc cgatggcaac   420
ttccaccggg gataccatct gcaggtgctc gtgaccccccg aagtgaccct gttccagaac   480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtactgtccc agccctctgt tcccggccc tagcaagcct   720
ttctgggtgc tggtggtggt cggagcgtg ctggcctgct acagcctgct ggtcaccgtg   780
gccttcatca tcttttgggt ccgcagcaag cggagcagag cgccacag cgactacatg   840
aacatgaccc ctagacggcc tggccccacc agaaagcact accagcccta cgcccctccc   900
cgggactttg ccgcctacag aagc                                         924

SEQ ID NO: 184            moltype = AA    length = 308
FEATURE                   Location/Qualifiers
REGION                    1..308
                          note = Synthetic sequence huCD200R-15aas-CD28Cys protein
source                    1..308
                          mol_type = protein
                          organism = synthetic construct
SEQUENCE: 184
MLCPWRTANL GLLLILTIFL VAASSSLCMD EKQITQNYSK VLAEVNTSWP VKMATNAVLC    60
```

```
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYCP SPLFPGPSKP   240
FWVLVVVGGV LACYSLLVTV AFIIFWVRSK RSRGGHSDYM NMTPRRPGPT RKHYQPYAPP   300
RDFAAYRS                                                            308

SEQ ID NO: 185              moltype = DNA   length = 700
FEATURE                     Location/Qualifiers
misc_feature                1..700
                            note = Synthetic sequence huFAStm-41BB construct
source                      1..700
                            mol_type = other DNA
                            organism = synthetic construct
SEQUENCE: 185
caccatgctg ggcatctgga ccctgctgcc tctggtgctg acaagcgtgg ccagactgag    60
cagcaagagc gtgaacgccc aagtgaccga catcaacagc aagggcctgg aactgagaaa   120
gaccgtgacc accgtggaaa cccagaacct ggaaggcctg caccacgacg gccagttctg   180
ccacaagcct tgtcccctg gcgagcggaa ggccagagac tgtactgtga acggcgacga   240
gccccgactgc gtgccctgtc aggaaggcaa agagtacacc gacaaggccc acttcagcag   300
caagtgccgg cggtgcagac tgtgtgatga gggccacggc ctggaagtgg aaatcaactg   360
cacccggacc cagaacacca gtgcagatg caagcccaac ttcttctgca acagcaccgt   420
gtgcgagcac tgcgacccct gtaccaagtg cgaacacgg atcatcaaag agtgcaccct   480
gacctccaac acaaagtgca aagaggaagg cagcagaagc aacctgggct ggctgtgcct   540
cctgctgctg cccatccctc tgatcgtgtg ggtcaagcgg ggcagaaaga agctgctgta   600
catcttcaag cagcctttca tgcggccggt gcagaccacc caggaagagg acggctgctc   660
ctgcagattc cccgaggaag aagaaggcgg ctgcgagctg                          700

SEQ ID NO: 186              moltype = AA   length = 232
FEATURE                     Location/Qualifiers
REGION                      1..232
                            note = Synthetic sequence huFAStm-41BB protein
source                      1..232
                            mol_type = protein
                            organism = synthetic construct
SEQUENCE: 186
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNLGWLCLL   180
LLPIPLIVWV KRGRKKLLYI FKQPFMRPVQ TTQEEDGCSC RFPEEEEGGC EL           232

SEQ ID NO: 187              moltype = DNA   length = 730
FEATURE                     Location/Qualifiers
misc_feature                1..730
                            note = Synthetic sequence huFAS-41BBtm construct
source                      1..730
                            mol_type = other DNA
                            organism = synthetic construct
SEQUENCE: 187
caccatgctg ggcatctgga ccctgctgcc tctggtgctg acaagcgtgg ccagactgag    60
cagcaagagc gtgaacgccc aagtgaccga catcaacagc aagggcctgg aactgagaaa   120
gaccgtgacc accgtggaaa cccagaacct ggaaggcctg caccacgacg gccagttctg   180
ccacaagcct tgtcccctg gcgagcggaa ggccagagac tgtactgtga acggcgacga   240
gccccgactgc gtgccctgtc aggaaggcaa agagtacacc gacaaggccc acttcagcag   300
caagtgccgg cggtgcagac tgtgtgatga gggccacggc ctggaagtgg aaatcaactg   360
cacccggacc cagaacacca gtgcagatg caagcccaac ttcttctgca acagcaccgt   420
gtgcgagcac tgcgacccct gtaccaagtg cgaacacgg atcatcaaag agtgcaccct   480
gacctccaac acaaagtgca aagaggaagg cagcagaagc aacatcatat ccttcttcct   540
ggcgttgacc tctaccgcgc tgcttttctt gctgttcttc cttacgctcc gcttcagtgt   600
ggttaagcgg ggcagaaaga agctgctgta catcttcaag cagcctttca tgcggccggt   660
gcagaccacc caggaagagg acggctgctc ctgcagattc cccgaggaag aagaaggcgg   720
ctgcgagctg                                                          730

SEQ ID NO: 188              moltype = AA   length = 242
FEATURE                     Location/Qualifiers
REGION                      1..242
                            note = Synthetic sequence huFAS-41BBtm protein
source                      1..242
                            mol_type = protein
                            organism = synthetic construct
SEQUENCE: 188
MLGIWTLLPL VLTSVARLSS KSVNAQVTDI NSKGLELRKT VTTVETQNLE GLHHDGQFCH    60
KPCPPGERKA RDCTVNGDEP DCVPCQEGKE YTDKAHFSSK CRRCRLCDEG HGLEVEINCT   120
RTQNTKCRCK PNFFCNSTVC EHCDPCTKCE HGIIKECTLT SNTKCKEEGS RSNIISFFLA   180
LTSTALLFLL FFLTLRFSVV KRGRKKLLYI FKQPFMRPVQ TTQEEDGCSC RFPEEEEGGC   240
EL                                                                  242

SEQ ID NO: 189              moltype = DNA   length = 705
FEATURE                     Location/Qualifiers
misc_feature                1..705
```

```
                        note = Synthetic sequence muFas tm-41BB construct
source                  1..705
                        mol_type = other DNA
                        organism = synthetic construct
SEQUENCE: 189
atgctgtgga tctgggccgt gctgcctctg gtgctggctg gatcacagct gagagtgcac    60
acccagggca ccaacagcat cagcgagagc ctgaagctga aagaagagt gcgcgagaca   120
gacaagaact gcagcgaggg cctgtaccag ggcggaccct tctgctgtca gccttgccag   180
cccggcaaga aaaaggtgga agattgcaag atgaacggcg gcaccccta ctgcgcccct    240
tgtacagagg gcaaagagta catggacaag aaccactacg ccgacaagtg cagacggtgc   300
accctgtgcg acgaggaaca cggcctgaa gtggaaacaa actgcaccct gacccagaac    360
accaagtgca agtgcaaacc cgacttctac tgcgacagcc ccggctgcga gcactgcgtc    420
agatgtgcct cttgcgagca cggcaccctg gaaccttgta ccgccaccag caacaccaac   480
tgccggaagc agagcccag aaacagactg tggctgctga ccatcctggt gctgctgatc    540
cccctggtgt tcatctacag cgtgctgaag tggatcagaa agaagttccc ccacatcttc    600
aagcagccct tcaagaaaac caccggcgct gcccaggaag aggacgcctg cagctgtaga    660
tgccctcagg aagaagaagg cggcggaggc ggctacgagc tgtga                   705

SEQ ID NO: 190           moltype = AA    length = 234
FEATURE                  Location/Qualifiers
REGION                   1..234
                         note = Synthetic sequence muFas tm-41BB protein
source                   1..234
                         mol_type = protein
                         organism = synthetic construct
SEQUENCE: 190
MLWIWAVLPL VLAGSQLRVH TQGTNSISES LKLRRRVRET DKNCSEGLYQ GGPFCCQPCQ    60
PGKKKVEDCK MNGGTPTCAP CTEGKEYMDK NHYADKCRRC TLCDEEHGLE VETNCTLTQN   120
TKCKCKPDFY CDSPGCEHCV RCASCEHGTL EPCTATSNTN CRKQSPRNRL WLLTILVLLI   180
PLVFIYSVLK WIRKKFPHIF KQPFKKTTGA AQEEDACSCR CPQEEEGGGG GYEL         234

SEQ ID NO: 191           moltype = DNA   length = 718
FEATURE                  Location/Qualifiers
misc_feature             1..718
                         note = Synthetic sequence muFas-41BBtm construct
source                   1..718
                         mol_type = other DNA
                         organism = synthetic construct
SEQUENCE: 191
caccatgctg tggatctggg ccgtgctgcc tctggtgctg gctggatcac agctgagagt    60
gcacacccag ggcaccaaca gcatcagcga gagcctgaag ctgagaagaa gagtgcgcga   120
gacagacaag aactgcagcg agggcctgta ccagggcgga ccttctgct gtcagccttg    180
ccagcccggc aagaaaaagg tggaagattg caagatgaac ggcggcaccc ctacctgcg    240
cccttgtaca gagggcaaag agtacatgga caagaaccac tacgccgaca gtgcagacg    300
gtgcaccctg tgcgacgagg aacacggcct ggaagtggaa acaaactgca ccctgaccca    360
gaacaccaag tgcaagtgca aacccgactt ctactgcgac agcccggct gcgagcactg    420
cgtcagatgt gcctcttgcg agcacggcac cctggaacct tgtaccgcca gcagcaaac    480
caactgccgg aagcagagcc ccagaaacag aacccttttc ctggctttga cctccgctct    540
cctcttggct ctgatcttca tcaccttct gtttagcgtg ctgaagtgga tcagaaagaa    600
gttcccccac atcttcaagc agcccttcaa gaaaaccacc ggcgctgccc aggaagagga    660
cgcctgcagc tgtagatgcc ctcaggaaga agaaggcggc ggaggcggct acgagctg     718

SEQ ID NO: 192           moltype = AA    length = 238
FEATURE                  Location/Qualifiers
REGION                   1..238
                         note = Synthetic sequence muFas-41BBtm protein
source                   1..238
                         mol_type = protein
                         organism = synthetic construct
SEQUENCE: 192
MLWIWAVLPL VLAGSQLRVH TQGTNSISES LKLRRRVRET DKNCSEGLYQ GGPFCCQPCQ    60
PGKKKVEDCK MNGGTPTCAP CTEGKEYMDK NHYADKCRRC TLCDEEHGLE VETNCTLTQN   120
TKCKCKPDFY CDSPGCEHCV RCASCEHGTL EPCTATSNTN CRKQSPRNRT LFLALTSALL   180
LALIFITLLF SVLKWIRKKF PHIFKQPFKK TTGAAQEEDA CSCRCPQEEE GGGGGYEL    238

SEQ ID NO: 193           moltype = DNA   length = 735
FEATURE                  Location/Qualifiers
misc_feature             1..735
                         note = Synthetic sequencemuFas-9aas-CD28Cys tm-41BBic
                           construct
source                   1..735
                         mol_type = other DNA
                         organism = synthetic construct
SEQUENCE: 193
atgctgtgga tctgggccgt gctgcctctg gtgctggctg gatcacagct gagagtgcac    60
acccagggca ccaacagcat cagcgagagc ctgaagctga agaagagt gcgcgagaca   120
gacaagaact gcagcgaggg cctgtaccag ggcggaccct tctgctgtca gccttgccag   180
cccggcaaga aaaaggtgga agattgcaag atgaacggcg gcaccccta ctgcgcccct    240
tgtacagagg gcaaagagta catggacaag aaccactacg ccgacaagtg cagacggtgc   300
```

```
accctgtgcg acgaggaaca cggcctggaa gtggaaacaa actgcaccct gacccagaac  360
accaagtgca agtgcaaacc cgacttctac tgcgacagcc ccggctgcga gcactgcgtc  420
agatgtgcct cttgcgagca cggcaccctg aaccttgta  ccgccaccag caacaccaac  480
tgccacaccc agagcagccc caagctgttc tgggccctgg tggtggtggc cggcgtgctg  540
ttttgttacg gcctgctcgt gaccgtggcc ctgtgcgtga tctggaccag cgtgctgaag  600
tggatcagaa agaagttccc ccacatcttc aagcagccct tcaagaaaac caccggcgct  660
gcccaggaag aggacgcctg cagctgtaga tgccctcagg aagaagaagg cggcggaggc  720
ggctacgagc tgtga                                                   735

SEQ ID NO: 194       moltype = AA  length = 244
FEATURE              Location/Qualifiers
REGION               1..244
                     note = Synthetic sequence muFas-9aas-CD28Cys tm-41BBic
                      protein
source               1..244
                     mol_type = protein
                     organism = synthetic construct
SEQUENCE: 194
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN CHTQSSPKLF WALVVVAGVL  180
FCYGLLVTVA LCVIWTSVLK WIRKKFPHIF KQPFKKTTGA AQEEDACSCR CPQEEEGGGG  240
GYEL                                                               244

SEQ ID NO: 195       moltype = DNA  length = 735
FEATURE              Location/Qualifiers
misc_feature         1..735
                     note = Synthetic sequence muFas-CD28tm-41BBic construct
source               1..735
                     mol_type = other DNA
                     organism = synthetic construct
SEQUENCE: 195
atgctgtgga tctgggccgt gctgcctctg gtgctggctg atcacagct  gagagtgcac   60
acccagggca ccaacagcat cagcgagagc ctgaagctga agaagagt  gcgcgagaca  120
gacaagaact gcagcgaggg cctgtaccag ggcggacct  tctgctgtca gccttgccag  180
cccggcaaga aaaaggtgga agattgcaag atgaacggcg gcaccccta  ctgcgcccct  240
tgtacagagg gcaaagagta catggacaag aaccactacg ccgacaagtg cagacggtgc  300
accctgtgcg acgaggaaca cggcctggaa gtggaaacaa actgcaccct gacccagaac  360
accaagtgca agtgcaaacc cgacttctac tgcgacagcc ccggctgcga gcactgcgtc  420
agatgtgcct cttgcgagca cggcaccctg aaccttgta  ccgccaccag caacaccaac  480
tgccggaagc agagccccag aaacagattc tgggccctgg tggtggtggc cggcgtgctg  540
ttttgttacg gcctgctcgt gaccgtggcc ctgtgcgtga tctggaccag cgtgctgaag  600
tggatcagaa agaagttccc ccacatcttc aagcagccct tcaagaaaac caccggcgct  660
gcccaggaag aggacgcctg cagctgtaga tgccctcagg aagaagaagg cggcggaggc  720
ggctacgagc tgtga                                                   735

SEQ ID NO: 196       moltype = AA  length = 244
FEATURE              Location/Qualifiers
REGION               1..244
                     note = Synthetic sequence muFas-CD28tm-41BBic protein
source               1..244
                     mol_type = protein
                     organism = synthetic construct
SEQUENCE: 196
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN CRKQSPRNRF WALVVVAGVL  180
FCYGLLVTVA LCVIWTSVLK WIRKKFPHIF KQPFKKTTGA AQEEDACSCR CPQEEEGGGG  240
GYEL                                                               244

SEQ ID NO: 197       moltype = DNA  length = 81
FEATURE              Location/Qualifiers
misc_feature         1..81
                     note = Synthetic sequence hu41BB transmembrane domain
source               1..81
                     mol_type = other DNA
                     organism = synthetic construct
SEQUENCE: 197
atcatatcct tcttcctggc gttgaccgtct accgcgctgc ttttcttgct gttcttcctt   60
acgctccgct tcagtgtggt t                                             81

SEQ ID NO: 198       moltype = AA  length = 27
FEATURE              Location/Qualifiers
REGION               1..27
                     note = Synthetic sequence hu41BB transmembrane protein
source               1..27
                     mol_type = protein
                     organism = synthetic construct
SEQUENCE: 198
```

```
IISFFLALTS TALLFLLFFL TLRFSVV                                      27

SEQ ID NO: 199          moltype = DNA   length = 507
FEATURE                 Location/Qualifiers
misc_feature            1..507
                        note = Synthetic sequence muFas extracellular domain
source                  1..507
                        mol_type = other DNA
                        organism = synthetic construct
SEQUENCE: 199
atgctgtgga tctgggccgt gctgcctctg gtgctggctg atcacagct gagagtgcac   60
acccagggca ccaacagcat cagcgagagc ctgaagctga aagaagagt gcgcgagaca  120
gacaagaact gcagcgaggg cctgtaccag ggcggaccct ctgctgtca gccttgccag  180
cccggcaaga aaaaggtgga agattgcaag atgaacggcg caccctac ctgcgcccct  240
tgtacagagg gcaaagagta catggacaag aaccactacg ccgacaagtg cagacggtgc  300
acctgtgccg acgaggaaca cggcctggaa gtggaaacaa actgcaccct gacccagaac  360
accaagtgca agtgcaaacc cgacttctac tgcgacagcc ccggctgcga gcactgcgtc  420
agatgtgcct cttgcgagca cggcaccctg aaccttgta ccgccaccag caacaccaac   480
tgccggaagc agagccccag aaacaga                                     507

SEQ ID NO: 200          moltype = AA   length = 169
FEATURE                 Location/Qualifiers
REGION                  1..169
                        note = Synthetic sequence muFas extracellular domain protein
source                  1..169
                        mol_type = protein
                        organism = synthetic construct
SEQUENCE: 200
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN CRKQSPRNR              169

SEQ ID NO: 201          moltype = DNA   length = 51
FEATURE                 Location/Qualifiers
misc_feature            1..51
                        note = Synthetic sequence muFas transmembrane domain
source                  1..51
                        mol_type = other DNA
                        organism = synthetic construct
SEQUENCE: 201
ctgtggctgc tgaccatcct ggtgctgctg atcccctgg tgttcatcta c            51

SEQ ID NO: 202          moltype = AA   length = 17
FEATURE                 Location/Qualifiers
REGION                  1..17
                        note = Synthetic sequence muFas transmembrane domain protein
source                  1..17
                        mol_type = protein
                        organism = synthetic construct
SEQUENCE: 202
LWLLTILVLL IPLVFIY                                                 17

SEQ ID NO: 203          moltype = DNA   length = 63
FEATURE                 Location/Qualifiers
misc_feature            1..63
                        note = Synthetic sequence mu41BB transmembrane domain
source                  1..63
                        mol_type = other DNA
                        organism = synthetic construct
SEQUENCE: 203
acccttttcc tggctttgac ctccgctctc ctcttggctc tgatcttcat cacccttctg   60
ttt                                                                63

SEQ ID NO: 204          moltype = AA   length = 21
FEATURE                 Location/Qualifiers
REGION                  1..21
                        note = Synthetic sequence mu41BB transmembrane protein
source                  1..21
                        mol_type = protein
                        organism = synthetic construct
SEQUENCE: 204
TLFLALTSAL LLALIFITLL F                                            21

SEQ ID NO: 205          moltype = DNA   length = 144
FEATURE                 Location/Qualifiers
misc_feature            1..144
                        note = Synthetic sequence mu41BB intracellular domain
source                  1..144
                        mol_type = other DNA
```

```
                                organism = synthetic construct
SEQUENCE: 205
agcgtgctga agtggatcag aaagaagttc ccccacatct tcaagcagcc cttcaagaaa   60
accaccggcg ctgcccagga agaggacgcc tgcagctgta gatgccctca ggaagaagaa  120
ggcggcggag gcggctacga gctg                                         144

SEQ ID NO: 206          moltype = AA  length = 48
FEATURE                 Location/Qualifiers
REGION                  1..48
                        note = Synthetic sequence mu41BB intracellular protein
source                  1..48
                        mol_type = protein
                        organism = synthetic construct
SEQUENCE: 206
SVLKWIRKKF PHIFKQPFKK TTGAAQEEDA CSCRCPQEEE GGGGGYEL                48

SEQ ID NO: 207          moltype = DNA  length = 480
FEATURE                 Location/Qualifiers
misc_feature            1..480
                        note = Synthetic sequence muFas extracellular domain -9aas
source                  1..480
                        mol_type = other DNA
                        organism = synthetic construct
SEQUENCE: 207
atgctgtgga tctgggccgt gctgcctctg gtgctggctg atcacagct  gagagtgcac   60
acccagggca ccaacagcat cagcgagagc ctgaagctga agaagagt  gcgcgagaca  120
gacaagaact gcagcgaggg cctgtaccag ggcggaccct tctgctgtca gccttgccag  180
cccggcaaga aaaaggtgga agattgcaag atgaacggcg gcacccctac ctgcgcccct  240
tgtacagagg gcaaagagta catggacaag aaccactacg ccgacaagtg cagacggtgc  300
accctgtgcg acgaggaaca cggcctggaa gtgaaacaa actgcaccct gacccagaac  360
accaagtgca agtgcaaacc cgacttctac tgcgacagcc ccggctgcga gcactgcgtc  420
agatgtgcct cttgcgagca cggcacccctg gaaccttgta ccgccaccag caacaccaac  480

SEQ ID NO: 208          moltype = AA  length = 160
FEATURE                 Location/Qualifiers
REGION                  1..160
                        note = Synthetic sequence muFas extracellular domain -9aas
                        protein
source                  1..160
                        mol_type = protein
                        organism = synthetic construct
SEQUENCE: 208
MLWIWAVLPL VLAGSQLRVH TQGTNSISES LKLRRRVRET DKNCSEGLYQ GGPFCCQPCQ   60
PGKKKVEDCK MNGGTPTCAP CTEGKEYMDK NHYADKCRRC TLCDEEHGLE VETNCTLTQN  120
TKCKCKPDFY CDSPGCEHCV RCASCEHGTL EPCTATSNTN                        160

SEQ ID NO: 209          moltype = DNA  length = 108
FEATURE                 Location/Qualifiers
misc_feature            1..108
                        note = Synthetic sequence muCD28Cys (108 nt)
source                  1..108
                        mol_type = other DNA
                        organism = synthetic construct
SEQUENCE: 209
tgccacaccc agagcagccc caagctgttc tgggccctgg tggtggtggc cggcgtgctg   60
ttttgttacg gcctgctcgt gaccgtggcc ctgtgcgtga tctggacc              108

SEQ ID NO: 210          moltype = AA  length = 36
FEATURE                 Location/Qualifiers
REGION                  1..36
                        note = Synthetic sequence muCD28Cys protein
source                  1..36
                        mol_type = protein
                        organism = synthetic construct
SEQUENCE: 210
CHTQSSPKLF WALVVVAGVL FCYGLLVTVA LCVIWT                             36

SEQ ID NO: 211          moltype = DNA  length = 81
FEATURE                 Location/Qualifiers
misc_feature            1..81
                        note = Synthetic sequence muCD28tm
source                  1..81
                        mol_type = other DNA
                        organism = synthetic construct
SEQUENCE: 211
ttctggggccc tggtggtggt ggccggcgtg ctgttttgtt acggcctgct cgtgaccgtg   60
gccctgtgcg tgatctggac c                                             81

SEQ ID NO: 212          moltype = AA  length = 27
```

```
FEATURE              Location/Qualifiers
REGION               1..27
                     note = Synthetic sequence muCD28tm protein
source               1..27
                     mol_type = protein
                     organism = synthetic construct
SEQUENCE: 212
FWALVVVAGV LFCYGLLVTV ALCVIWT                                          27

SEQ ID NO: 213       moltype = AA  length = 9
FEATURE              Location/Qualifiers
REGION               1..9
                     note = Synthetic sequence virus gag epitope
source               1..9
                     mol_type = protein
                     organism = synthetic construct
SEQUENCE: 213
CCLCLTVFL                                                               9
```

What is claimed is:

1. A method of treating a cancer or a tumor in a subject, the method comprising administering to the subject a therapeutically effective amount of a T cell, or of a pharmaceutical composition comprising the T cell and a pharmaceutically acceptable carrier, excipient, or diluent, wherein the T cell expresses:
   (1) a fusion protein comprising:
      (1)(a) an extracellular component comprising i) a CD95 (Fas) ectodomain that binds to CD95L (FasL) or ii) a CD95L (FasL)-binding fragment of the CD95 (Fas) ectodomain;
      (1)(b) an intracellular component comprising a CD137 (4-1BB) intracellular signaling domain or a signal-producing portion thereof; and
      (1)(c) a hydrophobic component connecting the extracellular and intracellular components, wherein the hydrophobic component comprises a transmembrane domain selected from the group consisting of CD2, CD3ε, CD3δ, CD3ζ, CD25, CD27, CD28, CD40, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, and Zap70; and
   (2) an antigen-specific T cell receptor (TCR) and/or an antigen-specific chimeric antigen receptor (CAR), wherein the antigen-specific TCR or the antigen-specific CAR specifically binds to a cancer-specific antigen, tumor-specific antigen, or tumor-associated antigen expressed by the cancer or tumor,
   and wherein the T cell is CD4+ or CD8+.

2. The method of claim 1, wherein the T cell is CD4+.

3. The method of claim 1, wherein the antigen-specific TCR is exogenous to the T cell.

4. The method of claim 1, wherein the antigen-specific TCR specifically binds to an HLA class I-restricted cancer or tumor antigen.

5. The method of claim 1, wherein the expression of the fusion protein in the T cell results in at least about a 1.5-fold, 2-fold, or 3-fold increase in survival, expansion, cytotoxicity, and/or cytokine secretion by the T cell in response to the cancer-specific antigen, tumor-specific antigen, or tumor-associated antigen, as compared to a response to the antigen by a T cell substantially the same as the T cell of claim 1, but not expressing the fusion protein.

6. The method of claim 1, wherein the extracellular component of the fusion protein comprises an amino acid sequence selected from the group consisting of SEQ ID NOs: 72, 74, and 76; the hydrophobic component of the fusion protein comprises an amino acid sequence selected from the group consisting of SEQ ID NOs: 27, 78, and 198; and the intracellular component of the fusion protein comprises the amino acid sequence set forth in SEQ ID NO: 36.

7. The method of claim 1, wherein the subject is human.

8. The method of claim 1, wherein the cancer or tumor is a hematological malignancy or a solid tumor.

9. The method of claim 8, wherein the cancer or tumor is a hematological malignancy comprising acute myeloid leukemia (AML); or is a solid tumor selected from a tumor of the pancreas, breast, ovary, prostate, lung, colon, liver, or heart; or a melanoma, a carcinoma, a squamous cell carcinoma, or a neuroblastoma.

10. The method of claim 1, wherein the cancer or tumor is ovarian cancer, pancreatic cancer, or AML, and the fusion protein comprises the CD95 (Fas) ectodomain that binds to CD95L (FasL).

11. The method of claim 2, comprising administering to the subject a therapeutically effective amount of the CD4+ T cell expressing the fusion protein, or of a pharmaceutical composition comprising the CD4+ T cell and a pharmaceutically acceptable carrier, excipient, or diluent, wherein:
   the extracellular component of the fusion protein comprises a binding domain that is, or has at least 95% identity to, a FasL-binding fragment of the amino acid sequence set forth in SEQ ID NO.: 72; and wherein the intracellular signaling domain of the fusion protein is, or contains at least 95% identity to, the amino acid sequence set forth in SEQ ID NO.: 36.

12. The method of claim 11, wherein the extracellular component of the fusion protein comprises a full-length mature extracellular portion of a Fas protein.

13. The method of claim 11, wherein:
   (a) the extracellular component of the fusion protein comprises the amino acid sequence set forth in SEQ ID NO: 72;
   (b) the hydrophobic component of the fusion protein comprises the amino acid sequence set forth in SEQ ID NO: 78 or 198; and (c) the intracellular component of the fusion protein comprises the amino acid sequence set forth in SEQ ID NO: 36.

14. The method of claim 11, wherein the fusion protein comprises the amino acid sequence set forth in SEQ ID NO: 186 or SEQ ID NO: 188.

15. The method of claim 11, wherein the subject is human.

16. The method of claim 11, wherein the cancer or tumor is a hematological malignancy or a solid tumor.

17. The method of claim 16, wherein cancer or tumor is a hematological malignancy comprising acute myeloid leukemia (AML); or is a solid tumor selected from a tumor of the pancreas, breast, ovary, prostate, lung, colon, liver, or heart; or is a melanoma, a carcinoma, a squamous cell carcinoma, or a neuroblastoma.

18. A method of treating a cancer or a tumor in a subject, the method comprising administering to the subject a therapeutically effective amount of a T cell, or of a pharmaceutical composition comprising the T cell and a pharmaceutically acceptable carrier, excipient, or diluent, wherein the T cell expresses:
   (i) a nucleic acid molecule encoding a fusion protein that specifically binds to a target, wherein the nucleic acid molecule comprises:
      (a) a nucleic acid molecule encoding an extracellular binding domain of the fusion protein, wherein the extracellular binding domain binds to the target and wherein the nucleic acid molecule is selected from the group consisting of SEQ ID NOs: 71, 73, and 75;
      (b) a nucleic acid molecule encoding a hydrophobic domain of the fusion protein, wherein said nucleic acid molecule is selected from the group consisting of SEQ ID NOs.: 4, 77, and 197; and
      (c) a nucleic acid molecule encoding an intracellular signaling domain of the fusion protein, wherein said nucleic acid molecule has the sequence set forth in SEQ ID NO.: 13; and wherein the hydrophobic domain connects the extracellular and intracellular domains of the fusion protein; and
   (ii) a nucleic acid molecule encoding an antigen-specific T cell receptor (TCR) and/or a nucleic acid molecule encoding an antigen-specific chimeric antigen receptor (CAR), wherein the antigen-specific TCR or the antigen-specific CAR specifically binds to a cancer-specific antigen, tumor-specific antigen, or tumor-associated antigen expressed by the cancer or tumor.

19. The method of claim 18, wherein the T cell is CD4+ or CD8+.

20. The method of claim 19, wherein the TCR is exogenous to the T cell.

21. The method of claim 19, wherein the antigen-specific TCR specifically binds to an HLA class I-restricted cancer or tumor antigen.

22. The method of claim 18, wherein the fusion protein consists essentially of (a) a CD95 (Fas) ectodomain, (b) a transmembrane domain of a CD137 (4-1BB), and (c) a CD137 (4-1BB) intracellular signaling domain.

23. The method of claim 18, wherein the subject is human.

24. The method of claim 18, wherein the cancer or tumor is a hematological malignancy or a solid tumor.

25. The method of claim 24, wherein the cancer or tumor is a hematological malignancy comprising acute myeloid leukemia (AML); or is a solid tumor selected from a tumor of the pancreas, breast, ovary, prostate, lung, colon, liver, or heart; or is a melanoma, a carcinoma, a squamous cell carcinoma, or a neuroblastoma.

26. The method of claim 19, wherein the expression of the fusion protein in the T cell results in at least about a 1.5-fold, 2-fold, or 3-fold increase in survival, expansion, cytotoxicity, and/or cytokine secretion by the T cell in response to the cancer-specific antigen, tumor-specific antigen, or tumor-associated antigen as compared to a response to the antigen by a cell substantially the same as the T cell but not expressing the fusion protein.

27. The method of claim 1, wherein treating the cancer or tumor comprises controlling or inhibiting cancer or tumor growth in the subject.

28. The method of claim 27, wherein the tumor is a liquid tumor or a solid tumor.

29. The method of claim 28, wherein the tumor is a solid tumor selected from a tumor of the pancreas, breast, ovary, prostate, lung, colon, liver, or heart; or a melanoma, a carcinoma, a squamous cell carcinoma, or a neuroblastoma.

30. The method of claim 27, wherein proliferation of T cells is increased, survival of T cells is increased, and/or T cell death is reduced in the subject following administration of the T cell or the pharmaceutical composition comprising the T cell.

31. The method of claim 1, wherein administering the therapeutically effective amount of the T cell or of the pharmaceutical composition comprising the T cell to the subject increases or enhances persistence of T cells in the subject.

32. The method of claim 31, wherein the subject has a liquid tumor or a solid tumor.

33. The method of claim 32, wherein the tumor is a solid tumor selected from a tumor of the pancreas, breast, ovary, prostate, lung, colon, liver, or heart; or a melanoma, a carcinoma, a squamous cell carcinoma, or a neuroblastoma.

34. The method of claim 31, wherein proliferation of T cells is increased, survival of T cells is increased, and/or T cell death is reduced in the subject following administration of the T cell or the pharmaceutical composition comprising the T cell.

35. A method of treating a cancer or a tumor in a subject, the method comprising administering to the subject a therapeutically effective amount of a T cell, or of a pharmaceutical composition comprising the T cell and a pharmaceutically acceptable carrier, excipient, or diluent, wherein the T cell comprises:
   (i) a fusion protein comprising:
      (i)(a) an extracellular component comprising a binding domain that specifically binds a target;
      (i)(b) an intracellular component comprising an intracellular signaling domain; and
      (i)(c) a hydrophobic component connecting the extracellular and intracellular components;
   wherein the binding domain is, or has at least 95% identity to, an inhibitory molecule binding domain and the intracellular signaling domain is, or has at least 95% identity to, a costimulatory or stimulatory molecule binding domain;
   wherein the inhibitory molecule is or comprises (i) a CD95 (Fas) ectodomain that binds to CD95L (FasL) or (ii) a CD95L (FasL)-binding fragment of (i), and the costimulatory or stimulatory molecule is or comprises an intracellular signaling domain or a signal-producing portion thereof from CD137 (4-1BB); and wherein the T cell is a CD4+ T cell or a CD8+ T cell; and
   (ii) an antigen-specific T cell receptor (TCR) and/or an antigen-specific chimeric antigen receptor (CAR), wherein the antigen-specific TCR or the antigen-specific CAR specifically binds to a cancer-specific antigen, tumor-specific antigen, or tumor-associated antigen expressed by the cancer or tumor.

36. The method of claim 35, wherein the extracellular component of the fusion protein comprises a full-length mature extracellular portion of a Fas protein.

37. The method of claim 35, wherein the subject is human.

38. The method of claim 35, wherein the cancer or tumor is a hematological malignancy or a solid tumor.

39. The method of claim 35, wherein the cancer or tumor is a hematological malignancy comprising acute myeloid leukemia (AML); or is a solid tumor selected from a tumor of the pancreas, breast, ovary, prostate, lung, colon, liver, or heart; or is a melanoma, a carcinoma, a squamous cell carcinoma, or a neuroblastoma.

40. The method of claim 35, wherein the expression of the fusion protein in the T cell results in at least about a 1.5-fold, 2-fold, or 3-fold increase in survival, expansion, cytotoxicity, and/or cytokine secretion by the T cell in response to the cancer-specific antigen, tumor-specific antigen, or tumor-associated antigen as compared to a response to the antigen by a cell substantially the same as the T cell but not expressing the fusion protein.

41. The method of claim 35, wherein administering the therapeutically effective amount of the T cell or of the pharmaceutical composition comprising the T cell to the subject increases or enhances persistence of T cells in the subject.

42. The method of claim 41, wherein proliferation of T cells is increased, survival of T cells is increased, and/or T cell death is reduced in the subject following administration of the T cell or the pharmaceutical composition comprising the T cell.

43. The method of claim 35, wherein the TCR is exogenous to the T cell.

* * * * *